US011261455B2

(12) United States Patent
Hill et al.

(10) Patent No.: US 11,261,455 B2
(45) Date of Patent: Mar. 1, 2022

(54) SUGARCANE MOSAIC VIRUS AS A TRANSIENT GENE EXPRESSION VECTOR

(71) Applicant: Iowa State University Research Foundation, Inc., Ames, IA (US)

(72) Inventors: John Hemmingson Hill, Ames, IA (US); Steven Alan Whitham, Ames, IA (US); Yu Mei, Ames, IA (US); Chunquan Zhang, Clinton, MS (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/929,711

(22) Filed: May 18, 2020

(65) Prior Publication Data
US 2021/0163970 A1 Jun. 3, 2021

Related U.S. Application Data

(60) Provisional application No. 62/942,407, filed on Dec. 2, 2019.

(51) Int. Cl.
*C12N 15/82* (2006.01)
(52) U.S. Cl.
CPC ................................ *C12N 15/8216* (2013.01)

(58) Field of Classification Search
None
See application file for complete search history.

(56) References Cited

U.S. PATENT DOCUMENTS 5,162,601 A * 11/1992 Slightom ............. C07K 14/005 435/320.1
5,766,885 A * 6/1998 Carrington et al. ......................... C12N 15/8203 435/70.1

OTHER PUBLICATIONS

Jander (2017) VIPER Grant Proposal, Boyce Thompson Int.*
Joshi et al. (1990) EMBO J 9(9):2663-69.*
Scofield et al., "Resources for Virus-Induced Gene Silencing in the Grasses", Plant Physiology, vol. 149, pp. 152-157, Jan. 2009.
Stewart et al., "Complete sequence and development of a full-lengh infectious clone of an Ohio isolate of Maize dwarf mosaic virus (MDMV)", Virus Research, vol. 165, pp. 219-224, Feb. 3, 2012.
Boyce Thompson Institute for Plant Research et al. "VIPER: Viruses and Insects as Plant Enhancement Resources", Proposal: vol. 1, 52 pages, submitted Jan. 17, 2017.

* cited by examiner

*Primary Examiner* — Russell T Boggs
(74) *Attorney, Agent, or Firm* — McKee, Voorhees & Sease, PLC

(57) ABSTRACT

The present invention provides plant virus vectors developed from the *Sugarcane mosaic* virus (SCMV). The vectors include a nucleic acid sequence encoding an infectious *Sugarcane mosaic* virus (SCMV) operably linked to one or more regulatory elements functional in a plant. The plant virus vectors may be used to infect monocot plants, such as maize, for gene expression applications.

21 Claims, 12 Drawing Sheets

Specification includes a Sequence Listing.

A

B

SUGARCANE MOSAIC VIRUS AS A TRANSIENT GENE EXPRESSION VECTOR

CROSS-REFERENCE TO RELATED APPLICATION

This application claims priority under 35 U.S.C. § 119 to Provisional Application U.S. Ser. No. 62/942,407, filed on Dec. 2, 2019, which is herein incorporated by reference in its entirety including without limitation, the specification, claims, and abstract, as well as any figures, tables, or examples thereof.

SEQUENCE LISTING

The instant application contains a Sequence Listing which has been submitted in ASCII format via EFS-Web and is hereby incorporated by reference in its entirety. Said ASCII copy, created on Apr. 28, 2020, is named HILL_P13045US01_SEQ_LISTING_ST25.txt and is 142,310 bytes in size.

FIELD OF THE INVENTION

The present invention relates to methods and compositions for genetic manipulation of monocot plants. More specifically, the invention describes the use of a *Sugarcane mosaic* virus (SCMV) based vector designed for foreign gene expression applications.

BACKGROUND OF THE INVENTION

Plant virus-based vectors for expressing heterologous proteins in plants present promising biotechnological tools to supplement conventional breeding and transgenic technologies. Considering the speed with which a virus infection becomes established throughout a plant and the high yield of viral-encoded proteins that accumulate in plants, the use of viral vectors provides an attractive and cost-effective means for the production of valuable proteins in plants and for rapid evaluation of new traits. Due to these advantages, many viral vectors have been developed and used, especially in dicot plants.

Virus-based expression vectors are used to transiently and rapidly express a wide range of recombinant proteins in plants. The use of viruses to deliver heterologous proteins overcomes the need for transgenic plant production, which is time consuming and costly in most crop species. A variety of foreign proteins have been expressed from various viruses including reporter proteins (e.g. green fluorescent protein (GFP) and β-glucuronidase (GUS)), selectable markers such as the bialaphos resistance (BAR) protein, and biopharmaceutical proteins (e.g. vaccine epitopes and therapeutic proteins), and pathogen effectors. The virus-mediated expression of heterologous proteins is useful not only for in planta protein production, but also the use of reporter-tagged viruses enables virus replication and movement to be easily tracked and quantified, which has greatly facilitated studies of virus-host interactions. In addition, viruses expressing selectable markers enabled high throughput genetic screens for plant lines with altered virus susceptibility.

Viruses in the sugarcane mosaic subgroup of the *Potyvirus* genus infect a wide range of plant species in the Graminae, including maize, sorghum, and sugarcane. The sugarcane mosaic subgroup contains four closely related but distinct viral species: *Sugarcane mosaic* virus (SCMV), *Maize dwarf mosaic* virus (MDMV), *Johnson grass mosaic* virus, and *Sorghum mosaic* virus. Similar to other potyviruses, SCMV has a positive sense, single-stranded RNA genome that is polyadenylated at the 3' terminus and encodes a large polyprotein that is cleaved into 10 mature proteins by three viral proteases. Co-infections of SCMV with the unrelated maize chlorotic mottle virus (MCMV) result in the destructive maize lethal necrosis disease that is a major problem for maize production in sub-Saharan Africa. The ability of SCMV to infect maize and other grass species where it may have utility for protein expression and its ability to participate in synergistic interactions with MCMV made SCMV an attractive candidate for developing infectious clones and expression vectors.

It is an object of the present invention to disclose an infectious plant virus vector system based on *Sugarcane mosaic* virus (SCMV) for foreign gene expression in maize and other monocots.

SUMMARY OF THE INVENTION

The present invention provides plant virus vectors developed from the *Sugarcane mosaic* virus (SCMV). According to the invention, the vector includes a nucleic acid construct with an infectious SCMV sequence operably linked to regulatory sequences functional in a plant cell. The SCMV vectors according to the invention may be full length, variant or truncated SCMV sequences. The SCMV sequence is engineered to include a heterologous multiple cloning site for insertion of sequences. The plant virus vectors may be used to infect monocot plants, such as maize.

In one embodiment optimized for foreign gene expression, the vector is engineered to include the multiple cloning site at the P1/HC-Pro junction. In some embodiments, the cloning sites are followed by NIa-Pro cleavage sites. Preferably, the SCMV sequence is rendered non-aphid transmissible by modification of the DAG amino acid motif near the N-terminus of CP.

The present invention also relates to a method of expressing foreign nucleotide sequences of interest in plant cells, including monocots such as maize. According to the invention, the SCMV sequence has the foreign nucleotide sequence inserted therein. In some embodiments, vectors are designed to be delivered directly into plant cells by biolistic inoculation.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION OF THE INVENTION

Figure 1:
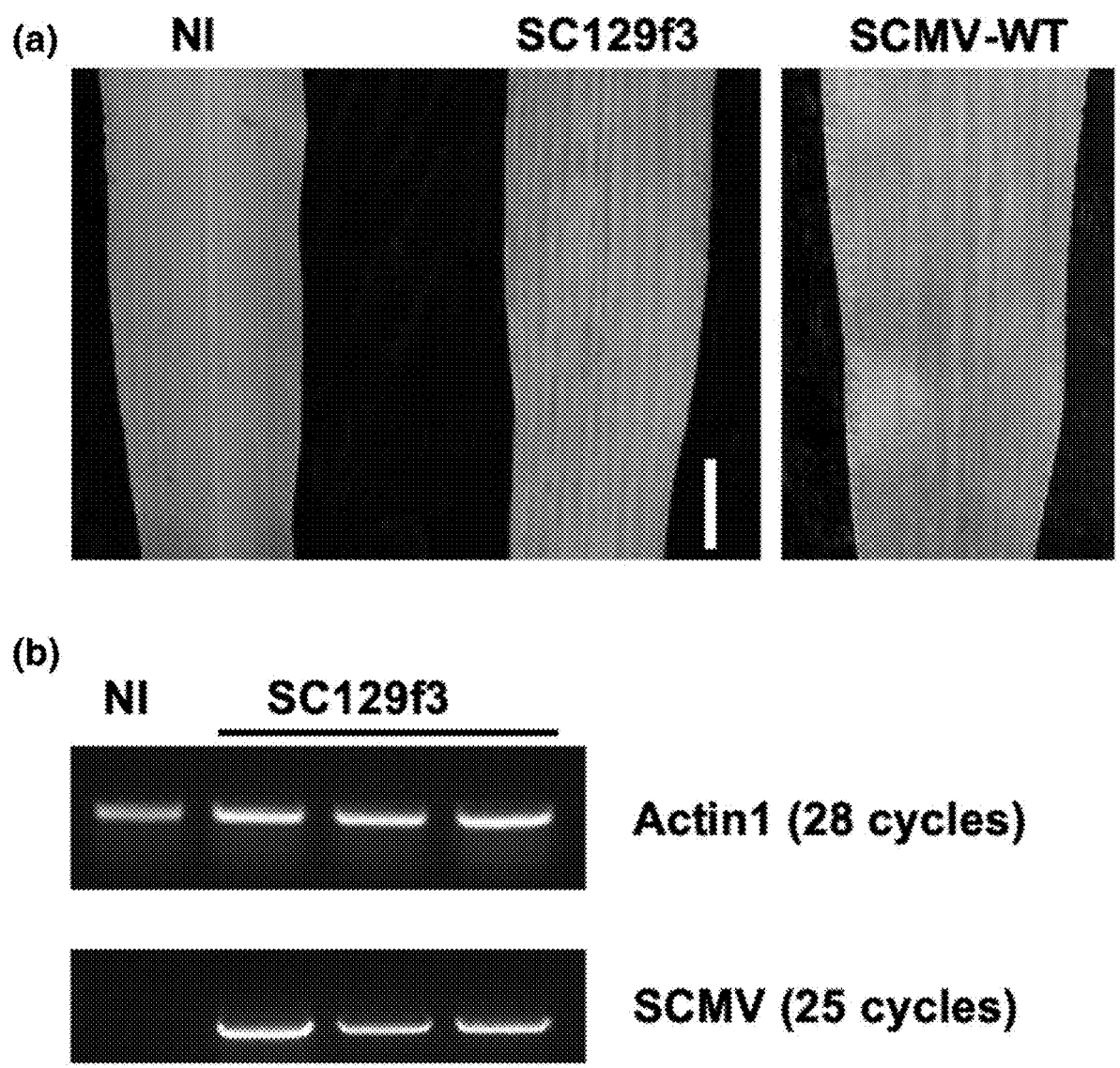
FIG. 1 shows confirmation of infectivity of the SCMV infectious clone. A. Typical mosaic symptoms were observed on an SC129f3-infected leaf but not on non-infected wild-type leaf (NI). The mosaic symptoms were indistinguishable from those caused by infection with the wild type SCMV (SCMV-WT). Bar=1 cm. B. RT-PCR amplification using primers for SCMV coat protein sequence on total RNA extracted from a non-infected plant (NI) and 3 plants inoculated with SC129f3. The SCMV fragment can only be detected in symptomatic leaves of plants inoculated with SC129f3. RT-PCR amplification of ZmActin1 was included as an internal positive control for RT-PCR.

Many viruses that infect dicot plants and belong to the *Potyvirus* genus have been engineered to express foreign proteins. An advantage of potyviruses is that their virions are filamentous, and therefore, the addition of a heterologous sequence results in a proportional increase in virion length. The mature viral proteins occur in the following order in the viral polyprotein: protein 1 (P1; SEQ ID NO: 1), helper component-proteinase (HC-Pro; SEQ ID NO: 2), protein 3 (P3; SEQ ID NO: 3)/6 kilo dalton 1 (6K1; SEQ ID NO: 4), cylindrical inclusion (CI; SEQ ID NO: 5), 6 kilo dalton 2 (6K2; SEQ ID NO: 6), viral protein genome-linked (VPg; SEQ ID NO: 7), nuclear inclusion proteinase a (NIa-Pro; SEQ ID NO: 8), nuclear inclusion b (Nib; SEQ ID NO: 9), and capsid protein (CP; SEQ ID NO: 10). The P1/HC-Pro junction is cleaved in cis by the P1 proteinase, the HC-Pro/P3 junction is cleaved in cis by HC-Pro, and all other junctions are cleaved in cis or trans by NIa-Pro. Potyviruses, including SCMV, encode an 11$^{th}$ protein, named PIPO, which is produced as a result of transcriptional slippage of the viral RNA polymerase at the amino-terminus of the coding sequence of the P3 protein.

Because potyviruses use a polyprotein expression strategy, the coding sequences of foreign proteins must be cloned in frame with the viral open reading frame. In addition, the insertion site(s) for foreign sequences must be flanked by amino acids comprising viral proteinase cleavage sites to ensure that the recombinant protein is processed from the mature viral proteins. Six different locations have been shown to be suitable for expressing proteins from potyviral genomes. The two most commonly used cloning sites are at the junctions of P1/HC-Pro and NIb/CP. P1 is a serine protease that cleaves its own C-terminus from the N-terminus of HC-Pro. Cloning sites using the P1/HC-Pro junction are engineered immediately after the cleavage site, which results in cleavage of the P1 C-terminus from the N-terminus of the foreign protein. A seven amino acid NIa-Pro cleavage site is added after the cloning site to process the C-terminus of the foreign protein away from the N-terminus of HC-Pro. Similarly, cloning sites at the NIb/CP junction utilize the naturally occurring NIa-Pro cleavage site at this junction along with an additional engineered NIa-Pro cleavage site after the cloning site.

Full-length SCMV infectious clones and modifications for gene expression in maize are disclosed. The junction of the P1 and HC-Pro cistrons was engineered to include a cloning site for inserting coding sequences of interest followed by a NIa protease cleavage site (SEQ ID NO: 15). This cloning strategy requires that the proteins of interest to be expressed in-frame with the viral polyprotein and then processed into their free forms by the viral-encoded P1 and NIa proteases. Two versions of the multiple cloning site (CS1 and CS2; SEQ ID NOs: 12 and 13) were made to provide different choices of restriction enzyme sites as dictated by the nucleotide sequences encoding proteins of interest. Both versions of the cloning site were confirmed to be stable after three serial passages in sweet corn using the marker gene GFP and the herbicide resistance gene BAR. A third version of the multiple cloning site (CS3; SEQ ID NOs: 14) is also provided. By mutating the DAG motif in the SCMV CP into the non-aphid transmissible DTG version, a non-aphid transmissible variant that prevents insect-vectored transmission of the recombinant virus was generated.

Many modifications and other embodiments of the invention will come to mind to one skilled in the art to which this invention pertains, having the benefit of the teachings presented in the descriptions and the drawings herein. As a result, it is to be understood that the invention is not to be limited to the specific embodiments disclosed and that modifications and other embodiments are intended to be included within the scope of the appended claims. Although specific terms are used in the specification, they are used in a generic and descriptive sense only and not for purposes of limitation.

In order to provide a clear and consistent understanding of the specification and the claims, including the scope given to such terms, the following definitions are provided. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, e.g., Sambrook et al. MOLECULAR CLONING: A LABORATORY MANUAL, 2d ed., Cold Spring Harbor Laboratory Press, 1989; 3d ed., 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press. San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The following definitions are provided to facilitate an understanding of the present invention.

Unless otherwise specified, "a," "an," "the," and "at least one" are used interchangeably and mean one or more than one.

"Plant" species of interest include, but are not limited to, corn (*Zea mays*), soybean (*Glycine max*), common bean (*Phaseolus vulgaris*), Peanuts (*Arachis hypogaea*), Medicago sativa, *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*)), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. In a preferred embodiment the plant is a monocot plant such as maize. The skilled person will appreciate that the tropism of the viral vectors disclosed herein varies. However, determining susceptibility to such viruses is well within the purview of the skilled person.

Maize is an important model for genetics and plant biology, and in addition, it is an important grain crop that is widely cultivated throughout the world. It is used in livestock feed and processed into a multitude of food and industrial products including starch, sweeteners, corn oil, beverage and industrial alcohol, and fuel ethanol. The current analysis of the maize B73 reference genome (B73 RefGen_v4) predicts 39,498 coding and 6,774 non-coding genes (gramene.org, accessed Nov. 8, 2018) (Schnable et al.

2009). Analysis of the function of these genes could be facilitated by new tools, such as viral vectors, that enable rapid analysis of gene functions through VIGS or protein expression. The SCMV vectors described herein represent a useful addition to the toolkit used for evaluating the functions of genes in maize.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

A "replicon" is any genetic element, for example, a plasmid, cosmid, bacmid, plastid, phage or virus that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" refers to a nucleic acid segment that may possess transcriptional and translational control sequences, such as promoters, enhancers, translational start signals (e.g., ATG or AUG codons), polyadenylation signals, terminators, and the like, and which facilitate the expression of a nucleic acid sequence in a host cell or organism.

By "host cell" is meant a cell which contains a vector of the present invention and supports the replication and/or expression of said vector. Host cells may be prokaryotic cells such as *E. coli*, or eukaryotic cells such as yeast, insect, amphibian, plant, or mammalian cells. Preferably, host cells are monocotyledonous plant cells, although dicotyledonous plant cells are encompassed as well. A particularly preferred monocotyledonous host cell is a maize host cell.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "introduce", shall refer to any method or means by which a nucleic acid is facilitated into a cell or host organism and may be used interchangeably to convey the same meaning. Such methods include, but are not limited to, transfection, electroporation, microinjection, PEG-fusion, *Agrobacterium* infection, and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant. A number of "selectable marker genes" are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I III, Laboratory Procedures and Their Applications Academic Press, New York, 1984. Particularly preferred selectable marker genes for use in the present invention would be genes which confer resistance to compounds such as antibiotics like kanamycin, and herbicides like glyphosate (Della-Cioppa et al., Bio/Technology 5(6), 1987, U.S. Pat. Nos. 5,463,175, 5,633,435). Other selection devices can also be implemented and would still fall within the scope of the present invention.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

"Native" refers to a naturally occurring ("wild-type") nucleic acid sequence.

"Heterologous" sequence refers to a sequence which originates from a foreign source or species or, if from the same source, is modified from its original form.

As used herein, the term "endogenous," when used in reference to a polypeptide, nucleic acid or gene, refers to a polypeptide, nucleic acid or gene that is expressed by a host or already present within a host plant.

A "coding sequence" or "coding region" refers to a nucleic acid molecule having sequence information necessary to produce a gene product, when the sequence is expressed.

"Genetic component" refers to any nucleic acid sequence or genetic element which may also be a component or part of an expression vector. Examples of genetic components include, but are not limited to promoter regions, 5' untranslated leaders or promoters, introns, genes, 3' untranslated regions or terminators, and other regulatory sequences or sequences which affect transcription or translation of one or more nucleic acid sequences.

"Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins. "Reduced gene expression" means that the expression of a plant endogenous sequence is reduced in a genetically modified plant cell or genetically modified plant containing a nucleic acid silencer molecule stably integrated in its genome when compared to a plant cell or plant which does not contain the nucleic acid silencer molecule. "Reduced gene expression" may involve a reduction of expression of a plant endogenous nucleic acid by at least 10%, 20%, 30%, 40%, 50%, 60%, 70%, 75%, 80%, 85%, 90%, 95% or 100%.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr et al., Science 232:1106 1112, 1986; Ellis et al., EMBO J. 6:1116, 1987; Strittmatter and Chua, Proc. Nat. Acad. Sci. USA 84:8986 8990, 1987; Poulsen and Chua, Mol. Gen. Genet. 214:16 23, 1988; Comai et al., Plant Mol. Biol. 15:373 381, 1991).

The 3' non-translated region of the gene constructs of the invention contain a transcriptional terminator, or an element having equivalent function, and, optionally, a polyadenylation signal, which functions in plants to cause the addition of polyadenylated nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (Nos) gene, and (2) plant genes such as the soybean storage protein genes and the small subunit of the ribulose-1,5-bisphosphate carboxylase (ssRUBISCO) gene. An example of another 3' region is that from the ssRUBISCO E9 gene from pea (European Patent Application 385,962, herein incorporated by reference in its entirety).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

As used herein, "transgenic plant" or "genetically modified plant" includes reference to a plant that comprises within its nuclear genome a heterologous polynucleotide. Generally, the heterologous polynucleotide is stably integrated within the nuclear genome such that the polynucleotide is passed on to successive generations. The heterologous polynucleotide may be integrated into the genome alone or as part of a recombinant expression cassette. "Transgenic" or "genetically modified" is used herein to include any cell, cell line, callus, tissue, plant part or plant, the genotype of which has been altered by the presence of heterologous nucleic acid including those initially so altered as well as those created by sexual crosses or asexual propagation from the initial transgenic or genetically modified plant. The term "transgenic" or "genetically modified" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide (e.g., SCMV-based constructs as described herein). Expression vectors of the present invention permit transcription of a nucleic acid inserted therein.

As used herein, "gene editing," "gene edited" "genetically edited" and "gene editing effectors" refer to the use of naturally occurring or artificially engineered nucleases, also referred to as "molecular scissors." The nucleases create specific double-stranded break (DSBs) at desired locations in the genome, which in some cases harnesses the cell's endogenous mechanisms to repair the induced break by natural processes of homologous recombination (HR) and/or nonhomologous end-joining (NHEJ). Gene editing effectors include Zinc Finger Nucleases (ZFNs), Transcription Activator-Like Effector Nucleases (TALENs), the Clustered Regularly Interspaced Short Palindromic Repeats/CAS9 (CRISPR/Cas9) system, and meganuclease re-engineered as homing endonucleases. The terms also include the use of transgenic procedures and techniques, including, for example, where the change is relatively small and/or does not introduce DNA from a foreign species. The terms "genetic manipulation" and "genetically manipulated" include gene editing techniques, as well as and/or in addition to other techniques and processes that alter or modify the nucleotide sequence of a gene or gene, or modify or alter the expression of a gene or genes.

As used herein, "VIGS" means virus-induced gene silencing.

As used herein, "viral silencing vector" means a DNA construct comprising (i) a sufficient portion of a viral genome to induce VIGS and (ii) a nucleotide sequence that is similar (i.e., a sequence that has a sufficient percent identity or a sufficient percent complementarity to effect down regulation) to at least a fragment of a target gene, wherein the target gene is down-regulated when the viral silencing vector is introduced into a cell. For example, in order to affect VIGS in a plant, the portion of the viral genome required to affect VIGS may include that portion responsible for viral movement and viral replication in the plant. As is known to those skilled in the art, each virus/host combination should be optimized for producing effective silencing vectors. However, it is to be understood that other optimized vectors can be used and are included within the scope of the applicant's teachings. For example, the silencing vector may include the origin of replication, the genes necessary for replication in a plant cell, and one or more nucleotide sequences with similarity to one or more target genes. The vector may also include those genes necessary for viral movement. The nucleotide sequence that is similar to at least a fragment of a target gene may replace any coding or non-coding region that is nonessential for the present purposes of gene silencing, may be inserted into the vector outside the viral sequences, or may be inserted just downstream of an endogenous viral gene, such that the viral gene and the nucleotide sequence are cotranscribed. The size of the nucleotide sequence that is similar to the target gene may depend on the site of insertion or replacement within the viral genome. Accordingly, there are many ways of producing silencing vectors, as known to those skilled in the art. The vectors of the invention may optionally include other sequences known to those of skill in the art such as marker genes, regulatory elements, terminators, antibiotic resistance genes, and the like.

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information World Wide Web at ncbi.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

Production of a genetically modified plant tissue either expressing or inhibiting expression of a gene of interest combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the plant species to be modified, the particular gene of interest, promoter elements and upstream elements used. Persons skilled in the art are able to select and use appropriate alternatives to achieve functionality. Culture conditions for expressing desired genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and gene selection are other parameters which may be optimized to achieve desired plant expression or inhibition as is known to those of skill in the art and taught herein.

The following is a non-limiting general overview of Molecular biology techniques which may be used in performing the invention Regulatory Elements Exemplary promoters for expression of a nucleic acid sequence in SCMV-based constructs include the CaMV 35S promoter (Odell et al., 1985), CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or R gene complex associated promoters (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that nucleic acids encoding a polypeptide as provided herein may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

Terminators

Transformation constructs prepared in accordance with the invention will typically include a 3' end DNA sequence that acts as a signal to terminate transcription and allow for the poly-adenylation of the mRNA produced by coding sequences operably linked to a promoter. Alternatively, a heterologous 3' end may enhance the expression of coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a. β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or a gene encoding for green fluorescent protein (Sheen et al., 1995; Haseloff et al., 1997; Reichel et al., 1996; Tian et al., 1997; WO 97/41228).

A heterologous nucleotide sequence of the present invention can be provided as its wild-type sequence. Alternatively, a synthetic sequence, such as a "plant-optimized" sequence mentioned above can be employed. A nucleotide sequence having a high degree of homology to these sequences, so that the encoded amino acid sequence remains substantially unchanged, are also contemplated. In particular, sequences at least 80%, more preferably 90%, homologous with an aforementioned nucleotide sequence are contemplated. In one embodiment, the SCMV-based transformation vectors as described herein comprise heterologous nucleic acids encoding genes producing increased agronomic traits (e.g., herbicide resistance, pathogen resistance, drought resistance, increased crop yield, etc.). Genes encoding beneficial agronomic traits are known to those in the art. It should be noted, however, that only that those epitopes of an expressed antigenic protein essential for generating the desired response need be present in the translated molecule. Accordingly, C- and/or N-terminal fragments, including portions of fusion proteins, presenting the essential epitopes are contemplated within the invention. Such fragments can be encoded in a vector construct of the invention or can be generated in vivo or in vitro by post-translation cleavage processes.

Gene Silencing

The vector is used to silence an endogenous target nucleic acid sequence present in a plant cell. The target sequences for silencing can be designed for the production of short hairpin RNA or silencing RNA against the target nucleic acid, gene, etc. Therefore vectors disclosed herein can include a silencing sequence encoding a gene, cDNA or mRNA of interest, or fragment thereof. The sequence can be 70%, 75%, 80%, 85%, 90%, 95%, 98%, 99%, or 100% identical to the sequence of the endogenous target gene, cDNA or mRNA, or 70%, 75%, 80%, 85%, 90%, 95%, 98%, 99%, or 100% identical to a complement thereof. The sequence is typically introduced to the constructs in reverse orientation.

The target polynucleotide of interest can be a full-length gene, or complement thereof. It can include non-coding regions including, but not limited to 5' untranslated region, 3' untranslated region, and one or more introns. The polynucleotide of interest can be a gene's coding region, or complement thereof, for example an mRNA or cDNA.

The polynucleotide can be a fragment of a full-length gene, mRNA, or cDNA. The polynucleotide can include the coding region, one or more introns, 5' untranslated region, 3' untranslated region or a combination thereof from a full-length gene. For example, the polynucleotide can at least 10, preferably at least 20, more preferably at least 30, most preferably at least 50 nucleotides of a gene, mRNA, or cDNA of interest. In some embodiments, the polynucleotide includes the first 10, 20, 30, 40, 50, 75, 100, 150, 200, 300, 400, 500, 750, or 1000 nucleotides of a gene or mRNA numbering for the 5' ATG start site. In some embodiments, the polynucleotide includes 10, 20, 30, 40, 50, 75, 100, 150, 200, 300, 400, 500, 750, or 1000 nucleotides beginning 3' of the ATG start site. In some embodiments, the polynucleotide includes the last 10, 20, 30, 40, 50, 75, 100, 150, 200, 300, 400, 500, 750, or 1000 nucleotides ending with the 3' stop codon. In some embodiments the polynucleotide includes the entire transcriptional unit of the gene, mRNA, or cDNA of interest.

In some embodiments the polynucleotide directs formation of tasiRNA against all splice variants of a gene or mRNA of interest by including sequences that are common to all of the splice variants. Likewise, the polynucleotide can direct formation of tasiRNA against related genes or mRNA of interest by including one or more sequences that are similar or related between the two related genes. For example, in some embodiments, the polynucleotide includes a sequence that 80%, 85%, 90%, 95%, 98%, 99%, or 100% identical to a sequence found in at least two different genes or mRNA of interest. The polynucleotide can also be specific for one or more splice variants of a gene when the sequence of the polynucleotide is unique that one or more splice variants.

The possible target genes of the compositions disclosed herein include but are not limited to those discussed below. The genes are generally related to one or more functions or pathways in a cell. It is also possible to target a single gene or mRNA. It is also possible to target more than one gene or mRNA simultaneously. Therefore, in some embodiments, the expression of at least two different target genes is reduced. The target genes can originate from a single group of genes direct to the same or related function or pathway. Alternatively, target genes can originate from genes directed to different or unrelated functions or pathways.

Another important application of plant viral vector systems is in studies on host gene function. With more plant genomic information available, a high throughput tool is required. Virus-induced gene silencing (VIGS) is an exceptional reverse genetics tool that can be employed to generate mutant phenotypes for conveying function to unknown genes. VIGS has many advantages over other methods, for example, it is quick and does not require plant transformation (Burch-Smith et al., 2004). In VIGS systems, viruses are designed to carry partial sequence of known or candidate genes in order to link their function to the mutant phenotype. Replication of the recombinant virus and generation of dsRNA intermediates trigger the RNA-mediated host defense system, resulting in degradation of RNA with sequence identity to the recombinant virus including mRNA of the gene of interest. The targets of VIGS can be a single gene, several members of a gene family, or several distinct genes (Lu et al., EMBO J. 22, 5690-5699 (2003a); Peele, et al., Plant J. 27:357-366 (2001); Turnage, et al., Plant J. 30:107-117 (2002)). Many model host plants including *N. benthamiana*, tomato, tobacco, *Arabidopsis*, and cassava have been explored (Burch-Smith, et al., Plant J. 39:734-746 (2004)). With the current abundance of genomic information on maize and other grass species (Stacey, et al., Plant Physiol. 135:59-70 (2004)), it is timely to apply VIGS to maize to enhance knowledge of gene function in such a major grain crop.

The invention additionally provides a method for virus-induced gene silencing in a maize plant and vectors useful in a method for virus-induced gene silencing. Such a method can include the step of inoculating a maize plant with *Sugarcane mosaic* virus (SCMV) RNA, wherein the SCMV RNA comprises a nucleic acid sequence encoding at least a portion of a gene endogenous to the maize plant. For virus-induced gene silencing, a partial or entire sequence of an endogenous gene can also be located in the untranslated regions (UTRs) of RNA2, or in RNA1 if the sequence is small enough to be accommodated, as discussed above, since it is the expression of the nucleic acid encoding at least a portion of an endogenous gene that results in gene silencing. For a virus-induced gene silencing vector, the insertion in the UTRs can be facilitated by engineering appropriate restriction sites for insertion of the endogenous gene, so long as the inserted endogenous sequence does not impair viral RNA replication and a sufficient amount of infective SCMV is produced.

The SCMV-based vector is suitable for use as a VIGS vector to study gene function maize. Maize is a major grain crop and an important source of food, feed, and biofuels. It is subject to a wide range of pathogens and VIGS is an ideal reverse genetics tool for maize functional genomics aimed at understanding host-microbe interaction.

It will generally be desirable that vectors provided by the invention be capable of systemic spread in an infected plant. However, such a systemic spread may not be essential for efficient gene silencing. A recombinant vector provided by the invention may or may not therefore include all cis-elements required for vascular movement of the vector or even its cell-to-cell spread. In this manner, modulation of plant gene expression in a collection of plant cells may be more efficiently carried out. Methods for inoculating plants and plant cells with recombinant viral vectors or viral particles are well known to those of skill in the art. Such vectors may, for example, be administered in a solution and may also contain any other desired ingredients including buffers, cis-elements, surfactants, solvents and similar components.

Plant Transformation Techniques

The transformation of suitable agronomic plant hosts using vectors can be accomplished with a variety of methods and plant tissues. Representative transformation procedures include *Agrobacterium*-mediated transformation, biolistics, rub inoculation, microinjection, electroporation, polyethylene glycol-mediated protoplast transformation, liposome-mediated transformation, and silicon fiber-mediated transformation (U.S. Pat. No. 5,464,765 to Coffee, et al.; "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga et al. eds.) Cold Spring Laboratory Press, New York (1995)).

Plants can be transformed by a number of reported procedures (U.S. Pat. No. 5,015,580 to Christou, et al.; U.S. Pat. No. 5,015,944 to Bubash; U.S. Pat. No. 5,024,944 to Collins, et al.; U.S. Pat. No. 5,322,783 to Tomes et al.; U.S. Pat. No. 5,416,011 to Hinchee et al.; U.S. Pat. No. 5,169,770 to Chee et al.). A number of transformation procedures have been reported for the production of transgenic maize plants including pollen transformation (U.S. Pat. No. 5,629,183 to Saunders et al.), silicon fiber-mediated transformation (U.S. Pat. No. 5,464,765 to Coffee et al.), electroporation of protoplasts (U.S. Pat. No. 5,231,019 Paszkowski et al.; U.S. Pat. No. 5,472,869 to Krzyzek et al.; U.S. Pat. No. 5,384,253 to Krzyzek et al.), gene gun (U.S. Pat. No. 5,538,877 to Lundquist et al. and U.S. Pat. No. 5,538,880 to Lundquist et al.), and *Agrobacterium*-mediated transformation (EP 0 604 662 A1 and WO 94/00977 both to Hiei Yukou et al.). The *Agrobacterium*-mediated procedure is particularly preferred as single integration events of the transgene constructs are more readily obtained using this procedure which greatly facilitates subsequent plant breeding. Cotton can be transformed by particle bombardment (U.S. Pat. No. 5,004,863 to Umbeck and U.S. Pat. No. 5,159,135 to Umbeck). Sunflower can be transformed using a combination of particle bombardment and *Agrobacterium* infection (EP 0 486 233 A2 to Bidney, Dennis; U.S. Pat. No. 5,030,572 to Power et al.). Flax can be transformed by either particle bombardment or *Agrobacterium*-mediated transformation. Switchgrass can be transformed using either biolistic or *Agrobacterium* mediated methods (Richards et al. Plant Cell Rep. 20: 48-54 (2001); Somleva et al. Crop Science 42: 2080-2087 (2002)). Methods for sugarcane transformation have also been described (Franks & Birch Aust. J. Plant Physiol. 18, 471-480 (1991); WO 2002/037951 to Elliott, Adrian, Ross et al.).

Transformation of most monocotyledon species has now become somewhat routine. Preferred techniques include direct gene transfer into protoplasts using PEG or electroporation techniques, particle bombardment into callus tissue or organized structures, as well as *Agrobacterium*-mediated transformation.

A. *Agrobacterium*-mediated Transformation

One method for introducing a *Sugarcane mosaic* virus-based expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10: 1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8: 238 (1989). See also, U.S. Pat. No. 5,563,055, (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector of the present invention is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559-563 (1988), Sanford, J. C., *Physiol Plant* 79: 206 (1990), Klein et al., *Biotechnology* 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors of the present invention into plants. Deshayes et al., *EMBO J.,* 4: 2731 (1985), Christou et al., *Proc Natl. Acad. Sci. U.S.A.* 84: 3962 (1987). Direct uptake of DNA into protoplasts using $CaCl_2$ precipitation, polyvinyl alcohol or poly-L-ornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495-1505 (1992) and Spencer et al., *Plant Mol. Biol.* 24: 51-61 (1994).

Following transformation of target tissues, expression of the above-described selectable marker genes allows for preferential selection of transformed cells, tissues and/or plants, using regeneration and selection methods now well known in the art.

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same SCMV-based vector, or physically separate on different vectors. A cell may be simultaneously transformed with more than one vector of the invention provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

The transformed cells may then be regenerated into a transgenic plant. The regenerated plants are transferred to standard soil conditions and cultivated in a conventional manner.

After the SCMV-based expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species this is accomplished rather easily by the use of another culture or isolated microspore culture. By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

Integration of a Heterologous Nucleic Acid Insert

Integration of an exogenous nucleic acid insert provided by the SCMV-based expression cassette as described herein can be accomplished by random integration into the plants genome or through site-specific integration. Site-specific integration of an exogenous nucleic acid at a native locus may be accomplished by any technique known to those of skill in the art. In some embodiments, integration of a heterologous nucleic acid insert at a native plant locus comprises contacting a cell (e.g., an isolated cell or a cell in a tissue) with a nucleic acid molecule of the present invention comprising the heterologous nucleic acid insert. In examples, such a nucleic acid molecule may comprise nucleotide sequences flanking the exogenous nucleic acid that facilitate homologous recombination between the nucleic acid molecule and at least one native locus. In particular examples, the nucleotide sequences flanking the exogenous nucleic acid that facilitate homologous recombination may be complementary to endogenous nucleotides of the native locus. In some embodiments, the heterologous nucleic acid insert provides for improved agronomic traits. In some embodiments, a plurality of exogenous nucleic acids may be integrated, such as in gene stacking.

Integration of a nucleic acid may be facilitated (e.g., catalyzed) in some embodiments by endogenous cellular machinery of a host cell, such as, for example and without limitation, endogenous DNA and endogenous recombinase enzymes. In some embodiments, integration of a nucleic acid may be facilitated by one or more factors (e.g., polypeptides) that are provided to a host cell. For example, nuclease(s), recombinase(s), and/or ligase polypeptides may be provided (either independently or as part of a chimeric polypeptide) by contacting the polypeptides with the host cell, or by expressing the polypeptides within the host cell via the SCMV-based expression vectors of the present invention. Accordingly, in some examples, a nucleic acid comprising a nucleotide sequence encoding at least one nuclease, recombinase, and/or ligase polypeptide may be introduced into the host cell, either concurrently or sequentially with a nucleic acid to be integrated site-specifically, wherein the at least one nuclease, recombinase, and/or ligase polypeptide is expressed from the nucleotide sequence in the host cell.

Targeted Endonuclease Systems

Genome editing tools such as transcription activator-like effector nucleases (TALENs) and zinc finger nucleases (ZFNs) have impacted the fields of biotechnology, functional genomic studies in many organisms, and are contemplated to be used with the SCMV-based expression systems describe herein. More recently, RNA-guided endonucleases (RGENs) are directed to their target sites by a complementary RNA molecule. The Cas9/CRISPR system is a REGEN. tracrRNA is another such tool. These are examples of targeted nuclease systems: these systems have a DNA-binding member that localizes the nuclease to a target site. The site is then cut by the nuclease. TALENs and ZFNs have the nuclease fused to the DNA-binding member. Cas9/CRISPR are cognates that find each other on the target DNA. The DNA-binding member has a cognate sequence in the chromosomal DNA. The DNA-binding member is typically designed in light of the intended cognate sequence so as to obtain a nucleolytic action at nor near an intended site. Certain embodiments are applicable to all such systems without limitation; including, embodiments that minimize nuclease re-cleavage, embodiments for making SNPs with precision at an intended residue, and placement of the allele that is being introgressed at the DNA-binding site.

In a preferred embodiment, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60) make up the gene sequences of the CRISPR/Cas nuclease system. CRISPR loci in microbial hosts contain a combination of Cas genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the foreign nucleic acid. Thus, in the bacterial cell, several Cas proteins are involved with the natural function of the CRISPR/Cas system and serve roles in functions such as insertion of the foreign DNA etc.

Compositions and methods for making and using CRISPR-Cas systems are described in U.S. Pat. No. 8,697,359, entitled "CRISPR-CAS SYSTEMS AND METHODS FOR ALTERING EXPRESSION OF GENE PRODUCTS," which is incorporated herein in its entirety.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

As used herein, the term "guide polynucleotide", relates to a polynucleotide sequence that can form a complex with a Cas endonuclease and enables the Cas endonuclease to recognize and optionally cleave a DNA target site (see also U.S. patent application Ser. No. 14/462,691, filed on Aug. 20, 2014, incorporated by reference herein). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

In particular embodiments, the SCMV-based vector comprises a DNA-binding polypeptide or guide RNA that specifically recognizes and binds to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

Vector Construction

Construction of vectors for use with the invention will be well known to those of skill in light of the current disclosure. Recombinant constructs preferably comprise restriction endonuclease sites to facilitate vector construction. Particularly useful are unique restriction endonuclease recognition sites. Examples of such restriction sites include sites for the restriction endonucleases HindIII, Tth 1111, BsmI, KpnI and XhoI. Endonucleases preferentially break the internal phosphodiester bonds of polynucleotide chains. They may be relatively unspecific, cutting polynucleotide bonds regardless of the surrounding nucleotide sequence. However, the endonucleases which cleave only a specific nucleotide sequence are called restriction enzymes. Restriction endonucleases generally internally cleave nucleic acid molecules at specific recognition sites, making breaks within "recognition" sequences that in many, but not all, cases exhibit two-fold symmetry around a given point. Such enzymes typically create double-stranded breaks.

Many of these enzymes make a staggered cleavage, yielding DNA fragments with protruding single-stranded 5' or 3' termini. Such ends are said to be "sticky" or "cohesive" because they will hydrogen bond to complementary 3' or 5' ends. As a result, the end of any DNA fragment produced by an enzyme, such as EcoRI, can anneal with any other fragment produced by that enzyme. This properly allows splicing of foreign genes into plasmids, for example. Some restriction endonucleases that may be particularly useful with the current invention include Bsu36I, HpaI, PspOMI, XbaI and XhoI.

Some endonucleases create fragments that have blunt ends, that is, that lack any protruding single strands. An alternative way to create blunt ends is to use a restriction enzyme that leaves overhangs, but to fill in the overhangs with a polymerase, such as Klenow, thereby resulting in blunt ends. When DNA has been cleaved with restriction enzymes that cut across both strands at the same position, blunt end ligation can be used to join the fragments directly together. The advantage of this technique is that any pair of ends may be joined together, irrespective of sequence.

Those nucleases that preferentially break off terminal nucleotides are referred to as exonucleases. For example, small deletions can be produced in any DNA molecule by treatment with an exonuclease which starts from each 3' end of the DNA and chews away single strands in a 3' to 5' direction, creating a population of DNA molecules with single-stranded fragments at each end, some containing terminal nucleotides. Similarly, exonucleases that digest DNA from the 5' end or enzymes that remove nucleotides from both strands have often been used. Some exonucleases which may be particularly useful in the present invention include Bal31, S1, and ExoIII. These nucleolytic reactions can be controlled by varying the time of incubation, the temperature, and the enzyme concentration needed to make deletions. Phosphatases and kinases also may be used to control which fragments have ends which can be joined. Examples of useful phosphatases include shrimp alkaline phosphatase and calf intestinal alkaline phosphatase. An example of a useful kinase is T4 polynucleotide kinase.

Once the source DNA sequences and vector sequences have been cleaved and modified to generate appropriate ends, they are incubated together with enzymes capable of mediating the ligation of the two DNA molecules. Particularly useful enzymes for this purpose include T4 ligase, *E. coli* ligase, or other similar enzymes. The action of these enzymes results in the sealing of the linear DNA to produce a larger DNA molecule containing the desired fragment (see, for example, U.S. Pat. Nos. 4,237,224; 4,264,731; 4,273,875; 4,322,499 and 4,336,336, which are specifically incorporated herein by reference).

It is to be understood that the termini of the linearized plasmid and the termini of the DNA fragment being inserted must be complementary or blunt in order for the ligation reaction to be successful. Suitable complementary ends can be achieved by choosing appropriate restriction endonucleases (i.e., if the fragment is produced by the same restriction endonuclease or one that generates the same overhang as that used to linearize the plasmid, then the termini of both molecules will be complementary). As discussed previously, in one embodiment of the invention, at least two classes of the vectors used in the present invention are adapted to receive the foreign oligonucleotide fragments in only one orientation. After joining the DNA segment to the vector, the resulting hybrid DNA can then be selected from among the large population of clones or libraries.

Once a DNA vector has been prepared, it will be readily understood to those of skill in the art that infective RNA transcripts may be made therefrom. For example, commercial kits are available for production of RNA transcripts. On example of such a kit that was used by the inventors is the mMeSSAGE mMACHINE transcription kit from Ambion (Austin, Tex.).

In certain embodiments of the invention, techniques may thus be used to assay gene expression and generally, the efficacy of a given gene silencing construct. While this may be carried out by visual observation of a change in plant phenotype, molecular tools may also be used. For example, expression may be evaluated by specifically identifying the nucleic acid or protein products of genes. Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently, the expression of a gene product is determined by evaluating the phenotypic results of its expression. These assays also may take many forms including but not limited to, analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may be observed, such as plant stature or growth.

Characterization of Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*.

Another example of an herbicide which is useful for selection of transformed cell lines in the practice of the invention is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on polypeptides encoded by the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use a bar-bialaphos or the EPSPS-glyphosate selective system, for example, transformed tissue can be cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be preferred, it is proposed that ranges of 0.1-50 mg/l bialaphos or 0.1-50 mM glyphosate will find utility.

Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

It is understood that modifications which do not substantially affect the activity the various embodiments of this invention are also provided within the definition of the invention provided herein. Accordingly, the following examples are intended to illustrate but not limit the present invention.

EXAMPLES

Example 1

Construction of an SCMV Full-Length Infectious Clone

The SCMV virus isolate ([MDMV-B] designated Iowa 66-188 [ATCC-PV53]) was first isolated in Iowa in 1966 (Ford et al. 1967; Hill et al. 1973) and maintained in sweet corn (Z. mays cv. 'Golden x Bantam'). The SCMV genome was obtained through reverse-transcription followed by PCR (RT-PCR) using total RNA extracted from SCMV-infected maize tissue. The full-length genome was placed under control of P35S and Tnos in the same plasmid backbone previously used for a Foxtail mosaic virus (FoMV) virus-induced gene silencing vector. Initial screening of SCMV full-length clones showed that no single clone was infectious when inoculated biolistically onto sweet corn seedlings. However, two pools of clones designated as set 129 (clones SC129, SC159, and SC163) and set 143 (clones SC143, SC147 and SC167) were infectious. The genomes of these six clones were sequenced and compared. Comparison of the predicted viral polyproteins of SC129, SC159, and SC163 identified differences at 15 amino acid positions (Table 1), and SC159 contains a frame shift that leads to early termination of the polyprotein at amino acid 1852. All three clones in set 143 carry the same amino acids at 13 of the 15 positions Q40, I100, P1103, L1216, C1229, M1528, V1536, G1983, L2354, D2504, L2736, F2953, and Q3076, but they differ at positions 555 and 558 (Table 1). With the exception of positions 100, 555, 558, and 2504, the amino acid residues in the set 143 clones are consistent with the consensus amino acid composition of the 18 full-length SCMV genomes identified in BLAST sequence alignments when SC129 was used as a query against the GenBank non-redundant (nr) database (Table 1). Based on these observations, we postulated that Q40, I100, P1103, L1216, C1229, M1528, V1536, G1983, L2354, D2504, L2736, F2953 and Q3076 were the correct amino acid residues at these 13 positions.

We also hypothesized that the preferred amino acids would predominate in virus accumulating in the systemically infected tissues following inoculation with a mixture of the SC129, SC159, and SC163 clones. RT-PCR was used to amplify five fragments of the viral genome encompassing the 15 amino acid positions. The RT-PCR products were cloned and 21 to 36 independent clones of each were sequenced (Table 2). The predominant amino acids at the 15 positions in question were: Q40, I100, S555, P558, P1103, L1216, C1229, M1528, V1536, G1983, L2354, D2504, L2736, F2953, and Q3076 (Table 2). These sequencing results were consistent with our in silico prediction based on sequence comparison of the full-length SCMV genomes, and they also demonstrated that S at position 555 and P at position 558 are preferred. SC129, which had the fewest differences from the consensus sequence, was modified by introducing amino acid substitutions F555S, S558P, P2354L, and G254D. The resulting construct was named SC129f3, and it was tested for infectivity following biolistic inoculation of sweet corn plants. Symptoms of leaf mosaic, mottling, and chlorosis occurred in the systemic leaves that were indistinguishable from symptoms caused by the wild type virus (FIG. 1A). These symptoms were observed as early as 6 days post inoculation (dpi) and persisted in all systemic leaves. RT-PCR analysis confirmed the presence of SCMV in symptomatic leaves of plants that had been biolistically inoculated with SC129f3 (FIG. 1B).

firmed to be infectious following biolistic inoculation using the same conditions as for the SC129f3 parental virus clone.

Example 3

Systemic Expression of GFP from SCMV

Figure 3:
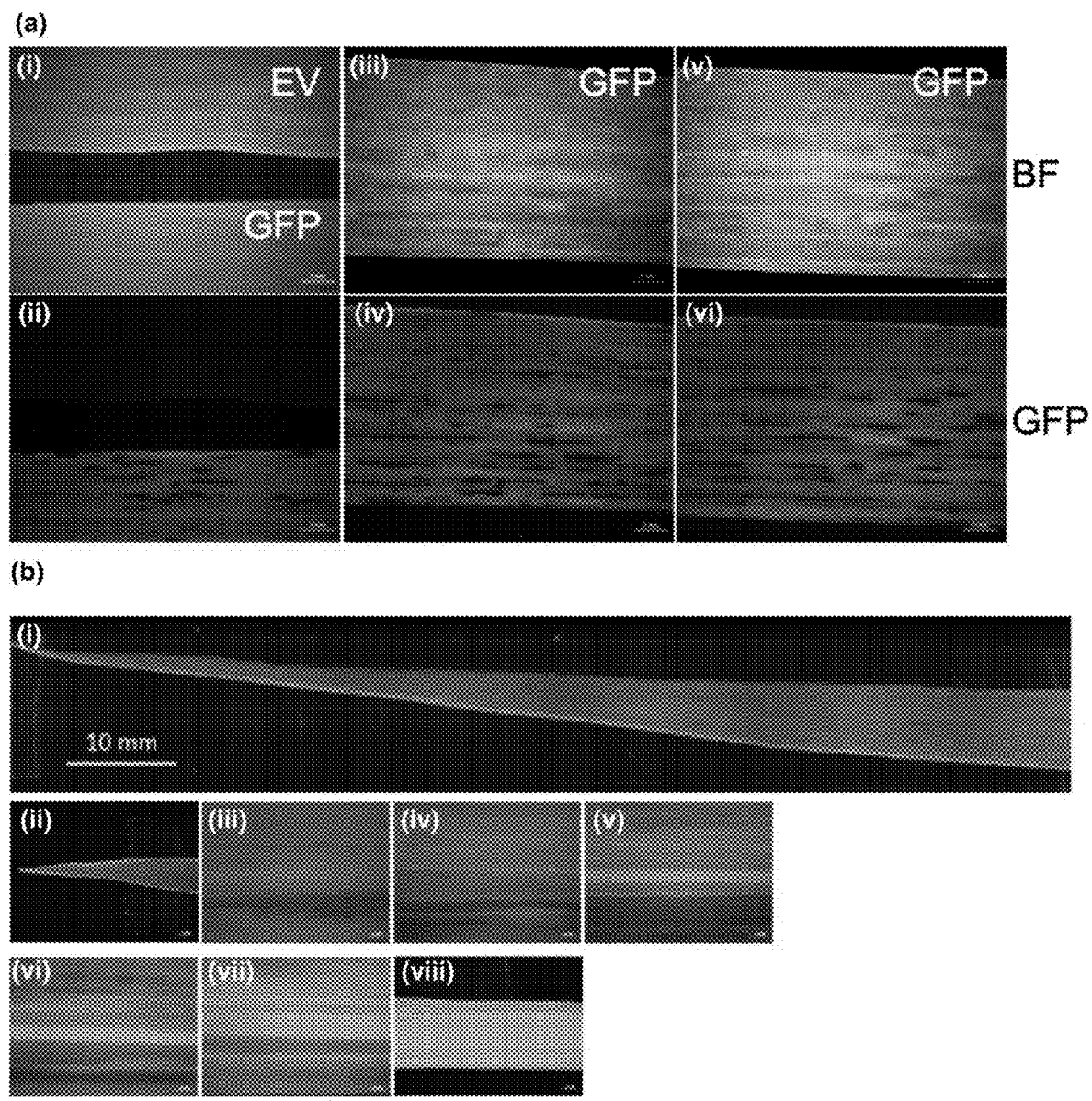
FIG. 3 shows SCMV-mediated GFP expression in sweet corn (Golden x Bantam). A. Green fluorescence was observed only in SCMV-CS1-GFP-infected leaves but not in leaves infected with the SCMV-CS1 empty vector (EV). i, iii, v, bright field; ii, iv, vi, the same leaf as in i, iii, v under green fluorescence channel. B. i, composite image of green fluorescence of a SCMV-CS1-GFP-infected half leaf (fifth leaf) 10 cm from the leaf tip. ii-viii, images of a 60 cm SCMV-CS1-GFP leaf (fifth leaf) at 10 cm intervals under the green fluorescence channel.

To investigate the potential of SCMV for protein expression in maize, the GFP coding sequence minus the stop codon was cloned into SCMV-CS1 to make pSCMV-CS1-GFP. At two-weeks after inoculation, typical mosaic symptoms were observed on leaves of plants infected with the SCMV-CS1-GFP and SCMV-CS1 empty vector (EV) plants (FIG. 3Ai, iii, v). The leaves of infected plants were exam-

TABLE 1

Sequence comparison among SCMV full-length infectious clones.

| | SCMV cistron Amino acid position in SCMV polyprotein | | | | | | | | | | | | | |
|---|---|---|---|---|---|---|---|---|---|---|---|---|---|---|
| | P1 | | HC-Pro | 6k1 | | CI | | | VPg | | NIb | | | CP |
| Clone[a] | 40 | 100 | 555 558 | 1103 | 1216 | 1229 | 1528 | 1536 | 1983 | 2354 | 2504 | 2736 | 2953 | 3076 |
| SC159[b] | R | I | S  P | Q | L | R | M | V | -(G) | -(L) | -(D) | -(L) | -(F) | -(Q) |
| SC163 | Q | T | S  P | P | P | C | T | A | E | L | D | P | L | P |
| SC129 | Q | I | F  S | P | L | C | M | V | G | P | G | L | F | Q |
| Set143[c] | Q | I | S/F P/S | P | L | C | M | V | G | L | D | L | F | Q |

[a]Amino acid differences are shown for the three individual clones of Set129 (SC129, SC159, and SC163). For Set143, a summary is provided.
[b]The predicted amino acid in parentheses is not made due to a frameshift.
[c]Amino acids in italics are conserved with 18 full length SCMV genomes in GenBank nr (release 192).

TABLE 2

Predominant amino acids observed in systemically infected plants inoculated with a combination of SC129, SC159, and SC163.

| Amino acid | Cloned RT-PCR fragment | | | | | | | | | | | | | |
|---|---|---|---|---|---|---|---|---|---|---|---|---|---|---|
| | 1 | | 2 | | 3 | | | | 4 | | | 5 | | |
| Position | 40 | 100 | 555 | 558 | 1103 | 1216 | 1229 | 1528 | 1536 | 1983 | 2354 | 2504 | 2736 | 2953 | 3076 |
| Residue | Q | I | S | P | P | L | C | M | V | G | L | D | L | F | Q |
| Number observed | 19 | 20 | 23 | 23 | 25 | 25 | 25 | 32 | 32 | 35 | 32 | 34 | 24 | 22 | 22 |
| Total clones | 21 | 21 | 24 | 24 | 36 | 36 | 36 | 36 | 36 | 36 | 36 | 36 | 24 | 24 | 24 |

Example 2

Expression of Heterologous Proteins from Modified SCMV Clones

Figure 2:
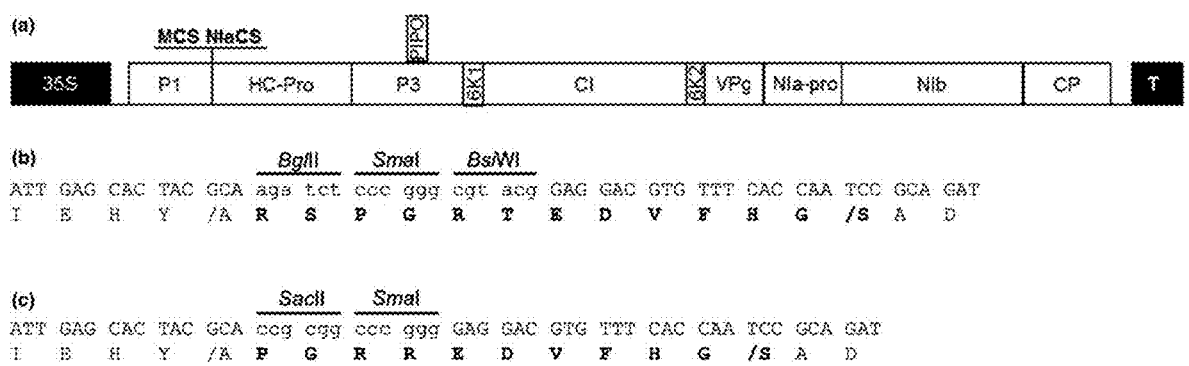
FIG. 2 is a diagram of SCMV expression constructs and cloning site modifications. A. Schematic representation of the modified SCMV genome. The positions of the multiple cloning site (MCS) and additional nuclear inclusion a proteinase cleavage site (NIaCS) engineered between P1 and HC-Pro are indicated. 35S, CaMV 35S promoter; P1, protein 1; HC-Pro, helper component proteinase; P3, protein 3; 6K1, 6 kiloDalton protein 1; CI, cylindrical inclusion; 6K2, 6 kiloDalton protein 2; VPg, genome-linked viral protein; NIa-pro, nuclear inclusion a proteinase; NIb, nuclear inclusion b (replicase); CP, coat protein; T, nopaline synthase terminator; and PIPO, pretty interesting potyviral open reading frame. B. Nucleotide and deduced amino acid sequences of the multiple cloning site in SCMV-CS1 (SEQ ID NOs: 85 and 86). The BglII, SmaI and BsiWI sites are shown with lowercase letters and the P1 and engineered NIa-Pro cleavage sites are represented by a forward slash. Bold letters indicate amino acids added to create the MCS1 and NIaCS. C. Nucleotide and deduced amino acid sequences of the multiple cloning site in SCMV-CS2 (SEQ ID NOs: 87 and 88). The SacII and SmaI sites are shown in lowercase letters and the P1 and engineered NIa-Pro cleavage sites are represented by a forward slash. Bold letters indicate amino acids added to create the MCS2 and NIaCS.
Figure 7:
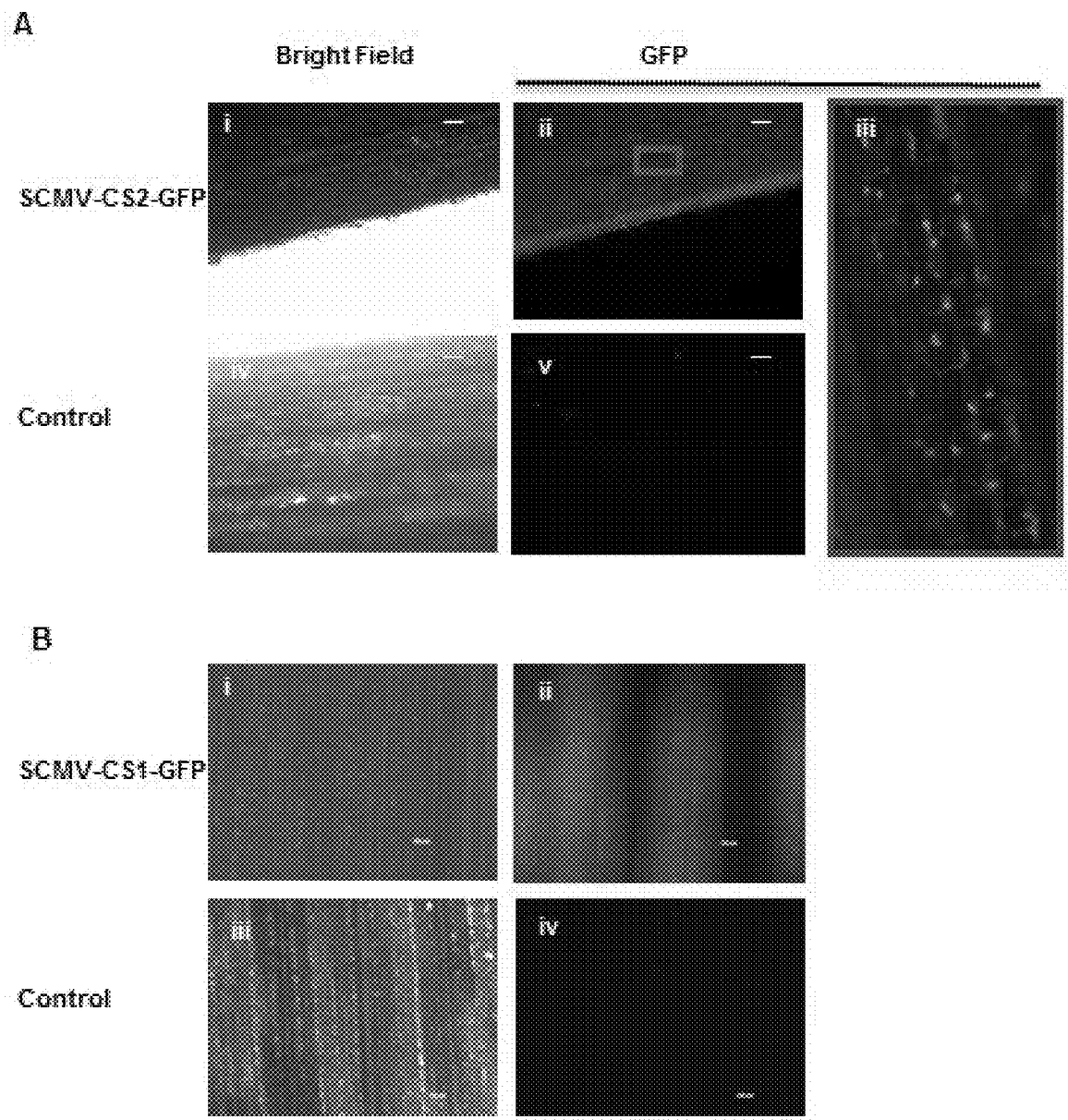
FIG. 7 shows SCMV-mediated GFP expression in sweet corn (Golden x Bantam) and B73. A. Green fluorescence was observed in SCMV-CS2-GFP-infected leaves but not in the control leaves. i, iv, bright field; ii, v, the same leaf as in i, iv under green fluorescence channel; iii, close-up image of the red rectangle in ii. B. SCMV-mediated GFP expression in B73. Green fluorescence was observed in SCMV-CS1-GFP rub inoculated B73 leaf (iii) but not in the control B73 leaf (iv). i, iii, bright field; ii, iv, the same leaf as in i, iii under green fluorescence channel. Bar=100 um.

In order to express heterologous proteins from SCMV, two different multiple cloning sites were inserted at the junction of the P1 and HC-Pro cistrons (FIG. 2A). This position has been used successfully for engineering several other potyviral vectors, including SMV, ZYMV, TEV, and ClYVV. The resulting clones, named SCMV-CS1 and SCMV-CS2, harbor different enzyme cloning sites BglII/SmaI/BsiWI and SacII/SmaI, respectively (FIG. 2B, C). A seven amino acid NIa-Pro cleavage site derived from the junction of SCMV NIb/CP was introduced after each cloning site (FIG. 2B, 2C). The third nucleotide of each codon was changed to avoid an exact duplication of the RNA sequence encoding the wild type NIa cleavage site at the NIb/CP junction. SCMV-CS1 and SCMV-CS2 were conined using a fluorescent dissecting microscope, and green fluorescence was detected only in SCMV-CS1-GFP-infected leaf tissue (FIG. 3Aii). The green fluorescence detected in the SCMV-CS1-GFP infected tissue occurred in a mosaic pattern throughout the leaves. To better visualize the distribution of GFP with respect to mosaic symptoms, we compared bright field and fluorescent images. In general, the lighter green to yellow areas in the bright field image corresponded with green fluorescent signal, whereas the dark green areas in the bright field had relatively less to no green fluorescence (FIG. 3Aiii-3Avi). To examine the expression of GFP across the length of a SCMV-CS1-GFP-infected leaf, a 10-cm section from the leaf tip was digitally reconstructed from 6 overlapping serial images (2 cm in length) (FIG. 3Bi). In addition, 7 images (2 cm in length) were taken from a 60-cm long leaf at 10-cm intervals (FIG. 3Bii-viii). Green fluorescence was seen in all the areas examined, indicating the presence of GFP from the base to the tip of the leaf. GFP was also expressed from the SCMV-CS2 vector with similar results (FIG. 7A).

Figure 4:
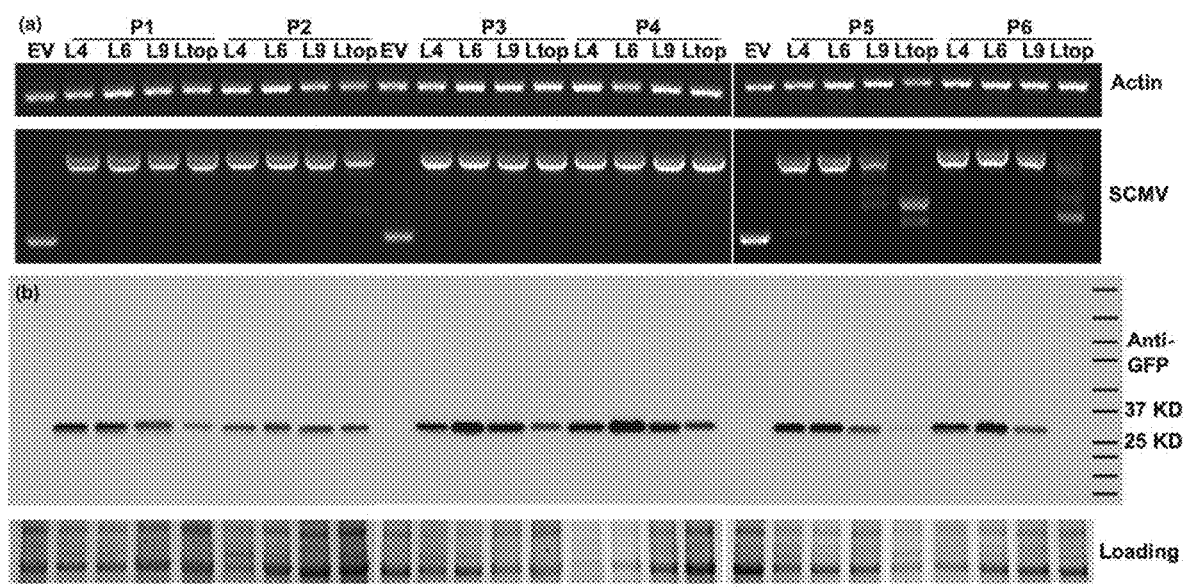
FIG. 4 shows SCMV mediated GFP expression in sweet corn (Golden x Bantam). A. RT-PCR analyses for the GFP insert stability in SCMV-CS1-GFP-infected plants. The upper gel image is the RT-PCR control showing amplification of a single maize actin1 mRNA fragment in all samples. The lower gel image is RT-PCR amplification across the SCMV cloning site. EV indicates the SCMV-CS1 empty vector that carries no insert. L4, L6, L9, Ltop indicate the leaf number that was sampled. B. Western blot analysis showing GFP expression in SCMV-CS1-GFP-infected leaf tissues that are presented in panel A. The upper panel shows the 27 kDa band corresponding to GFP protein detected using anti-GFP antibody and chemiluminescence. The lower panel shows the protein loading control.

To investigate the stability of the GFP coding sequence, infected leaves were harvested over a two-month time course. RT-PCR analysis using primers that flanked the GFP insertion site was performed to determine if the GFP insert was intact or if deletions occurred. A 344-nt RT-PCR product was detected in tissue infected with the SCMV-CS1 empty vector, and a 1055 nt product was detected in the SCMV-CS1-GFP infected tissue, indicating the presence of the GFP insert (FIG. 4A). A single product of 1055 nt was seen in the $4^{th}$ and $6^{th}$ leaf samples. An additional band of smaller size was detected in one of the six leaf 9 samples indicating minor deletion had occurred and increasing numbers of plants were observed with deletions in the top leaf samples. Consistent with the RT-PCR results, western blot assay using an anti-GFP antibody detected GFP in all the L4, L6, and L9 samples and also in most of the top leaf samples where GFP appeared to be less abundant. These results indicate that SCMV-mediated GFP expression is robust and long-lasting, but the integrity of the GFP insertion may decrease over extended periods of time.

Example 4

Expression of BAR and GUS from SCMV

Figure 5:
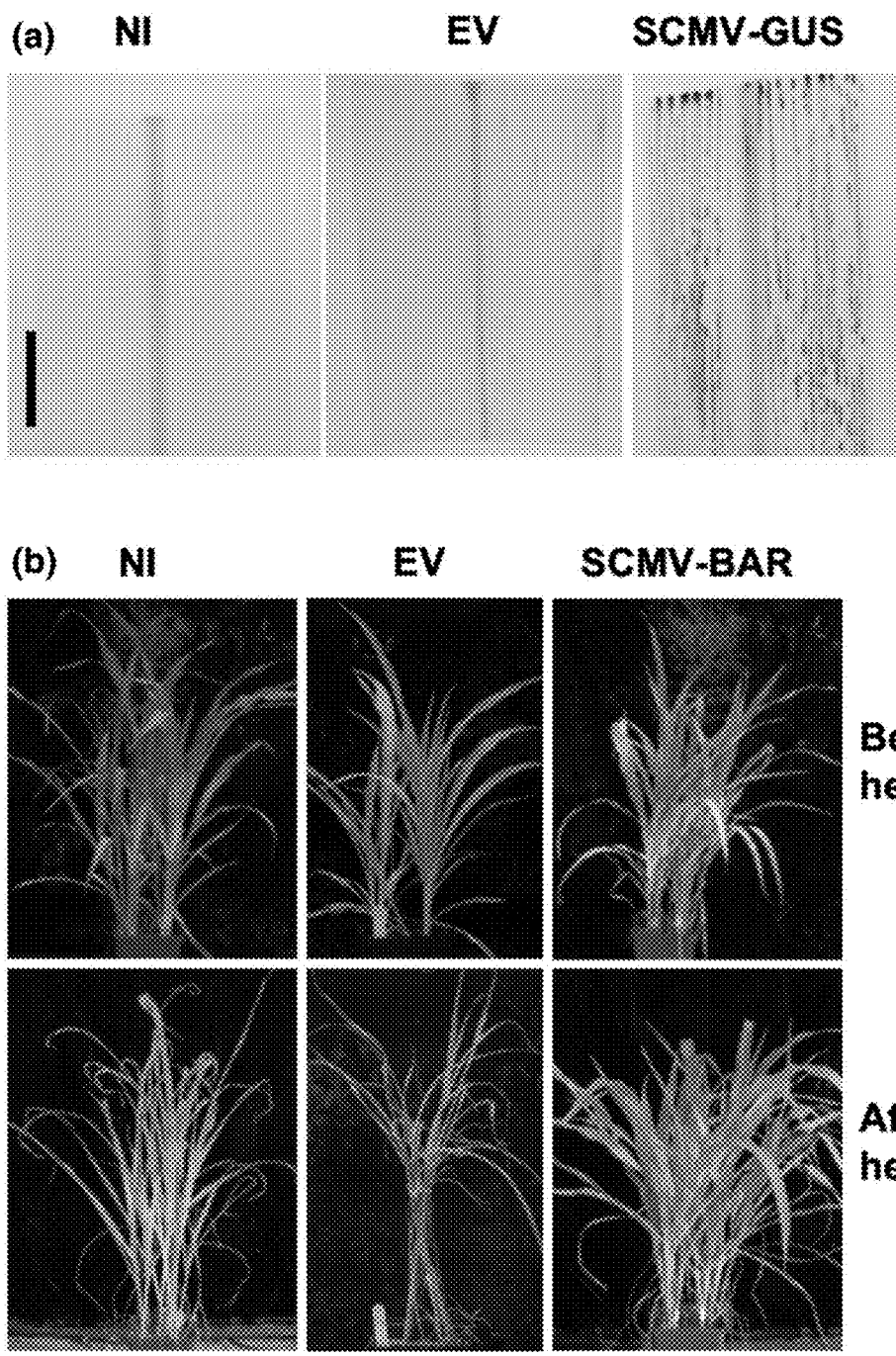
FIG. 5 shows expression of GUS and BAR proteins from the SCMV expression vector in sweet corn leaves. A. The leaf on left is from a non-infected (NI) plant; the middle leaf is from a SCMV empty vector (EV)-infected plant, and the leaf on the right from a plant infected with SCMV-CS2-GUS (biolistically inoculated). Blue indicates presence of GUS protein in leaves stained with X-Gluc and cleared with ethanol. B. SCMV-CS2-BAR protects plants from effects of Finale® (Agrevo) herbicide, which contains glufosinate-ammonium as the active ingredient. The herbicide killed non-infected plants (NI) and plants infected by SCMV empty vector (EV) (Rub inoculation R1).
Figure 8:
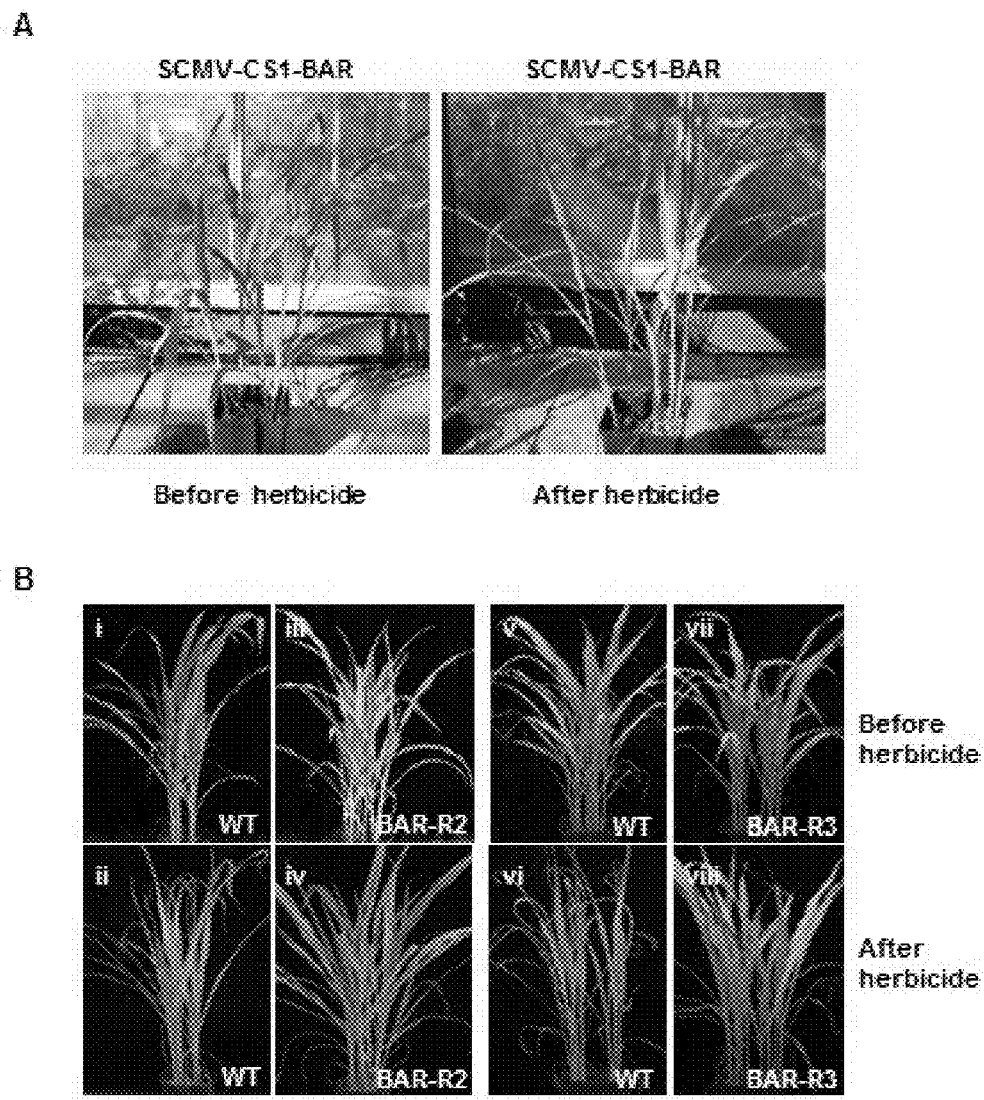
FIG. 8 shows SCMV-BAR protects plants from effects of Finale® (Agrevo) herbicide. A. Sweet corn seedlings were biolistically inoculated with pSCMV-CS1-BAR, and later treated with of Finale® (Agrevo) herbicide. The surviving plant was confirmed to be infected by SCMV-CS1-BAR. B. SCMV-CS2-BAR infection protected plants from herbicide in rub-inoculated passage 2 (BAR-R2) and passage 3 plants (BAR-R3).

To further investigate the ability of SCMV to express functional proteins of different sizes, the BAR (183 amino acids) and GUS (603 amino acids) proteins were tested. The BAR (549 nucleotides (nt)) or GUS (1809 nt) coding sequences minus the stop codons were cloned into pSCMV-CS1 or pSCMV-CS2 to produce pSCMV-CS2-BAR or pSCMV-CS1-GUS, respectively. Similar to the SCMV clones expressing GFP, the infectivity of SCMV-CS1-GUS or SCMV-CS2-BAR was confirmed by leaf mosaic symptoms and the expression of functional proteins was then tested. In SCMV-CS1-GUS-infected plants, GUS activity was detected throughout the leaves while no background activity was seen in SCMV-CS1 empty vector-infected leaves (FIG. 5A). Plants infected by the SCMV-CS2 empty vector and then sprayed with Finale® (Agrevo) herbicide were killed, whereas all the SCMV-CS2-BAR-infected plants survived (FIG. 5B). Similarly, plants infected with the SCMV-CS1-BAR virus also survived herbicide application (FIG. 8A). These results further confirmed that the modified SCMV vectors have the capability to express different foreign proteins that maintain their biological functions.

Example 5

Gene Expression by SCMV Vectors Following Virus Passages

Figure 6:
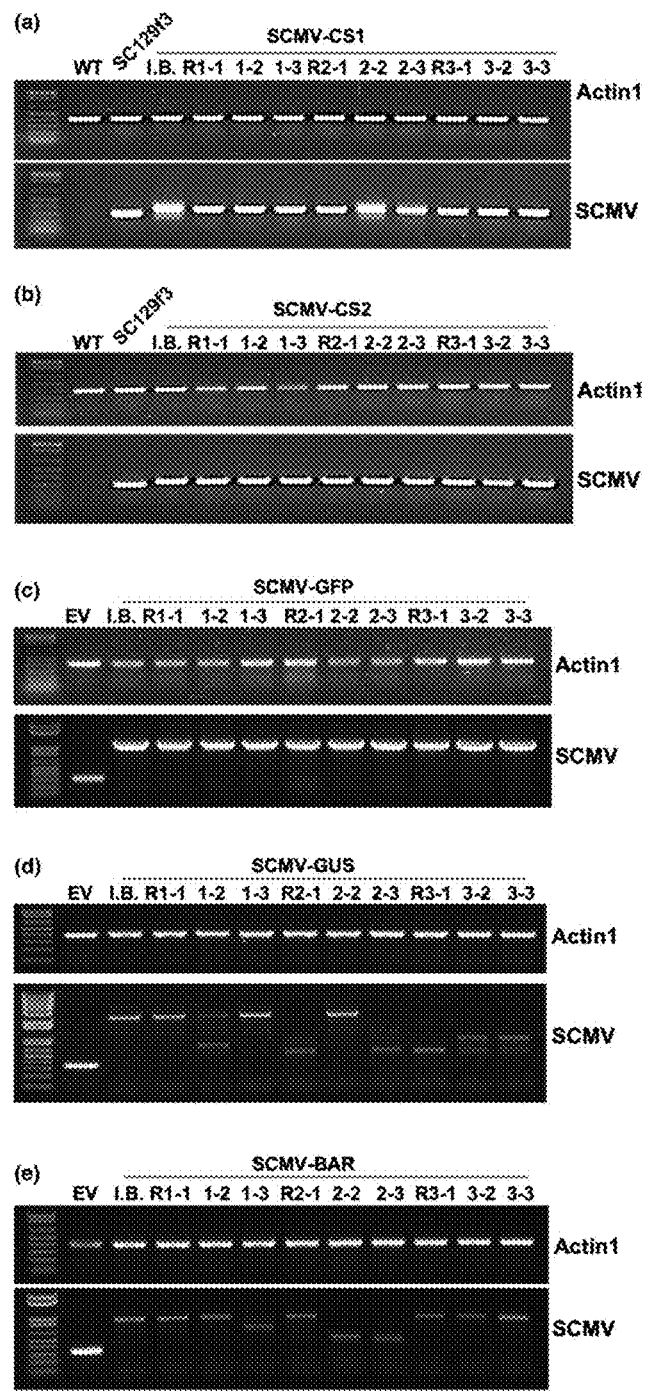
FIG. 6 shows the stability of foreign sequences carried by SCMV vectors. RT-PCR analysis of plants inoculated with SCMV-CS1 (A), SCMV-CS2 (B), SCMV-CS2-GFP (C), SCMV-CS1-GUS (D), SCMV-CS2-BAR (E). I.B., Initial Bombardment; R1, Rub inoculation passage 1; R2, Rub inoculation passage 2; R3, Rub inoculation passage 3; EV, Empty vector. SCMV primers flanking the insertion site were used to detect the stability of the insertion and Zmactin1 was used as internal control.

We demonstrated that the SCMV vectors can be successfully used to express three different reporter genes following biolistic inoculation. Next, we tested if these recombinant viruses could maintain protein expression when they were passed to new plants via rub-inoculation. To test this, we evaluated the stability of inserted genes following three successive passages by RT-PCR using primers in the P1 and HC-Pro cistrons that flanked the cloning site. During each passage, leaves 5 and 6 were collected at 2-3 weeks post inoculation and used as inoculum for the next set of plants and for RNA extraction. As a control, the SCMV-CS1 and SCMV-CS2 empty vectors, which have insertions of 42 nt and 36 nt, respectively, were tested first. A unique product of 302 nt was detected in SC129f3-infected plants indicating infection by the wild-type SCMV infectious clone while a larger band of approximately 340 nt was detected in all the SCMV-CS1 or SCMV-CS2 infected plants demonstrating the stability of the empty CS1 and CS2 modifications (FIGS. 6A, 6B).

The stability of GUS, GFP, and BAR was tested in the same way. Only the expected fragment of 1061 nt was detected in the SCMV-CS1-GFP-infected plants (FIG. 6C). Furthermore, fluorescence due to the expression of GFP was readily detected in leaf cells from all the plants tested among three passage generations. For GUS, the expected fragment of 2147 nt was detected in the initial biolistically inoculated plant. After serial passages, the 2147 nt band was detected in the first two passage generations along with other smaller bands, indicating partial deletion of the GUS coding sequence (FIG. 6D). When GUS activity was tested, 10 of 10 plants from the first passage and 13 of 14 plants from the second passage tested positive. None of the ten plants tested in the third passage possessed GUS activity. The lack of GUS activity after the third passage is consistent with the presence of bands in RT-PCR assays that were all less than 2147 nt (FIG. 6D). When SCMV-CS2-BAR infected plants were tested, the expected band of 893 nt was detected in the initial biolistically inoculated plant. This band was present in all three-passage generations although partial deletion was also detected in some plants (FIG. 6E). One plant out of eight from the second passage was killed by Finale® (Agrevo) herbicide while all the others survived as a result of expression of the BAR protein (10 of 10 plants survived in serial passage 1, 7 of 8 plants survived in serial passage 2, and 8 of 8 plants survived in serial passage 3) (FIG. 8B).

Example 6

Engineering SCMV to be Non-Aphid Transmissible

SCMV, like other potyviruses, is naturally transmitted by aphids in a non-persistent manner. The DAG amino acid motif near the N-terminus of the CP plays a critical role in the aphid transmissibility of several potyviruses. For example, mutation of DAG to DAL or DAS completely abolished the aphid transmissibility of Tobacco vein mottling virus, and a mutation of DAG to DTG in Zucchini yellow mosaic virus rendered the virus non-aphid transmissible. To prevent aphid transmission of the recombinant SCMV clones, the DAG motif of the SCMV-CS1 CP was mutated to DTG, and the virulence and aphid transmissibility of $SCMV_{DAG}$-CS1 and $SCMV_{DTG}$-CS1 were compared. As expected, $SCMV_{DAG}$ and $SCMV_{DTG}$ caused symptoms that were indistinguishable on sweet corn plants, indicating that the DAG to DTG mutation did not affect SCMV virulence. To test aphid transmission of $SCMV_{DAG}$ and $SCMV_{DTG}$, aphids were allowed to feed on symptomatic plants, and then 10 aphids were transferred to each of 5 healthy plants and allowed to feed overnight. The aphid-inoculated plants were grown and examined for symptoms up to 21 dpi. $SCMV_{DAG}$ was transmitted by M. persicae in the range of 40%-100% with a mean of 65%. In four replications of the experiment, 2 of 5, 2 of 5, 4 of 5, and 5 and 5 plants developed symptoms. However, 0 of 5 plants infected with $SCMV_{DTG}$ were symptomatic in each of the four replications of the experiment. These data demonstrate that SCMV clones carrying the DTG mutation in the CP cannot be transmitted by M. persicae.

Example 7

SCMV Infection of Maize Inbred Lines

Figure 9:
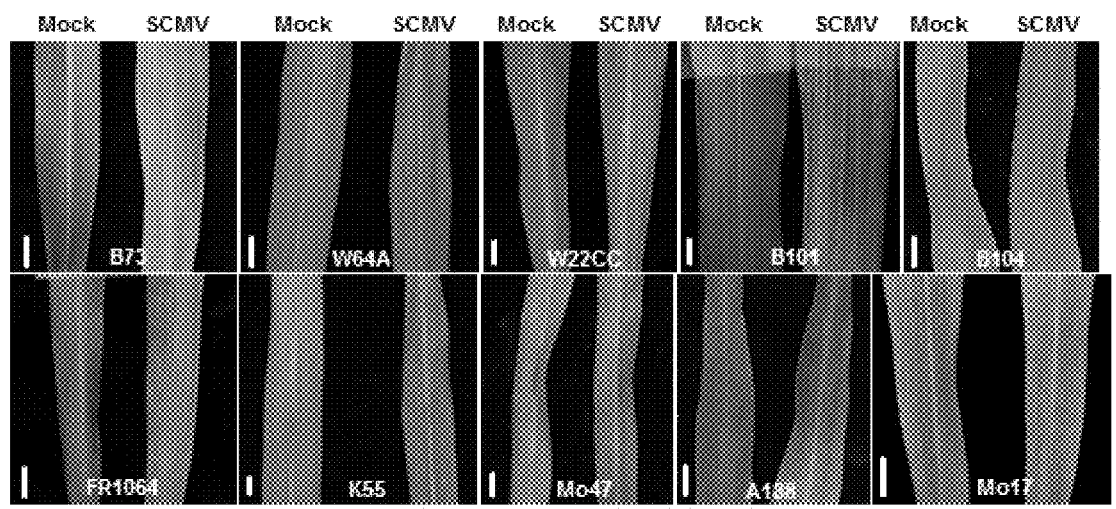
FIG. 9 shows SCMV infection of 10 maize inbred lines. A. Mosaic symptoms caused by SCMV infection were observed on systemic leaves of maize inbred lines (B73, W64A, W22CC, B101, B104, FR1064, K55, Mo47, A188 and Mo17). Bar=1 cm. B. ELISA confirmed SCMV infection in sweet corn and the 10 maize inbred lines. The presence of the SCMV-CP can only be detected in plants inoculated with SCMV but not in mock-treated plants. Grinding buffer only was used as negative control.
Figure 9:
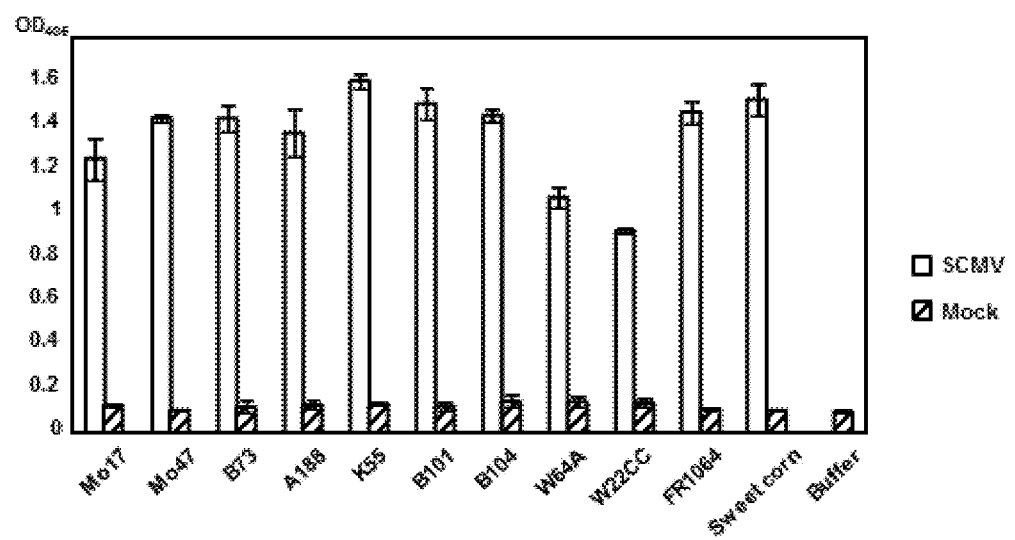
Figure 10:
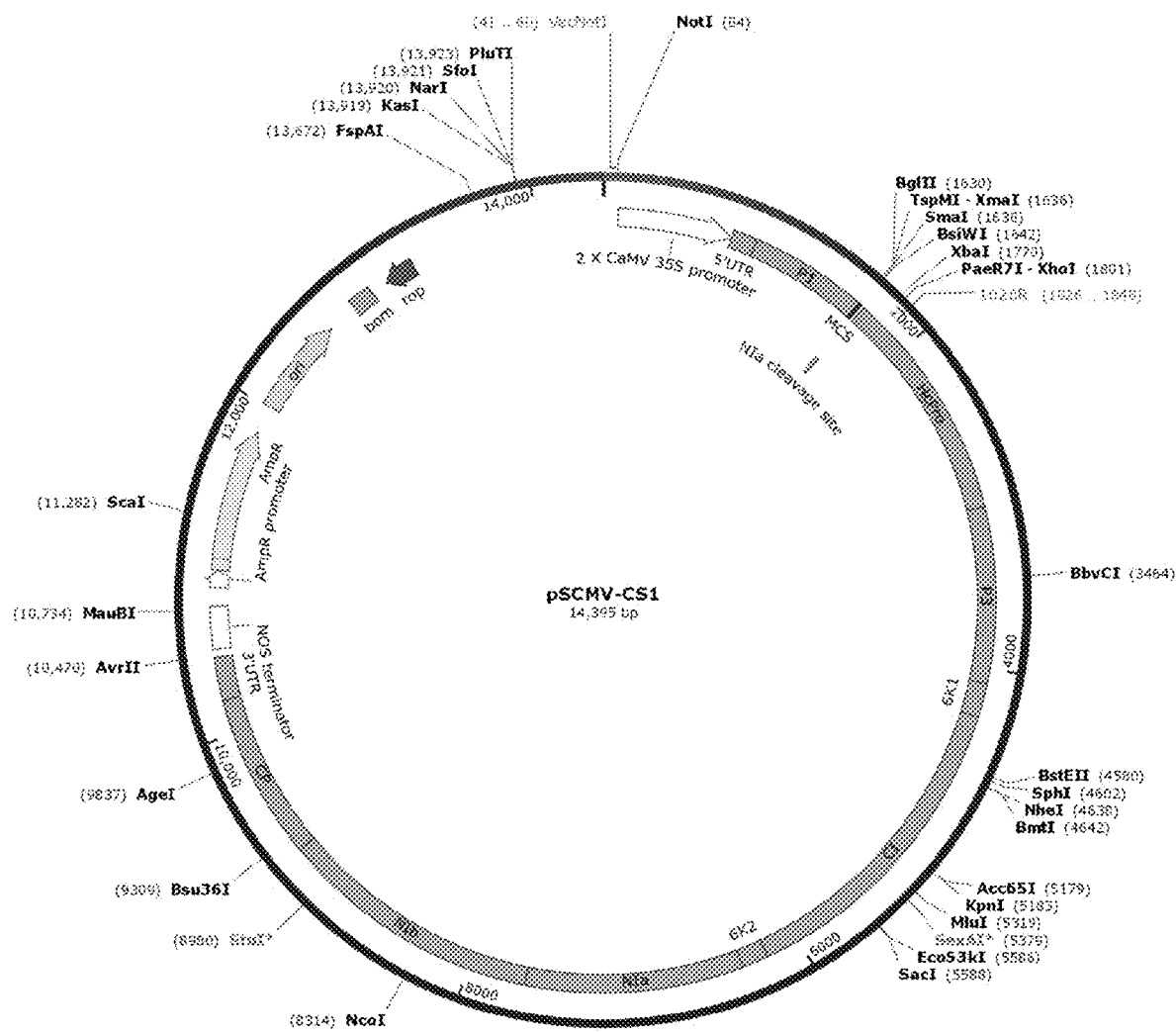
FIG. 10 is a map of the pSCMV-CS1 vector (SEQ ID NO: 19).
Figure 11:
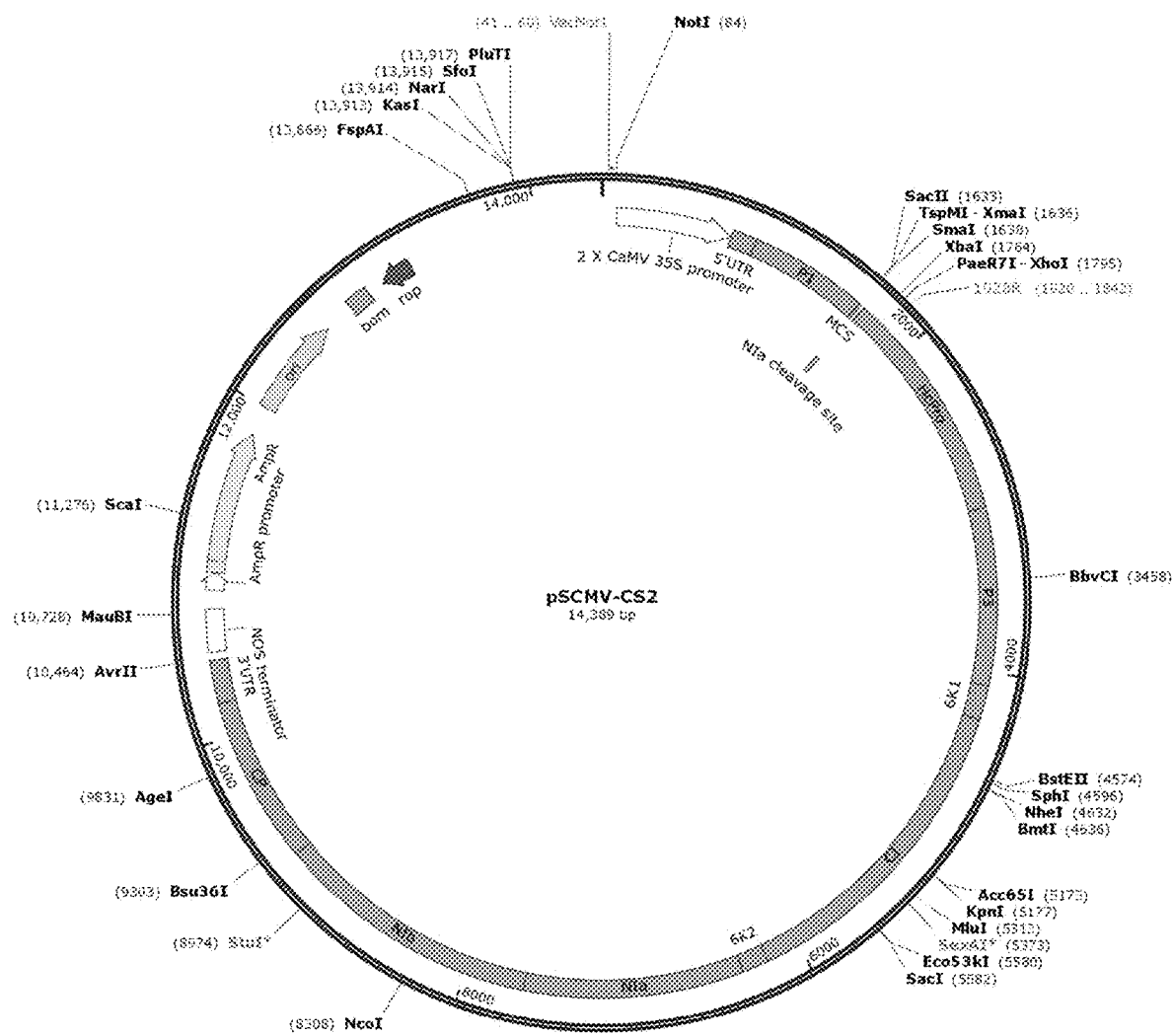
FIG. 11 is a map of the pSCMV-CS2 vector (SEQ ID NO: 20).
Figure 12:
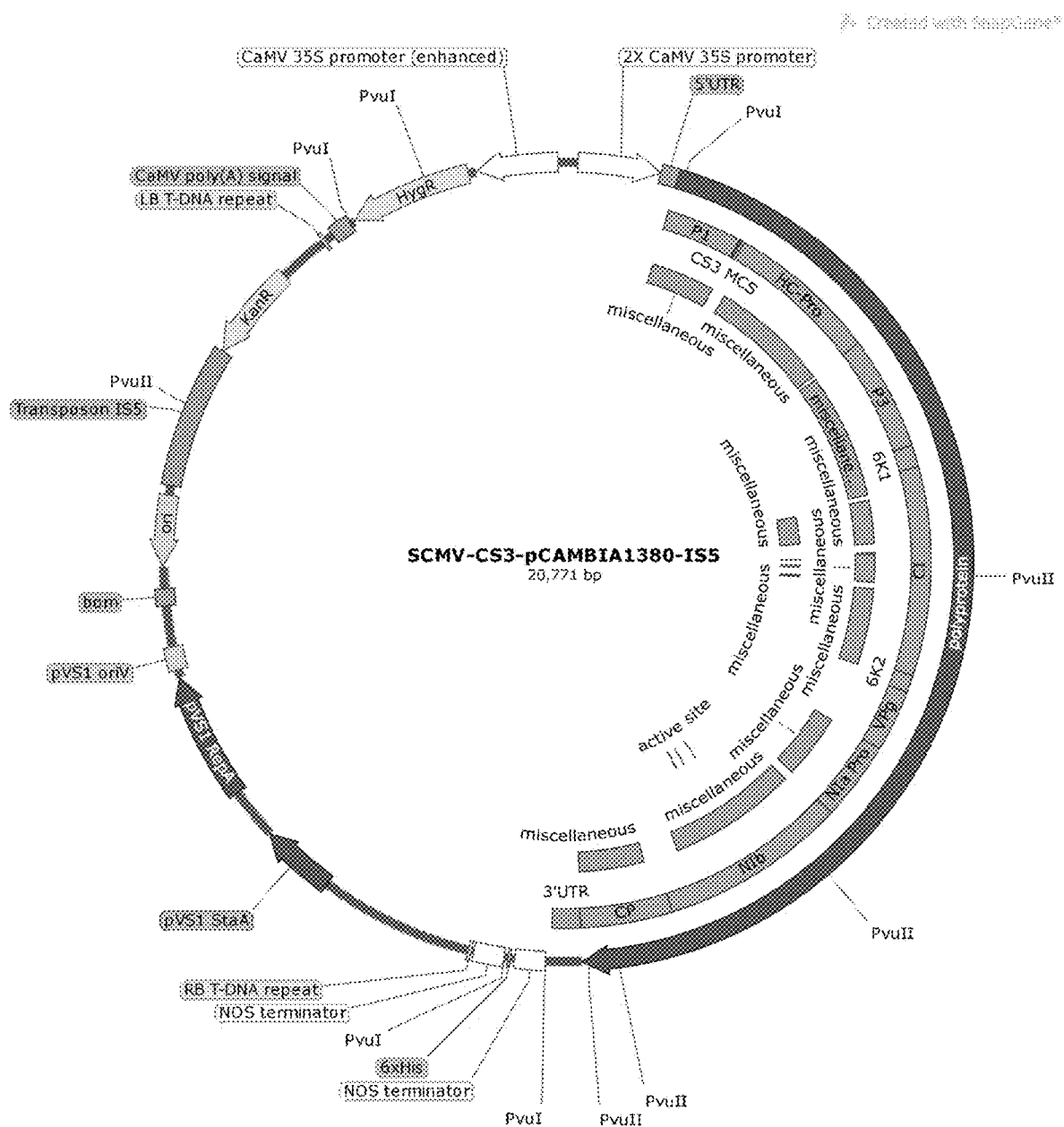
FIG. 12 is a map of the pSCMV-CS3 vector (SEQ ID NO: 21).

To test the potential of the SCMV expression system to be used in different maize genetic backgrounds, seedlings of 10 different inbred lines of dent corn were rub inoculated with the SCMV wild-type parental virus. Mosaic symptoms were observed on leaves of all the maize inbred lines tested, including B73, Mo17, Mo47, B101, B104, W22CC, K55, FR1064, A188, and W64A (FIG. 9A). An ELISA test was performed to confirm SCMV infection in the systemic leaves of the 10 inbred lines (FIG. 9B). We rub-inoculated B73 seedlings with SCMV-CS1-GFP, and observed GFP expression similar to that in sweet corn demonstrating the potential for protein expression in dent corn inbred lines (FIG. 7B). These results indicate the SCMV expression vectors can be used in a wide variety of genetic backgrounds of interest to the maize research community.

TABLE 3

Oligonucleotide primers.

| Name | Sequence (5' → 3') |
|---|---|
| *Primers used to clone and sequence full-length SCMV genomes* | |
| SC-5end | AAAAACAACAAAACTCAACACAACACAACAAAA (SEQ ID NO: 22) |
| SC-415R | TGCTTTGTTCGCGGATTTTCCA (SEQ ID NO: 23) |
| SC-745F | GAGGGAGCAGTGGTCTCA (SEQ ID NO: 24) |
| SC-2120R | CGCGCATTTCACTATCCATAGA (SEQ ID NO: 25) |
| SC-2859F | ACAATATATCAGCTACGCATCTAA (SEQ ID NO: 26) |
| SC-2859R | TTAGATGCGTAGCTGATATATTGT (SEQ ID NO: 27) |
| SC-2916F | AGCTCTACTTTAACCAAACTCCG (SEQ ID NO: 28) |
| SC-2916R | CGGAGTTTGGTTAAAGTAGAGCT (SEQ ID NO: 29) |
| SC-3239R | TGACACCTGTGTGAGTTAAGT (SEQ ID NO: 30) |
| SC-3601F | TGAAGATTGGTGGTCAAATCAA (SEQ ID NO: 31) |
| SC-3748F | TAGAGGAGCAGTCGGCTCGGGAA (SEQ ID NO: 32) |
| SC-3748R | TTCCCGAGCCGACTGCTCCTCTA (SEQ ID NO: 33) |
| SC-4404F | GAGAATGGCGTCACACTAGA (SEQ ID NO: 34) |
| SC-4533F | CGATTGGGTCGTGTTGGCA (SEQ ID NO: 35) |
| SC-5244F | ATGAAAGATCACACGAAGGA (SEQ ID NO: 36) |
| SC-5350F | GGCTCTCAACACAGTTATTCA (SEQ ID NO: 37) |
| SC-5647F | TCGGATCTGCTTACACTAAGAA (SEQ ID NO: 38) |
| SC-6004F | TAGCAGGTTTCCCAGAGTATGA (SEQ ID NO: 39) |
| SC-6495F | AGTGTAACAGCACCAAAAGGAA (SEQ ID NO: 40) |
| SC-6721F | ACAAGTGGGAAAAAGGATGGCA (SEQ ID NO: 41) |
| SC-6721R | TGCCATCCTTTTTCCCACTTGT (SEQ ID NO: 42) |
| SC-7014F | TATGACAAAAGCAGATTAAACAGA (SEQ ID NO: 43) |
| SC-7788F | GTCGACAACACACTCATGGT (SEQ ID NO: 44) |
| SC-8200F | GGCAACTTGGCGTATGGAA (SEQ ID NO: 45) |
| SC-8690F | GAAAATGCGCTTACCTAAAGCAA (SEQ ID NO: 46) |
| SC-8870R | GTGTCATCAATTTCGTATTCCT (SEQ ID NO: 47) |
| SC-9118F | CAATCTCACCGACTATAGCTTA (SEQ ID NO: 48) |
| SC-9200R | TGGCATCATACCATCTATCAAACT (SEQ ID NO: 49) |
| SC-3end | TTTTTTTTTTTTTTTTTTTGTCTCTCACCAAGAGACTCGCA (SEQ ID NO: 50) |
| 35S-Seq | ACG CAC AAT CCC ACT ATC (SEQ ID NO: 51) |
| Nos-Rev | AGA CCG GCA ACA GGA TTC A (SEQ ID NO: 52) |
| *Primers used to amplify the five fragments encompassing the 15 amino acid differences* | |
| 157F | GAACGTGGACCTACGTGACA (SEQ ID NO: 53) 123 |
| 745R | GTGAGACCACTGCTCCCTCT (SEQ ID NO: 54) |
| 1487F | TAGGGAATACCACGCCAAAC (SEQ ID NO: 55) |
| 2120R | CGCGCATTTCACTATCCATAGA (SEQ ID NO: 56) |
| 3338F | TGATCCACAGAAAAGCGATG (SEQ ID NO: 57) |
| 4955R | CGGAATTTTGACGTGGTCTT (SEQ ID NO: 58) |
| 6015F | CCAGAATATGAAGGAACACTTC (SEQ ID NO: 59) |
| 7897R | TCATCACCATTCGCAAACAT (SEQ ID NO: 60) |
| 8232F | GCAAATCTCGCAAAAGAAGG (SEQ ID NO: 61) |
| 9614R | CCAAGAGACTCGCAACACAA (SEQ ID NO: 62) |
| *Primers used to introduce cloning sites and the NIa-Pro cleavage site* | |
| VecNotI | AAGGAGCTGACTGGGTTGAA (SEQ ID NO: 63) |
| 848R + 1 | ACACGTCCTCCGTACGCCCGGGAGATCTTGCGTAGTGCTCAATATCCAA (SEQ ID NO: 64) |
| 848F + 1 | CGGGCGTACGGAGGACGTGTTTCACCAATCCGCAGATCCCCAGGCTAAC (SEQ ID NO: 65) |
| 848R + 2 | AAACACGTCCTCCCCGGGCCGCGGTGCGTAGTGCTCAATATCCAA (SEQ ID NO: 66) |
| 848F + 2 | CCCGGGGAGGACGTGTTTCACCAATCCGCAGATCCCCAGGCTAAC (SEQ ID NO: 67) |
| 1028R | GCATGTCTTGCATGTAATTTTGA (SEQ ID NO: 68) |
| *Primers used to introduce the DTG mutation in CP* | |
| 7474F | TTCACATCATTTAGAAGGTCCA (SEQ ID NO: 69) |
| DAGR | CCTTGTGCACCCGTATCAA (SEQ ID NO: 70) |
| DAGF | TTGATACGGGTGCACAAGG (SEQ ID NO: 71) |
| 8510R | TACACCAGTTCCAGCTCCTG (SEQ ID NO: 72) |

TABLE 3-continued

Oligonucleotide primers.

| Name | Sequence (5' → 3') |
|---|---|
| Primers used to insert GUS, GFP, and BAR coding sequences in SCMV-CS1 and SCMV-CS2 | |
| GUSS-1 | GAAGATCTATGGTCCGTCCTGTAGAAACC (SEQ ID NO: 73) |
| GUSA-1 | CCGCGTACGTTGTTTGCCTCCCTGCTG (SEQ ID NO: 74) |
| GUSS-2 | TCCCCGCGGATGGTCCGTCCTGTAGAAACC (SEQ ID NO: 75) |
| GUSA-2 | TCCCCGCGGTTGTTTGCCTCCCTGCTG (SEQ ID NO: 76) |
| GFPS-1 | GAAGATCTATGGTGAGCAAGGGAGAGGA (SEQ ID NO: 77) |
| GFPA-1 | CCGCGTACGCTTGTACAGCTCGTCCATGC (SEQ ID NO: 78) |
| GFPS-2 | TCCCCGCGGATGGTGAGCAAGGGAGAGGA (SEQ ID NO: 79) |
| GFPA-2 | TCCCCGCGGCTTGTACAGCTCGTCCATGC (SEQ ID NO: 80) |
| BARS | TCCCCCGGGATGAGCCCAGAACGACG (SEQ ID NO: 81) |
| BARA | TCCCCCGGGGATCTCGGTGACGGGCA (SEQ ID NO: 82) |
| Primers used to amplify maize actin gene (control for RT-PCR) | |
| ZmAct1F | CCTGAAGATCACCCTGTGCT (SEQ ID NO: 83) |
| ZmAct1R | GCAGTCTCCAGCTCCTGTTC (SEQ ID NO: 84) |

Sequences

>P1 nucleotide sequence (SEQ ID NO: 1)
ATGGCGGGAACGTGGACCTACGTGACACGTAAGTGGCAGCCAGATGTTAACAACGATCGTCACATTAAAAGAG
TGATGGAAATGTTTGCAGCAAAACATCAACATTACTCAGAAGAACAGCGACTTGCCCATAATATGAAATTATT
GAGGAAGGCAAGTGTTGTAAGCGTTGAGCCTGCGAAACCAAAGCAGAAGCAGGCAACTCAACAGATGTGGGTT
GAGAAATGTGATCACAATCCTGTTGATCACTTAGTATATCCACGACTTGGAAAATCCGCGAACAAAGCAGATA
TGAGTATTAAAAGTGCATCTGTAAGCAAACTAACCAGAGAGATTTTAGAAATCTCAAAGGTTAGCGGCCTTAA
GGTTGAACTAATTGATAAACGAAAAAGATTCAAAACACAGTTATCAATCAAAAGGTTCAATGGCAAAAATTTC
CTCCACTGCAAAACGAATCACGAAAACAATTTATTTAAGAGGAAAGACATAGCCATTGGGCACAAATGGTTTC
CAACGATTGAAGCCATTGCTAGATGCTATAGCACGATGAATCGAGAAGAACTACAAAGCCTTTATAGAGGGAG
CAGTGGTCTCACATTCATTCAAAACGATGAATTGTTCATTGTCAGAGGAAGAATGAATGGTGAACTTGTCAAT
AGCTTGTACGAGACAAATCGGGTTTTGGATATTGAGCACTAC >HC-Pro nucleotide sequence (SEQ ID NO: 2)
GCAGATCCCCAGGCTAACGATTTCTGGAGGGGATACACAAATGCTTACGTAGAGAATCGTAACATTTCGACTA
CTCATACAGAGCACACCCCTACAATCAATCTAGAAGAATGTGGAAAACGAATGGCTCTACTCGAGATACTATT
TCACTCTACATTCAAAATTACATGCAAGACATGCAACATTGATGATCTTGAATTATCGGATGATGAATTTGGA
GCTAAACTCTACAAGAATTTGCAACGTATCGAAGAGAAACAACGAGAGTATCTTGCAAAGGATCAAAAACTAT
CCAGAATGATACAATTTATCAAAGAAAGGTGCAATCCAAAATTTTCGCATTTACCAACGCTATGGCAAGTTGC
GGAAACAATAGGGCACTATACTGATAACCAGTCAAAGCAAATAATGGATATTAGCGAAGCGCTCATCAAAGTT
AATACTCTGACTCCTGATGATGCTATGAAAGCAAGCGCAGCGTTACTTGAAGTGTCGCGATGGTATAAGAATC
GTAAGGAGTCACTCAAAACTGACTCATTGGAATCTTTTAGAAATAAAATATCACCAAAGAGTACAATAAATGC
AGCTTTAATGTGCGATAATCAATTGGATAAAAATGCAAATTTTGTATGGGGTAATAGGGAATACCACGCCAAA
CGATTTTTCGCAAACTATTTTGAAGCAGTGGATCCCACAGATGCATATGAAAAGCACGTCACACGGTTCAACC
CTAATGGTCAACGAAAGTTATCAATAGGAAAGTTAGTTATCCCACTAGACTTTCAAAAGATTAGAGAATCATT
TGTTGGACTCTCGATAAATAGACAACCGCTGGATAAATGTTGTGTTAGCAAGATCGAAGGAGGGTATATATAC
CCATGTTGCTGCGTCACAACAGAATTTGGTAAACCAGCATACTCTGAGATAATACCTCCAACGAAAGGGCATA
TAACAATAGGCAATTCTATTGATCCAAAGATTGTGGACTTGCCAAATACAACACCACCCAGCATGTACATTGC
TAAGGATGGGTATTGCTATATCAACATCTTTTTAGCAGCCATGATCAACGTTAATGAAGAATCTGCCAAGGAT
TACACGAAATTTTTGAGGGACGAACTAGTTGAGCGTCTCGGAAAGTGGCCAAAGCTTAAAGACGTAGCAACAG
CGTGTTATGCATTATCTGTAATGTTTCCAGAAATTAAGAATGCTGAGCTACCTCCAATTCTAGTTGACCATGA
AAATAAATCAATGCACGTAATTGATTCATATGGTTCACTAAGCGTTGGATTTCACATATTAAAAGCAAGCACG
ATTGGTCAATTAATCAAATTTCAATATGAGTCTATGGATAGTGAAATGCGCGAATACATAGTAGGA >P3 nucleotide sequence (SEQ ID NO: 3)
GGAACTCTCACACAACAGACATTCAACACACTTCTTAAGATGCTTACGAAAAACATGTTCAAACCAGAGCGCA
TCAAGCAGATAATTGAAGAGGAACCCTTCTTACTTATGATGGCGATTGCGTCTCCAACGGTATTAATAGCACT
ATATAATAATTGTTATATTGAGCAAGCTATGACATACTGGATCGTTAAGAATCAAGGAGTTGCAGCCATATTC
GCACAACTCGAAGCATTAGCCAAGAAAACATCCCAGGCTGAGCTATTAGTTCTACAAATGCAGATACTTGAAA
AAGCATCTAACCAATTAAGATTAGCAGTTTCAGGACTTAGCCATATCGACCCAGCAAAGCGACTTTTGTGGTC
ACACCTTGAAGCGATGTCAACACGATCAGAAATGAACAAGGAGTTAATAGCTGAGGGGTATGCACTATATGAC
GAGCGCCTATACACCCTGATGGAAAAAAGTTACGTAGATCAATTAAACCAATCATGGGCAGAATTGTCATACT
GTGGAAAATTTTCAGCAATATGGCGTGTGTTCAGAGTCAGGAAGTATTACAAACCGTCTTTAACCGTGAGAAA
AAGCGTAGATTTAGGCGCTGTATACAATATATCAGCTACGCATCTAATATCAGATTTAGCGCGGAAAAGTCAA
GATCAAGTCAGCTCTACTTTAACCAAACTCCGCAACGGTTTCTATGATAAATTAGAGAAAGTTAGAATACGAA
CTATAAAAACGGTTTATTGGTTTATACCTGATATATTTAGACTCGTGCACATATTCATAGTTTTGAGTTTATT
AACTACCATCGCTAACACTATCATAGTAACTATGAATGACTACAAGAAATTGAAGAAGCAACAAAGAGAAGAC
GAATATGAAGCAGAAATTAACGAAGTTCGCAGAATCCATTCTACCTTAATGGAAGAGCGGAAGGACAATCTGA
CGTGTGAACAATTTATTGAGTATATGCGTCAAAATCATCCACGGCTAGTTGAAGCAACACTGGACTTAACTCA
CACAGGTGTCATACATGAA

| Sequences |
|---|
| >6K1 nucleotide sequence (SEQ ID NO: 4)<br>GGGAAATCCAATCTCGAAACCAATTTGGAACAGGCAATGGCAGTTGGAACCTTGATAACAATGATACTTGATC<br>CACAGAAAAGCGATGCTGTCTATAAGGTGTTGAACAAAATGCGGACAGTAATTAGTACAATTGAACAAAACGT<br>CCCATTCCCTTCAGTGAATTTCTCCAACATCTTAACACCTCCAGTGGCACAACAG<br><br>>CI nucleotide sequence (SEQ ID NO: 5)<br>AGTGTAGATGTTGATGAGCCATTAACACTTAGCACTGATAAAAATTTAACAATAGACTTTGACACAAATCAAG<br>ATTTACCTGCCGATACATTCAGTAATGATGTGACATTTGAAGATTGGTGGTCAAATCAATTAAGCAACAACAG<br>AACAGTGCCACACTACCGACTTGGGGGAAAGTTCATTGAATTCACACGAGAAAACGCAGCCCACACGAGCATC<br>GAACTTGCACACTCAAACATTGAGAGGGAATTCTTGCTTAGAGGAGCAGTCGGCTCGGGAAAATCCACTGGGT<br>TACCATACCATCTTAGCATGCGCGGAAAAGTGCTTCTACTAGAGCCTACAAGACCGCTAGCTGAGAACGTGTG<br>TAGGCAACTACAAGGACCGCCATTTAACGTAAGTCCAACTCTTCAAATGCGTGGATTAAGTTCTTTTGGATGC<br>ACTCCAATCACAATCATGACATCTGGTTTTGCATTGCACATGTACGCAAATAATCCAGATAAAATATCTGAGT<br>ACGATTTCATAATCTTTGATGAATGTCATATAATGGAAGCACCAGCGATGGCCTTTTATTGCTTACTCAAAGA<br>ATATGAATATCGAGGAAAAATTATCAAGGTATCAGCTACGCCTCCAGGAAGGGAGTGTGAATTCACAACACAA<br>CATCCAGTAGACATCCATGTTTGTGAGAATCTAACTCAGCAACAGTTTGTTATGGAACTCGGGACTGGTTCAA<br>CCGCAGATGCTACGAAGTACGGAAATAATATCTTAGTTTATGTAGCAAGCTATAATGACGTCGATTCATTGTC<br>GCAAGCACTAGTCGAACTTAAATTTTCCGTAATCAAAGTGGATGGCCGAACAATGAAACAAAACACAACAGGA<br>ATCATTACAAACGGTACCGCACAAAAGAAGTGTTTTGTTGTCGCAACGAATATAATTGAGAATGGCGTCACAC<br>TAGATATTGATGTTGTTGTCGACTTCGGACTTAAGGTCTCAGCTGACTTGGACGTTGACAACAGGGCGGTATT<br>GTATAAACGCGTAAGTATATCATATGGTGAACGCATACAACGATTGGGTCGTGTTGGCAGAAATAAACCTGGT<br>ACAGTTATTCGAATCGGAAAAACAATGAAAGGTTTGCAGGAAATTCCAGCAATGATCGCAACAGAAGCAGCCT<br>TCATGTGTTTCGCTTACGGTCTTAAAGTTATCACTCATAATGTTTCAACGACCCATCTTGCAAAGTGCACAGT<br>TAAACAAGCGAGAACCATGATGCAATTTGAATTATCACCATTTGTCATGGCTGAGCTCGTTAAGTTTGATGGT<br>TCAATGCATCCACAAATACATGAGGCACTAGTAAAATACAAACTTAGAGATTCTGTCATAATGCTCAGACCGA<br>ATGCACTTCCAAGGGTCAATTTACATAATTGGCTTACAGCCCGAGATTATAATAGAATAGGATGTTCATTAGA<br>ACTCGAAGACCACGTCAAAATTCCGTACTACATTAGGGGAGTTCCTGACAAGTTGTATGGAAAGCTATATGAT<br>ATTATCTTACAGTATAGTCCAACTAGTTGCTACGGTAGACTATCAAGTGCGTGTGCAGGTAAAGTAGCATATA<br>CTCTGCGAACTGATCCATTTTCACTTCCAAGAACAATAGCAATAATTAATGCCTTAATCACGGAGGAGTATGC<br>GAAGAGAGATCACTATCGTAACATGATTTCAAACCCATCTTCATCACACGCATTCTCACTCAATGGGTTGGTG<br>TCTATGATCGCTACTAGATATATGAAAGACCCATACAAAGGAGAATATTGACAAACTCATTAGAGTGCGTGATC<br>AATTACTTGAGTTTCAAGGTACTGGAATGCAATTTCAAGATCCATCAGAACTCATGGAAATTGGGGCTCTCAA<br>CACAGTTATTCACCAA<br><br>>6K2 nucleotide sequence (SEQ ID NO: 6)<br>GGAATGGACGCAACTGCAGCTTGTATTGGGTTACAAGGACGATGGAATGCTTCACTTATACAACGCGATCTCC<br>TGATTGCAGGTGGAGTTTTTATCGGAGGCATTTTGATGATGTGGAGCCTATTTACTAAATGGAGTAACACAAA<br>TGTCTCACATCAG<br><br>>NIa-VPg nucleotide sequence (SEQ ID NO: 7)<br>GGGAAGAACAAACGCAGTAGACAAAAACTTCGATTCAAAGAAGCAAGAGACAACAAATATGCATATGATGTCA<br>CAGGATCGGAAGAATGCCTTGGCGAGAATTTTGGAACAGCCTATACAAAGAAAGGTAAAGGAAAAGGAACTAA<br>AGTTGGACTCGGTGTGAAGCAGCATAAAATTCCATATGATGTACGGTTTCGATCCCCAAGAGTACAACCTAATT<br>CGGTTTGTCGATCCACTCACGGGAGCAACTCTTGATGAACAAATCCGATATACGCTTAATTCAAGAGC<br>ACTTCGCTGAAATTCGTGAGGAGGCAGTGATTAATGACACAATTGAAAGGCAGCAGATTTACGGCAATCCTGG<br>ACTACAAGCATTTTTCATACAAAATGGGTCAGCAAACGCTCTGAGAGTTGATTTAACACCACATTCACCTACA<br>CGAGTTGTCACAGGTAATAACATAGCAGGGTTCCCAGAATATGAAGGAACACTTCGTCAGACTGGAACAGCTA<br>TAACTATACCCATTGGTCAAGTCCCAATCGCAAATGAAGCAGGGGTTGCACACGAG<br><br>>NIa-Pro nucleotide sequence (SEQ ID NO: 8)<br>TCAAAATCCATGATGAACGGGTTGGGTGATTACACACCAATATCGCAACAATTGTGTCTAGTACAAAATGACT<br>CGGATGGGGTAAAGCGGAATGTATTTTCAATTGGATATGGCTCATATCTTATTTCACCAGCGCACTTATTCAA<br>ATATAACAATGGTGAAATAACAATTGATCATCAAGAGGATTGTACAAAATTCGTAATTCTGTGGATTTAAAA<br>TTACATCCAATTGCACACAGAGACATGGTCATAATTCAACTCCCAAAGGATTTCCCACCGTTCCCAATGCGCT<br>TGAAATTCAAACAACCATCACGAGATATGCGAGTCTGCCTAGTAGGTGTCAACTTCCAACAGAATTATAGCAC<br>TTGCATCGTATCAGAAAGTAGTGTGACAGCACCAAAAGGAAATGGAGACTTTTGGAACATTGGATATCAACA<br>GTCGACGGTCAATGTGGACTACCATTGGTAGATACTAAGAGCAAACATATTGTCGGAATTCATAGTCTTGCAT<br>CAACAAGTGGAAACACTAATTTCTTTGTCGCTGTGCCTGGGAACTTTAATGAATACATCAATGGACTTGTGCA<br>AGCAAATAAATGGGAAAAGGATGGCACTATAATCCGAATCTCATATCCTGGTGTGGACTAAATTTAGTTGAT<br>TCTGCCCCAAAAGGTTTGTTTAAAACGTCAAAATTGGTAGAAGACTTGGACGCGAGCGTTGAAGAGCAA<br><br>>NIb nucleotide sequence (SEQ ID NO: 9)<br>TGCAAGATCACCGAAACATGGCTCACAGAGCAATTACAAGATAATTTGCAAGTGGTTGCGAAATGTCCAGGCC<br>AACTTGTTACCAAGCATGTTGTTAAGGGTCAATGCCCACACTTTCAATTGTACTTATCAACACATGACGATGC<br>CAAAGAATACTTCGCACCCATGCTTGGAAAATACGACAAGAGTAGGCTTAACAGAGCAGCTTTTATCAAGAC<br>ATATCAAAATATGCAAAACCAATTTATATTGGAGAAATCAAGTATGATATCTTTGATAGAGCTGTACAGCGGG<br>TTGTCAATATTCTCAAAAATGTTGGAATGCAACAATGCGTTTATGTCACAGATGAAGAAGAAATTTTCAGATC<br>ACTTAACCTGAACGCAGCTGTCGGAGCATTGTATACAGGAAAGAAGAAAATTACTTTGAAAATTTTTCAAGC<br>GAAGACAAAGAAGAGATCGTGATGAGATCCTGTGAACGTATTTACAATGGGCAACTTGGCGTATGGAATGGAT<br>CGCTCAAAGCTGAGATCAGATCAATAGAGAAAACCATGCTGAATCTGCGAACCTTCACAGCAGCCCCATT<br>AGAAACTTTGCTCGGAGGAAAAGTGTGCGTGGATGATTTTAATAATCAATTCTATTCACATCATTTAGAAGGT<br>CCATGGACTGTTGGGATAACAAAATTCTATGGAGGTTGGAATCGCTTACTTGAGAAGTTACCAGAAGGATGGG<br>TTTACTGCGATGCTGACGGGTCTCAATTTGATAGTTCGTTAACACCCATATCTCATCAATGCAGTATTAAATAT<br>TCGATTGCAATTTATGGAAGATTGGGATATAGGAGCGCAAATGCTAAAGAACCTGTACACTGAGATTGTTTAC<br>ACACCAATCGCAACGCCAGACGGATCAATCGTGAAGAAATTCAAGGTAACAATAGCGGACAACCTTCTACAG<br>TAGTGGACAACACATTGATGGTTATAATAGCTTTCAACTATGCCATGCTATCAAGTGGTATCAAAGAAGAAGA |

-continued

| Sequences |
|---|
| AATCGATAATTGCTGTAGAATGTTTGCGAATGGTGATGACTTACTCCTAGCAGTGCATCCTGATTTTGAGTTC<br>ATTTTAGATGAATTTCAAAATCACTTTGGGAATCTTGGGCTGAACTTCGAATTTACATCACGAACACGAGACA<br>AATCCGAACTGTGGTTCATGTCCACAAGAGGCATCAAGTATGAAGGAATTTACATACCAAAGCTTGAGAAAGA<br>AAGAATAGTCGCCATACTTGAATGGGATCGATCAAACTTGCCTGAACATAGGTTGGAAGCTATATGTGCAGCG<br>ATGGTTGAGGCCTGGGGATATTCCGATCTCGTTCATGAAATACGAAAGTTCTATGCGTGGCTTTTGGAAATGC<br>AACCTTTTGCAAATCTCGCAAAAGAAGGGTTGGCCCCATACATTGCCGAGACAGCACTCCGCAATCTCTATCT<br>TGGAACGGGTATCAAAGAGGAAGAAATTGAAAAATATCTTAAACAATTCATTAAGGATCTTCCCGGATACATA<br>GAAGATTACAATGAAGATGTATTCCATCAG |
| >CP nucleotide sequence (SEQ ID NO: 10)<br>TCGGGAACTGTTGATGCGGGTGCACAAGGCGGCAGTGGAAGCCAAGGGACAACACCACCAGCAACAGGTAGTG<br>GAGCAAAACCAGCCACCTCAGGGGCAGGATCTGGTAGTGGCACAGGAGCTGGAACTGGTGTAACTGGAGGTCA<br>AGCAAGGACTGGCAGTGGCACTGGGACGGGATCTGGAGCAACCGGAGGCCAATCAGGATCTGGAAGTGGCACT<br>GAACAGGTTAACACGGGTTCAGCAGGAACTAATGCAACTGGAGGCCAAAGAGATAGGGATGTGGATGCAGGTA<br>CAACAGGAAAAATTTCTGTACCAAAGCTCAAGGCCATGTCAAAGAAAATGCGCTTACCTAAAGCAAAAGGAAA<br>AGATGTGCTACATTTGGATTTTCTATTGACATACAAACCACAACAACAAGACATATCAAACACTAGAGCAACC<br>AAGGAAGAGTTTGATAGATGGTATGATGCCATAAAGAAGGAATACGAAATTGATGACACACAAATGACAGTTG<br>TCATGAGTGGCCTTATGGTATGGTGCATCGAAAATGGTTGCTCACCAAACATAAACGGAAATTGGACAATGAT<br>GGATGAAGATGAACAAAGGGTCTTTCCACTCAAACCGGTCATTGAGAATGCATCTCCAACTTTCCGACAAATT<br>ATGCATCATTTCAGTGATGCAGCTGAAGCGTACATAGAGTACAGAAACTCTACTGAGCGATATATGCCAAGAT<br>ACGGACTTCAGCGCAATCTCACCGACTATAGCTTAGCACGGTATGCATTTGATTTCTATGAAATGACTTCACG<br>CACACCTGCTAGAGCTAAAGAAGCCCACATGCAGATGAAAGCCGCAGCAGTTCGTGGTTCAAACACACGACTG<br>TTCGGTTTGGACGGAAATGTCGGCGAGACTCAGGAGAATACAGAGAGACACACAGCTGGCGATGTTAGTCGCA<br>ACATGCACTCTCTGTTGGGAGTGCAGCAGCACCACTAG |
| >Full-length SCMV (SEQ ID NO: 11)<br>AAAAACAACAAAACTCAACACAACACAACAAAACACAACCAAGCAAATCCAATTTACTTGCGCTCAGATTGTA<br>GTGAACGGCTCGAACGAAACGGTTCTTCGAGATCACTCTCTGATTCTTCCTCATCTTTCAATTTCTTTCGAAA<br>GAAATGGCGGGAACGTGGACCTACGTGACACGTAAGTGGCAGCCAGATGTTAACAACGATCGTCACATTAAAA<br>GAGTGATGGAAATGTTTGCAGCAAAACATCAACATTACTCAGAAGAACAGCGACTTGCCCATAATATGAAATT<br>ATTGAGGAAGGCAAGTGTTGTAAGCGTTGAGCCTGCGAAACCAAAGCAGAAGCAGGCAACTCAACAGATGTGG<br>GTTGAGAAATGTGATCACAATCCTGTTGATCACTTAGTATATCCACGACTTGGAAAATCCGCGAACAAAGCAG<br>ATATGAGTATTAAAAGTGCATCTGTAAGCAAACTAACCAGAGAGATTTTAGAAATCTCAAAGGTTAGCGGCCT<br>TAAGGTTGAACTAATTGATAAACGAAAAAGATTCAAAACACAGTTATCAATCAAAAGGTTCAATGGCAAAAAT<br>TTCCTCCACTGCAAAACGAATCACGAAAACAATTTATTTAAGAGGAAAGACATAGCCATTGGGCACAAATGGT<br>TTCCAACGATTGAAGCCATTGCTAGATGCTATAGCACGATGAATCGAGAAGAACTACAAAGCCTTTATAGAGG<br>GAGCAGTGGTCTCACATTCATTCAAAACGATGAATTGTTCATTGTCAGAGGAAGAATGAATGGTGAACTTGTC<br>AATAGCTTGTACGAGACAAATCGGGTTTTGGATATTGAGCACTACGCAGATCCCCAGGCTAACGATTTCTGGA<br>GGGGATACACAAATGCTTACGTAGAGAATCGTAACATTTCGACTACTCATACAGAGCACACCCCTACAATCAA<br>TCTAGAAGAATGTGGAAAACGAATGGCTCTACTCGAGATACTATTTCACTCTACATTCAAAATTACATGCAAG<br>ACATGCAACATTGATGATCTTGAATTATCGGATGATGAATTTGGAGCTAAACTCTACAAGAATTTGCAACGTA<br>TCGAAGAGAAACAACGAGAGTATCTTGCAAAGGATCAAAAACTATCCAGAATGATACAATTTATCAAAGAAAG<br>GTGCAATCCAAAATTTTCGCATTTACCAACGCTATGGCAAGTTGCGGAAACAATAGGGCACTATACTGATAAC<br>CAGTCAAAGCAAATAATGGATATTAGCGAAGCGCTCATCAAAGTTAATACTCTGACTCCTGATGATGCTATGA<br>AAGCAAGCGCAGCGTTACTTGAAGTGTCGCGATGGTATAAGAATCGTAAGGAGTCACTCAAAACTGACTCATT<br>GGAATCTTTTAGAAATAAAATATCACCAAAGAGTACAATAAATGCAGCTTTAATGTGCGATAATCAATTGGAT<br>AAAAATGCAAATTTTGTATGGGGTAATAGGGAATACCACGCCAAACGATTTTTCGCAAACTATTTTGAAGCAG<br>TGGATCCCACAGATGCATATGAAAAGCACGTCACACGGTTCAACCCTAATGGTCAACGAAAGTTATCAATAGG<br>AAAGTTAGTTATCCCACTAGACTTTCAAAAGATTAGAGAATCATTTGTTGGACTCTCGATAAATAGACAACCG<br>CTGGATAAATGTTGTGTTAGCAAGATCGAAGGAGGGTATATATACCCATGTTGCTGCGTCACAACAGAATTTG<br>GTAAACCAGCATACTCTGAGATAATACCTCCAACGAAAGGGCATATAACAATAGGCAATTCTATTGATCCAAA<br>GATTGTGGACTTGCCAAATACAACACCACCCAGCATGTACATTGCTAAGGATGGGTATTGCTATATCAACATC<br>TTTTTAGCAGCCATGATCAACGTTAATGAAGAATCTGCCAAGGATTACACGAAATTTTTGAGGGACGAACTAG<br>TTGAGCGTCTCGGAAAGTGGCCAAAGCTTAAAGACGTAGCAACAGCGTGTTATGCATTATCTGTAATGTTTCC<br>AGAAATTAAGAATGCTGAGCTACCTCCAATTCTAGTTGACCATGAAAATAAATCAATGCACGTAATTGATTCA<br>TATGGTTCACTAAGCGTTGGATTTCACATATTAAAAGCAAGCACGATTGGTCAATTAATCAAATTTCAATATG<br>AGTCTATGGATAGTGAAATGCGCGAATACATAGTAGGAGGAACTCTCACACAACAGACATTCAACACACTTCT<br>TAAGATGCTTACGAAAAACATGTTCAAACCAGAGCGCATCAAGCAGATAATTGAAGAGGAACCCTTCTTACTT<br>ATGATGGCGATTGCGTCTCCAACGGTATTAATAGCACTATATAATAATTGTTATATTGAGCAAGCTATGACAT<br>ACTGGATCGTTAAGAATCAAGGAGTTGCAGCCATATTCGCACAACTCGAAGCATTAGCCAAGAAAACATCCCA<br>GGCTGAGCTATTAGTTCTACAAATGCAGATACTTGAAAAAGCATCTAACCAATTAAGATTAGCAGTTTGAGGA<br>CTTAGCCATATCGACCCAGCAAAGCGACTTTTGTGGTCACACCTTGAAGCGATGTCAACACGATCAGAAATGA<br>ACAAGGAGTTAATAGCTGAGGGGTATGCACTATATGACGAGCGCCTATACACCCTGATGGAAAAAAGTTACGT<br>AGATCAATTAAACCAATCATGGGCAGAATTGTCATACTGTGGAAAATTTTCAGCAATATGGCGTGTGTTCAGA<br>GTCAGGAAGTATTACAAACCGTCTTTAACCGTGAGAAAAAGCGTAGATTTAGGCGCTGTATACAATATATCAG<br>CTACGCATCTAATATCAGATTTAGCGCGGAAAAGTCAAGATCAAGTCAGCTCTACTTTAACCAAACTCCGCAA<br>CGGTTTCTATGATAAATTAGAGAAAGTTAGAATACGAACTATAAAAACGGTTTATTGGTTTATACCTGATATA<br>TTTAGACTCGTGCACATATTCATAGTTTTGAGTTTATTAACTACCATCGCTAACACTATCATAGTAACTATGA<br>ATGACTACAAGAAATTGAAGAAGCAACAAAGAGAAGACGAATATGAAGCAGAAATTAACGAAGTTCGCAGAAT<br>CCATTCTACCTTAATGGAAGAGCGGAAGGACAATCTGACGTGTGAACAATTTATTGAGTATATGCGTCAAAAT<br>CATCCACGGCTAGTTGAAGCAACACTGGACTTAACTCACACAGGTGTCATACATGAAGGGAAATCCAATCTCG<br>AAACCAATTTGGAACAGGCAATGGCAGTTGGAACCTTGATAACAATGATACTTGATCCACAGAAAAGCGATGC<br>TGTCTATAAGGTGTTGAACAAAATGCGGACAGTAATTAGTACAATTGAACAAAACGTCCCATTCCCTTCAGTG<br>AATTTCTCCAACATCTTAACACCTCCAGTGGCACAACAGAGTGTAGATGTTGATGAGCCATTAACACTTAGCA<br>CTGATAAAAATTTAACAATAGACTTTGACACAAATCAAGATTTACCTGCCGATACATTCAGTAATGATGTGAC<br>ATTTGAAGATTGGTGGTCAAATCAATTAAGCAACAACAGAACAGTGCCACACTACCGACTTGGGGGAAAGTTC<br>ATTGAATTCACACGAGAAAACGCAGCCCACACGAGCATCGAACTTGCACACTCAAACATTGAGAGGGAATTCT |

| Sequences |
| --- |
| TGCTTAGAGGAGCAGTCGGCTCGGGAAAATCCACTGGGTTACCATACCATCTTAGCATGCGCGGAAAAGTGCT |
| TCTACTAGAGCCTACAAGACCGCTAGCTGAGAACGTGTGTAGGCAACTACAAGGACCGCCATTTAACGTAAGT |
| CCAACTCTTGAAATGCGTGGATTAAGTTCTTTTGGATGCACTCCAATCACAATCATGACATCTGGTTTTGCAT |
| TGCACATGTACGCAAATAATCCAGATAAAATATCTGAGTACGATTTCATAATCTTTGATGAATGTCATATAAT |
| GGAAGCACCAGCGATGGCCTTTTATTGCTTACTCAAAGAATATGAATATCGAGGAAAAATTATCAAGGTATCA |
| GCTACGCCTCCAGGAAGGGAGTGTGAATTCACAACACAACATCCAGTAGACATCCATGTTTGTGAGAATCTAA |
| CTCAGCAACAGTTTGTTATGGAACTCGGGACTGGTTCAACCGCAGATGCTACGAAGTACGGAAATAATATCTT |
| AGTTTATGTAGCAAGCTATAATGACGTCGATTCATTGTCGCAAGCACTAGTCGAACTTAAATTTTCCGTAATC |
| AAAGTGGATGGCCGAACAATGAAACAAAACACAACAGGAATCATTACAAACGGTACCGCACAAAAGAAGTGTT |
| TTGTTGTCGCAACGAATATAATTGAGAATGGCGTCACACTAGATATTGATGTTGTTGTCGACTTCGGACTTAA |
| GGTCTCAGCTGACTTGGACGTTGACAACAGGGCGGTATTGTATAAACGCGTAAGTATATCATATGGTGAACGC |
| ATACAACGATTGGGTCGTGTTGGCAGAAATAAACCTGGTACAGTTATTCGAATCGGAAAAACAATGAAAGGTT |
| TGCAGGAAATTCCAGCAATGATCGCAACAGAAGCAGCCTTCATGTGTTTCGCTTACGGTCTTAAAGTTATCAC |
| TCATAATGTTTCAACGACCCATCTTGCAAAGTGCACAGTTAAACAAGCGAGAACCATGATGCAATTTGAATTA |
| TCACCATTTGTCATGGCTGAGCTCGTTAAGTTTGATGGTTCAATGCATCCACAAATACATGAGGCACTAGTAA |
| AATACAAACTTAGAGATTCTGTCATAATGCTCAGACCGAATGCACTTCCAAGGGTCAATTTACATAATTGGCT |
| TACAGCCCGAGATTATAATAGAATAGGATGTTCATTAGAACTCGAAGACCACGTCAAAATTCCGTACTACATT |
| AGGGGAGTTCCTGACAAGTTGTATGGAAAGCTATATGATATTATCTTACAGTATAGTCCAACTAGTTGCTACG |
| GTAGACTATCAAGTGCGTGTGCAGGTAAAGTAGCATATACTCTGCGAACTGATCCATTTTCACTTCCAAGAAC |
| AATAGCAATAATTAATGCCTTAATCACGGAGGAGTATGCGAAGAGAGATCACTATCGTAACATGATTTCAAAC |
| CCATCTTCATCACACGCATTCTCACTCAATGGGTTGGTGTCTATGATCGCTACTAGATATATGAAAGACCATA |
| CAAAGGAGAATATTGACAAACTCATTAGAGTGCGTGATCAATTACTTGAGTTTCAAGGTACTGGAATGCAATT |
| TCAAGATCCATCAGAACTCATGGAAATTGGGGCTCTCAACACAGTTATTCACCAAGGAATGGACGCAACTGCA |
| GCTTGTATTGGGTTACAAGGACGATGGAATGCTTCACTTATACAACGCGATCTCCTGATTGCAGGTGGAGTTT |
| TTATCGGAGGCATTTTGATGATGTGGAGCCTATTTACTAAATGGAGTAACACAAATGTCTCACATCAGGGGAA |
| GAACAAACGCAGTAGACAAAAACTTCGATTCAAAGAAGCAAGAGACAACAAATATGCATATGATGTCACAGGA |
| TCGGAAGAATGCCTTGGCGAGAATTTTGGAACAGCCTATACAAAGAAAGGTAAAGGAAAAGGAACTAAAGTTG |
| GACTCGGTGTGAAGCAGCATAAATTCCATATGATGTACGGTTTCGATCCCCAAGAGTACAACCTAATTCGGTT |
| TGTCGATCCACTCACGGGAGCAACTCTTGATGAACAAATCCATGCCGATATACGCTTAATTCAAGAGCACTTC |
| GCTGAAATTCGTGAGGAGGCAGTGATTAATGACACAATTGAAAGGCAGCAGATTTACGGCAATCCTGGACTAC |
| AAGCATTTTTCATACAAAATGGGTCAGCAAACGCTCTGAGAGTTGATTTAACACCACATTCACCTACACGAGT |
| TGTCACAGGTAATAACATAGCAGGGTTCCCAGAATATGAAGGAACACTTCGTCAGACTGGAACAGCTATAACT |
| ATACCCATTGGTCAAGTCCCAATCGCAAATGAAGCAGGGGTTGCACACGAGTCAAAATCCATGATGAACGGGT |
| TGGGTGATTACACACCAATATCGCAACAATTGTGTCTAGTACAAAATGACTCGGATGGGGTAAAGCGGAATGT |
| ATTTTCAATTGGATATGGCTCATATCTTATTTCACCAGCGCACTTATTCAAATATAACAATGGTGAAATAACA |
| ATTAGATCATCAAGAGGATTGTACAAAATTCGTAATTCTGTGGATTTAAAATTACATCCAATTGCACACAGAG |
| ACATGGTCATAATTCAACTCCCAAAGGATTTCCCACCGTTCCCAATGCGCTTGAAATTCAAACAACCATCACG |
| AGATATGCGAGTCTGCCTAGTAGGTGTCAACTTCCAACAGAATTATAGCACTTGCATCGTATCAGAAAGTAGT |
| GTGACAGCACCAAAAGGAAATGGAGACTTTTGGAAACATTGGATATCAACAGTCGACGGTCAATGTGGACTAC |
| CATTGGTAGATACTAAGAGCAAACATATTGTCGGAATTCATAGTCTTGCATCAACAAGTGGAAACACTAATTT |
| CTTTGTCGCTGTGCCTGGGAACTTTAATGAATACATCAATGGACTTGTGCAAGCAAATAAATGGGAAAAAGGA |
| TGGCACTATAATCCGAATCTCATATCCTGGTGTGGACTAAATTTAGTTGATTCTGCCCCAAAAGGTTTGTTTA |
| AAACGTCAAAATTGGTAGAAGACTTGGACGCGAGCGTTGAAGAGCAATGCAAGATCACCGAAACATGGCTCAC |
| AGAGCAATTACAAGATAATTTGCAAGTGGTTGCGAAATGTCCAGGCCAACTTGTTACCAAGCATGTTGTTAAG |
| GGTCAATGCCCACACTTTCAATTGTACTTATCAACACATGACGATGCCAAAGAATACTTCGCACCCATGCTTG |
| GAAAATACGACAAGAGTAGGCTTAACAGAGCAGCTTTTATCAAAGACATATCAAAATATGCAAAACCAATTTA |
| TATTGGAGAAATCAAGTATGATATCTTTGATAGAGCTGTACAGCGGGTTGTCAATATTCTCAAAAATGTTGGA |
| ATGCAACAATGCGTTTATGTCACAGATGAAGAAGAAATTTTCAGATCACTTAACCTGAACGCAGCTGTCGGAG |
| CATTGTATACAGGAAAGAAGAAAATTACTTTGAAAATTTTTCAAGCGAAGACAAGAAGAGATCGTGATGAG |
| ATCCTGTGAACGTATTTACAATGGGCAACTTGGCGTATGGAATGGATCGCTCAAAGCTGAGATCAGATCAATA |
| GAGAAAACCATGCTGAATAAGACTCGAACCTTCACAGCAGCCCCATTAGAAACTTTGCTCGGAGGAAAGTGT |
| GCGTGGATGATTTTAATAATCAATTCTATTCACATCATTTAGAAGGTCCATGGACTGTTGGGATAACAAAATT |
| CTATGGAGGTTGGAATCGCTTACTTGAGAAGTTACCAGAAGGATGGGTTTACTGCGATGCTGACGGGTCTCAA |
| TTTGATAGTTCGTTAACACCATATCTCATCAATGCAGTATTAAATATTCGATTGCAATTTATGGAAGATTGGG |
| ATATAGGAGCGCAAATGCTAAAGAACCTGTACACTGAGATTGTTTACACACCAATCGCAACGCCAGACGGATC |
| AATCGTGAAGAAATTCAAAGGTAACAATAGCGGACAACCTTCTACAGTAGTGGACAACACATTGATGGTTATA |
| ATAGCTTTCAACTATGCCATGCTATCAAGTGGTATCAAAGAAGAAAGAAATCGATAATTGCTGTAGAATGTTTG |
| CGAATGGTGATGACTTACTCCAGCAGTGCATCCTGATTTTGAGTTCATTTTAGATGAATTTCAAAATCACTT |
| TGGGAATCTTGGGCTGAACTTCGAATTTACATCACGAACACGAGACAAATCCGAACTGTGGTTCATGTCCACA |
| AGAGGCATCAAGTATGAAGGAATTTACATACCAAAGCTTGAGAAAGAAAGAATAGTCGCCATACTTGAATGGG |
| ATCGATCAAACTTGCCTGAACATAGGTTGGAAGCTATATGTGCAGCGATGGTTGAGGCCTGGGGATTCTCGA |
| TCTCGTTCATGAAATACGAAAGTTCTATGCGTGGCTTTTGGAAATGCAACCTTTTGCAAATCTCGCAAAAGAA |
| GGGTTGGCCCCATACATTGCCGAGACAGCACTCCGCAATCTCTATCTTGGAACGGGTATCAAAGAGGAAGAAA |
| TTGAAAAATATCTTAAACAATTCATTAAGGATCTTCCCGGATACATAGAAGATTACAATGAAGATGTATTCCA |
| TCAGTCGGGAACTGTTGATGCGGGTGCACAAGGCGGCAGTGGAAGCCAAGGGACAACACCACCAGCAACAGGT |
| AGTGGACAAAACCAGCCACCTCAGGGGCAGGATCTGGTAGTGGCAAGGATCTGGAAGGCAAATGCAACTTGAA |
| GTCAAGCAAGGACTGGCAGTGGCACTGGGACGGGATCTGGAGCAACCGGAGGCCAATCAGGATCTGGAAGTGG |
| CACTGAACAGGTTAACACGGGTTCAGCAGGAACTAATGCAACTGGAGGCCAAAGAGATAGGGATGTGGATGCA |
| GGTACAACAGGAAAATTTCTGTACCAAAGCTCAAGGCCATGTCAAAGAAATGCGCTTACCTAAAGCAAAAG |
| GAAAAGATGTGCTACATTTGGATTTTCTATTGACATACAAACCACAACAACAAGACATATCAAACACTAGAGC |
| AACAAGGAAGAGTTTGATAGATGGTATGATGCCATAAAGAAGGAAATCGATGACACACAAATGACA |
| GTTGTCATGAGTGGCCTTATGGTATGGTGCATCGAAAATGGTTGCTCACCAAACATAAACGGAAATTGGACAA |
| TGATGGATGAAGATGAACAAAGGGTCTTTCCACTCAAACCGGTCATTGAGAATGCATCTCCAACTTTCCGACA |
| AATTATGCATCATTTCAGTGATGCAGCTGAAGCGTACATAGAGTACAGAAACTCTACTGAGCGATATATGCCA |
| AGATACGGACTTCAGCGCAATCTCACCGACTATAGCTTAGCACGGTATGCATTTGATTTCTATGAAATGACTT |
| CACGCACACCTGCTAGAGCTAAAGAAGCCCACATGCAGATGAAGCCGCAGCAGTTCGTGGTTCAAACACACG |
| ACTGTTCGGTTTGGACGGAAATGTCGGCGAGACTCAGGAGAATACAGAGAGACACACAGCTGGCGATGTTAGT |

| Sequences |
| --- |
| CGCAACATGCACTCTCTGTTGGGAGTGCAGCAGCACCACTAGTCTCCTGGAAACCCTGTTTGCAGTACCAATA<br>ATATGTACTAATATATAGTATTTTAGTGAGGTTTTACCTCGTCTTTACTGTTTTATTACGTATGTATTTAAAG<br>CGTGAACCAGTCTGCAACATACAGGGTTGGACCCAGTGTGTTCTGGTGTAGCGTGTACTAGCGTCGAGCCATG<br>AGATGGACTGCACTGGGTGTGGTTTTGCCACTTGTGTTGCGAGTCTCTTGGTGAGAGACAAAAAAAAAAAAAA<br>AAAAAA<br><br>>CS1 cloning site (SEQ ID NO: 12)<br>AGATCTCCCGGGCGTACG<br><br>>C52 cloning site (SEQ ID NO: 13)<br>CCGCGGCCCGGG<br><br>>CS3 cloning site (SEQ ID NO 14)<br>GGGCCCTGTTTAAACGCCTGCAGG<br><br>>NIA cleavage site (SEQ ID NO: 15)<br>GAGGACGTGTTTCACCAATCCGCA<br><br>>SCMV-CS1 (SEQ ID NO: 16)<br>AAAAACAACAAAACTCAACACAACACAACAAAACACAACCAAGCAAATCCAATTTACTTGCGCTCAGATTGTA<br>GTGAACGGCTCGAACGAAACGGTTCTTCGAGATCACTCTCTGATTCTTCCTCATCTTTCAATTTCTTTCGAAA<br>GAAATGGCGGGAACGTGGACCTACGTGACACGTAAGTGGCAGCCAGATGTTAACAACGATCGTCACATTAAAA<br>GAGTGATGGAAATGTTTGCAGCAAAACATCAACATTACTCAGAAGAACAGCGACTTGCCCATAATATGAAATT<br>ATTGAGGAAGGCAAGTGTTGTAAGCGTTGAGCCTGCGAAACCAAAGCAGGCAACTCAACAGATGTGG<br>GTTGAGAAATGTGATCACAATCCTGTTGATCACTTAGTATATCCACGACTTGGAAAATCCGCGAACAAAGCAG<br>ATATGAGTATTAAAAGTGCATCTGTAAGCAAACTAACCAGAGAGATTTTAGAAATCTCAAAGGTTAGCGGCCT<br>TAAGGTTGAACTAATTGATAAACGAAAAAGATTCAAAACACAGTTATCAATCAAAAGGTTCAATGGCAAAAAT<br>TTCCTCCACTGCAAAACGAATCACGAAAACAATTTATTTAAGAGGAAAGACATAGCCATTGGGCACAAATGGT<br>TTCCAACGATTGAAGCCATTGCTAGATGCTATAGCACGATGAATCGAGAAGAACTACAAAGCCTTTATAGAGG<br>GAGCAGTGGTCTCACATTCATTCAAAACGATGAATTGTTCATTGTCAGAGGAAGAATGAATGGTGAACTTGTC<br>AATAGCTTGTACGAGACAAATCGGGTTTTGGATATTGAGCACTACGCAAGATCTCCCGGGCGTACGGAGGACG<br>TGTTTCACCAATCCGCAGATCCCCAGGCTAACGATTTCTGGAGGGGATACACAAATGCTTACGTAGAGAATCG<br>TAACATTTCGACTACTCATACAGAGCACACCCCTACAATCAATCTAGAGAATGTGGAAAACGAATGGCTCTA<br>CTCGAGATACTATTTCACTCTACATTCAAAATTACATGCAAGACATGCAACATTGATGATCTTGAATTATCGG<br>ATGATGAATTTGGAGCTAAACTCTACAAGAATTTGCAACGTATCGAAGAGAAACAACGAGAGTATCTTGCAAA<br>GGATCAAAAACTATCCAGAATGATACAATTTATCAAAGAAAGGTGCAATCCAAAATTTTCGCATTTACCAACG<br>CTATGGCAAGTTGCGGAAACAATAGGGCACTATACTGATAAACAGTCAAAGCAAATAATGGATATTAGCGAAG<br>CGCTCATCAAAGTTAATACTCTGACTCCTGATGATGCTATGAAAGCAAGCGCAGCGTTACTTGAAGTGTCGCG<br>ATGGTATAAGAATCGTAAGGAGTCACTCAAAACTGACTCATTGGAATCTTTTAGAAATAAAATATCACCAAAG<br>AGTACAATAAATGCAGCTTTAATGTGCGATAATCAATTGGATAAAAATGCAAATTTTGTATGGGGTAATAGGG<br>AATACCACGCCAAACGATTTTTCGCAAACTATTTTGAAGCAGTGGATCCCACAGATGCATATGAAAAGCACGT<br>CACACGGTTCAACCCTAATGGTCAACGAAAGTTATCAATAGGAAAGTTAGTTATCCCACTAGACTTTCAAAAG<br>ATTAGAGAATCATTTGTTGGACTCTCGATAAATAGACAACCGCTGGATAAATGTTGTGTTAGCAAGATCGAAG<br>GAGGGTATATATACCCATGTTGCTGCGTCACAACAGAATTTGGTAAACCAGCATACTCTGAGATAATACCTCC<br>AACGAAAGGGCATATAACAATAGGCAATTCTATTGATCCAAAGATTGTGGACTTGCCAAATACAACACCACCC<br>AGCATGTACATTGCTAAGGATGGGTATTGCTATATCAACATCTTTTTAGCAGCCATGATCAACGTTAATGAAG<br>AATCTGCCAAGGATTACACGAAATTTTTGAGGGACGAACTAGTTGAGCGTCTCGGAAAGTGGCCAAAGCTTAA<br>AGACGTAGCAACAGCGTGTTATGCATTATCTGTAATGTTTCCAGAAATTAAGAATGCTGAGCTACCTCCAATT<br>CTAGTTGACCATGAAATAAATCAATGCACGTAATTGATTCATATGGTTCACTAAGCGTTGGATTTCACATAT<br>TAAAAGCAAGCACGATTGGTCAATTAATCAAATTTCAATATGAGTCTATGGATAGTGAAATGCGCGAATACAT<br>AGTAGGAGGAACTCTCACACAACAGACATTCAACACACTTCTTAAGATGCTTACGAAAAACATGTTCAAACCA<br>GAGCGCATCAAGCAGATAATTGAAGAGGAACCCTTCTTACTTATGATGGCGATTGCGTCTCCAACGGTATTAA<br>TAGCACTATATAATAATTGTTATATTGAGCAAGCTATGACATACTGGATCGTTAAGAATCAAGGAGTTGCAGC<br>CATATTCGCACAACTCGAAGCATTAGCCAAGAAAACATCCCAGGCTGAGCTATTAGTTCTACAAATGCAGATA<br>CTTGAAAAGCATCTAACCAATTAAGATTAGCAGTTTCAGGACTTAGCCATATCGACCCAGCAAAGCGACTTT<br>TGTGGTCACACCTTGAAGCGATGTCAACACGATCAGAAATGAACAAGGAGTTAATAGCTGAGGGGTATGCACT<br>ATATGACGAGCGCCTATACACCCTGATGGAAAAAAGTTACGTAGATCAATTAAACCAATCATGGGCAGAATTG<br>TCATACTGTGGAAAATTTTCAGCAATATGGCGTGTGTTCAGAGTCAGGAAGTATTACAAACCGTCTTTAACCG<br>TGAGAAAAAGCGTAGATTTAGGCGCTGTATACAATATATCAGCTACGCATCTAATATCAGATTTAGCGCGGAA<br>AAGTCAAGATCAAGTCAGCTCTACTTTAACCAAACTCCGCAACGGTTTCTATGATAAATTAGAGAAAGTTAGA<br>ATACGACTATAAAAACGGTTTATTGGTTTATACCTGATATATTTAGACTCGTGCACATATTCATAGTTTTGA<br>GTTTATTAACTACCATCGCTAACACTATCATAGTAACTATGAATGACTACAAGAAATTGAAGAAGCAACAAAG<br>AGAAGACGAATATGAAGCAGAATTAACGAAGTTCGCAGAATCCATTCTACCTTAATGGAAGAGCGGAAGGAC<br>AATCTGACGTGTGAACAATTTATTGAGTATATGCGTCAAAATCATCCACGGCTAGTTGAAGCAACACTGGACT<br>TAACTCACACAGGTGTCATACATGAAGGGAAATCCAATCTCGAAACCAATTTGGAACAGGCAATGGCAGTTGG<br>AACCTTGATAACAATGATACTTGATCCACAGAAAAGCGATGCTGTCTATAAGGTGTTGAACAAAATGCGGACA<br>GTAATTAGTACAATTGAACAAAACGTCCCATTCCCTTCAGTGAATTTCTCCAACATCTTAACACCTCCAGTGG<br>CACAACAGAGTGTAGATGTTGATGAGCCATTAACACTTAGCACTGATAAAATTTAACAATAGACTTTGACAC<br>AAATCAAGATTTACCTGCCGATACATTCAGTAATGATGTGACATTTGAAGATTGGTGGTCAAATCAATTAAGC<br>AACAACAGAACAGTGCCACACTACCGACTTGGGGAAAGTTCATTGAATTCACACGAGAAACGCAGCCCACA<br>CGAGCATCGAACTTGCACACTCAAACATTGAGAGGGAATTCTTGCTTAGAGGAGCAGTCGGCTCGGGAAAATC<br>CACTGGGTTACCATACCATCTTAGCATGCGCGG7AAAGTGCTTCTACTAGAGCCTACAAGACCGCTAGCTGAG<br>AACGTGTGTAGGCAACTACAAGGACCGCCATTTAACGTAAGTCCAACTCTTCAAATGCGTGGATTAAGTTCTT<br>TTGGATGCACTCCAATCACAATCATGACATCTGGTTTTGCATTGCACATGTACGCAAATAATCCAGATAAAAT<br>ATCTGAGTACGATTTCATAATCTTTGATGAATGTCATATAATGGAAGCACCAGCGATGGCCTTTTATTGCTTA<br>CTCAAAGAATATGAATATCGAGGAAAAATTATCAAGGTATCAGCTACGCCTCCAGGAAGGGAGTGTGAATTCA<br>CAACACAACATCCAGTAGACATCCATGTTTGTGAGAATCTAACTCAGCAACAGTTTGTTATGGAACTCGGGAC |

| Sequences |
|---|
| TGGTTCAACCGCAGATGCTACGAAGTACGGAAATAATATCTTAGTTTATGTAGCAAGCTATAATGACGTCGAT |
| TCATTGTCGCAAGCACTAGTCGAACTTAAATTTTCCGTAATCAAAGTGGATGGCCGAACAATGAAACAAACA |
| CAACAGGAATCATTACAAACGGTACCGCACAAAAGAAGTGTTTTGTTGTCGCAACGAATATAATTGAGAATGG |
| CGTCACACTAGATATTGATGTTGTTGTCGACTTCGGACTTAAGGTCTCAGCTGACTTGGACGTTGACAACAGG |
| GCGGTATTGTATAAACGCGTAAGTATATCATATGGTGAACGCATACAACGATTGGGTCGTGTTGGCAGAAATA |
| AACCTGGTACAGTTATTCGAATCGGAAAAACAATGAAAGGTTTGCAGGAAATTCCAGCAATGATCGCAACAGA |
| AGCAGCCTTCATGTGTTTCGCTTACGGTCTTAAAGTTATCACTCATAATGTTTCAACGACCCATCTTGCAAAG |
| TGCACAGTTAAACAAGCGAGAACCATGATGCAATTTGAATTATCACCATTTGTCATGGCTGAGCTCGTTAAGT |
| TTGATGGTTCAATGCATCCACAAATACATGAGGCACTAGTAAAATACAAACTTAGAGATTCTGTCATAATGCT |
| CAGACCGAATGCACTTCCAAGGGTCAATTTACATAATTGGCTTACAGCCCGAGATTATAATAGAATAGGATGT |
| TCATTAGAACTCGAAGACCACGTCAAAATTCCGTACTACATTAGGGGAGTTCCTGACAAGTTGTATGGAAAGC |
| TATATGATATTATCTTACAGTATAGTCCAACTAGTTGCTACGGTAGACTATCAAGTGCGTGTGCAGGTAAAGT |
| AGCATATACTCTGCGAACTGATCCATTTTCACTTCCAAGAACAATAGCAATAATTAATGCCTTAATCACGGAG |
| GAGTATGCGAAGAGAGATCACTATCGTAACATGATTTCAAACCCATCTTCATCACACGCATTCTCACTCAATG |
| GGTTGGTGTCTATGATCGCTACTAGATATATGAAAGACCATACAAAGGAGAATATTGACAAACTCATTAGAGT |
| GCGTGATCAATTACTTGAGTTTCAAGGTACTGGAATGCAATTTCAAGATCCATCAGAACTCATGGAAATTGGG |
| GCTCTCAACACAGTTATTCACCAAGGAATGGACGCAACTGCAGCTTGTATTGGGTTACAAGGACGATGGAATG |
| CTTCACTTATACAACGCGATCTCCTGATTGCAGGTGGAGTTTTTATCGGAGGCATTTTGATGATGTGGAGCCT |
| ATTTACTAAATGGAGTAACACAAATGTCTCACATCAGGGGAAGAACAAACGCAGTAGACAAAAACTTCGATTC |
| AAAGAAGCAAGAGACAACAAATATGCATATGATGTCACAGATCGGAAGAATGCCTTGGCGAGAATTTTGGAA |
| CAGCCTATACAAAGAAAGGTAAAGGAAAAGGAACTAAAGTTGGACTCGGTGTGAAGCAGCATAAATTCCATAT |
| GATGTACGGTTTCGATCCCCAAGAGTACAACCTAATTCGGTTTGTCGATCCACTCACGGGAGCAACTCTTGAT |
| GAACAAATCCATGCCGATATACGCTTAATTCAAGAGCACTTCGCTGAAATTCGTGAGGAGGCAGTGATTAATG |
| ACACAATTGAAAGGCAGCAGATTTACGGCAATCCTGGACTACAAGCATTTTTCATACAAAATGGGTCAGCAAA |
| CGCTCTGAGAGTTGATTTAACACCACATTCACCTACACGAGTTGTCACAGGTAATAACATAGCAGGGTTCCCA |
| GAATATGAAGGAACACTTCGTCAGACTGGAACAGCTATAACTATACCCATTGGTCAAGTCCCAATCGCAAATG |
| AAGCAGGGGTTGCACACGAGTCAAAATCCATGATGAACGGGTTGGGTGATTACACACCAATATCGCAACAATT |
| GTGTCTAGTACAAAATGACTCGGATGGGGTAAAGCGGAATGTATTTTCAATTGGATATGGCTCATATCTTATT |
| TCACCAGCGCACTTATTCAAATATAACAATGGTGAAATAACAATTGATCATCAAGAGGATTGTACAAAATTC |
| GTAATTCTGTGGATTTAAAATTACATCCAATTGCACACAGAGACATGGTCATAATTCAACTCCCAAAGGATTT |
| CCCACCGTTCCCAATGCGCTTGAAATTCAAACAACCATCACGAGATATGCGAGTCTGCCTAGTAGGTGTCAAC |
| TTCCAACAGAATTATAGCACTTGCATCGTATCAGAAAGTAGTGTGACAGCACCAAAAGGAAATGGAGACTTTT |
| GGAAACATTGGATATCAACAGTCGACGGTCAATGTGGACTACCATTGGTGAACGTATTAAGAGCAAACATATTGT |
| CGGAATTCATAGTCTTGCATCAACAAGTGGAAACACTAATTTCTTTGTCGCTGTGCCTGGGAACTTTAATGAA |
| TACATCAATGGACTTGTCAAGCAAATAAATGGGAAAAAGGATGGCACTATAATCCGAATCTCATATCCTGGT |
| GTGGACTAAATTTAGTTGATTCTGCCCCAAAAGGTTTGTTTAAAACGTCAAAATTGGTAGAAGACTTGGACGC |
| GAGCGTTGAAGAGCAATGCAAGATCACCGAAACATGGCTCACAGAGCAATTACAAGATAATTTGCAAGTGGTT |
| GCGAAATGTCCAGGCCAACTTGTTACCAAGCATGTTGTTAAGGGTCAATGCCCACACTTTCAATTGTACTTAT |
| CAACACATGACGATGCCAAAGAATACTTCGCACCCATGCTTGGAAAATACGACAAGAGTAGGCCTTAACAGAGC |
| AGCTTTTATCAAAGACATATCAAAATATGCAAAACCAATTTATATTGGAGAAATCAAGTATGATATCTTTGAT |
| AGAGCTGTACAGCGGGTTGTCAATATTCTCAAAAATGTTGGAATGCAACAATGCGTTTATGTCACAGATGAAG |
| AAGAAATTTTCAGATCACTTAACCTGAACGCAGCTGTCGGAGCATTGTATACAGGAAAGAAGAAAAATTACTT |
| TGAAAATTTTCAAGCGAAGACAAAGAAGAGATCGTGATGAGATCCTGTGAACGTATTTACAATGGGCAACTT |
| GGCGTATGGAATGGATCGCTCAAAGCTGAGATCAGATCAATAGAGAAAACCATGCTGAATAAGACTCGAACCT |
| TCACAGCAGCCCCATTAGAAACTTTGCTCGGAGGAAAAGTGTGCGTGGATGATTTTAATAATCAATTCTATTC |
| ACATCATTTAGAAGGTCCATGGACTGTTGGGATAACAAAATTCTATGGAGGTTGGAATCGCTTACTTGAGAAG |
| TTACCAGAAGGATGGGTTTACTGCGATGCTGACGGGTCTCAATTTGATAGTTCGTTAACACCATATCTCATCA |
| ATGCAGTATTAAATATTCGATTGCAATTTATGGAAGATTGGGATATAGGAGCGCAAATGCTAAAGAACCTGTA |
| CACTGAGATTGTTTACACACACCAATCGCAACGCCAGACGGATCAATCGTGAAGAAATTCAAAGGTAACAATAGC |
| GGACAACCTTCTACAGTAGTGGACAACACATTGATGGTTATAATAGCTTTCAACTATGCCATGCTATCAAGTG |
| GTATCAAAGAAGAAGAAATCGATAATTGCTGTAGAATGTTTGCGAATGGTGATGACTTACTCCTAGCAGTGCA |
| TCCTGATTTTGAGTTCATTTTAGATGAATTTCAAAATCACTTTGGGAATCTTGGGCTGAACTTCGAATTTACA |
| TCACGAACACGAGACAAATCCGAACTGTGGTTCATGTCCACAAGAGGCATCAAGTATGAAGGAATTTACATAC |
| CAAAGCTTGAGAAAGAAAGAATAGTCGCCATACTTGAATGGGATCCATCAAACTTGCCTGAACATAGGTTGGA |
| AGCTATATGTGCAGCGATGGTTGAGGCCTGGGGATATTCCGATCTCGTTCATGAAATACGAAAGTTCTATGCG |
| TGGCTTTTGGAAATGCAACCTTTTGCAAATCTCGCAAAAGAAGGGTTGGCCCCATCATTGCCGAGACAGCAC |
| TCCGCAATCTCTATCTTGGAACGGGTATCAAAGAGGAAGAAATTGAAAAATATCTTAAACAATTCATTAAGGA |
| TCTTCCCGGATACATAGAAGATTACAATGAAGATGTATTCCATCAGTCGGGAACTGTTGATGCGGGTGCACAA |
| GGCGGCAGTGGAAGCCAAGGGACAACACCACCAGCAACAGGTAGTGGAAGCCACCTCAGGGGCAG |
| GATCTGGTAGTGGCACAGGAGCTGGAACTGGTGTAACTGGAGGTCAAGCAAGGACTGGCAGTGGCACTGGGAC |
| GGGATCTGGAGCAACCGGAGGCCAATCAGGATCTGGAAGTGGCACTGAACAGGTTAACACGGGTTCAGCAGGA |
| ACTAATGCAACTGGAGGCCAAAGAGATAGGGATGTGGATGCAGGTACAACAGGAAAAATTTCTGTACCAAAGC |
| TCAAGGCCATGTCAAAGAAAATGCGCTTACCTAAAGCAAAAGGAAAAGATGTGCTACATTTGGATTTTCTATT |
| GACATACAAACCACAACAACAAGACATATCAAACACTAGAGCAACCAAGGAAGAGTTTGATAGATGGTATGAT |
| GCCATAAAGAAGGAATACGAAATTGATGACACACAAATGACAGTTGTCATGAGTGGCCTTATGGTATGGTGCA |
| TCGAAAATGGTTGCTCACCAAACATAAACGGAAATTGGACAATGATGGATGAAGATGAACAAAGGGTCTTTCC |
| ACTCAAACCGGTCATTGAGAATGCATCTCCAACTTTCCGACAAATTATGCATCATTTCAGTGATGCAGCTGAA |
| GCGTACATAGAGTACAGAAACTCTACTGAGCGATATATGCCAAGATACGGACTTCAGCGCAATCTCACCGACT |
| ATAGCTTAGCACGTATGCATTTGATTTCTATGAAATGACTTCACGCACCTGCTAGAGCTAAAGAAGCCCA |
| CATGCAGATGAAAGCCGCAGCAGTTCGTGGTTCAAACACACGACTGTTCGGTTTGGACGGAAATGTCGGCGAG |
| ACTCAGGAGAATACAGAGAGACACACAGCTGGCGATGTTAGTCGCAACATGCACTCTCTGTTGGGAGTGCAGC |
| AGCACCACTAGTCTCCTGGAAACCCTGTTTGCAGTACCAATAATATGTACTAATATATAGTATTTTAGTGAGG |
| TTTTACCTCGTCTTTACTGTTTTATTACGTATGTATTTAAAGCGTGAACCAGTCTGCAACATACAGGGTTGGA |
| CCCAGTGTGTTCTGGTGTAGCGTGTACTAGCGTCGAGCCATGAGATGGACTGCACTGGGTGTGGTTTTGCCAC |
| TTGTGTTGCGAGTCTCTTGGTGAGAGACAAAAAAAAAAAAAAAAAAA |

-continued

Sequences

>SCMV-CS2 (SEQ ID NO: 17)
AAAAACAACAAAACTCAACACAACAACAAAAACACAACCAAGCAAATCCAATTTACTTGCGCTCAGATTGTA
GTGAACGGCTCGAACGAAACGGTTCTTCGAGATCACTCTCTGATTCTTCCTCATCTTTCAATTTCTTTCGAAA
GAAATGGCGGGAACGTGGACCTACGTGACACGTAAGTGGCAGCCAGATGTTAACAACGATCGTCACATTAAAA
GAGTGATGGAAATGTTTGCAGCAAAACATCAACATTACTCAGAAGAACAGCGACTTGCCCATAATATGAAATT
ATTGAGGAAGGCAAGTGTTGTAAGCGTTGAGCCTGCGAAACCAAAGCAGAAGCAGGCAACTCAACAGATGTGG
GTTGAGAAATGTGATCACAATCCTGTTGATCACTTAGTATATCCACGACTTGGAAAATCCGCGAACAAAGCAG
ATATGAGTATTAAAAGTGCATCTGTAAGCAAACTAACCAGAGAGATTTTAGAAATCTCAAAGGTTAGCGGCCT
TAAGGTTGAACTAATTGATAAACGAAAAAGATTCAAAACACAGTTATCAATCAAAAGGTTCAATGGCAAAAAT
TTCCTCCACTGCAAAACGAATCACGAAAACAATTTATTTAAGAGGAAAGACATAGCCATTGGGCACAAATGGT
TTCCAACGATTGAAGCCATTGCTAGATGCTATAGCACGATGAATCGAGAAGAACTACAAAGCCTTTATAGAGG
GAGCAGTGGTCTCACATTCATTCAAAACGATGAATTGTTCATTGTCAGAGGAAGAATGAATGGTGAACTTGTC
AATAGCTTGTACGAGACAAATCGGGTTTTGGATATTGAGCACTACGCACCGCGGCCCGGGGAGGACGTGTTTC
ACCAATCCGCAGATCCCCAGGCTAACGATTTCTGGAGGGGATACACAAATGCTTACGTAGAGAATCGTAACAT
TTCGACTACTCATACAGAGCACACCCCTACAATCAATCTAGAAGAATGTGGAAAACGAATGGCTCTACTCGAG
ATACTATTTCACTCTACATTCAAAATTACATGCAAGACATGCAACATTGATGATCTTGAATTATCGGATGATG
AATTTGGAGCTAAACTCTACAAGAATTTGCAACGTATCGAAGAGAAACAACGAGAGTATCTTGCAAAGGATCA
AAAACTATCCAGAATGATACAATTTATCAAAGAAAGGTGCAATCCAAAATTTTCGCATTTACCAACGCTATGG
CAAGTTGCGGAAACAATAGGGCACTATACTGATAACCAGTCAAGCAAATAATGGATATTAGCGAAGCGCTCA
TCAAAGTTAATACTCTGACTCCTGATGATGCTATGAAAGCAAGCGCAGCGTTACTTGAAGTGTCGCGATGGTA
TAAGAATCGTAAGGAGTCACTCAAAACTGACTCATTGGAATCTTTTAGAAATAAAATATCACCAAAGAGTACA
ATAAATGCAGCTTTAATGTGCGATAATCAATTGGATAAAAATGCAAATTTTGTATGGGGTAATAGGGAATACC
ACGCCAAACGATTTTTCGCAAACTATTTTGAAGCAGTGGATCCCACAGATGCATATGAAAAGCACGTCACACG
GTTCAACCCTAATGGTCAACGAAAGTTATCAATAGGAAAGTTAGTTATCCCACTAGACTTTCAAAAGATTAGA
GAATCATTTGTTGGACTCTCGATAAATAGACAACCGCTGGATAAATGTTGTGTTAGCAAGATCGAAGGAGGGT
ATATATACCCATGTTGCTGCGTCACAACAGAATTTGGTAAACCAGCATACTCTGAGATAATACCTCCAACGAA
AGGGCATATAACAATAGGCAATTCTATTGATCCAAAGATTGTGGACTTGCCAAATACAACACCACCCAGCATG
TACATTGCTAAGGATGGGTATTGCTATATCAACATCTTTTTAGCAGCCATGATCAACGTTAATGAAGAATCTG
CCAAGGATTACACGAAATTTTTGAGGGACGAACTAGTTGAGCGTCTCGGAAAGTGGCCAAAGCTTAAAGACGT
AGCAACAGCGTGTTATGCATTATCTGTAATGTTTCCAGAAATTAAGAATGCTGAGCTACCTCCAATTCTAGTT
GACCATGAAAATAAATCAATGCACGTAATTGATTCATATGGTTCACTAAGCGTTGGATTTCACATATTAAAAG
CAAGCACGATTGGTCAATTAATCAAATTTCAATATGAGTCTATGGATAGTGAAATGCGCGAATACATAGTAGG
AGGAACTCTCACACAACAGACATTCAACACACTTCTTAAGATGCTTACGAAAACATGTTCAAACCAGAGCGC
ATCAAGCAGATAATTGAAGAGGAACCCTTCTTACTTATGATGGCGATTGCGTCTCCAACGGTATTAATAGCAC
TATATAATAATTGTTATATTGAGCAAGCTATGACATACTGGATCGTTAAGAATCAAGGAGTTGCAGCCATATT
CGCACAACTCGAAGCATTAGCCAAGAAAACATCCCAGGCTGAGCTATTAGTTCTACAAATGCAGATACTTGAA
AAAGCATCTAAGCAATTAAGGATTAGCAGTTTCAGGACTTAGCCATATCGACCCAGCAAAGCGACTTTTGTGGT
CACACCTTGAAGCGATGTCAACACGATCAGAAATGAACAAGGAGTTAATAGCTGAGGGGTATGCACTATATGA
CGAGCGCCTATACACCCTGATGGAAAAAAGTTACGTAGATCAATTAAACCAATCATGGGCAGAATTGCTACAC
TGTTGGAAAATTTTCAGCAATATGGCGTGTGTTCAGAGTCAGGAAGTATTACAAACCGTCTTTAACCGTGAGAA
AAAGCGTAGATTTAGGCGCTGTATACAATATATCAGCTACGCATCTAATATCAGATTTAGCGCGGAAAAGTCA
AGATCAAGTCAGCTCTACTTTAACCAAACTCCGCAACGGTTTCTATGATAAATTAGAGAAAGTTAGAATACGA
ACTATAAAAACGGTTTATTGGTTTATACCTGATATATTTAGACTCGTGCACATATTCATAGTTTTGAGTTTAT
TAACTACCATCGCTAACACTATCATAGTAACTATGAATGACTACAGAAAATTGAAGAAGCAACAAGAGAAGA
CGAATATGAAGCAGAAATTAACGAAGTTCGCAGAATCCATTCTACCTTAATGGAAGAGCGGAAGGACAATCTG
ACGTGTGAACAATTTATTGAGTATATGCGTCAAAATCATCCACGGCTAGTTGAAGCAACACTGGACTTAACTC
ACACAGGTGTCATACATGAAGGGAAATCCAATCTCGAAACCAATTTGGAACAGGCAATGGCAGTTGGAACCTT
GATAACAATGATACTTGATCCACAGAAAAGCGATGCTGTCTATAAGGTGTTGAACAAAATGCGGACAGTAATT
AGTACAATTGAACAAAACGTCCCATTCCCTTCAGTGAATTTCTCCAACATCTTAACACCTCCAGTGGCACAAC
AGAGTGTAGATGTTGATGAGCCATTAACACTTAGCACTGATAAAAATTTAACAATAGACTTTGACACAAATCA
AGATTTACCTGCCGATACATTCAGTAATGATGTGACATTTGAAGATTGGTGGTCAAATCAATTAAGCAACAAC
AGAACAGTGCCACACTACCGACTTGGGGGAAAGTTCATTGAATTCACACGAGAAAACGCAGCCCACACGAGCA
TCGAACTTGCACACTCAAACATTGAGAGGGAATTCTTGCTTAGAGGAGCAGTCGGCTCGGGAAAATCCACTGG
GTTACCATACCATCTTAGCATGCGCGGAAAAGTGCTTCTACTAGAGCCTACAAGACCGCTAGCTGAGAACGTG
TGTAGGCAACTACAAGGACCGCCATTTAACGTAAGTCCAACTCTTCAAATGCGTGGATTAAGTTCTTTTGGAT
GCACTCCAATCACAATCATGACATCTGGTTTTGCATTGCACATGTACGCAAATAATTCAGATAAAATATCTGA
GTACGATTTCATAATCTTTGATGAATGTCATATAATGGAAGCACCAGCGATGGCCTTTTATTGCTTACTCAAA
GAATATGAATATCGAGGAAAAATTATCAAGGTATCAGCTACGCCTCCAGGAAGGGAGTGTGAATTCACAACAC
AACATCCAGTAGACATCCATGTTTGTGAGAATCTAACTCAGCAACAGTTTGTTATGGAACTCGGGACTGGTTC
AACCGCAGATGCTACGAAGTACGGAAATAATATCTTAGTTTATGTAGCAAGCTATAATGACGTCGATTCATTG
TCGCAAGCACTAGTCGAACTTAAATTTTCCGTAATCAAAGTGGATGGCCAACAATGAAACAAAACACAACAG
GAATCATTACAAACGGTACCGCACAAAAGAAGTGTTTTGTTGTCGCAACGAATATAATTGAGAATGGCGTCAC
ACTAGATATTGATGTTGTTGTCGACTTCGGACTTAAGGTCTCAGCTGACTTGGACGTTGACAACAGGGCGGTA
TTGTATAAACGCGTAAGTATATCATATGGTGAACGCATACAACGATTGGGTCGTGTTGGCAGAAATAAACCTG
GTACAGTTATTCGAATCGGAAAAACAGAAAGGGTTTTGCAGGAAATTCCAGCAATGATCGCACAGAGAAGCAGC
CTTCATGTGTTTCGCTTACGGTCTTAAAGTTATCACTCATAATGTTTCAACGACCCATCTTGCAAAGTGCACA
GTTAAACAAGCGAGAACCATGATGCAATTTGAATTATCACCATTTGTCATGGCTGAGCTCGTTAAGTTTGATG
GTTCAATGCATCCACAAATACATGAGGCACTAGTAAAATACAAACTTAGAGATTCTGTCATAATGCTCAGACC
GAATGCACTTCCAAGGGTCAATTTACATAATTGGCTTACAGCCCGAGATTATAATAGAATAGGATGTTCATTA
GAACTCGAAGACCACGTCAAAATTCCGTACTACATTAGGGGAGTTCCTGACAGTTGATTGGGAAAGCTCATG
ATATTATCTTACAGTATAGTCCAACTAGTTGCTACGGTAGACTATCAAGTGCGTGTGCAGGTAAAGTAGCATA
TACTCTGCGAACTGATCCATTTTCACTTCCAAGAACAATAGCAATAATTAATGCCTTAATCACGGAGGAGTAT
GCGAAGAGAGATCACTATCGTAACATGATTTCAAACCCATCTTCATCACACGCATTCTCACTCAATGGGTTGG
TGTCTATGATCGCTACTAGATATGAAAGACCATACAAAGGAGAATATTGACAAACTCATTAGAGTGCGTGA
TCAATTACTTGAGTTTCAAGGTACTGGAATGCAATTTCAAGATCCATCAGAACTCATGGAAATTGGGCTCTC
AACACAGTTATTCACCAAGGAATGGACGCAACTGCAGCTTGTATTGGGTTACAAGGACGATGGAATGCTTCAC

-continued

| Sequences |
|---|
| TTATACAACGCGATCTCCTGATTGCAGGTGGAGTTTTTATCGGAGGCATTTTGATGATGTGGAGCCTATTTAC |
| TAAATGGAGTAACACAAATGTCTCACATCAGGGGAAGAACAAACGCAGTAGACAAAAACTTCGATTCAAAGAA |
| GCAAGAGACAACAAATATGCATATGATGTCACAGGATCGGAAGAATGCCTTGGCGAGAATTTTGGAACAGCCT |
| ATACAAAGAAAGGTAAAGGAAAAGGAACTAAAGTTGGACTCGGTGTGAAGCAGCATAAATTCCATATGATGTA |
| CGGTTTCGATCCCCAAGAGTACAACCTAATTCGGTTTGTCGATCCACTCACGGGAGCAACTCTTGATGAACAA |
| ATCCATGCCGATATACGCTTAATTCAAGAGCACTTCGCTGAAATTCGTGAGGAGGCAGTGATTAATGACACAA |
| TTGAAAGGCAGCAGATTTACGGCAATCCTGGACTACAAGCATTTTTTCATACAAAATGGGTCAGCAAACGCTCT |
| GAGAGTTGATTTAACACCACATTCACCTACACGAGTTGTCACAGGTAATAACATAGCAGGGTTCCCAGAATAT |
| GAAGGAACACTTCGTCAGACTGGAACAGCTATAACTATACCCATTGGTCAAGTCCCAATCGCAAATGAAGCAG |
| GGGTTGCACACGAGTCAAAATCCATGATGAACGGGTTGGGTGATTACACACCAATATCGCAACAATTGTGTCT |
| AGTACAAAATGACTCGGATGGGGTAAAGCGGAATGTATTTTCAATTGGATATGGCTCATATCTTATTTCACCA |
| GCGCACTTATTCAAATATAACAATGGTGAAATAACAATTAGATCATCAAGAGGATTGTACAAAATTCGTAATT |
| CTGTGGATTTAAAATTACATCCAATTGCACACAGAGACATGGTCATAATTCAACTCCCAAAGGATTTCCCACC |
| GTTCCCAATGCGCTTGAAATTCAAACAACCATCACGAGATATGCGAGTCTGCCTAGTAGGTGTCAACTTCCAA |
| CAGAATTATAGCACTTGCATCGTATCAGAAAGTAGTGTGACAGCACCAAAAGGAAATGGAGACTTTTGGAAAC |
| ATTGGATATCAACAGTCGACGGTCAATGTGGACTACCATTGGTAGATACTAAGAGCAAACATATTGTCGGAAT |
| TCATAGTCTTGCATCAACAAGTGGAAACACTAATTTCTTTGTCGCTGTGCCTGGGAACTTTAATGAATACATC |
| AATGGACTTGTGCAAGCAAATAAATGGGAAAAAGGATGGCACTATAATCCGAATCTCATATCCTGGTGTGGAC |
| TAAATTTAGTTGATTCTGCCCCAAAAGGTTTGTTTAAAACGTCAAAATTGGTAGAAGACTTGGACGCGAGCGT |
| TGAAGAGCAATGCAAGATCACCGAAACATGGCTCACAGAGCAATTAGAAGATAATTTGCAAGTGGTTGCGAAA |
| TGTCCAGGCGAACTTGTTACCAAGCATGTGTTAAGGGTCAATGCCCACACTTTCAATTGTACTTATCAACAC |
| ATGACGATGCCAAAGAATACTTCGCACCCATGCTTGGAAAATACGACAAGAGTAGGCTTAACAGAGCAGCTTT |
| TATCAAAGACATATCAAAATATGCAAAACCAATTTATATTGGAGAAATCAAGTATGATATCTTTGATAGAGCT |
| GTACAGCGGGTTGTCAATATTCTCAAAAATGTTGGAATGCAACAATGCGTTTATGTCACAGATGAAGAAGAAA |
| TTTTCAGATCACTTAACCTGAACGCAGCTGTCGGAGCATTGTATACAGGAAAGAAGAAAAATTACTTTGAAAA |
| TTTTTCAAGCGAAGACAAAGAAGAGATCGTGATGAGATCCTGTGAACGTATTTACAATGGGCAACTTGGCGTA |
| TGGAATGGATCGCTCAAAGCTGAGATCAGATCAATAGAGAAAACCATGCTGAATAAGACTCGAACCTTCACAG |
| CAGCCCCATTAGAAACTTTGCTCGGAGGAAAAGTGTGCGTGGATGATTTTAATAATCAATTCTATTCACATCA |
| TTTAGAAGGTCCATGGACTGTTGGGATAACAAAATTCTATGGAGGTTGGAATCGCTTACTTGAGAAGTTACCA |
| GAAGGATGGGTTTACTGCGATGCTGACGGGTCTCAATTTGATAGTTCGTTAACACCCATATCTCATCAATGCAG |
| TATTAAATATTCGATTGCAATTTATGGAAGATTGGGATATAGGAGCGCAAATGCTAAAGAACCTGTACACTGA |
| GATTGTTTACACACCAATCGCAACGCCAGACGGATCAATCGTGAAGAAATTCAAAGGTAACAATAGCGGACAA |
| CCTTCTACAGTAGTGGACAACACATTGATGGTTATAATAGCTTTCAACTATGCCATGCTATCAAGTGGTATCA |
| AAGAAGAAGAAATCGATAATTGCTGTAGAATGTTTGCGAATGGTGATGACTTACTCCTAGCAGTGCATCCTGA |
| TTTTGAGTTCATTTTAGATGAATTTCAAAATCACTTTGGGAATCTTGGGCTGAACTTCGAATTTACATCACGA |
| ACACGAGACAATCCGAACTGTGGTTCATGTCCACAAGAGGCATCAAGTATGAAGGAATTTACATACCAAAGC |
| TTGAGAAAGAAAGAATAGTCGCCATACTTGAATGGGATCGATCAAACTTGCCTGAACATAGGTTGGAAGCTAT |
| ATGTGCAGCGATGGTTGAGGCCTGGGGATATTCCGATCTCGTTCATGAAATACGAAAGTTCTATGCGTGGCTT |
| TTGGAAATGCAACCTTTTGCAAATCTCGCAAAAGAAGGGTTGGCCCCATACATTGCCGAGACAGCACTCCGCA |
| ATCTCTATCTTGGAACGGGTATCAAAGAGGAAGAAATTGAAAAATATCTTAAACAATTCATTAAGGATCTTCC |
| CGGATACATAGAAGATTACAATGAAGATGTATTCCATCAGTCGGGAACTGTTGATGCGGGTGCACAAGGCGGC |
| AGTGGAAGCCAAGGGACAACACCACCAGCAACAGGTAGTGGAGCAAAACCAGCCACCTCAGGGGCAGGATCTG |
| GTAGTGGCACAGGAGCTGGAACTGGTGTAACTGGAGGTCAAGCAAGGACTGGCAGTGGCACTGGGACGGGATC |
| TGGAGCAACCGGAGGCCAATCAGGATCTGGAAGTGGCACTGAACAGGTTAACACGGGTTCAGCAGGAACTAAT |
| GCAACTGGAGGCCAAAGAGATAGGGATGTGGATGCAGGTACAACAGGAAAAATTTCTGTACCAAAGCTCAAGG |
| CCATGTCAAAGAAAATGCGCTTACCTAAAGCAAAAGGAAAAGATGTGCTACATTTGGATTTTCTATTGACATA |
| CAAACCACAACAACAAGACATATCAAACACTAGAGCAACCAAGGAAGAGTTTGATAGATGGTATGATGCCATA |
| AAGAAGGAATACGAAATTGATGACACACAAATGACAGTTGTCATGAGTGGCCTTATGGTATGGTGCATCGAAA |
| ATGGTTGCTCACCAAACATAAACGGAAATTGGACAATGATGGATGAAGATGAACAAAAGGGTCTTTCCACTCAA |
| ACCGGTCATTGAGAATGCATCTCCAACTTTCCGACAAATTATGCATCATTTCAGTGATGCAGCTGAAGCGTAC |
| ATAGAGTACAGAAACTCTACTGAGCGATATATGCCAAGATACGGACTTCAGCGCAATCTCACCGACTATAGCT |
| TAGCACGGTATGCATTTGATTTCTATGAAATGACTTCACGCACACCTGCTAGAGCTAAAGAAGCCCACATGCA |
| GATGAAAGCCGCAGCAGTTCGTGGTTCAAACACACGACTGTTCGGTTTGGACGGAAATGTCGGCGAGACTCAG |
| GAGAATACAGAGAGACACACAGCTGGCGATGTTAGTCGCAACATGCACTCTCTGTTGGGAGTGCAGCAGCACC |
| ACTAGTCTCCTGGAAACCCTGTTTGCAGTACCAATAATATGTACTAATATATAGTATTTTAGTGAGGTTTTAC |
| CTCGTCTTTACTGTTTTATTACGTATGTATTTAAAGCGTGAACCAGTCTGCAACATACAGGGTTGGACCCAGT |
| GTGTTCTGGTGTAGCGTGTACTAGCGTCGAGCCATGAGATGGACTGCACTGGGTGTGGTTTTGCCACTTGTGT |
| TGCGAGTCTCTTGGTGAGAGACAAAAAAAAAAAAAAAAAAAAAA |

>SCMV-CS3 (SEQ ID NO: 18)
AAAAACAACAAAACTCAACACAACACAACAAAAACACAACCAAGCAAATCCAATTTACTTGCGCTCAGATTGTA
GTGAACGGCTCGAACGAAACGGTTCTTCGAGATCACTCTCTGATTCTTCCTCATCTTTCAATTTCTTTCGAAA
GAAATGGCGGGAACGTGGACCTACGTGACACGTAAGTGGCAGCCAGATGTTAACAACGATCGTCACATTAAAA
GAGTGATGGAAATGTTTGCAGCAAAACATCAACATTACTCAGAAGAACAGCGACTTGCCCATAATATGAAATT
ATTGAGGAAGGCAAGTGTTGTAAGCGTTGAGCCTGCGAAACCAAAGCAGAAGCAGGCAACTCAACAGATGTGG
GTTGAGAAATGTGATCACAATCCTGTTGATCACTTAGTATATCCAGACTTTGGAAAATCCGCGAACAAAGCAG
ATATGAGTATTAAAAGTGCATCTGTAAGCAAACTAACCAGAGAGATTTTAGAAATCTCAAAGGTTAGCGGCCT
TAAGGTTGAACTAATTGATAAACGAAAAAGATTCAAAACACAGTTATCAATCAAAAGGTTCAATGGCAAAAAT
TTCCTCCACTGCAAAACGAATCACGAAAACAATTTATTTAAGAGGAAAGACATAGCCATTGGGCACAAATGGT
TTCCAACGATTGAAGCCATTGCTAGATGCTATAGCACGATGAATCGAGAAGAACTACAAAGCCTTTATAGAGG
GAGCAGTGGTCTCACATTCATTCAAAACGATGAATTGTTCATTGTCAGAGGAAGAATGAATGGTGAACTTGTC
AATAGCTTGTACGAGACAAATCGGGTTTTGGATATTGAGCACTACGCAGGGCCCTGTTTAAACGCCTGCAGGG
AGGACGTGTTTCACCAATCCGCAGATCCCCAGGCTAACGATTTCTGGAGGGGATACACAAATGCTTACGTAGA
GAATCGTAACATTTCGACTACTCATCAGAGCACACCCCTACAATCAATCTAGAAGAATGTGGAAAACGAATG
GCTCTACTCGAGATACTATTTCACTCTACATTCAAAATTACATGCAAGACATGCAACATTGATGATCTTGAAT
TATCGGATGATGAATTTGGAGCTAAACTCTACAAGAATTTGCAACGTATCGAAGAGAAACAACGAGAGTATCT
TGCAAAGGATCAAAAACTATCCAGAATGATACAATTTATCAAAGAAAGGTGCAATCCAAAATTTTCGCATTTA

-continued

| Sequences |
|---|
| CCAACGCTATGGCAAGTTGCGGAAACAATAGGGCACTATACTGATAACCAGTCAAAGCAAATAATGGATATTA |
| GCGAAGCGCTCATCAAAGTTAATACTCTGACTCCTGATGATGCTATGAAAGCAAGCGCAGCGTTACTTGAAGT |
| GTCGCGATGGTATAAGAATCGTAAGGAGTCACTCAAAACTGACTCATTGGAATCTTTTAGAAATAAAATATCA |
| CCAAAGAGTACAATAAATGCAGCTTTAATGTGCGATAATCAATTGGATAAAAATGCAAATTTTGTATGGGGTA |
| ATAGGGAATACCACGCCAAACGATTTTTCGCAAACTATTTTGAAGCAGTGGATCCCACAGATGCATATGAAAA |
| GCACGTCACACGGTTCAACCCTAATGGTCAACGAAAGTTATCAATAGGAAAGTTAGTTATCCCACTAGACTTT |
| CAAAAGATTAGAGAATCATTTGTTGGACTCTCGATAAATAGACAACCGCTGGATAAATGTTGTGTTAGCAAGA |
| TCGAAGGAGGGTATATATACCCATGTTGCTGCGTCACAACAGATTTGGTAAACCAGCATACTCTGAGATAAT |
| ACCTCCAACGAAAGGGCATATAACAATAGGCAATTCTATTGATCCAAAGATTGTGGACTTGCCAAATACAACA |
| CCACCCAGCATGTACATTGCTAAGGATGGGTATTGCTATATCAACATCTTTTTAGCAGCCATGATCAACGTTA |
| ATGAAGAATCTGCCAAGGATTACACGAAATTTTTGAGGGACGAACTAGTTGAGCGTCTCGGAAAGTGGCCAAA |
| GCTTAAAGACGTAGCAACAGCGTGTTATGCATTATCTGTAATGTTTCCAGAAATTAAGAATGCTGAGCTACCT |
| CCAATTCTAGTTGACCATGAAAATAAATCAATGCACGTAATTGATTCATATGGTTCACTAAGCGTTGGATTTC |
| ACATATTAAAAGCAAGCACGATTGGTCAATTAATCAAATTTCAATATGAGTCTATGGATAGTGAAATGCGCGA |
| ATACATAGTAGGAGGAACTCTCACACAACAGACATTCAACACACTTCTTAAGATGCTTACGAAAAACATGTTC |
| AAACCAGAGCGCATCAAGCAGATAATTGAAGAGGAACCCTTCTTACTTATGATGGCGATTGCGTCTCCAACGG |
| TATTAATAGCACTATATAATAATTGTTATATTGAGCAAGCTATGACATACTGGATCGTTAAGAATCAAGGAGT |
| TGCAGCCATATTCGCACAACTCGAAGCATTAGCCAAGAAAACATCCCAGGCTGAGCTATTAGTTCTACAAATG |
| CAGATACTTGAAAAAGCATCTAACCAATTAAGATTAGCAGTTTCAGGACTTAGCCATATCGACCCAGCAAAGC |
| GACTTTTGTGGTCACACCTTGAAGCGATGTCAACACGATCAGAAATGAACAAGGAGTTAATAGCTGAGGGGTA |
| TGCACTATATGACGAGCGCCTATACACCCTGATGGAAAAAGTTACGTAGATCAATTAAACCAATCATGGGCA |
| GAATTGTCATACTGTGGAAAATTTTCAGCAATATGGCGTGTGTTCAGAGTCAGGAAGTATTACAAACCGTCTT |
| TAACCGTGAGAAAAAGCGTAGATTTAGGCGCTGTATACAATATATCAGCTACGCATCTAATATCAGATTTAGC |
| GCGGAAAAGTCAAGATCAAGTCAGCTCTACTTTAACCAAACTCCGCAACGGTTTCTATGATAAATTAGAGAAA |
| GTTAGAATACGAACTATAAAAACGGTTTATTGGTTTATACCTGATATATTTAGACTCGTGCACATATTCATAG |
| TTTTGAGTTTATTAACTACCATCGCTAACACTATCATAGTAACTATGAATGACTACAAGAAATTGAAGAAGCA |
| ACAAAGAGAAGACGAATATGAAGCAGAAATTAACGAAGTTCGCAGAATCCATTCTACCTTAATGGAAGAGCGG |
| AAGGACAATCTGACGTGTGAACAATTTATTGAGTATATGCGTCAAAATCATCCACGGCTAGTTGAAGCAACAC |
| TGGACTTAACTCACACAGGTGTCATACATGAAGGGAAATCCAATCTCGAAACCAATTTGGAACAGGCAATGGC |
| AGTTGGAACCTTGATAACAATGATACTTGATCCACAGAAAAGCGATGCTGTCTATAAGGTGTTGAACAAAATG |
| CGGACAGTAATTAGTACAATTGAACAAAACGTCCCATTCCCTTCAGTGAATTTCTCCAACATCTTAACACCTC |
| CAGTGGCACAACAGAGTGTAGATGTTGATGAGCCATTAACACTTAGCACTGATAAAAATTTAACAATAGACTT |
| TGACACAAATCAAGATTTACCTGCCGATACATTCAGTAATGATGTGACATTTGAAGATTGGTGGTCAAATCAA |
| TTAAGCAACAACAGAACAGTGCCACACTACCGACTTGGGGGAAAGTTCATTGAATTCACACGAGAAAACGCAG |
| CCCACACGAGCATCGAACTTGCACACTCAAACATTGAGAGGGAATTCTTGCTTAGAGGAGCAGTCGGCTCGGG |
| AAAATCCACTGGGTTACCATACCATCTTAGCATGCGCGGAAATGCTTCTACTAGAGCCTACAAGACCGCTA |
| GCTGAGAACGTGTGTAGGCAACTACAAGGACCGCCATTTAACGTAAGTCCAACTCTTCAAATGCGTGGATTAA |
| GTTCTTTTGGATGCACTCCAATCACAATCATGACATCTGGTTTTGCATTGCACATGTACGCAAATAATCCAGA |
| TAAAATATCTGAGTACGATTTCATAATCTTTGATGAATGTCATATAATGGAAGCACCAGCGATGGCCTTTTAT |
| TGCTTACTCAAAGAATATGAATATCGAGGAAAATTATCAAGGTATCAGCTACGCCTCCAGGAAGGGAGTGTG |
| AATTCACAACACAACATCCAGTAGACATCCATGTTTGTGAGAATCTAACTCAGCAACAGTTTGTTATGGAACT |
| CGGGACTGGTTCAACCGCAGATGCTACGAAGTACGGAAATAATATCTTAGTTTATGTAGCAAGCTATAATGAC |
| GTCGATTCATTGTCGCAAGCACTAGTCGAACTTAAATTTTCCGTAATCAAAGTGGATGGCCGAACAATGAAAC |
| AAAACACAACAGGAATCATTACAAACGGTACCGCACAAAAGAAGTGTTTTGTTGTCGCAACGAATATAATTGA |
| GAATGGCGTCACACTAGATATTGATGTTGTTGTCGACTTCGGACTTAAGGTCTCAGCTGACTTGGACGTTGAC |
| AACAGGGCGGTATTGTATAAACGCGTAAGTATATCATATGGTGAACGCATACAACGATTGGGTCGTGTTGGCA |
| GAAATAAACCTGGTACAGTTATTCGAATCGGAAAAACAATGAAAGGTTTGCAGGAAATTCCAGCAATGATCGC |
| AACAGAAGCAGCCTTCATGTGTTTCGCTTACGGTCTTAAAGTTATCACTCATAATGTTTCAACGACCCATCTT |
| GCAAAGTGCACAGTTAAACAAGCGAGAACCATGATGCAATTTGAATTTACCATTTGTCATGGCTGAGCTCG |
| TTAAGTTTGATGGTTCAATGCATCCACAAATACATGAGGCACTAGTAAAATACAAACTTAGAGATTCTGTCAT |
| AATGCTCAGACCGAATGCACTTCCAAGGGTCAATTTACATAATTGGCTTACAGCCCGAGATTATAATAGAATA |
| GGATGTTCATTAGAACTCGAAGACCACGTCAAAATTCCGTACTACATTAGGGGAGTTCCTGACAAGTTGTATG |
| GAAAGCTATATGATATTATCTTACAGTATAGTCCAACTAGTTGCTACAGACATCAAGTGCGTGTGCAGG |
| TAAAGTAGCATATACTCTGCGAACTGATCCATTTTCACTTCCAAGAACAATAGCAATAATTAATGCCTTAATC |
| ACGGAGGAGTATGCGAAGAGAGATCACTATCGTAACATGATTTCAAACCCATCTTCATCACACGCATTCTCAC |
| TCAATGGGTTGGTGTCTATGATCGCTACTAGATATATGAAAGACCATACAAAGGAGAATATTGACAAACTCAT |
| TAGAGTGCGTGATCAATTACTTGAGTTTCAAGGTACTGGAATGCAATTTCAAGATCCATCAGAACTCATGGAA |
| ATTGGGGCTCTCAACACAGTTATTCACCAAGGAATGGACGCAACTGCAGCTTGTATTGGGTTACAAGGACGAT |
| GGAATGCTTCACTTATACAACGCGATCTCCTGATTGCAGGTGGAGTTTTTATCGGAGGCATTTTGATGATGTG |
| GAGCCTATTTACTAAATGGAGTAACACAAATGTCTCACATCAGGGGAAGAACAAACGCAGTAGACAAAAACTT |
| CGATTCAAAGAAGCAAGAGACAACAAATATGCATATGATGTCACAGGATCGGAAGAATGCCTTGGCGAGAATT |
| TTGGAACAGCCTATACAAAGAAAGGTAAAGGAAAAGGAACTAAAGTTGGACTCGGTGTGAAGCAGCATAAATT |
| CCATATGATGTACGGTTTCGATCCCCAAGAGTACAACCTAATTCGGTTTGTCGATCCACTCACGGGAGCAACT |
| CTTGATGAACAAATCCATGCCGATATACGCTTAATTCAAGAGCACTTCGCTGAAATTCGTGAGGAGGCAGTGA |
| TTAATGACACAATTGAAAGGCAGCAGATTTACGGCAATCCTGGACTACAAGCATTTTTCATACAAAATGGGTC |
| AGCAAACGCTCTGAGAGTTGATTTAACACCACATTCACCTACACGAGTTGTCACAGGTAATAACATAGCAGGG |
| TTCCCAGAATATGAAGGAACACTTCGTCAGACTGGAACAGCTATAACTATACCCATTGGTCAAGTCCCAATCG |
| CAAATGAAGCAGGGGTTGCACACGAGTCAAAATCCATGATGAACGGGTTGGGTGATTACACACCAATATCGCA |
| ACAATTGTGTCTAGTACAAAATGACTCGGATGGGGTAAAGCGGAATGTATTTTCAATTGGATATGGCTCATAT |
| CTTATTTCACCAGCGCACTTATTCAAATATAACAATGGTGAAATAACAATTAGTCATCAAGAGGATTGTACA |
| AAATTCGTAATTCTGTGGATTTAAAATTACATCCAATTGCACACAGAGACATGGTCATAATTCAACTCCCAAA |
| GGATTTCCCACCGTTCCCAATGCGCTTGAAATTCAAACAACCATCACGAGATATGCGAGTCTGCCTAGTAGGT |
| GTCAACTTCCAACAGAATTATAGCACTTGCATCGTATCAGAAAGTAGTGTGACAGCACCAAAAGGAAATGGAG |
| ACTTTTGGAAACATTGGATATCAACAGTCGACGGTCAATGTGGACTACCATTGGTAGATACTAAGAGCAAACA |
| TATTGTCGGAATTCATAGTCTTGCATCAACAAGTGGAAACACTAATTTCTTTGTCGCTGTGCCTGGGAACTTT |
| AATGAATACATCAATGGACTTGTGCAAGCAAATAAATGGGAAAAAGGATGGCACTATAATCCGAATCTCATAT |
| CCTGGTGTGGACTAAATTTAGTTGATTCTGCCCCAAAAGGTTTGTTTAAAACGTCAAAATTGGTAGAAGACTT |

| Sequences |
| --- |
| GGACGCGAGCGTTGAAGAGCAATGCAAGATCACCGAAACATGGCTCACAGAGCAATTACAAGATAATTTGCAA |
| GTGGTTGCGAAATGTCCAGGCCAACTTGTTACCAAGCATGTTGTTAAGGGTCAATGCCCACACTTTCAATTGT |
| ACTTATCAACACATGACGATGCCAAAGAATACTTCGCCACCCATGCTTGGAAAATACGACAAGAGTAGGCTTAA |
| CAGAGCAGCTTTTATCAAAGACATATCAAAATATGCAAAACCAATTTATATTGGAGAAATCAAGTATGATATC |
| TTTGATAGAGCTGTACAGCGGGTTGTCAATATTCTCAAAAATGTTGGAATGCAACAATGCGTTTATGTCACAG |
| ATGAAGAAGAAATTTTCAGATCACTTAACCTGAACGCAGCTGTCGGAGCATTGTATACAGGAAAGAAGAAAAA |
| TTACTTTGAAAATTTTTCAAGCGAAGACAAAGAAGAGATCGTGATGAGATCCTGTGAACGTATTTACAATGGG |
| CAACTTGGCGTATGGAATGGATCGCTCAAAGCTGAGATCAGATCAATAGAGAAAACCATGCTGAATAAGACTC |
| GAACCTTCACAGCAGCCCCATTAGAAACTTTGCTCGGAGGAAAGTGTGCGTGGATGATTTTAATAATCAATT |
| CTATTCACATCATTTAGAAGGTCCATGGACTGTTGGGATAACAAAATTCTATGGAGGTTGGAATCGCTTACTT |
| GAGAAGTTACCAGAAGGATGGGTTTACTGCGATGCTGACGGGTCTCAATTTGATAGTTCGTTAACACCATATC |
| TCATCAATGCAGTATTAAATATTCGATTGCAATTTATGGAAGATTGGGATATAGGAGCGCAAATGCTAAAGAA |
| CCTGTACACTGAGATTGTTTACACACCAATCGCAACGCCAGACGGATCAATCGTGAAGAAATTCAAAGGTAAC |
| AATAGCGGACAACCTTCTACAGTAGTGGACAACACATTGATGGTTATAATAGCTTTCAACTATGCCATGCTAT |
| CAAGTGGTATCAAAGAAGAAGAAATCGATAATTGCTGTAGAATGTTTGCGAATGGTGATGACTTACTCCTAGC |
| AGTGCATCCTGATTTTGAGTTCATTTTAGATGAATTTCAAAATCACTTTGGGAATCTTGGGCTGAACTTCGAA |
| TTTACATCACGAACACGAGACAAATCCGAACTGTGGTTCATGTCCACAAGAGGCATCAAGTATGAAGGAATTT |
| ACATACCAAAGCTTGAGAAAGAAAGAATAGTCGCCATACTTGAATGGGATCGATCAAACTTGCCTGAACATAG |
| GTTGGAAGCTATATGTGCAGCGATGGTTGAGGCCTGGGGATATTCCGATCTCGTTCATGAAATACGAAAGTTC |
| TATGCGTGGCTTTTGGAAATGCAACCTTTTGCAAATCTCGCAAAAGAAGGGTTGGCCCCATACATTGCCGAGA |
| CAGCACTCCGCAATCTCTATCTTGGAACGGGTATCAAAGAGGAAGAAATTGAAAAATATCTTAAACAATTCAT |
| TAAGGATCTTCCCGGATACATAGAAGATTACAATGAAGATGTATTCCATCAGTCGGGAACTGTTGATGCGGGT |
| GCACAAGGCGGCAGTGGAAGCCAAGGGACAACACCACCAGCAACAGGTAGTGGAGCAAAACCAGCCACCTCAG |
| GGGCAGGATCTCGGTAGTGGCACAGGAGCTGGAACTGGTGTAACTGGAGGTCAAGCAAGGACTGGCAGTGGCAC |
| TGGGACGGGATCTGGAGCAACCGGAGGCCAATCAGGATCTGGAAGTGGCACTGAACAGGTTAACACGGGTTCA |
| GCAGGAACTAATGCAACTGGAGGCCAAAGAGATAGGGATGTGGATGCAGGTACAACAGGAAAATTTCTGTAC |
| CAAAGCTCAAGGCCATGTCAAAGAAATGCGCTTACCTAAAGCAAAAGGAAAAGATGTGCTACATTTGGATTT |
| TCTATTGACATACAAACCACAACAACAGACATATCAAACACTAGGACATAATGCCAAGATACGGACTTCAGCGCAATCTCA |
| TATGATGCCATAAAGAAGGAATACGAAATTGATGACACACAAATGACAGTTGTCATGAGTGGCCTTATGGTAT |
| GGTGCATCGAAAATGGTTGCTCACCAAACATAAACGGAAATTGGACAATGATGGATGAAGATGAACAAAGGGT |
| CTTTCCACTCAAACCGGTCATTGAGAATGCATCTCCAACTTTCCGACAAATTATGCATCATTTCAGTGATGCA |
| GCTGAAGCGTACATAGAGTACAGAAACTCTACTGAGCGATATATGCCAAGATACGGACTTCAGCGCAATCTCA |
| CCGACTATAGCTTAGCACGGTATGCATTTGATTTCTATGAAATGACTTCACGCACACCTGCTAGAGCTAAAGA |
| AGCCCACATGCAGATGAAAGCCGCAGCAGTTCGTGGTTCAAACACGACTGTTCGGTTTGGACGGAAATGTC |
| GGCGAGACTCAGGAGAATACAGAGAGACACACAGCTGGCGATGTTAGTCGCAACATGCACTCTCGTTGGGAG |
| TGCAGCAGCACCACTAGTCTCCTGGAAACCCTGTTTGCAGTACCAATAATATGTACTAATATATAGTATTTTA |
| GTGAGGTTTTACCTCGTCTTTACTGTTTTATTACGTATGTATTTAAAGCGTGAACCAGTCTGCAACATACAGG |
| GTTGGACCCAGTGTGTTCTGGTGTAGCGTGTACTAGCGTCGAGCCATGAGATGGACTGCACTGGGTGTGGTTT |
| TGCCACTTGTGTTGCGAGTCTCTTGGTGAGAGACAAAAAAAAAAAAAAAAAAAA | pSCMV-CS1 (SEQ ID NO: 19)
CATAAGTGCGGCGACGATAGTCATGCCCCGCGCCCACCGGAAGGAGCTGACTGGGTTGAAGGCTCTCAAGGGC
ATCGGTCGAGCGGCCGCCCTCCAAAAATATCAAAGATACAGTCTCAGAAGACCAAAGGGCAATTGAGACTTTT
CAACAAAGGGTAATATCCGGAAACCTCCTCGGATTCCATTGCCCAGCTATCTGTCACTTTATTGTGAAGATAG
TGGAAAAGGAAGGTGGCTCCTACAAATGCCATCATTGCGATAAAGGAAAGGCCATCGTTGAAGATGCCTCTGC
CGACAGTGGTCCCAAAGATGGACCCCCACCCACGAGGAGCATCGTGGAAAAAGAAGACGTTCCAACCACGTCT
TCAAAGCAAGTGGATTGATGTGATACTCCAAAAATATCAAAGATACAGTCTCAGAAGACCAAAGGGCAATTGA
GACTTTTCAACAAAGGGTAATATCCGGAAACCTCCTCGGATTCCATTGCCCAGCTATCTGTCACTTTATTGTG
AAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAAC
CACGTCTTCAAAGCAAGTGGATTGATGTGATATCTCCACTGACGTAAGGGATGACGCACAATCCCACTATCCT
TCGCAAGACCCTTCCTCTATATAAGGAAGTTCATTTCATTTGGAGAGGAAAAACAACAAAACTCAACACAACA
CAACAAACACAACCAAGCAAATCCAATTTACTTGCGCTCAGATTGTAGTGAACGGCTCGAACGAAACGGTTC
TTCGAGATCACTCTCTGATTCTTCCTCATCTTTCAATTTCTTTCGAAAGAAATGGCGGGAACGTGGACCTACG
TGACACGTAAGTGGCAGCCAGATGTTAACAACGATCGTCACATTAAAAGAGTGATGGAAATGTTTGCAGCAAA
ACATCAACATTACTCAGAAGAACAGCGACTTGCCCATAATATGAAATTATTGAGGAAGGCAAGTGTTGTAAGC
GTTGAGCCTGCGAAACCAAAGCAGAAGCAGGCAACTCAACAGATGTGGGTTGGAAATGTGATCACAATCCTG
TTGATCACTTAGTATATCCACGACTTGGAAAATCCGCGAACAAAGCAGATATGAGTATTAAAAGTGCATCTGT
AAGCAAACTAACCAGAGAGATTTTAGAAATCTCAAAGGTTAGCGGCCTTAAGGTTGAACTAATTGATAAACGA
AAAAGATTCAAAACACAGTTATCAATCAAAAGGTTCAATGGCAAAAATTTCCTCCACTGCAAAACGAATCACG
AAAACAATTTATTTAAGAGGAAAGACATAGCCATTGGGCACAAATGTTCCAACGATTGAAGCCATTGCCTAG
ATGCTATAGCACGATGAATCGAGAAGAACTACAAAGCCTTTATAGAGGGAGCAGTGGTCTCACATTCATTCAA
AACGATGAATTGTTCATTGTCAGAGGAAGAATGAATGGTGAACTTGTCAATAGCTTGTACGAGACAAATCGGG
TTTTGGATATTGAGCACTACGCAAGATCTCCCGGGCGTACGGAGGACGTGTTTCACCAATCCGCAGATCCCCA
GGCTAACGATTTCTGGAGGGGATACACAAATGCTTACGTAGAGAATCGTAACATTTCGACTACTCATACAGAG
CACACCCCTACAATCAATCTAGAAGAATGTGGAAAACGAATGGCTCTACTCGAGATACTATTTCACTCTACAT
TCAAAATTACATGCAAGACATGCAACATTGATGATCTTGAATTATCGGATGATGAATTTGGAGCTAAACTCTA
CAAGAATTTGCAACGTATCGAAGAGAAACAACGAGAGTATCTTGCAAAGGATCAAAAACTATCCAGAATGATA
CAATTTATCAAAGAAAGGTGCAATCCAAAATTTTCGCATTTACCAACGCTATGGCAAGTTGCGGAAACAATAG
GGCACTATACTGATAACCAGTCAAAGCAAATAATGGATATTAGCGAAGCGCTCATCAAAGTTAATACTCTGAC
TCCTGATGATGCTATGAAAGCAAGCGCAGCGTTACTTGAAGTGTCGCGATGGTATAAGAATCGTAAGGAGTCA
CTCAAAACTGACTCATTGGAATCTTTTAGAAATAAAATCACCAAAGAGTACAATAAATGCAGCTTTAATGT
GCGATAATCAATTGGATAAAAATGCAAATTTTGTATGGGTAATAGGGAATACCACGCCAAACGATTTTTCGC
AAACTATTTTGAAGCAGTGGATCCCACAGATGCATATGAAAGCACGTCACACGGTTCAACCCTAATGGTCAA
CGAAAGTTATCAATAGGAAAGTTAGTTATCCCACTAGACTTTCAAAAGATTAGAGAATCATTTGTTGGACTCT
CGATAAATAGACAACCGCTGGATAAATGTTGTGTTAGCAAGATCGAAGGAGGGTATATATACCCATGTTGCTG
CGTCACAACAGAATTTGGTAAACCAGCATACTCTGAGATAATACCTCAACGAAAGGGCATATAACAATAGGC

-continued

| Sequences |
|---|
| AATTCTATTGATCCAAAGATTGTGGACTTGCCAAATACAACACCCACCCAGCATGTACATTGCTAAGGATGGGT |
| ATTGCTATATCAACATCTTTTTAGCAGCCATGATCAACGTTAATGAAGAATCTGCCAAGGATTACACGAAATT |
| TTTGAGGGACGAACTAGTTGAGCGTCTCGGAAAGTGGCCAAAGCTTAAAGACGTAGCAACAGCGTGTTATGCA |
| TTATCTGTAATGTTTCCAGAAATTAAGAATGCTGAGCTACCTCCAATTCTAGTTGACCATGAAAATAAATCAA |
| TGCACGTAATTGATTCATATGGTTCACTAAGCGTTGGATTTCACATATTAAAAGCAAGCACGATTGGTCAATT |
| AATCAAATTTCAATATGAGTCTATGGATAGTGAAATGCGCGAATACATAGTAGGAGGAACTCTCACACAACAG |
| ACATTCAACACACTTCTTAAGATGCTTACGAAAAACATGTTCAAACCAGAGCGCATCAAGCAGATAATTGAAG |
| AGGAACCCTTCTTACTTATGATGGCGATTGCGTCTCCAACGGTATTAATAGCACTATATAATAATTGTTATAT |
| TGAGCAAGCTATGACATACTGGATCGTTAAGAATCAAGGAGTTGCAGCCATATTCGCACAACTCGAAGCATTA |
| GCCAAGAAAACATCCCAGGCTGAGCTATTAGTTCTACAAATGCAGATACTTGAAAAAGCATCTAACCAATTAA |
| GATTAGCAGTTTCAGGACTTAGCCATATCGACCCAGCAAAGCGACTTTTGTGGTCACACCTTGAAGCGATGTC |
| AACACGATCAGAAATGAACAAGGAGTTAATAGCTGAGGGGTATGCACTATATGACGAGCGCCTATACACCCTG |
| ATGGAAAAAGTTACGTAGATCAATTAAACCAATCATGGGCAGAATTGTCATACTGTGGAAAATTTTCAGCAA |
| TATGGCGTGTGTTCAGAGTCAGGAAGTATTACAAACCGTCTTTAACCGTGAGAAAAGCGTAGATTTAGGCGC |
| TGTATACAATATATCAGCTACGCATCTAATATCAGATTTAGCGCGGAAAGTCAAGATCAAGTCAGCTCTACT |
| TTAACCAAACTCCGCAACGGTTTCTATGATAAATTAGAGAAAGTTAGAATACGAACTATAAAAACGGTTTATT |
| GGTTTATACCTGATATATTTAGACTCGTGCACATATTCATAGTTTTGAGTTTATTAACTACCATCGCTAACAC |
| TATCATAGTAACTATGAATGACTACAAGAAATTGAAGAAGCAACAAAGAGAAGACGAATATGAAGCAGAAATT |
| AACGAAGTTCGCAGAATCCATTCTACCTTAATGGAAGAGCGGAAGGACAATCTGACGTGTGAACAATTTATTG |
| AGTATATGCGTCAAAATCATCCACGGCTAGTTGAAGCAACACTGGACTTAACTCACACAGGTGTCATACATGA |
| AGGGAAATCCAATCTCGAAACCAATTTGGAACAGGCAATGGCAGTTGGAACCTTGATAACAATGATACTTGAT |
| CCACAGAAAAGGGATGCTGTCTATAAGGTGTTGAACAAAATGCGGACAGTAATTAGTACAATTGAACAAAACG |
| TCCCATTCCCTTCAGTGAATTTCTCCAACATCTTAACACCTCCAGTGGCACAACAGAGTGTAGATGTTGATGA |
| GCCATTAACACTTAGCACTGATAAAAATTTAACAATTAGACTTTGACACAAATCAAGATTTACCTGCCGATACA |
| TTCAGTAATGATGTGACATTTGAAGATTGGTGGTCAAATCAATTAAGCAACAACAGAACAGTGCCACACTACC |
| GACTTGGGGGAAAGTTCATTGAATTCACACGAGAAAACGCAGCCCACACGAGCATCGAACTTGCACACTCAAA |
| CATTGAGAGGGAATTCTTGCTTAGAGGAGCAGTCGGCTCGGGAAAATCCACTGGGTTACCATACCATCTTAGC |
| ATGCGCGGAAAAGTGCTTCTACTAGAGCCTACAAGACCGCTAGCTGCAGTTAACTCAGTTAAACAAGCGAGAA |
| CGCCATTTAACGTAAGTCCAACTCTTCAAATGCGTGGATTAAGTTCTTTTGGATGCACTCCAATCACAATCAT |
| GACATCTGGTTTTGCATTGCACATGTACGCAAATAATCCAGATAAAATATCTGAGTACGATTTCATAATCTTT |
| GATGAATGTCATATAATGGAAGCACCAGCGATGGCCTTTTATTGCTTACTCAAAGAATATGAATATCGAGGAA |
| AAATTATCAAGGTATCAGCTACGCCTCCAGGAAGGGAGTGTGAAATAGCATATACTCTGCGAACTGATCCA |
| TGTTTGTGAGAATCTAACTCAGCAACAGTTTGTTATGGAACTCGGGACTGGTTCAACCGCAGATGCTACGAAG |
| TACGGAAATAATATCTTAGTTTATGTAGCAAGCTATAATGACGTCGATTCATTGTCGCAAGCACTAGTCGAAC |
| TTAAATTTTCCGTAATCAAAGTGGATGGCCGAACAATGAAACAAAACACAACAGGAATCATTACAAACGGTAC |
| CGCACAAAAGAAGTGTTTTGTTGTCGCAACGAATATAATTGAAGAATGGCGTCACACTAGATATTGATGTTGTT |
| GTCGACTTCGGACTTAAGGTCTCAGCTGACTTGGACGTTGACAACAGGGCGGTATTGTATAAACGCGTAAGTA |
| TATCATATGGTGAACGCATACAACGATTGGGTCGTGTTGGCAGAAATAAACCTGGTACAGTTATTCGAATCGG |
| AAAAACAATGAAAGGTTTGCAGGAAATTCCAGCAATGATCGCAACAGAAGCAGCCTTCATGTGTTTCGCTTAC |
| GGTCTTAAAGTTATCACTCATAATGTTTCAACGACCCATCTTGCAAAGTGCACAGTTAAACAAGCGAGAACCA |
| TGATGCAATTTGAATTATCACCATTTGTCATGGCTGAGCTCGTTAAGTTTGATGGTTCAATGCATCCACAAAT |
| ACATGAGGCACTAGTAAAATACAAACTTAGAGATTCTGTCATAATGCTCAGACCGAATGCACTTCCAAGGGTC |
| AATTTACATAATTGGCTTACAGCCCGAGATTATAATAGAATAGGATGTTCATTAGAACTCGAAGACCACGTCA |
| AAATTCCGTACTACATTAGGGGAGTTCCTGACAAGTTGTATGGAAAGCTATATGATATTATCTTACAGTATAG |
| TCCAACTAGTTGCTACGGTAGACTATCAAGTGCGTGTGCAGGTAAAGTAGCATATACTCTGCGAACTGATCCA |
| TTTTCACTTCCAAGAACAATAGCAATAATTAATGCCTTAATCACGGAGGAGTATGCGAAGAGAGATCACTATC |
| GTAACATGATTTCAAACCCATCTTCATCACACGCATTCTCACTCAATGGGTTGGTGTCTATGATCGCTACTAG |
| ATATATGAAAGACCATACAAAGGAGAATATTGACAAACTCATTAGAGTGCGTGATCAATTACTTGAGTTTCAA |
| GGTACTGGAATGCAATTTCAAGATCCATCAGAACTCATGGAAATTGGGATTCTCAACACAGTTATTCACCAAG |
| GAATGGACGCAACTGCAGCTTGTATTGGGTTACAAGGACGATGGAATGCTTCACTTATACAACGCGATCTCCT |
| GATTGCAGGTGGAGTTTTTATCGGAGGCATTTTGATGATGTGGAGCCTATTTACTAAATGGAGTAACACAAAT |
| GTCTCACATCAGGGGAAGAACAAACGCAGTAGACAAAAACTTCGATTCAAAGAAGCAAGAGCAACAAATATG |
| CATATGATGTCACAGGATCGGAAGAATGCCTTGGCGAGAATTTTGGAACAGCCTATACAAAGAAAGGTAAAGG |
| AAAAGGAACTAAAGTTGGACTCGGTGTGAAGCAGCATAAATTCCATATGATGTACGGTTTCGATCCCCAAGAG |
| TACAACCTAATTCGGTTTGTCGATCCACTCACGGGAGCAACTCTTGATGAACAAATCCATGCCGATATACGCT |
| TAATTCAAGAGCACTTCGCTGAAATTCGTGAGGAGGCAGTGATTAATGACACAATTGAAAGGCAGCAGATTTA |
| CGGCAATCCTGGACTACAAGCATTTTTCATACAAAATGGGTCAGCAAACGCTCTGAGAGTTGATTTAACACCA |
| CATTCACCTACACGAGTTGTCACAGGTAATAACATAGCAGGGTTCCCAGAATATGAAGGAACACTTCGTCAGA |
| CTGGAACAGCTATAACTATACCCATTGGTCAAGTCCCAATCGCAAATGAAGCAGGGGTTGCACACGAGTCAAA |
| ATCCATGATGAACGGGTTGGGTGATTACACACCAATATCGCAACAATTGTGTCTAGTACAAAATGACTCGGAT |
| GGGGTAAAGCGGAATGTATTTTCAATTGGATATGGCTCATATCTTATTTCACCAGCGCACTTATTCAAATATA |
| ACAATGGTGAAATAACAATTAGATCATCAAGAGGATTGTACAAAATTCGTAATTCTGTGGATTTAAAATTACA |
| TCCAATTGCACACAGAGACATGGTCATAATTCAACTCCCAAAGGATTTCCCACCGTTCCCAATGCGCTTGAAA |
| TTCAAACAACCATCACGAGATATGCGAGTCTGCCTAGTAGGTGTCAACTTCCAACAGAATTATAGCACTTGCA |
| TCGTATCAGAAAGTAGTGTGACAGCACCAAAAGGAAATGGAGACTTTTGGAAACATTGGATATCAACAGTCGA |
| CGGTCAATGTGACTACCATTGGTAGATACTAAGAGCAAACATATTGTCGGAATTCATAGTCTTGCATCAACA |
| AGTGGAAACACTAATTTCTTTGTCGCTGTGCCTGGGAACTTTAATGAATACATCAATGGACTTGTGCAAGCAA |
| ATAAATGGGAAAAGGATGGCACTATAATCCGAATCTCATATCCTGGTGTGGACTAAATTTAGTTGATTCTGC |
| CCCAAAAGGTTTGTTTAAAACGTCAAAATTGGTAGAAGACTTGGACGCGAGCGTTGAAGAGCAATGCAAGATC |
| ACCGAAACATGGCTCACAGAGCAATTACAAGATAAATTTGCAAGTGGTTGCGAAATGTCCAGGCCAACTTGTA |
| CCAAGCATGTTGTTAAGGGTCAATGCCCACACTTTCAATTGTACTTATCAACACATGACGATGCCAAAGAATA |
| CTTCGCACCCATGCTTGGAAAATACGACAAGAGTAGGCTTAACAGAGCAGCTTTTATCAAAGACATATCAAAA |
| TATGCAAAACCAATTTATATTGGAGAAATCAAGTATGATATCTTTGATAGAGCTGTACAGCGGGTTGTCAATA |
| TTCTCAAAAATGTTGGAATGCAACAATGCGTTTATGTCACAGATGAAGAAGAAATTTTCAGATCACTTAACCT |
| GAACGCAGCTGTCGGAGCATTGTATACAGGAAAGAAGAAAAATTACTTTGAAAATTTTTCAAGCGAAGACAAA |
| GAAGAGATCGTGATGAGATCCTGTGAACGTATTTACAATGGGCAACTTGGCGTATGGAATGGATCGCTCAAAG |
| CTGAGATCAGATCAATAGAGAAAACCATGCTGAATAAGACTCGAACCTTCACAGCAGCCCCATTAGAAACTTT |

-continued

| Sequences |
| --- |
| GCTCGGAGGAAAAGTGTGCGTGGATGATTTTAATAATCAATTCTATTCACATCATTTAGAAGGTCCATGGACT |
| GTTGGGATAACAAAATTCTATGGAGGTTGGAATCGCTTACTTGAGAAGTTACCAGAAGGATGGGTTTACTGCG |
| ATGCTGACGGGTCTCAATTTGATAGTTCGTTAACACCATATCTCATCAATGCAGTATTAAATATTCGATTGCA |
| ATTTATGGAAGATTGGGATATAGGAGCGCAAATGCTAAAGAACCCTGTACACTGAGATTGTTTACACACCAATC |
| GCAACGCCAGACGGATCAATCGTGAAGAAATTCAAAGGTAACAATAGCGGACAACCTTCTACAGTAGTGGACA |
| ACACATTGATGGTTATAATAGCTTTCAACTATGCCATGCTATCAAGTGGTATCAAAGAAGAAGAAATCGATAA |
| TTGCTGTAGAATGTTTGCGAATGGTGATGACTTACTCCTAGCAGTGCATCCTGATTTTGAGTTCATTTTAGAT |
| GAATTTCAAAATCACTTTGGGAATCTTGGGCTGAACTTCGAATTTACATCACGAACACGAGACAAATCCGAAC |
| TGTGGTTCATGTCCACAAGAGGCATCAAGTATGAAGGAATTTACATACCAAAGCTTGAGAAAGAAAGAATAGT |
| CGCCATACTTGAATGGGATCGATCAAACTTGCCTGAACATAGGTTGGAAGCTATATGTGCAGCGATGGTTGAG |
| GCCTGGGGATATTCCGATCTCGTTCATGAAATACGAAAGTTCTATGCGTGGCTTTTGGAAATGCAACCTTTTG |
| CAAATCTCGCAAAAGAAGGGTTGGCCCCATACATTGCCGAGACAGCACTCCGCAATCTCTATCTTGGAACGGG |
| TATCAAAGAGGAAGAAATTGAAAAATATCTTAAACAATTCATTAAGGATCTTCCCGGATACATAGAAGATTAC |
| AATGAAGATGTATTCCATCAGTCGGGAACTGTTGATGCGGGTGCACAAGGCGGCAGTGGAAGCCAAGGGACAA |
| CACCACCAGCAACAGGTAGTGGAGCAAAACCAGCCACCTCAGGGGCAGGATCTGGTAGTGGCACAGGAGCTGG |
| AACTGGTGTAACTGGAGGTCAAGCAAGGACTGGCAGTGGCACTGGGACGGGATCTGGAGCAACCGGAGGCCAA |
| TCAGGATCTGGAAGTGGCACTGAACAGGTTAACACGGGTTCAGCAGGAACTAATGCAACTGGAGGCCAAAGAG |
| ATAGGGATGTGGATGCAGGTACAACAGGAAAAATTTCTGTACCAAAGCTCAAGGCCATGTCAAAGAAAATGCG |
| CTTACCTAAAGCAAAAGGAAAAGATGTGCTACATTTGGATTTTCTATTGACATACAAACCACAACAACAAGAC |
| ATATCAAACACTAGAGCAACCAAGGAAGAGTTTGATAGATGGTATGATGCCATAAAGAAGGAATACGAAATTG |
| ATGACACACAAATGACAGTTGTCATGAGTGGCCTTATGGTATGGTGCATCGAAAATGGTTGCTCACCAAACAT |
| AAACGGAAATTGGACAATGATGGATGAAGATGAACAAGGGTCTTTCCACTCAAACCGGTCATTGAGAATGCA |
| TCTCCAACTTTCCGACAAATTATGCATCATTTCAGTGATGCAGCTGAAGCGTACATAGAGTACAGAAACTCTA |
| CTGAGCGATATATGCCAAGATACGACTTCAGCGCAATCTCACCGACTATAGCTTAGCACGGTATGCATTTGA |
| TTTCTATGAAATGACTTCACGCACACCTGCTAGAGCTAAAGAAGCCCACATGCAGATGAAAGCCGCAGCAGTT |
| CGTGGTTCAAACACGACTGTTCGGTTTGGACGGAAATGTCGGCGAGACTCAGGAGAATACAGAGAGACACA |
| CAGCTGGCGATGTTAGTCGCAACATGCACTCTCTGTTGGGAGTGCAGCAGCACCACTAGTCTCCTGGAAACCC |
| TGTTTGCAGTACCAATAATATGTACTAATATATAGTATTTTAGTGAGGTTTTACCTCGTCGTTTACTGTTTTAT |
| TACGTATGTATTTAAAGCGTGAACCAGTCTGCAACATACAGGGTTGGACCCAGTGTGTTCTGGTGTAGCGTGT |
| ACTAGCGTCGAGCCATGAGATGGACTGCACTGGGTGTGGTTTTGCCACTTGTGTTGCGAGTCTCTTGGTGAGA |
| GACAAAAAAAAAAAAAAAAAAAAACCTGGATCCTAGGTTCACAAAGTGTCATCGATAGCTCGAATTTCCCCGAT |
| CGTTCAAACATTTGGCAATAAAGTTTCTTAAGATTGAATCCTGTTGCCGGTCTTGCGATGATTATCATATAAT |
| TTCTGTTGAATTACGTTAAGCATGTAATAATTAACATGTAATGCATGACGTTATTTATGAGATGGGTTTTTAT |
| GATTAGAGTCCCGCAATTATACATTTAATACGCGATAGAAAACAAATATAGCGCGCAAACTAGGATAAATTA |
| TCGCGCGCGGTGTCATCTATGTTACTAGATCGGGAATTCTTGAAGACGAAAGGGCCTCGTGATACGCCTATTT |
| TTATAGGTTAATGTCATGATAATAATGGTTTCTTAGACGTCAGGTGGCACTTTTCGGGGAAATGTGCGCGGAA |
| CCCCTATTTGTTTATTTTTCTAAATACATTCAAATATGTATCCGCTCATGAGACAATAACCCTGATAAATGCT |
| TCAATAATATTGAAAAGGAAGAGTATGAGTATTCAACATTTCCGTGTCGCCCTTATTCCCTTTTTTGCGGCA |
| TTTTGCCTTCCTGTTTTTGCTCACCCAGAAACGCTGGTGAAAGTAAAAGATGCTGAAGATCAGTTGGGTGCAC |
| GAGTGGGTTACATCGAACTGGATCTCAACAGCGGTAAGATCCTTGAGAGTTTTCGCCCCGAAGAACGTTTTCC |
| AATGATGAGCACTTTTAAAGTTCTGCTATGTGGCGCGGTATTATCCCGTGTTGACGCCGGGCAAGAGCAACTC |
| GGTCGCCGCATACACTATTCTCAGAATGACTTGGTTGAGTACTCACCAGTCACAGAAAAGCATCTTACGGATG |
| GCATGACAGTAAGAGAATTATGCAGTGCTGCCATAACCATGAGTGATAACACTGCGGCCAACTTACTTCTGAC |
| AACGATCGGAGGACCGAAGGAGCTAACCGCTTTTTTGCACAACATGGGGGATCATGTAACTCGCCTTGATCGT |
| TGGGAACCGGAGCTGAATGAAGCCATACCAAACGACGAGCGTGACACCACGATGCCTGCAGCAATGGCAACAA |
| CGTTGCGCAAACTATTAACTGGCGAACTACTTACTCTAGCTTCCCGGCAACAATTAATAGACTGGATGGAGGC |
| GGATAAAGTTGCAGGACCACTTCTGCGCTCGGCCCTTCCGGCTGGCTGGTTTATTGCTGATAAATCTGGAGCC |
| GGTGAGCGTGGGTCTCGCGGTATCATTGCAGCACTGGGGCCAGATGGTAAGCCCTCCCGTATCGTAGTTATCT |
| ACACGACGGGAGTCAGGCAACTATGGATGAACGAAATAGACAGATCGCTGAGATAGGTGCCTCACTGATTAA |
| GCATTGGTAACTGTCAGACCAAGTTTACTCATATATACTTTAGATTGATTTAAAACTTCATTTTTAATTTAAA |
| AGGATCTAGGTGAAGATCCTTTTTGATAATCTCATGACCAAAATCCCTTAACGTGAGTTTTCGTTCCACTGAG |
| CGTCAGACCCCGTAGAAAAGATCAAAGGATCTTCTTGAGATCCTTTTTTTCTGCGCGTAATCTGCTGCTTGCA |
| AACAAAAAAACCACCGCTACCAGCGGTGGTTTGTTTGCCGGATCAAGAGCTACCAACTCTTTTTCCGAAGGTA |
| ACTGGCTTCAGCAGAGCGCAGATACCAAATACTGTCCTTCTAGTGTAGCCGTAGTTAGGCCACCACTTCAAGA |
| ACTCTGTAGCACCGCCTACATACCTCGCTCTGCTAATCCTGTTACCAGTGGCTGCTGCCAGTGGCGATAAGTC |
| GTGTCTTACCGGGTTGGACTCAAGACGATAGTTACCGGATAAGGCGCAGCGGTCGGGCTGAACGGGGGGTTCG |
| TGCACACAGCCCAGCTTGGAGCGAACGACCTACACCGAACTGAGATACCTACAGCGTGAGCTATGAGAAAGCG |
| CCACGCTTCCCGAAGGGAGAAAGGCGGACAGGTATCCGGTAAGCGGCAGGGTCGGAACAGGAGAGCGCACGAG |
| GGAGCTTCCAGGGGGAAACGCCTGGTATCTTTATAGTCCTGTCGGGTTTCGCCACCTCTGACTTGAGCGTCGA |
| TTTTTGTGATGCTCGTCAGGGGGGCGGAGCCTATGGAAAAACGCCAGCAACGCGGCCTTTTTACGGTTCCTGG |
| CCTTTTGCTGGCCTTTTGCTCACATGTTCTTTCCTGCGTTATCCCCTGATTCTGTGGATAACCGTATTACCGC |
| CTTTGAGTGAGCTGATACCGCTCGCCGCAGCCGAACGACCGAGCGCAGCGAGTCAGTGAGCGAGGAAGCGGAA |
| GAGCGCCTGATGCGGTATTTTCTCCTTACGCATCTGTGCGGTATTTCACACCGCATATGGTGCACTCTCAGTA |
| CAATCTGCTCTGATGCCGCATAGTTAAGCCAGTATACACTCCGCTATCGCTACGTGACTGGGTCATGGCTGCG |
| CCCCGACACCCGCCAACACCCGCTGACGCGCCCTGACGGGCTTGTCTGCTCCCGGCATCCGCTTACAGACAAG |
| CTGTGACCGTCTCCGGGAGCTGCATGTGTCAGAGGTTTTCACCGTCATCACCGAAACGCGCGAGGCAGCTGCG |
| GTAAAGCTCATCAGCGTGGTCGTGAAGCGATTCACAGATGTCTGCCTGTTCATCCGCGTCCAGCTCGTTGAGT |
| TTCTCCAGAAGCGTTAATGTCTGGCTTCTGATAAAGCGGGCCATGTTAAGGGCGGTTTTTTCCTGTTTGGTCA |
| CTGATGCCTCCGTGTAAGGGGGATTTCTGTTCATGGGGGTAATGATACCGATGAAACGAGAGAGGATGCTCAC |
| GATACGGGTTACTGATGATGAACATGCCCGGTTACTGGAACGTTGTGAGGGTAAACAACTGGCGGTATGGATG |
| CGGCGGGACCAGAGAAAAATCACTCAGGGTCAATGCCAGCGCTTCGTTAATACAGATGTAGGTGTTCCACAGG |
| GTAGCCAGCAGCATCCTGCGATGCAGATCCGGAACATAATGGTGCAGGGCGCTGACTTCCGCGTTTCCAGACT |
| TTACGAAACACGGAAACCGAAGACCATTCATGTTGTTGCTCAGGTCGCAGACGTTTTGCAGCAGCAGTCGCTT |
| CACGTTCGCTCGCGTATCGGTGATTCATTCTGCTAACCAGTAAGGCAACCCCGCCAGCCTAGCCGGGTCCTCA |
| ACGACAGGAGCACGATCATGCGCACCCGTGGCCAGGACCCAACGCTGCCCGAGATGCGCCGCGTGCGGCTGCT |
| GGAGATGGCGGACGCGATGGATATGTTCTGCCAAGGGTTGGTTTGCGCATTCACAGTTCTCCGCAAGAATTGA |
| TTGGCTCCAATTCTTGGAGTGGTGAATCCGTTAGCGAGGTGCCGCCGGCTTCCATTCAGGTCGAGGTGGCCCG |

| Sequences |
|---|
| GCTCCATGCACCGCGACGCAACGCGGGGAGGCAGACAAGGTATAGGGCGGCGCCTACAATCCATGCCAACCCG
TTCCATGTGCTCGCCGAGGCGGCATAAATCGCCGTGACGATCAGCGGTCCAATGATCGAAGTTAGGCTGGTAA
GAGCCGCGAGCGATCCTTGAAGCTGTCCCTGATGGTCGTCATCTACCTGCCTGCCTGGACAGCATGGCCTGCAACGC
GGGCATCCCGATGCCGCCGGAAGCGAGAAGAATCATAATGGGGAAGGCCATCCAGCCTCGCGTCGCGAACGCC
AGCAAGACGTAGCCCAGCGCGTCGGCCGCCATGCCGGCGATAATGGCCTGCTTCTCGCCGAAACGTTTGGTGG
CGGGACCAGTGACGAAGGCTTGAGCGAGGGCGTGCAAGATTCCGAATACCGCAAGCGACAGGCCGATCATCGT
CGCGCTCCAGCGAAAGCGGTCCTCGCCGAAAATGACCCAGAGCGCTGCCGGCACCTGTCCTACGAGTTGCATG
ATAAAGAAGACAGT |
| pSCMV-CS2 (SEQ ID NO: 20) |
| CATAAGTGCGGCGACGATAGTCATGCCCCGCGCCCACCGGAAGGAGCTGACTGGGTTGAAGGCTCTCAAGGGC
ATCGGTCGAGCGGCCGCCCTCCAAAAATATCAAAGATACAGTCTCAGAAGACCAAAGGGCAATTGAGACTTTT
CAACAAAGGGTAATATCCGGAAACCTCCTCGGATTCCATTGCCCAGCTATCTGTCACTTTATTGTGAAGATAG
TGGAAAAGGAAGGTGGCTCCTACAAATGCCATCATTGCGATAAAGGAAAGGCCATCGTTGAAGATGCCTCTGC
CGACAGTGGTCCCAAAGATGGACCCCCACCCACGAGGAGCATCGTGGAAAAAGAAGACGTTCCAACCACGTCT
TCAAAGCAAGTGGATTGATGTGATACTCCAAAAATATCAAAGATACAGTCTCAGAAGACCAAAGGGCAATTGA
GACTTTTCAACAAAGGGTAATATCCGGAAACCTCCTCGGATTCCATTGCCCAGCTATCTGTCACTTTATTGTG
AAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAAC
CACGTCTTCAAAGCAAGTGGATTGATGTGATATCTCCACTGACGTAAGGGATGACGCACAATCCCACTATCCT
TCGCAAGACCCTTCCTCTATATAAGGAAGTTCATTTCATTTGGAGAGGAAAAACAACAAAACTCAACACAACA
CAACAAAACACAACCAAGCAAATCCAATTTACTTGCGCTCAGATTGTAGTGAACGGCTCGAACGAAACGGTTC
TTCGAGATCACTCTCTGATTCTTCCTCATCTTTCAATTTCTTTCGAAAGAAATGGCGGGAACGTGGACCTACG
TGACACGTAAGTGGCAGCCAGATGTTAACAACGATCGTCACATTAAAAGAGTGATGGAAATGTTTGCAGCAAA
ACATCAACATTACTCAGAAGAACAGCGACTTGCCCATAATATGAAATTATTGAGGAAGGCAAGTGTTGTAAGC
GTTGAGCCTGCGAAACCAAAGCAGAAGCAGGCAACTCAACAGATGTGGGTTGAGAAATGTGATCACAATCCTG
TTGATCACTTAGTATATCCACGACTTGGAAAATCCGCGAACAAAGCAGATATGAGTATTAAAAGTGCATCTGT
AAGCAAACTAACCAGAGAGATTTTAGAAATCTCAAAGGTTAGCGGCCTTAAGGTTGAACTAATTGATAAACGA
AAAAGATTCAAAACACAGTTATCAATCAAAAGGTTCAATGGCAAAAATTTCCTCCACTGCAAAACGAATCACG
AAAACAATTTATTTAAGAGGAAAGACATAGCCATTGGGCACAAATGTTTCCAACGATTGAAGCCATTGCTAG
ATGCTATAGCACGATGAATCGAGAAGAACTACAAAGCCTTTATAGAGGGAGCAGTGGTCTCACATTCATTCAA
AACGATGAATTGTTCATTGTCAGAGGAAGAATGAATGGTGAACTTGTCAATAGCTTGTACGAGACAAATCGGG
TTTTGGATATTGAGCACTACGCACCGCGGCCCGGGGAGGACGTGTTTCACCAATCCGCAGATCCCCAGGCTAA
CGATTTCTGGAGGGGATACACAAATGCTTACGTAGAGAATCGTAACATTTCGACTACTCATACAGAGCACACC
CCTACAATCAATCTAGAAGAATGTGGAAAACGAATGGCTCTACTCGAGATACTATTTCACTCTACATTCAAAA
TTACATGCAAGCACATGCAACATTGATGATCTTGAATTATCGGATGATGAATTTGGAGCTAAACTCTACAAGAA
TTTGCAACGTATCGAAGAGAAACAACGAGAGTATCTTGCAAAGGATCAAAAACTATCCAGAATGATACAATTT
ATCAAAGAAAGGTGCAATCCAAATTTTCGCATTTACCAACGCTATGGCAAGTTGCGGAAACAATAGGGCACT
ATACTGATAACCAGTCAAAGCAAATAATGGATATTAGCGAAGCGCTCATCAAAGTTAATACTCTGACTCCTGA
TGATGCTATGAAAGCAAGCGCAGCGTTACTTGAAGTGTCGCGATGGTATAAGAATCGTAAGGAGTCACTCAAA
ACTGACTCATTGGAATCTTTTAGAAATAAAATATCACCAAAGAGTACAATAAATGCAGCTTTAATGTGCGATA
ATCAATTGGATAAAAATGCAAATTTTGTATGGGGTAATAGGGAATACCACGCCAAACGATTTTTCGCAAACTA
TTTTGAAGCAGTGGATCCCACAGATGCATATGAAAAGCACGTCACACGGTTCAACCCTAATGGTCAACGAAAG
TTATCAATAGGAAAGTTAGTTATCCCACTAGACTTTCAAAAGATTAGAGAATCATTTGTTGGACTCTCGATAA
ATAGACAACCGCTGGATAAATGTTGTGTTAGCAAGATCGAAGGAGGGTATATATACCCATGTTGCTGCGTCAC
AACAGAATTTGGTAAACCAGCATACTCTGAGATAATACCTCCAACGAAAGGGCATATAACAATAGGCAATTCT
ATTGATCCAAAGATTGTGGACTTGCCAAATACAACACCACCCAGCATGTACATTGCTAAGGATGGGTATTGCT
ATATCAACATCTTTTTAGCAGCCATGATCAACGTTAATGAAGAATCTGCCAAGGATTACACGAAATTTTTGAG
GGACGAACTAGTTGAGCGTCTCGGAAAGTGGCCAAAGCTTAAAGACGTAGCAACAGCGTGTTATGCATTATCT
GTAATGTTTCCAGAAATTAAGAATGCTGAGCTACCTCCAATTCTAGTTGACCATGAAAATAAATCAATGCACG
TAATTGATTCATATGGTTCACTAAGCGTTGGATTTCACATATTAAAAGCAAGCACGATTGGTCAATTAATCAA
ATTTCAATATGAGTCTATGGATAGTGAAATGCGCGAATACATAGTAGGAGGAACTCTCACACAACAGACATTC
AACACACTTCTTAAGATGCTTACGAAAAACATGTTCAAACCAGCAGCGCATCAAGCAGATAATTGAAGAGGAAC
CCTTCTTACTTATGATGGCGATTGCGTCTCCAACGGTATTAATAGCACTATATAATAATTGTTATATTGAGCA
AGCTATGACATACTGGATCGTTAAGAATCAAGGAGTTGCAGCCATATTCGCACAACTCGAAGCATTAGCCAAG
AAAACATCCCAGGCTGAGCTATTAGTTCTACAAATGCAGATACTTGAAAAAGCATCTAACCAATTAAGATTAG
CAGTTTCAGGACTTAGCCATATGACCCAGCAAAGCGACTTTTGTGGTCACACCTTGAAGCGATGTCAACACG
ATCAGAAATGAACAAGGAGTTAATAGCTGAGGGGTATGCACTATATGACGAGCGCCTATACACCCTGATGGAA
AAAAGTTACGTAGATCAATTAAACCAATCATGGGCAGAATTGTCATACTGTGGAAAATTTTCAGCAATATGGC
GTGTGTTCAGAGTCAGGAAGTATTACAAACCGTCTTTAACCGTGAGAAAAAGCGTAGATTTAGGCGCTGTATA
CAATATATCAGCTACGCATCTAATATCAGATTTAGCGCGGAAAAGTCAAGATCAAGTCAGCTCTACTTTAACC
AAACTCCGCAACGGTTTCTATGATAAATTAGAGAAAGTTAGAATACGAACTATAAAACGGTTATTGGTTTA
TACCTGATATATTTAGACTCGTGCACATATTCATAGTTTTGAGTTTATTAACTACCATCGCTAACACTATCAT
AGTAACTATGAATGACTACAAGAAATTGAAGAAGCAACAAAGAGAAGACGAATATGAAGCAGAAATTAACGAA
GTTCGCAGAATCCATTCTACCTTAATGGAAGAGCGGAAGGACAATCTGACGTGTGAACAATTTATTGAGTATA
TGCGTCAAAATCATCCACGGCTAGTTGAAGCAACACTGGACTTAACTCACAGCAGGTGTCATACATGAAGGGAA
ATCCAATCTCGAAACCAATTTGGAACAGGCAATGGCAGTTGGAACCTTGATAACAATGATACTTGATCCACAG
AAAAGCGATGCTGTCTATAAGGTGTTGAACAAAATGCGGACAGTAATTAGTACAATTGAACAAAACGTCCCAT
TCCCTTCAGTGAATTTCTCCAACATCTTAACACCTCCAGTGGCACAACAGAGTGTAGATGTTGATGAGCCATT
AACACTTAGCACTGATAAAAATTTAACAATAGACTTTGACACAAATCAAGATTTACCTGCCGATACATTCAGT
AATGATGTGACATTTGAAGATTGGTGGTCAAATCAATTAAGCAACAACAGAAGAGTGCCACACTACCGACTTG
GGGGAAAGTTCATTGAATTCACACGAGAAAACGCAGCCCACACGAGCATCGAACTTGCACACTCAAACATTGA
GAGGGAATTCTTGCTTAGAGGAGCAGTCGGCTCGGGAAAATCCACTGGGTTACCATACCATCTTAGCATGCGC
GGAAAAGTGCTTCTACTAGAGCCTACAAGACCGCTAGCTGAGAACGTGTGTAGGCAACTACAAGGACCGCCAT
TTAACGTAAGTCCAACTCTTCAAATGCGTGGATTAAGTTCTTTTGGATGCACTCCAATCACAATCATGACATC
TGGTTTTGCATTGCACATGTACGCAAATAATCCAGATAAAATATCTGAGTACGATTTCATAATCTTTGATGAA
TGTCATATAATGGAAGCACCAGCGATGGCCTTTTATTGCTTACTCAAAGAATATGAATATCGAGGAAAAATTA |

-continued

| Sequences |
|---|
| TCAAGGTATCAGCTACGCCTCCAGGAAGGGAGTGTGAATTCACAACACAACATCCAGTAGACATCCATGTTTG |
| TGAGAATCTAACTCAGCAACAGTTTGTTATGGAACTCGGGACTGGTTCAACCGCAGATGCTACGAAGTACGGA |
| AATAATATCTTAGTTTATGTAGCAAGCTATAATGACGTCGATTCATTGTCGCAAGCACTAGTCGAACTTAAAT |
| TTTCCGTAATCAAAGTGGATGGCCGAACAATGAAACAAAACACAACAGGAATCATTACAAACGGTACCGCACA |
| AAAGAAGTGTTTTGTTGTCGCAACGAATATAATTGAGAATGGCGTCACACTAGATATTGATGTTGTTGTCGAC |
| TTCGGACTTAAGGTCTCAGCTGACTTGGACGTTGACAACAGGGCGGTATTGTATAAACGCGTAAGTATATCAT |
| ATGGTGAACGCATACAACGATTGGGTCGTGTTGGCAGAAATAAACCTGGTACAGTTATTCGAATCGGAAAAAC |
| AATGAAAGGTTTGCAGGAAATTCCAGCAATGATCGCAACAGAAGCAGCCTTCATGTGTTTCGCTTACGGTCTT |
| AAAGTTATCACTCATAATGTTTCAACGACCCATCTTGCAAAGTGCACAGTTAAACAAGCGAGAACCATGATGC |
| AATTTGAATTATCACCATTTGTCATGGCTGAGCTCGTTAAGTTTGATGGTTCAATGCATCCACAAATACATGA |
| GGCACTAGTAAAATACAAACTTAGAGATTCTGTCATAATGCTCAGACCGAATGCACTTCCAAGGGTCAATTTA |
| CATAATTGGCTTACAGCCCGAGATTATAATAGAATAGGATGTTCATTAGAACTCGAAGACCACGTCAAAATTC |
| CGTACTACATTAGGGGAGTTCCTGACAAGTTGTATGGAAAGCTATATGATATTATCTTACAGTATAGTCCAAC |
| TAGTTGCTACGGTAGACTATCAAGTGCGTGTGCAGGTAAAGTAGCATATACTCTGCGAACTGATCCATTTTCA |
| CTTCCAAGAACAATAGCAATAATTAATGCCTTAATCACGGAGGAGTATGCGAAGAGAGATCACTATCGTAACA |
| TGATTTCAAACCCATCTTCATCACACGCATTCTCACTCAATGGGTTGGTGTCTATGATCGCTACTAGATATAT |
| GAAAGACCATACAAAGGAGAATATTGACAAACTCATTAGAGTGCGTGATCAATTACTTGAGTTTCAAGGTACT |
| GGAATGCAATTTCAAGATCCATCAGAACTCATGGAAATTGGGGCTCTCAACACAGTTATTCACCAAGGAATGG |
| ACGCAACTGCAGCTTGTATTGGGTTACAAGGACGATGGAATGCTTCACTTATACAACGCGATCTCCTGATTGC |
| AGGTGGAGTTTTTATCGGAGGCATTTTGATGATGTGGAGCCTATTTACTAAATGGAGTAACACAAATGTCTCA |
| CATCAGGGGAAGAACAAACGCAGTAGACAAAAACTTCGATTCAAAGAAGCAAGAGACAACAAATATGCATATG |
| ATGTCACAGGATCGGAAGAATGCCTTGGCGAGAATTTTGGAACAGCCTATACAAAGAAAGGTAAAGGAAAAGG |
| AACTAAAGTTGGACTCGGTGTGAAGCAGCATAAATTCCATATGATGTACGGTTTCGATCCCCAAGAGTACAAC |
| CTAATTCGGTTTGTCGATCCACTCACGGGAGCAACTCTTGATGAACAAATCCATGCCGATATACGCTTAATTC |
| AAGAGCACTTCGCTGAAATTCGTGAGGAGGCAGTGATTAATGACACAATTGAAAGGCAGCAGATTTACGGCAA |
| TCCTGGACTACAAGCATTTTTTCATACAAAATGGGTCAGCAAACGCTCTGAGAGTTGATTTAACACCACATTCA |
| CCTACACGAGTTGTCACAGGTAATAACATAGCAGGGTTCCCAGAATATGAAGGAACACTTCGTCAGACTGGAA |
| CAGCTATAACTATACCCATTGGTCAAGTCCCAATCGCAAATGAAGCAGGGGTTGCACACGAGTCAAAATCCAT |
| GATGAACGGGTTGGGTGATTACACACCAATATCGCAACAATTGTGTCTAGTACAAAATGACTCGGATGGGGTA |
| AAGCGGAATGTATTTTCAATTGGATATGGCTCATATCTTATTTCACCAGCGCACTTATTCAAATATAACAATG |
| GTGAAATAACAATTAGATCATCAAGAGGATTGTACAAAATTCGTAATTCTGTGGATTTAAAATTACATCCAAT |
| TGCACACAGAGACATGGTCATAATTCAACTCCCAAAGGATTTCCCACCGTTCCCAATGCGCTTGAAATTCAAA |
| CAACCATCACGAGATATGCGAGTCTGCCTAGTAGGTGTCAACTTCCAACAGAATTATAGCACTTGCATCGTAT |
| CAGAAAGTAGTGTGACAGCACCAAAAGGAAATGGAGACTTTTGGAAACATTGGATATCAACAGTCGACGGTCA |
| ATGTGGACTACCATTGGTAGATACTAAGAGCAAACATATTGTCGGAATTCATAGTCTTGCATCAACAAGTGGA |
| AACACTAATTTCTTTGCTCGTCGTGCCTGGGAACTTTAATGAATACATCAATGACTTGTGCAAGCAAATAAAT |
| GGGAAAAAGGATGGCACTATAATCCGAATCTCATATCTGGTGTGGACTAAATTTAGTTGATTCTGCCCCAAA |
| AGGTTTGTTTAAAACGTCAAAATTGGTAGAAGACTTGGACGCGAGCGTTGAAGAGCAATGCAAGATCACCGAA |
| ACATGGCTCACAGAGCAATTACAAGATAATTTGCAAGTGGTTGCGAAATGTCCAGGCCAACTTGTTACCAAGC |
| ATGTTGTTAAGGGTCAATGCCCACACTTTCAATTGTACTTATCAACACATGACGATGCCAAAGAATACTTCGC |
| ACCCATGCTTGGAAAATACGACAAGAGTAGGCTTAACAGAGCAGCTTTTATCAAAGACATATCAAAATATGCA |
| AAACCAATTTATATTGGAGAAATCAAGTATGATATCTTTGATAGAGCTGTACAGCGGGTTGTCAATATTCTCA |
| AAAATGTTGGAATGCAACAATGCGTTTATGTCACAGATGAAGAAGAAATTTTCAGATCACTTAACCTGAACGC |
| AGCTGTCGGAGCATTGTATACAGGAAAGAAGAAAATTACTTTGAAAATTTTTCAAGCGAAGACAAAGAAGAG |
| ATCGTGATGAGATCCTGTGAACGTATTTACAATGGGCAACTTGGCATCCTGATTTTGGAATGGATCGCTCAAAGCTGAGA |
| TCAGATCAATAGAGAAAACCATGCTGAATAAGACTCGAACCTTCACAGCAGCCCCATTAGAAACTTTGCTCGG |
| AGGAAAAGTGTGCGTGGATGATTTTAATAATCAATTCTATTCACATCATTTAGAAGGTCCATGGACTGTTGGG |
| ATAACAAAATTCTATGGAGGTTGGAATCGCTTACTTGAGAAGTTACCAGAAGGATGGGTTTACTGCGATGCTG |
| ACGGGTCTCAATTTGATAGTTCGTTAACACCATATCTCATCAATGCAGTATTTAAATATTCGATTGCAATTTAT |
| GGAAGATTGGGATATAGGAGCGCAAATGCTAAAGAACCTGTACACTGAGATTGTTTACACACCAATCGCAACG |
| CCAGACGGATCAATCGTGAAGAAATTCAAAGGTAACAATAGCGGACAACCTTCTACAGTAGTGGACAACACAT |
| TGATGGTTATAATAGCTTTCAACTATGCCATGCTATCAAGTGGTATCAAAGAAGAAGAAATCGATAATTGCTG |
| TAGAATGTTTGCGAATGGTGATGACTTACTCCTAGCAGTGCATCCTGATTTTGGTCATTTTAGATGAATTT |
| CAAAATCACTTTGGGAATCTTGGGCTGAACTTCGAATTTACATCACGAACACGAGACAAATCCGAACTGTGGT |
| TCATGTCCACAAGAGGCATCAAGTATGAAGGAATTTACATACCAAAGCTTGAGAAAGAAAGAATAGTCGCCAT |
| ACTTGAATGGGATCGATCAAACTTGCCTGAACATAGGTTGGAAGCTATATGTGCAGCGATGGTTGAGGCCTGG |
| GGATATTCCGATCTCGTTCATGAAATACGAAAGTTCTATGCGTGCTTTTGGAAGTGCAACCTTTTGCAAATC |
| TCGCAAAAGAAGGGTTGGCCCCATACATTGCCGAGACAGCACTCCGCAATCTCTATCTTGGAACGGGTATCAA |
| AGAGGAAGAAATTGAAAAATATCTTAAACAATTCATTAAGGATCTTCCCGGATACATAGAAGATTACAATGAA |
| GATGTATTCCATCAGTCGGGAACTGTTGATGCGGGTGCACAAGGCGGCAGTGGAAGCCAAGGGACAACACCAC |
| CAGCAACAGGTAGTGGAGCAAAACCAGCCACCTCAGGGGCAGGATCTGGTAGTGGCACAGGAGCTGGAACTGG |
| TGTAACTGGAGGTCAAGCAAGGACTGGCAGTGGCACTGGGACGGATCTGGAGCAACCGGAGGCCAATCAGGA |
| TCTGGAAGTGGCACTGAACAGGTTAACACGGGTTCAGCAGGAACTAATGCAACTGGAGGCCAAAGAGATAGGG |
| ATGTGGATCAGGTACAACAGGAAAAATTTCTGTACCAAAGCTCAAGGCCATGTCAAAGAAAATGCGCTTACC |
| TAAAGCAAAGGAAAGATGTGCTACATTTGGATTTTCTATTGACATACAAACCACAACAACAAGACATATCA |
| AACACTAGAGCAACCAAGGAAGAGTTTGATGATGGTATGATGCCAAAAGAAGGAATACGAAATTGATGACA |
| CACAAATGACAGTTGTCATGAGTGGCCTTATGGTATGGTGCATCGAAAATGGTTGCTCACCAAACATAAACGG |
| AAATTGGACAATGATGGATGAAGATGAACAAAGGGTCTTTCCACTCAAACCGGTCATTGAGAATGCATCTCCA |
| ACTTTCCGACAAATTATGCATCATTTCAGTGATGCAGCTGAAGCGTACATAGAGTACAGAAACTCTACTGAGC |
| GATATATGCCAAGATACGGACTTCAGCGCAATCTCACCGACTATAGCTTAGCACGGTATGCATTTGATTTCTA |
| TGAAATGACTTCACGCACACCTGCTAGAGCTAAAGAAGCCCACATGCAGATGAAAGCCGCAGCAGTTCGTGGT |
| TCAAACACACGACTGTTCGGTTTGGACGGAAATGTCGGCGAGACTCAGGAGAATACAGAGAGACACACAGCTG |
| GCGATGTTAGTCGCAACATGCACTCTCTGTTGGGAGTGCAGCAGCACCACTAGTCTCCTGGAAACCCTGTTTG |
| CAGTACCAATAATATGTACTAATATATAGTATTTTAGTGAGGTTTTACCTCGTCTTTACTGTTTTATTACGTA |
| TGTATTTAAAGCGTGAACCAGTCTGCAACATACAGGGTTGGACCCAGTGTGTTCTGGTGTAGCGTGTACTAGC |
| GTCGAGCCATGAGATGGACTGCACTGGGTGTGGTTTTGCCACTTGTGTTGCAGTCTCTTGGTGAGAGACAAA |
| AAAAAAAAAAAAAAAAACCTGGATCCTAGGTTCACAAAGTGTCATCGATAGCTCGAATTTCCCCGATCGTTCA |

| Sequences |
| --- |
| AACATTTGGCAATAAAGTTTCTTAAGATTGAATCCTGTTGCCGGTCTTGCGATGATTATCATATAATTTCTGT |
| TGAATTACGTTAAGCATGTAATAATTAACATGTAATGCATGACGTTATTTATGAGATGGGTTTTTATGATTAG |
| AGTCCCGCAATTATACATTTAATACGCGATAGAAAACAAAATATAGCGCGCAAACTAGGATAAATTATCGCGC |
| GCGGTGTCATCTATGTTACTAGATCGGGAATTCTTGAAGACGAAAGGGCCTCGTGATACGCCTATTTTTATAG |
| GTTAATGTCATGATAATAATGGTTTCTTAGACGTCAGGTGGCACTTTTCGGGGAAATGTGCGCGGAACCCCTA |
| TTTGTTTATTTTTCTAAATACATTCAAATATGTATCCGCTCATGAGACAATAACCCTGATAAATGCTTCAATA |
| ATATTGAAAAAGGAAGAGTATGAGTATTCAACATTTCCGTGTCGCCCTTATTCCCTTTTTTGCGGCATTTTGC |
| CTTCCTGTTTTTGCTCACCCAGAAACGCTGGTGAAAGTAAAAGATGCTGAAGATCAGTTGGGTGCACGAGTGG |
| GTTACATCGAACTGGATCTCAACAGCGGTAAGATCCTTGAGAGTTTTCGCCCCGAAGAACGTTTTCCAATGAT |
| GAGCACTTTTAAAGTTCTGCTATGTGGCGCGGTATTATCCCGTGTTGACGCCGGGCAAGAGCAACTCGGTCGC |
| CGCATACACTATTCTCAGAATGACTTGGTTGAGTACTCACCAGTCACAGAAAAGCATCTTACGGATGGCATGA |
| CAGTAAGAGAATTATGCAGTGCTGCCATAACCATGAGTGATAACACTGCGGCCAACTTACTTCTGACAACGAT |
| CGGAGGACCGAAGGAGCTAACCGCTTTTTTGCACAACATGGGGGATCATGTAACTCGCCTTGATCGTTGGGAA |
| CCGGAGCTGAATGAAGCCATACCAAACGACGAGCGTGACACCACGATGCCTGCAGCAATGGCAACAACGTTGC |
| GCAAACTATTAACTGGCGAACTACTTACTCTAGCTTCCCGGCAACAATTAATAGACTGGATGGAGGCGGATAA |
| AGTTGCAGGACCACTTCTGCGCTCGGCCCTTCCGGCTGGCTGGTTTATTGCTGATAAATCTGGAGCCGGTGAG |
| CGTGGGTCTCGCGGTATCATTGCAGCACTGGGGCCAGATGGTAAGCCCTCCCGTATCGTAGTTATCTACACGA |
| CGGGGAGTCAGGCAACTATGGATGAACGAAATAGACAGATCGCTGAGATAGGTGCCTCACTGATTAAGCATTG |
| GTAACTGTCAGACCAAGTTTACTCATATATACTTTAGATTGATTTAAAACTTCATTTTTAATTTAAAAGGATC |
| TAGGTGAAGATCCTTTTTGATAATCTCATGACCAAAATCCCTTAACGTGAGTTTTCGTTCCACTGAGCGTCAG |
| ACCCCGTAGAAAAGATCAAAGGATCTTCTTGAGATCCTTTTTTTCTGCGCGTAATCTGCTGCTTGCAAACAAA |
| AAAACCACCGCTACCAGCGGTGGTTTGTTTGCCGGATCAAGAGCTACCAACTCTTTTTCCGAAGGTAACTGGC |
| TTCAGCAGAGCGCAGATACCAAATACTGTCCTTCTAGTGTAGCCGTAGTTAGGCCACCACTTCAAGAACTCTG |
| TAGCACCGCCTACATACCTCGCTCTGCTAATCCTGTTACCAGTGGCTGCTGCCAGTGGCGATAAGTCGTGTCT |
| TACCGGGTTGGACTCAAGACGATAGTTACCGGATAAGGCGCAGCGGTCGGGCTGAACGGGGGGTTCGTGCACA |
| CAGCCCAGCTTGGAGCGAACGACCTACACCGAACTGAGATACCTACAGCGTGAGCTATGAGAAAGCGCCACGC |
| TTCCCGAAGGGAGAAAGGCGGACAGGTATCCGGTAAGCGGCAGGGTCGGAACAGGAGAGCGCACGAGGGAGCT |
| TCCAGGGGGAAACGCCTGGTATCTTTATAGTCCTGTCGGGTTTCGCCACCTCTGACTTGAGCGTCGATTTTTG |
| TGATGCTCGTCAGGGGGCGGAGCCTATGGAAAAACGCCAGCAACGCGGCCTTTTTACGGTTCCTGGCCTTTT |
| GCTGGCCTTTTGCTCACATGTTCTTTCCTGCGTTATCCCTGATTCTGTGGATAACCGTATTACCGCCTTTGA |
| GTGAGCTGATACCGCTCGCCGCAGCCGAACGACCGAGCGCAGCGAGTCAGTGAGCGAGGAAGCGGAAGAGCGC |
| CTGATGCGGTATTTTCTCCTTACGCATCTGTGCGGTATTTCACACCGCATATGGTGCACTCTCAGTACAATCT |
| GCTCTGATGCCGCATAGTTAAGCCAGTATACACTCCGCTATCGCTACGTGACTGGGTCATGGCTGCGCCCCGA |
| CACCCGCCAACACCCGCTGACGCGCCCTGACGGGCTTGTCTGCTCCCGGCATCCGCTTACAGACAAGCTGTGA |
| CCGTCTCCGGGAGCTGCATGTGTCAGAGGTTTTCACCGTCATCACCGAAACGCGCGAGGCAGCTGCGGTAAAG |
| CTCATCAGCGTGGTCGTGAAGCGATTCACAGATGTCTGCCTGTTCATCCGCGTCCAGCTCGTTGAGTTTCTCC |
| AGAAGCGTTAATGTCTGGCTTCTGATAAAGCGGGCCATGTTAAGGGCGGTTTTTTCCTGTTTGGTCACTGATG |
| CCTCCGTGTAAGGGGGATTTCTGTTCATGGGGGTAATGATACCGATGAAACGAGAGAGGATGCTCACGATACG |
| GGTTACTGATGATGAACATGCCCGGTTACTGGAACGTTGTGAGGGTAAACAACTGGCGGTATGGATGCGGCGG |
| GACCAGAGAAAAATCACTCAGGGTCAATGCCAGCGCTTCGTTAATACAGATGTAGGTGTTCCACAGGGTAGCC |
| AGCAGCATCCTGCGATGCAGATCCGGAACATAATGGTGCAGGGCGCTGACTTCCGCGTTTCCAGACTTTACGA |
| AACACGGAAACCGAAGACCATTCATGTTGTTGCTCAGGTCGCAGACGTTTTGCAGCAGCAGTCGCTTCACGTT |
| CGCTCGCGTATCGGTGATTCATTCTGCTAACCAGTAAGGCAACCCCGCCAGCCTAGCCGGGTCCTCAACGACA |
| GGAGCACGATCATGCGCACCCGTGGCCAGGACCCAACGCTGCCCGAGATGCGCCGCGTGCGGCTGCTGGAGAT |
| GGCGGACGCGATGGATATGTTCTGCCAAGGGTTGGTTTGCGCATTCACAGTTCTCCGCAAGAATTGATTGGCT |
| CCAATTCTTGGAGTGGTGAATCCGTTAGCGAGGTGCCGCCGGCTTCCATTCAGGTCGAGGTGGCCCGGCTCCA |
| TGCACCGCGACGCAACGCGGGGAGGCAGACAAGGTATAGGGCGGCGCCTACAATCCATGCCAACCCGTTCCAT |
| GTGCTCGCCGAGGCGGCATAAATCGCCGTGACGATCAGCGGTCCAATGATCGAAGTTAGGCTGGTAAGAGCCG |
| CGAGCGATCCTTGAAGCTGTCCCTGATGGTCGTCATCTACCTGCCTGGACAGCATGGCCTGCAACGCGGGCAT |
| CCCGATGCCGCCGGAAGCGAGAAGAATCATAATGGGGAAGGCCATCCAGCCTCGCGTCGCGAACGCCAGCAAG |
| ACGTAGCCCAGCGCGTCGGCCGCCATGCCGGCGATAATGGCCTGCTTCTCGCCGAAACGTTTGGTGGCGGGAC |
| CAGTGACGAAGGCTTGAGCGAGGGCGTGCAAGATTCCGAATACCGCAAGCGACAGGCCGATCATCGTCGCGCT |
| CCAGCGAAAGCGGTCCTCGCCGAAAATGACCCAGAGCGCTGCCGGCACCTGTCCTACGAGTTGCATGATAAAG |
| AAGACAGT | pSCMV-CS3 (SEQ ID NO: 21)
GAGAGTGTCGTGCTCCACCATGTTGCATAAGTGCGGCGACGATAGTCATGCCCCGCGCCCACCGGAAGGAGCT
GACTGGGTTGAAGGCTCTCAAGGGCATCGGTCGAGCGGCCGCCCTCCAAAAATATCAAAGATACAGTCTCAGA
AGACCAAAGGGCAATTGAGACTTTTCAACAAAGGGTAATATCCGGAAACCTCCTCGGATTCCATTGCCCAGCT
ATCTGTCACTTTATTGTGAAGATAGTGGAAAAGGAAGGTGGCTCCTACAAATGCCATCGTTGCGATAAAGGAA
AGGCCATCGTTGAAGATGCCTCTGCCGACAGTGGTCCCAAAGATGGACCCCCACCCACGAGGAGCATCGTGGA
AAAAGAAGACGTTCCAACCACGTCTTCAAAGCAAGTGGATTGATGTGATACTCCAAAAATATCAAAGATACAG
TCTCAGAAGACCAAAGGGCAATTGAGACTTTTCAACAAAGGGTAATATCCGGAAACCTCCTCGGATTCCATTG
CCCAGCTATCTGTCACTTTATTGTGAAGATAGTGGAAAAGGAAGGTGGCTCCTACAAATGCCATCATTGCGAT
AAAGGAAAGGCCATCGTTGAAGATGCCTCTGCCGACAGTGGTCCCAAAGATGGACCCCCACCCACGAGGAGCA
TCGTGGAAAAAGAAGACGTTCCAACCACGTCTTCAAAGCAAGTGGATTGATGTGATATCCACTGACGTAAG
GGATGACGCACAATCCCACTATCCTTCGCAAGACCCTTCCTCTATATAAGGAAGTTCATTTCATTTGGGGAG
GAAAACAACAAAACTCAACACAACACAACAAAACACAACCAAGCAAATCCAATTTACTTGCGCTCAGATTGT
AGTGAACGGCTCGAACGAAACGGTTCTTGAGATCACTCTCTGATTCTTCCTCATCTTTCAATTTCTTTCGAA
AGAAATGGCGGGAACGTGGACCTACGTGACACGTAAGTGGCAGCCAGATGTTAACAACGATCGTCACATTAAA
AGAGTGATGGAAATGTTTGCAGCAAAACATCAACATTACTCAGAAGAACAGCGACTTGCCCATAATATGAAAT
TATTGAGGAAGGCAAGTGTTGTAAGCGTTGAGCCTGCGAAACAAAGCAGAAGCAGGCAACTCAACAGATGTG
GGTTGAGAAATGTGATCACAATCCTGTTGATCACTTAGTATATCCACGACTTGGAAAATCCGCGAACAAAGCA
GATATGAGTATTAAAGTGCATCTGTAAGCAAACTAACCAGAGAGATTTAGAAATCTCAAAGGTTAGCGGCC
TTAAGGTTGAACTAATTGATAAACGAAAAAGATTCAAAACACAGTTATCAATCAAAAGGTTCAATGGCAAAAA
TTTCCTCCACTGCAAAACGAATCACGAAAACAATTTATTTAAGAGGAAAGACATAGCCATTGGGCACAAATGG
TTTCCAACGATTGAAGCCATTGCTAGATGCTATAGCACGATGAATCGAGAAGAACTACAAAGCCTTTATAGAG

| Sequences |
|---|
| GGAGCAGTGGTCTCACATTCATTCAAAACGATGAATTGTTCATTGTCAGAGGAAGAATGAATGGTGAACTTGT |
| CAATAGCTTGTACGAGACAAATCGGGTTTTGGATATTGAGCACTACGCAGGGCCCTGTTTAAACGCCTGCAGG |
| GAGGACGTGTTTCACCAATCCGCAGATCCCCAGGCTAACGATTTCTGGAGGGGATACACAAATGCTTACGTAG |
| AGAATCGTAACATTTCGACTACTCATACAGAGCACACCCCTACAATCAATCTAGAAGAATGTGGAAAACGAAT |
| GGCTCTACTCGAGATACTATTTCACTCTACATTCAAAATTACATGCAAGACATGCAACATTGATGATCTTGAA |
| TTATCGGATGATGAATTTGGAGCTAAACTCTACAAGAATTTGCAACGTATCGAAGAGAAACAACGAGAGTATC |
| TTGCAAAGGATCAAAAACTATCCAGAATGATACAATTTATCAAAGAAAGGTGCAATCCAAAATTTTCGCATTT |
| ACCAACGCTATGGCAAGTTGCGGAAACAATAGGGCACTATACTGATAACCAGTCAAAGCAAATAATGGATATT |
| AGCGAAGCGCTCATCAAAGTTAATACTCTGACTCCTGATGATGCTATGAAAGCAAGCGCAGCGTTACTTGAAG |
| TGTCGCGATGGTATAAGAATCGTAAGGAGTCACTCAAAACTGACTCATTGGAATCTTTTAGAAATAAAATATC |
| ACCAAAGAGTACAATAAATGCAGCTTTAATGTGCGATAATCAATTGGATAAAAATGCAAATTTTGTATGGGGT |
| AATAGGGAATACCACGCCAAACGATTTTTCGCAAACTATTTTGAAGCAGTGGATCCCACAGATGCATATGAAA |
| AGCACGTCACACGGTTCAACCCTAATGGTCAACGAAAGTTATCAATAGGAAAGTTAGTTATCCCACTAGACTT |
| TCAAAAGATTAGAGAATCATTTGTTGGACTCTCGATAAATAGACAACCGCTGGATAAATGTTGTGTTAGCAAG |
| ATCGAAGGAGGGTATATATACCCATGTTGCTGCGTCACAACAGAATTTGGTAAACCAGCATACTCTGAGATAA |
| TACCTCCAACGAAAGGGCATATAACAATAGGCAATTCTATTGATCCAAAGATTGTGGACTTGCCAAATACAAC |
| ACCACCCAGCATGTACATTGCTAAGGATGGGTATTGCTATATCAACATCTTTTTAGCAGCCATGATCAACGTT |
| AATGAAGAATCTGCCAAGGATTACACGAAATTTTTGAGGGACGAACTAGTTGAGCGTCTCGGAAAGTGGCCAA |
| AGCTTAAAGACGTAGCAACAGCGTGTTATGCATTATCTGTAATGTTTCCAGAAATTAAGAATGCTGAGCTACC |
| TCCAATTCTAGTTGACCATGAAAATAAATCAATGCACGTAATTGATTCATATGGTTCACTAAGCGTTGGATTT |
| CACATATTAAAAGCAAGCACGATTGGTCAATTAATCAAATTTCAATATGAGTCTATGGATAGTGAAATGCGCG |
| AATACATAGTAGGAGGAACTCTCACACAACAGACATTCAACACACTTCTTAAGATGCTTACGAAAAACATGTT |
| CAAACCAGAGCGCATCAAGCAGATAATTGAAGAGGAACCCTTCTTACTTATGATGGCGATTGCGTCTCCAACG |
| GTATTAATAGCACTATATAATAATTGTTATATTGAGCAAGCTATGACATACTGGATCGTTAAGAATCAAGGAG |
| TTGCAGCCATATTCGCACAACTCGAAGCATTAGCCAAGAAAACATCCCAGGCTGAGCTATTAGTTCTACAAAT |
| GCAGATACTTGAAAAAGCATCTAACCAATTAAGGATTAGCAGTTTCAGGACTTAGCCATATCGACCCAGCAAG |
| CGACTTTTGTGGTCACACCTTGAAGCGATGTCAACACGATCAGAAATGAACAAGGAGTTAATAGCTGAGGGGT |
| ATGCACTATATGACGAGCGCCTATACACCCTGATGGAAAAAAGTTACGTAGATCAATTAAACCAATCATGGGC |
| AGAATTGTCATACTGTGGAAAATTTTCAGCAATATGGCGTGTGTTCAGAGTCAGGAAGTATTACAAACCGTCT |
| TTAACCGTGAGAAAAAGCGTAGATTTAGGCGCTGTATACAATATATCAGCTACGCATCTAATATCAGATTTAG |
| CGCGGAAAAGTCAAGATCAAGTCAGCTCTACTTTAACCAAACTCCGCAACGGTTTCTATGATAAATTAGAGAA |
| AGTTAGAATACGAACTATAAAAACGGTTTATTGGTTTATACCTGATATATTTAGACTCGTGCACATATTCATA |
| GTTTTGAGTTTATTAACTACCATCGCTAACACTATCATAGTAACTATGAATGACTACAAGAAATTGAAGAAGC |
| AACAAAGAGAAGACGAATATGAAGCAGAAATTAACGAAGTTCGCAGAATCCATTCTACCTTAATGGAAGAGCG |
| GAAGGACAATCTGACGTGTGAACAATTTATTGAGTATATGCGTCAAAATCATCCACGGCTAGTTGAAGCAACA |
| CTGGACTTAACTCACACAGGTGTCATACATGAAGGGAAATCCAATCTCGAAACCAATTTGGAACAGGCAATGG |
| CAGTTGGAACCTTGATAACAATGATACTTGATCCACAGAAAAGCGATGCTGTCTATAAGGTGTTGAACAAAAT |
| GCGGACAGTAATTAGTACAATTGAACAAAACGTCCCATTCCCTTCAGTGAATTTCTCCAACATCTTAACACCT |
| CCAGTGGCACAACAGAGTGTAGATGTTGATGAGCCATTAACACTTAGCACTGATAAAAATTTAACAATAGACT |
| TTGACACAAATCAAGATTTACCTGCCGATACATTCAGTAATGATGTGACATTTGAAGATTGGTGGTCAAATCA |
| ATTAAGCAACAACAGAACAGTGCCACACTACCGACTTGGGGGAAAGTTCATTGAATTCACACAGAAAAACGCA |
| GCCCACACGAGCATCGAACTTGCACACTCAAACATTGAGAGGGAATTCTTGCTTAGAGGAGCAGTCGGCTCGG |
| GAAAATCCACTGGGTTACCATACCATCTTAGCATGCGCGGAAAAGTGCTTCTACTAGAGCCTACAAGACCGCT |
| AGCTGAGAACGTGTGTAGGCAACTACAAGGACCGCCATTTAACGTAAGTCCAACTCTTCAAATGCGTGGATTA |
| AGTTCTTTTGGATGCACTCCAATCACAATCATGACATCTGGTTTTGCATTGCACATGTACGCAAATAATCCAG |
| ATAAAATATCTGAGTACGATTTCATAATCTTTGATGAATGTCATATAATGGAAGCACCAGCGATGGCCTTTTA |
| TTGCTTACTCAAAGAATATGAATATCGAGGAAAATTATCAAGGTATCAGCTACGCCTCCAGGAAGGGAGTGT |
| GAATTCACAACACAACATCCAGTAGACATCCATGTTTGTGAGAATCTAACTCAGCAACAGTTTGTTATGGAAC |
| TCGGGACTGGTTCAACCGCAGATGCTACGAAGTACGGAAATAATATCTTAGTTTATGGTAGCAAGCTATAATGA |
| CGTCGATTCATTGTCGCAAGCACTAGTCGAACTTAAATTTTCCGTAATCAAAGTGGATGGCCGAACAATGAAA |
| CAAAACACAACAGGAATCATTACAAACGGTACCGCACAAAAGAAGTGTTTTGTTGTCGCAACGAATATAATTG |
| AGAATGGCGTCACACTAGATATTGATGTTGTTGTCGACTTCGGACTTAAGGTCTCAGCTGACTTGGACGTTGA |
| CAACAGGGCGGTATTGTATAAACGCGTAAGTATATCATATGGTGAACGCATACAACGATTGGGTCGTGTTGGC |
| AGAAATAAACCTGGTACAGTTATTCGAATCGGAAAAACAATGAAAGGTTTGCAGGGAAATTCCAGCAATGATCG |
| CAACAGAAGCAGCCTTCATGTGTTTCGCTTACGGTCTTAAAGTTATCACTCATAATGTTTCAACGACCCATCT |
| TGCAAAGTGCACAGTTAAACAAGCGAGAACCATGATGCAATTTGAATTATCACCATTTGTCATGGCTGAGCTC |
| GTTAAGTTTGATGGTTCAATGCATCCACAAATACATGAGGCACTTGTAGAAATACAAACTTAGAGATTCTGTCA |
| TAATGCTCAGACCGAATGCACTTCCAAGGGTCAATTTACATAATTGGCTTACAGCCCGAGATTATAATAGAAT |
| AGGATGTTCATTAGAACTCGAAGACCACGTCAAAATTCCGTACTACATTAGGGGAGTTCCTGACAAGTTGTAT |
| GGAAAGCTATATGATATTATCTTACAGTATAGTCCAACTAGTTGCTACGGTAGACTATCAAGTGCGTGTGCAG |
| GTAAAGTAGCAATACTCTGCGAACTGATCCCATTTTCACTTCCAAGAACAATAGCAATAATTAATGCCTTAAT |
| CACGGAGGAGTATGCGAAGAGAGATCACTATCGTAACATGATTTCAAACCCATCTTCATCACACGCATTCTCA |
| CTCAATGGGTTGGTGTCTATGATCGCTACTAGATATATGAAAGACCATACAAAGGAGAATATTGACAAACTCA |
| TTAGAGTGCGTGATCAATTACTTGAGTTTCAAGGTACTGGAATGCAATTTCAAGATCCATCAGAACTCATGGA |
| AATTGGGCTCTCAACACAGTTATTCACCAAGGAATGGACGCAACTGCAGCTTGTATTGGGTTACAAGGACGA |
| TGGAATGCTTCACTTATACAACGCGATCTCCTGATTGCAGGTGGAGTTTTTATCGGAGGCATTTTGATGATGT |
| GGAGCCTATTTACTAAATGGAGTAACACAAATGTCTCACATCAGGGGAAGAACAAACGCAGTAGACAAAAACT |
| TCGATTCAAAGAAGCAAGAGACAACAAATATGCATATGATGTCACAGGATCGGAAGAATGCCTTGGCGAGAAT |
| TTTGGAACAGCCTATCAAAGAAAGGTAAAGGAAAAGGAACTAAAGTTGGACTCGGTGTGAAGCAGCATAAAT |
| TCCATATGATGTACGGTTTCGATCCCCAAGAGTACAACCTAATTCGGTTTGTCGATCCACTCACGGGAGCAAC |
| TCTTGATGAACAAATCCATGCCGATATACGCTTAATTCAAGAGCACTTCGCTGAAATTCGTGAGGAGGCAGTG |
| ATTAATGACACAATTGAAAGGCAGCAGATTTACGGCAATCCTGGACTACAAGCATTTTTCATACAAAATGGGT |
| CAGCAAACGCTCTGAGAGTTGATTTAACACCACATTCACCTACACGAGTTGTCACAGGTAATAACATAGCAGG |
| GTTCCCAGAATATGAAGGAACACTTCGTCAGACTGGAACAGCTATAACTATACCCATTGGTCAAGTCCCAATC |
| GCAAATGAAGCAGGGGTTGCACACGAGTCAAAATCCATGATGAACGGGTTGGGTGATTACACACCAATATCGC |
| AACAATTGTGTCTAGTACAAAATGACTCGGATGGGGTAAAGCGGAATGTATTTTCAATTGGATATGGCTCATA |
| TCTTATTTCACCAGCGCACTTATTCAAATATAACAATGGTGAAATAACAATTAGATCATCAAGAGGATTGTAC |

| Sequences |
| --- |
| AAAATTCGTAATTCTGTGGATTTAAAATTACATCCAATTGCACACAGAGACATGGTCATAATTCAACTCCCAA
AGGATTTCCCACCGTTCCCAATGCGCTTGAAATTCAAACAACCATCACGAGATATGCGAGTCTGCCTAGTAGG
TGTCAACTTCCAACAGAATTATAGCACTTGCATCGTATCAGAAAGTAGTGTGACAGCACCAAAAGGAAATGGA
GACTTTTGGAAACATTGGATATCAACAGTCGACGGTCAATGTGGACTACCATTGGTAGATACTAAGAGCAAAC
ATATTGTCGGAATTCATAGTCTTGCATCAACAAGTGGAAACACTAATTTCTTTGTCGCTGTGCCTGGGAACTT
TAATGAATACATCAATGGACTTGTGCAAGCAAATAAATGGGAAAAAGGATGGCACTATAATCCGAATCTCATA
TCCTGGTGTGGACTAAATTTAGTTGATTCTGCCCCAAAAGGTTTGTTTAAAACGTCAAAATTGGTAGAAGACT
TGGACGCGAGCGTTGAAGAGCAATGCAAGATCACCGAAACATGGCTCACAGAGCAATTACAAGATAATTTGCA
AGTGGTTGCGAAATGTCCAGGCCAACTTGTTACCAAGCATGTTGTTAAGGGTCAATGCCCACACTTTCAATTG
TACTTATCAACACATGACGATGCCAAAGAATACTTCGCACCCATGCTTGGAAAATACGACAAGAGTAGGCTTA
ACAGAGCAGCTTTTATCAAAGACATATCAAAATATGCAAAACCAATTTATATTGGAGAAATCAAGTATGATAT
CTTTGATAGAGCTGTACAGCGGGTTGTCAATATTCTCAAAAATGTTGGAATGCAACAATGCGTTTATGTCACA
GATGAAGAAGAATTTTCAGATCACTTAACCTGAACGCAGCTGTCGGAGCATTGTATACAGGAAAGAAGAAAA
ATTACTTTGAAAATTTTTCAAGCGAAGACAAAGAAGAGATCGTGATGAGATCCTGTGAACGTATTTACAATGG
GCAACTTGGCGTATGGAATGGATCGCTCAAAGCTGAGATCAGATCAATAGAGAAAACCATGCTGAATAAGACT
CGAACCTTCACAGCAGCCCCATTAGAAACTTTGCTCGGAGGAAAAGTGTGCGTGGATGATTTTAATAATCAAT
TCTATTCACATCATTTAGAAGGTCCATGGACTGTTGGGATAACAAAATTCTATGGAGGTTGGAATCGCTTACT
TGAGAAGTTACCAGAAGGATGGGTTTACTGCGATGCTGACGGGTCTCAATTTGATAGTTCGTTAACACCATAT
CTCATCAATGCAGTATTAAATATTCGATTGCAATTTATGGAAGATTGGGATATAGGAGCGCAAATGCTAAAGA
ACCTGTACACTGAGATTGTTTACACACCAATCGCAACGCCAGACGGATCAATCGTGAAGAAATTCAAAGGTAA
CAATAGCGGACAACCTTCTACAGTAGTGGACAACACATTGATGGTTATAATAGCTTTCAACTATGCCATGCTA
TCAAGTGGTATCAAAGAAGAAGAAATCGATAATTGCTGTAGAATGTTTGCGAATGGTGATGACTTACTCCTAG
CAGTGCATCCTGATTTTGAGTTCATTTTAGATGAATTTCAAAATCACTTTGGGAATCTTGGGCTGAACTTCGA
ATTTACATCACGAACACGAGACAAATCCGAACTGTGGTTCATGTCCACAAGAGGCATCAAGTATGAAGGAATT
TACATACCAAAGCTTGAGAAAGAAAGAATAGTCGCCATACTTGAATGGGATCGATCAAACTTGCCTGAACATA
GGTTGGAAGCTATATGTGCAGCGATGGTTGAGGCCTGGGGATATTCCGATCTCGTTCATGAAATACGAAAGTT
CTATGCGTGGCTTTTGGAAATGCAACCTTTTGCAAATCTCGCAAAAGAAGGGTTGGCCCCATACATTGCCGAG
ACAGCACTCCGCAATCTCTATCTTGGAACGGGTATCAAAGAGGAAGAAATTGAAAAATATCTTAAACAATTCA
TTAAGGATCTTCCCGGATACATAGAAGATTACAATGAAGATGTATTCCATCAGTCGGGAACTGTTGATGCGGG
TGCACAAGGCGGCAGTGGAAGCCAAGGGACAACACCACCAGCAACAGGTAGTGGAGCAAAACCAGCCACCTCA
GGGGCAGGATCTGGTAGTGGCACAGGAGCTGGAACTGGTGTAACTGGAGGTCAAGCAAGGACTGGCAGTGGCA
CTGGGACGGGATCTGGAGCAACCGGAGGCCAATCAGGATCTGGAAGTGGCACTGAACAGGTTAACACGGGTTC
AGCAGGAACTAATGCAACTGGAGGCCAAAGAGATAGGGATGTGGATGCAGGTACAACAGGAAAAATTTCTGTA
CCAAAGCTCAAGGCCATGTCAAAGAAAATGCGCTTACCTAAAGCAAAAGGAAAAGATGTGCTACATTTGGATT
TTCTATTGACATACAAACCACAACAACAAGACATATCAAACACTAGAGCAACCAAGGAAGAGTTTGATAGATG
GTATGATGCCATAAAGAAGGAATACGAAATTGATGACACACAAATGTACAGTTGTCATGAGTGGCCTTATGGTA
TGGTGCATCGAAAATGGTTGCTCACCAAACATAAACGGAAATTGGACAATGATGGATGAAGATGAACAAAGGG
TCTTTCCACTCAAACCGGTCATTGAGAATGCATCTCCAACTTTCCGACAAATTATGCATCATTTCAGTGATGC
AGCTGAAGCGTACATAGAGTACAGAAACTCTACTGAGCGATATATGCCAAGATACGGACTTCAGCGCAATCTC
ACCGACTATAGCTTAGCACGGTATGCATTTGATTTCTATGAAATGACTTCACGCACACCTGCTAGAGCTAAAG
AAGCCCACATGCAGATGAAAGCCGCAGCAGTTCGTGGTTCAAACACACGACTGTTCGGTTTGGACGGAAATGT
CGGCGAGACTCAGGAGAATACAGAGAGACACACAGCTGGCGATGTTAGTCGCAACATGCACTCTCTGTTGGGA
GTGCAGCAGCACCACTAGTCTCCTGGAAACCCTGTTTGCAGTACCAATAATATGTACTAATATAGTATTTT
AGTGAGGTTTTACCTCGTCTTTACTGTTTTATTACGTATGTATTTAAAGCGTGAACCAGTCTGCAACATACAG
GGTTGGACCCAGTGTGTTCTGGTGTAGCGTGTACTAGCGTCGAGCCATGAGGTGGACTGCACTGGGTGTGGTT
TTGCCACTTGTGTTGCGAGTCTCTTGGTGAGAGACAAAAAAAAAAAAAAAAAAAAAACCTGGATCCTAGGTTCAC
AAAGTGTCATCGATAGCTCGAATTTCCCCGATCGTTCAAACATTTGGCAATAAAGTTTCTTAAGATTGAATCC
TGTTGCCGGTCTTGCGATGATTATCATATAATTTCTGTTGAATTACGTTAAGCATGTAATAATTAACATGTAA
TGCATGACGTTATTTATGAGATGGGTTTTTATGATTAGAGTCCCGCAATTACATTTAATACGCGATAGAAAGA
ACAAAATATAGCGCGCAAACTAGGATAAATTATCGCGCGCGGTGTCATCTATGTTACTAGATCGGGAATTCTT
GAAGACGAAAGGGCCTCAACGCTAGCCACCACCACCACCACCACGTGTGAATTACAGGTGACCAGCTCGAATT
TCCCCGATCGTTCAAACATTTGGCAATAAAGTTTCTTAAGATTGAATCCTGTTGCCGGTCTTGCGATGATTAT
CATATAATTTCTGTTGAATTACGTTAAGCATGTAATAATTAACATGTAATGCATGACGTTATTTATGAGATGG
GTTTTTATGATTAGAGTCCCGCAATTATACATTTAATACGCGATAGAAAACAAAATATAGCGCGCAAACTAGG
ATAAATTATCGCGCGCGGTGTCATCTATGTTACTAGATCGGGAATTAAACTATCAGTGTTTGACAGGATATAT
TGGCGGGTAAACCTAAGAGAAAAGAGCGTTTATTAGAATAACGGATATTTAAAAGGGCGTGAAAAGGTTTATC
CGTTCGTCCATTTGTATGTGCATGCCAACCACAGGGTTCCCCTCGGGATCAAAGTACTTTGATCCAACCCCTC
CGCTGCTATAGTGCAGTCGGCTTCTGACGTTCAGTGCAGCCGTCTTCTGAAAACGACATGTCGCACAAGTCCT
AAGTTACGCGACAGGCTGCCGCCCTGCCCTTTTCCTGGCGTTTTCTTGTCGCGTGTTTTAGTCGCATAAAGTA
GAATACTTGCGACTAGAACCGGAGACATTACGCCATGAACAAGAGCGCCGCCGCTGGCCTGCTGGGCTATGCC
CGCGTCAGCACCGACGACCAGGACTTGACCAACCAACGGGCCGAACTGCACGCGGCCGGCTGCACCAAGCTGT
TTTCCGAGAAGATCACCGGCACCAGGCGCGACCGCCCGGAGCTGGCCAGGATGCTTGACCACCTACGCCCTGG
CGACGTTGTGACAGTGACCAGGCTAGACCGCCTGGCCCGCAGCACCCGCGACCTACTGGACATTGCCGAGCGC
ATCCAGGAGGCCGGCGCGGGCCTGCGTAGCCTGGCAGAGCCGTGGGCCGACACCACCACGCCGGCCGGCCGCA
TGGTGTTGACCGTGTTCGCCGGCATTGCCGAGTTCGAGCGTTCCCTAATCATCGACCGCACCCGGAGCGGGCG
CGAGGCCGCCAAGGCCCGAGGCGTGAAGTTTGGCCCCCGCCCTACCCTCACCCCGGCACAGATCGCGCACGCC
CGCGAGCTGATCGACCAGGAAGGCCGCACCGTGAAAGAGGCGGCTGCACTGCTTGGCGTGCATCGCTCGACCC
TGTACCGCGCACTTGAGCGCAGCGAGGAAGTGACGCCCACCGAGGCCAGGCGGCGCGGTGCCTTCCGTGAGGA
CGCATTGACCGAGGCCGACGCCCTGGCGGCCGCCGAGAATGAACGCCAAGAGGAACAAGCATGAAACCGCACC
AGGACGGCCAGGACGAACCGTTTTTCATTACCGAAGAGATCGAGGCGGAGATGATCGCGGCCGGGTACGTGTT
CGAGCCGCCCGCGCACGTCTCAACCGTGCGGCTGCATGAAATCCTGGCCGGTTTGTCTGATGCCAAGCTGGCG
GCCTGGCCGGCCAGCTTGGCCGCTGAAGAAACCGAGCGCCGCCGTCTAAAAAGGTGATGTGTATTTGAGTAAA
ACAGCTTGCGTCATGCGGTCGCTGCGTATATGATGCGATGAGTAAATAAACAAATACGCAAGGGGAACGCATG
AAGGTTATCGCTGTACTTAACCAGAAAGGCGGGTCAGGCAAGACGACCATCGCAACCCATCTAGCCCGCGCCC
TGCAACTCGCCGGGGCCGATGTTCTGTTAGTCGATTCCGATCCCCAGGGCAGTGCCCGCGATTGGGCGGCCGT
GCGGGAAGATCAACCGCTAACCGTTGTCGGCATCGACCGCCCGACGATTGACCGCGACGTGAAGGCCATCGGC
CGGCGCGACTTCGTAGTGATCGACGGAGCGCCCCAGGCGGCGGACTTGGCTGTGTCCGCGATCAAGGCAGCCG |

| Sequences |
| --- |
| ACTTCGTGCTGATTCCGGTGCAGCCAAGCCCTTACGACATATGGGCCACCGCCGACCTGGTGGAGCTGGTTAA |
| GCAGCGCATTGAGGTCACGGATGGAAGGCTACAAGCGGCCTTTGTCGTGTCGCGGGCGATCAAAGGCACGCGC |
| ATCGGCGGTGAGGTTGCCGAGGCGCTGGCCGGGTACGAGCTGCCCATTCTTGAGTCCCGTATCACGCAGCGCG |
| TGAGCTACCCAGGCACTGCCGCCGCCGGCACAACCGTTCTTGAATCAGAACCCGAGGGCGACGCTGCCCGCGA |
| GGTCCAGGCGCTGGCCGCTGAAATTAAATCAAAACTCATTTGAGTTAATGAGGTAAAGAGAAAATGAGCAAAA |
| GCACAAACACGCTAAGTGCCGGCCGTCCGAGCGCACGCAGCAGCAAGGCTGCAACGTTGGCCAGCCTGGCAGA |
| CACGCCAGCCATGAAGCGGGTCAACTTTCAGTTGCCGGCGGAGGATCACACCAAGCTGAAGATGTACGCGGTA |
| CGCCAAGGCAAGACCATTACCGAGCTGCTATCTGAATACATCGCGCAGCTACCAGAGTAAATGAGCAAATGAA |
| TAAATGAGTAGATGAATTTTAGCGGCTAAAGGAGGCGGCATGGAAAATCAAGAACAACCAGGCACCGACGCCG |
| TGGAATGCCCCATGTGTGGAGGAACGGGCGGTTGGCCAGGCGTAAGCGGCTGGGTTGCCTGCCGGCCCTGCAA |
| TGGCACTGGAAGCCCCAAGCCCGAGGAATCGGCGTGAGCGGTCGCAAACCATCCGGCCCGGTACAAATCGGCG |
| CGGCGCTGGGTGATGACCTGGTGGAGAAGTTGAAGGCCGCGCAGGCCGCCCAGCGGCAACGCATCGAGGCAGA |
| AGCACGCCCGGTGAATCGTGGCAAGCGGCCGCTGATCGAATCCGCAAAGAATCCCGGCAACCGCCGGCAGCC |
| GGTGCGCCGTCGATTAGGAAGCCGCCCAAGGGCGACGAGCAACCAGATTTTTTCGTTCCGATGCTCTATGACG |
| TGGGCACCCGCGATAGTCGCAGCATCATGGACGTGGCCGTTTTCCGTCTGTCGAAGCGTGACCGACGAGCTGG |
| CGAGGTGATCCGCTACGAGCTTCCAGACGGGCACGTAGAGGTTTCCGCAGGGCCGGCCGGCATGGCCAGTGTG |
| TGGGATTACGACCTGGTACTGATGGCGGTTTCCCATCTAACCGAATCCATGAACCGATACCGGGAAGGGAAGG |
| GAGACAAGCCCGGCCGCGTGTTCCGTCCACACGTTGCGGACGTACTCAAGTTCTGCCGGCGAGCCGATGGCGG |
| AAAGCAGAAAGACGACCTGGTAGAAACCTGCATTCGGTTAAACACCACGCACGTTGCCATGCAGCGTACGAAG |
| AAGGCCAAGAACGGCCGCCTGGTGACGGTATCCGAGGGTGAAGCCTTGATTAGCCGCTACAAGATCGTAAAGA |
| GCGAAACCGGGCGGCCGGAGTACATCGAGATCGAGCTAGCTGATTGGATGTACCGCGAGATCACAGAAGGCAA |
| GAACCCGGACGTGCTGACGGTTCACCCCGATTACTTTTTGATCGATCCCGGCATCGGCCGTTTTCTCTACCGC |
| CTGGCACGCCGCGCCGCAGGCAAGGCAGAAGCCAGATGGTTGTTCAAGACGATCTACGAACGCAGTGGCAGCG |
| CCGGAGAGTTCAAGAAGTTCTGTTTCACCGTGCGCAAGCTGATCGATGTCAAATGACCTGCCGGAGTACGATTT |
| GAAGGAGGAGGCGGGGCAGGCTGGCCCGATCCTAGTCATGCGCTACCGCAACCTGATCGAGGGCGAAGCATCC |
| GCCGGTTCCTAATGTACGGAGCAGATGCTAGGGCAAATTGCCCTAGCAGGGGAAAAAGGTCGAAAAGGTCTCT |
| TTCCTGTGGATAGCACGTACATTGGGAACCCAAAGCCGTACATTGGGAACCGGAACCCGTACATTGGGAACCC |
| AAAGCCGTACATTGGGAACCGGTCACACATGTAAGTGACTGATATAAAAGAGAAAAAAGGCGATTTTTCCGCC |
| TAAAACTCTTTAAAACTTATTAAAACTCTTAAAACCCGCCTGGCCTGTGCATAACTGTCTGGCCAGCGCACAG |
| CCGAAGAGCTGCAAAAAGCGCCTACCCTTCGGTCGCTGCGCTCCCTACGCCCCGCCGCTTCGCGTCGGCCTAT |
| CGCGGCCGCTGGCCGCTCAAAAATGGCTGGCCTACGGCCAGGCAATCTACCAGGGCGCGGACAAGCCGCGCCG |
| TCGCCACTCGACCGCCGGCGCCCACATCAAGGCACCCTGCCTCGCGCGTTTCGGTGATGACGGTGAAAACCTC |
| TGACACATGCAGCTCCCGGAGACGGTCACAGCTTGTCTGTAAGCGGATGCCGGGAGCAGACAAGCCCGTCAGG |
| GCGCGTCAGCGGGTGTTGGCGGGTGTCGGGGCGCAGCCATGACCCAGTCACGTAGCGATAGCGGAGTGTATAC |
| TGGCTTAACTATGCGGCATCAGAGCAGATTGTACTGAGAGTGCACCATATGCGGTGTGAAATACCGCACAGAT |
| GCGTAAGGAGAAAATACCGCATCAGGCGCTCTTCCGCTTCCTCGCTCACTGACTCGCTGCGCTCGGTCGTTCG |
| GCTGCGGCGAGCGGTATCAGCTCACTCAAAGGCGGTAATACGGTTATCCACAGAATCAGGGGATAACGCAGGA |
| AAGAACATGTGAGCAAAAGGCCAGCAAAAGGCCAGGAACCGTAAAAAGGCCGCGTTGCTGGCGTTTTTCCATA |
| GGCTCCGCCCCCTGACGAGCATCACAAAAATCGACGCTCAAGTCAGAGGTGGCGAAACCCGACAGGACTATA |
| AAGATACCAGGCGTTTCCCCCTGGAAGCTCCCTCGTGCGCTCTCCTGTTCCGACCCTGCCGCTTACCGGATAC |
| CTGTCCGCCTTTCTCCCTTCGGGAAGCGTGGCGCTTTCTCATAGCTCACGCTGTAGGTATCTCAGTTCGGTGT |
| AGGTCGTTCGCTCCAAGCTGGGCTGTGTGCACGAACCCCCCGTTCAGCCCGACCGCTGCGCCTTATCCGGTAA |
| CTATCGTCTTGAGTCCAACCCGGTAAGACACGACTTATCGCCACTGGCAGCAGCCACTGGTAACAGGATTAGC |
| AGAGCGAGGTATGTAGGCGGTGCTACAGAGTTCTTGAAGTGGTGGCCTAACTACGGCTACACTAGAAGGACAG |
| TATTTGGTATCTGCGCTCTGCTGAAGCCAGTTACCTTCGGAAAAAGAGTTGGTAGCTCTTGATCCGGCAAACA |
| AACCACCGCTGGTAGCGGTGGTTTTTTTGTTTGCAAGCAGCAGATTACGCGCAGAAAAAAAGGATCTCAAGAA |
| GATCCTTTGATCTTTTCTACGGGGTCTGACGCTCAGTGGAACGAAAACTCACGTTAAGGGATTTTGGTCATGC |
| ATTCTAGGGAAGGTGCGAACAAGTCCCTGATATGAGATCATGTTTGTCATCTGGAGCCATAGAACAGGGTTCA |
| TCATGAGTCATCAACTTACCTTCGCCGACAGTGAATTCAGCAGTAAGCGCCGTCAGACCAGAAAAGAGATTTT |
| CTTGTCCCGCATGGAGCAGATTCTGCCATGGCAAAACATGGTGGAAGTCATCGAGCCGTTTTACCCCAAGGCT |
| GGTAATGCCCGGCGACCTTATCCGCTGGAAACCATGCTACGCATTCACTGCATGCAGCATTGGTACAACCTGA |
| GCGATGCGCGATGGAAGATGCTCTGTACGAAATCGCCTCCATGCGTCTGTTTGCCCGGTTATCCCTGGATAG |
| CGCCTTGCCGGACCGCCACCACCATCATGAATTTCCGCCACCTGCTGGAGGACGCATCAACTGGCCCGCAATTG |
| TTCAAGACCATCAATCGCTGGCTGGCCGAAGCAGGCGTCATGATGACTCAAGGCACCTTGGTCGATGCCACCA |
| TCATTGAGGCACCCAGCTCGACCAAGAACAAAGAGCAGCAACGCGATCCGGAGATGCATCAGACCAAGAAAGG |
| CAATCAGTGGCACTTTGGCATGAAGGCCCACATTGGTGTCGATGCCAAGAGTGGCCTGACCCACAGCCTGGTC |
| ACCACCGCGGCCAACGAGCATGACTCAATCAGCTGGGTAATCTGCTGCATGGAGAGGAGCAATTTGTCTCAG |
| CCGATGCCGGCTACCAAGGGGCGCCACAGCGCGAGGAGCTGGCCGAGGTGGATGTGGACTGGCTGATCGCCGA |
| GCGCCCCGGCAAGGTAAGAACCTTGAAACAGCATCCACGCAAGAACAAACGGCCATCAACATCGAATACATG |
| AAAGCCAGCATCCGGGCCAGGGTGGAGCACCCATTTCGCATCATCAAGCGACAGTTCGGCTTCGTGAAAGCCA |
| GATACAAGGGGTTGCTGAAAAACGATAACCAACTGGCGATGTTATTCACGCTGGCCAACCTGTTTCGGGCGGA |
| CCAAATGATACGTCAGTGGGAGATCTCACTAAAAACTGGGGATAACGCCTTAAATGCGGAAGAAAACGGTCT |
| AAATAGGCTGATTCAAGGCATTTACGGGAGAAAAAATCGGCTCAAACATGAAGAAATGAAATGACTGAGTCAG |
| CCGAGAAGAATTTCCCCGCTTATTCGCACCTTCCCTAGGTACTAAAACAATTCATCCAGTAAAATATAATATT |
| TTATTTTCTCCCAATCAGGCTTGATCCCCAGTAAGTCAAAAAATAGCTCGACATACTGTTCTTCCCCGATATC |
| CTCCCTGATCGACCGGACGCAGAAGGCAATGTCATACCACTTGTCCGCCCTGCCGCTTCTCCCAAGATCAATA |
| AAGCCACTTACTTTGCCATCTTTCACAAAGATGTTGCTGTCTCCCAGGTCGCCGTGGGAAAAGACAAGTTCCT |
| CTTCGGGCTTTTCCGTCTTTAAAAAATCATACAGCTCGCGCGGATCTTTAAATGGAGTGTCTTCTTCCCAGTT |
| TTCGCAATCCACATCGGCCAGATCGTTATTCAGTAAGTAATCCAATTCGGCTAAGCGGCTGTCTAAGCTATTC |
| GTATAGGGACAATCCGATATGTCGATGGAGTGAAAGAGCCTGATGCACTCCGCATACAGCTCGATAATCTTTT |
| CAGGGCTTTGTTCATCTTCATACTCTTCCGAGCAAAGGACGCCATCGGCCTCACTCATGAGCAGATTGCTCCA |
| GCCATCATGCCGTTCAAAGTGCAGGACCTTTGGAACAGGCAGCTTTCCTTCCAGCCATAGCATCATGTCCTTT |
| TCCCGTTCCACATCATAGGTGGTCCCTTTATACCGGCTGTCCGTCATTTTTAAATATAGGTTTTCATTTTCTC |
| CCACCAGCTTATATACCTTAGCAGGAGACATTCCTTCCGTATCTTTTACGCAGCGGTATTTTTCGATCAGTTT |
| TTTCAATTCCGGTGATATTCTCATTTTAGCCATTTATTTTTCCTTCCTCTTTTTCTACAGTATTTAAAGATAC |
| CCCAAGAAGCTAATTATAACAAGACGAACTCCAATTCACTGTTCCTTGCATTCTAAAACCTTAAATACCAGAA |
| AACAGCTTTTTCAAAGTTGTTTTCAAAGTTGGCGTATAACATAGTATCGACGGAGCCGATTTTGAAACCGCGG |

-continued

| Sequences |
|---|
| TGATCACAGGCAGCAACGCTCTGTCATCGTTACAATCAACATGCTACCCTCCGCGAGATCATCCGTGTTTCAA |
| ACCCGGCAGCTTAGTTGCCGTTCTTCCGAATAGCATCGGTAACATGAGCAAAGTCTGCCGCCTTACAACGGCT |
| CTCCCGCTGACGCCGTCCCGGACTGATGGGCTGCCTGTATCGAGTGGTGATTTTGTGCCGAGCTGCCGGTCGG |
| GGAGCTGTTGGCTGGCTGGTGGCAGGATATATTGTGGTGTAAACAAATTGACGCTTAGACAACTTAATAACAC |
| ATTGCGGACGTTTTTAATGTACTGAATTAACGCCGAATTAATTCGGGGGATCTGGATTTTAGTACTGGATTTT |
| GGTTTTAGGAATTAGAAATTTTATTGATAGAAGTATTTTACAAATACAAATACATACTAAGGGTTTCTTATAT |
| GCTCAACACATGAGCGAAACCCTATAGGAACCCTAATTCCCTTATCTGGGAACTACTCACACATTATTATGGA |
| GAAACTCGAGCTTGTCGATCGACAGATCCCGGTCGGCATCTACTCTATTTCTTTGCCCTCGGACGAGTGCTGG |
| GGCGTCGGTTTCCACTATCGGCGAGTACTTCTACACAGCCATCGGTCCAGACGGCCGCGCTTCTGCGGGCGAT |
| TTGTGTACGCCCGACAGTCCCGGCTCCGGATCGGACGATTGCGTCGCATCGACCCTGCGCCCAAGCTGCATCA |
| TCGAAATTGCCGTCAACCAAGCTCTGATAGAGTTGGTCAAGACCAATGCGGAGCATATACGCCCGGAGTCGTG |
| GCGATCCTGCAAGCTCCGGATGCCTCCGCTCGAAGTAGCGCGTCTGCTGCTCCATACAAGCCAACCACGGCCT |
| CCAGAAGAAGATGTTGGCGACCTCGTATTGGGAATCCCCGAACATCGCCTCGCTCCAGTCAATGACCGCTGTT |
| ATGCGGCCATTGTCCGTCAGGACATTGTTGGAGCCGAAATCCGCGTGCACGAGGTGCCGGACTTCGGGGCAGT |
| CCTCGGCCCAAAGCATCAGCTCATCGAGAGCCTGCGCGACGGACGCACTGACGGTGTCGTCCATCACAGTTTG |
| CCAGTGATACACATGGGGATCAGCAATCGCGCATATGAAATCACGCCATGTAGTGTATTGACCGATTCCTTGC |
| GGTCCGAATGGGCCGAACCCGCTCGTCTGGCTAAGATCGGCCGCAGCGATCGCATCCATAGCCTCCGCGACCG |
| GTTGTAGAACAGCGGGCAGTTCGGTTTCAGGCAGGTCTTGCAACGTGACACCCTGTGAACGGCGGGAGATGCA |
| ATAGGTCAGGCTCTCGCTAAACTCCCCAATGTCAAGCACTTCCGGAATCGGGAGCGCGGCCGATGCAAAGTGC |
| CGATAAACATAACGATCTTTGTAGAAACCATCGGCGCAGCTATTTACCCGCAGGACATATCCACGCCCTCCTA |
| CATCGAAGCTGAAAGCACGAGATTCTTCGCCCTCCGAGAGCTGCATCAGGTCGGAGACGCTGTCGAACTTTTC |
| GATCAGAAACTTCTCGACAGACGTCGCGGTGAGTTCAGGCTTTTTCATATCTCATTGCCCCCCGGATCTGCGA |
| AAGCTCGAGAGAGATAGATTTGTAGAGAGAGACTGGTGATTTCAGCGTGTCCTCTCCAAATGAAATGAACTTC |
| CTTATATAGAGGAAGGTCTTGCGAAGGATAGTGGGATTGTGCGTCATCCCTTACGTCAGTGGAGATATCACAT |
| CAATCCACTTGCTTTGAAGACGTGGTTGGAACGTCTTCTTTTTCCACGATGCTCCTCGTGGGTGGGGGTCCAT |
| CTTTGGGACCACTGTCGGCAGAGGCATCTTGAACGATAGCCTTTCCTTTATCGCAATGATGGCATTTGTAGGT |
| GCCACCTTCCTTTTCTACTGTCCTTTTGATGAAGTGACAGATAGCTGGGCAATGGAATCCGAGGAGGTTTCCC |
| GATATTACCCTTTGTTGAAAAGTCTCAATAGCCCTTTGGTCTTCTGAGACTGTATCTTTGATATTCTTGGAGT |
| AGACGAGAGTGTCGTGCTCCACCATGTTATCACATCAATCCACTTGCTTTGAAGACGTGGTTGGAACGTCTTC |
| TTTTTCCACGATGCTCCTCGTGGGTGGGGGTCCATCTTTGGGACCACTGTCGGCAGAGGCATCTTGAACGATA |
| GCCTTTCCTTTATCGCAATGATGGCATTTGTAGGTGCCACCTTCCTTTTCTACTGTCCTTTTGATAAAGTGAC |
| AGATAGCTGGGCAATGGAATCCGAGGAGGTTTCCGGATATTACCCTTTGTTGAAAAGTCTCAATTGCCCTTTG |
| GTCTTCTGAGACTGTATCTTTGATATTCTTGGAGTAGAC |

What is claimed is:

1. A vector for expression of a foreign nucleotide sequence in a plant comprising:
   a nucleic acid molecule encoding an infectious *Sugarcane mosaic* virus (SCMV) operably linked to one or more regulatory elements functional in a plant cell, wherein the SCMV is at least 95% identical to the sequence set forth in SEQ ID NO: 16, 17, or 18.

2. The vector of claim 1, wherein the SCMV includes a multiple cloning site between the P1 and HC-Pro encoding sequences of the SCMV for insertion of the foreign nucleotide sequence.

3. The vector of claim 2, wherein the multiple cloning site is the sequence set forth in SEQ ID NO: 12, 13, or 14.

4. The vector of claim 2, wherein the SCMV encodes a NIa-Pro cleavage site following the multiple cloning site.

5. The vector of claim 1, wherein the SCMV is modified to be non-aphid transmissible.

6. The vector of claim 1, wherein one of the one or more regulatory elements is a promoter.

7. The vector of claim 1, wherein one of the one or more regulatory elements is a terminator sequence.

8. The vector of claim 1, further comprising a foreign nucleotide sequence inserted between the P1 and HC-Pro encoding sequences of the SCMV.

9. The vector of claim 1, wherein the SCMV is the sequence set forth in SEQ ID NO: 16, 17, or 18.

10. The vector of claim 1, wherein the nucleotide sequence of the vector is the sequence set forth in SEQ ID NO: 19, 20, or 21.

11. A plant cell, tissue or organ comprising the vector of claim 8.

12. A method of expressing a foreign nucleotide sequence of interest in a plant cell comprising:

introducing to said plant cell a vector comprising a nucleic acid molecule encoding an infectious SCMV operably linked to one or more regulatory elements functional in a plant cell, wherein the SCMV is at least 95% identical to the sequence set forth in SEQ ID NO: 16, 17, or 18, and wherein the SCMV has the foreign nucleotide sequence inserted therein.

13. The method of claim 12, wherein the foreign nucleotide sequence is inserted in a multiple cloning site between the P1 and HC-Pro encoding sequences of the SCMV.

14. The method of claim 13, wherein the SCMV encodes a NIa-Pro cleavage site following the multiple cloning site.

15. The method of claim 12, wherein the SCMV is modified to be non-aphid transmissible.

16. The method of claim 12, wherein one of the one or more regulatory elements is a promoter.

17. The method of claim 12, wherein one of the one or more regulatory elements is a terminator sequence.

18. The method of claim 12, wherein the plant cell is a monocot plant cell.

19. The method of claim 12, wherein the SCMV is the sequence set forth in SEQ ID NO: 16, 17, or 18.

20. The method of claim 12, wherein the nucleotide sequence of the vector is the sequence set forth in SEQ ID NO: 19, 20, or 21.

21. The method of claim 12, wherein the introducing is by biolistic inoculation, rub inoculation, or *Agrobacterium*-mediated transformation.

* * * * *

SEQUENCE LISTING

<160> NUMBER OF SEQ ID NOS: 88

<210> SEQ ID NO 1
<211> LENGTH: 699
<212> TYPE: DNA
<213> ORGANISM: Sugarcane mosaic virus

<400> SEQUENCE: 1
atggcgggaa cgtggaccta cgtgacacgt aagtggcagc cagatgttaa caacgatcgt 60
cacattaaaa gagtgatgga aatgtttgca gcaaaacatc aacattactc agaagaacag 120
cgacttgccc ataatatgaa attattgagg aaggcaagtg ttgtaagcgt tgagcctgcg 180
aaaccaaagc agaagcaggc aactcaacag atgtgggttg agaaatgtga tcacaatcct 240
gttgatcact tagtatatcc acgacttgga aaatccgcga acaaagcaga tatgagtatt 300
aaaagtgcat ctgtaagcaa actaaccaga gagattttag aaatctcaaa ggttagcggc 360
cttaaggttg aactaattga taaacgaaaa agattcaaaa cacagttatc aatcaaaagg 420
ttcaatggca aaaatttcct ccactgcaaa acgaatcacg aaaacaattt atttaagagg 480
aaagacatag ccattgggca caaatggttt ccaacgattg aagccattgc tagatgctat 540
agcacgatga atcgagaaga actacaaagc ctttatagag ggagcagtgg tctcacattc 600
attcaaaacg atgaattgtt cattgtcaga ggaagaatga atggtgaact tgtcaatagc 660
ttgtacgaga caaatcgggt tttggatatt gagcactac 699

<210> SEQ ID NO 2
<211> LENGTH: 1380
<212> TYPE: DNA

<213> ORGANISM: Sugarcane mosaic virus

<400> SEQUENCE: 2

```
gcagatcccc aggctaacga tttctggagg ggatacacaa atgcttacgt agagaatcgt    60
aacatttcga ctactcatac agagcacacc cctacaatca atctagaaga atgtggaaaa   120
cgaatggctc tactcgagat actatttcac tctacattca aaattacatg caagacatgc   180
aacattgatg atcttgaatt atcggatgat gaatttggag ctaaactcta caagaatttg   240
caacgtatcg aagagaaaca acgagagtat cttgcaaagg atcaaaaact atccagaatg   300
atacaattta tcaaagaaag gtgcaatcca aaattttcgc atttaccaac gctatggcaa   360
gttgcggaaa caatagggca ctatactgat aaccagtcaa agcaaataat ggatattagc   420
gaagcgctca tcaaagttaa tactctgact cctgatgatg ctatgaaagc aagcgcagcg   480
ttacttgaag tgtcgcgatg gtataagaat cgtaaggagt cactcaaaac tgactcattg   540
gaatctttta gaaataaaat atcaccaaag agtacaataa atgcagcttt aatgtgcgat   600
aatcaattgg ataaaaatgc aaattttgta tggggtaata gggaatacca cgccaaacga   660
tttttcgcaa actatttttga agcagtggat cccacagatg catatgaaaa gcacgtcaca   720
cggttcaacc ctaatggtca acgaaagtta tcaataggaa agttagttat cccactagac   780
tttcaaaaga ttagagaatc atttgttgga ctctcgataa atagacaacc gctggataaa   840
tgttgtgtta gcaagatcga aggagggtat atatacccat gttgctgcgt cacaacagaa   900
tttggtaaac cagcatactc tgagataata cctccaacga aagggcatat aacaataggc   960
aattctattg atccaaagat tgtggacttg ccaaatacaa caccacccag catgtacatt  1020
gctaaggatg ggtattgcta tatcaacatc ttttttagcag ccatgatcaa cgttaatgaa  1080
gaatctgcca aggattacac gaaattttg agggacgaac tagttgagcg tctcggaaag  1140
tggccaaagc ttaaagacgt agcaacagcg tgttatgcat tatctgtaat gtttccagaa  1200
attaagaatg ctgagctacc tccaattcta gttgaccatg aaaataaatc aatgcacgta  1260
attgattcat atggttcact aagcgttgga tttcacatat aaaaagcaag cacgattggt  1320
caattaatca aatttcaata tgagtctatg gatagtgaaa tgcgcgaata catagtagga  1380
```

<210> SEQ ID NO 3
<211> LENGTH: 1041
<212> TYPE: DNA
<213> ORGANISM: Sugarcane mosaic virus

<400> SEQUENCE: 3

```
ggaactctca cacaacagac attcaacaca cttcttaaga tgcttacgaa aaacatgttc    60
aaaccgagagc gcatcaagca gataattgaa gaggaaccct tcttacttat gatggcgatt   120
gcgtctccaa cggtattaat agcactatat aataattgtt atattgagca agctatgaca   180
tactggatcg ttaagaatca aggagttgca gccatattcg cacaactcga agcattagcc   240
aagaaaacat cccaggctga gctattagtt ctacaaatgc agatacttga aaaagcatct   300
aaccaattaa gattagcagt ttcaggactt agccatatcg acccagcaaa gcgacttttg   360
tggtcacacc ttgaagcgat gtcaacacga tcagaaatga acaaggagtt aatagctgag   420
gggtatgcac tatatgacga gcgcctatac accctgatgg aaaaaagtta cgtagatcaa   480
ttaaccaat catgggcaga attgtcatac tgtggaaaat tttcagcaat atggcgtgtg   540
ttcagagtca ggaagtatta caaaccgtct ttaaccgtga gaaaagcgt agatttaggc   600
gctgtataca atatatcagc tacgcatcta atatcagatt tagcgcggaa aagtcaagat   660
```
caagtcagct ctactttaac caaactccgc aacggtttct atgataaatt agagaaagtt 720
agaatacgaa ctataaaaac ggtttattgg tttatacctg atatatttag actcgtgcac 780
atattcatag ttttgagttt attaactacc atcgctaaca ctatcatagt aactatgaat 840
gactacaaga aattgaagaa gcaacaaaga gaagacgaat atgaagcaga aattaacgaa 900
gttcgcagaa tccattctac cttaatggaa gagcggaagg acaatctgac gtgtgaacaa 960
tttattgagt atatgcgtca aaatcatcca cggctagttg aagcaacact ggacttaact 1020
cacacaggtg tcatacatga a 1041

<210> SEQ ID NO 4
<211> LENGTH: 201
<212> TYPE: DNA
<213> ORGANISM: Sugarcane mosaic virus

<400> SEQUENCE: 4
gggaaatcca atctcgaaac caatttggaa caggcaatgg cagttggaac cttgataaca 60
atgatacttg atccacagaa aagcgatgct gtctataagg tgttgaacaa aatgcggaca 120
gtaattagta caattgaaca aaacgtccca ttcccttcag tgaatttctc caacatctta 180
acacctccag tggcacaaca g 201

<210> SEQ ID NO 5
<211> LENGTH: 1914
<212> TYPE: DNA
<213> ORGANISM: Sugarcane mosaic virus

<400> SEQUENCE: 5
agtgtagatg ttgatgagcc attaacactt agcactgata aaaatttaac aatagacttt 60
gacacaaatc aagatttacc tgccgataca ttcagtaatg atgtgacatt tgaagattgg 120
tggtcaaatc aattaagcaa caacagaaca gtgccacact accgacttgg gggaaagttc 180
attgaattca cacgagaaaa cgcagcccac acgagcatcg aacttgcaca ctcaaacatt 240
gagagggaat tcttgcttag aggagcagtc ggctcgggaa aatccactgg gttaccatac 300
catcttagca tgcgcggaaa agtgcttcta ctagagccta caagaccgct agctgagaac 360
gtgtgtaggc aactacaagg accgccattt aacgtaagtc caactcttca aatgcgtgga 420
ttaagttctt ttggatgcac tccaatcaca atcatgacat ctggttttgc attgcacatg 480
tacgcaaata atccagataa aatatctgag tacgatttca taatctttga tgaatgtcat 540
ataatggaag caccagcgat ggccttttat tgcttactca aagaatatga atatcgagga 600
aaaattatca aggtatcagc tacgcctcca ggaagggagt gtgaattcac aacacaacat 660
ccagtagaca tccatgtttg tgagaatcta actcagcaac agtttgttat ggaactcggg 720
actggttcaa ccgcagatgc tacgaagtac ggaaataata tcttagttta tgtagcaagc 780
tataatgacg tcgattcatt gtcgcaagca ctagtcgaac ttaaattttc cgtaatcaaa 840
gtggatggcc gaacaatgaa acaaaacaca acaggaatca ttacaaacgg taccgcacaa 900
aagaagtgtt ttgttgtcgc aacgaatata attgagaatg gcgtcacact agatattgat 960
gttgttgtcg acttcggact taaggtctca gctgacttgg acgttgacaa cagggcggta 1020
ttgtataaac gcgtaagtat atcatatggt gaacgcatac aacgattggg tcgtgttggc 1080
agaaataaac ctggtacagt tattcgaatc ggaaaaacaa tgaaaggttt gcaggaaatt 1140
ccagcaatga tcgcaacaga agcagccttc atgtgtttcg cttacggtct taaagttatc 1200

-continued

```
actcataatg tttcaacgac ccatcttgca aagtgcacag ttaaacaagc gagaaccatg   1260
atgcaatttg aattatcacc atttgtcatg gctgagctcg ttaagtttga tggttcaatg   1320
catccacaaa tacatgaggc actagtaaaa tacaaactta gagattctgt cataatgctc   1380
agaccgaatg cacttccaag ggtcaattta cataattggc ttacagcccg agattataat   1440
agaataggat gttcattaga actcgaagac cacgtcaaaa ttccgtacta cattagggga   1500
gttcctgaca agttgtatgg aaagctatat gatattatct tacagtatag tccaactagt   1560
tgctacggta gactatcaag tgcgtgtgca ggtaaagtag catatactct gcgaactgat   1620
ccattttcac ttccaagaac aatagcaata attaatgcct taatcacgga ggagtatgcg   1680
aagagagatc actatcgtaa catgatttca aacccatctt catcacacgc attctcactc   1740
aatgggttgg tgtctatgat cgctactaga tatatgaaag accatacaaa ggagaatatt   1800
gacaaactca ttagagtgcg tgatcaatta cttgagtttc aaggtactgg aatgcaattt   1860
caagatccat cagaactcat ggaaattggg gctctcaaca cagttattca ccaa         1914
```

```
<210> SEQ ID NO 6
<211> LENGTH: 159
<212> TYPE: DNA
<213> ORGANISM: Sugarcane mosaic virus

<400> SEQUENCE: 6
ggaatggacg caactgcagc ttgtattggg ttacaaggac gatggaatgc ttcacttata     60
caacgcgatc tcctgattgc aggtggagtt tttatcggag gcattttgat gatgtggagc    120
ctatttacta aatggagtaa cacaaatgtc tcacatcag                           159
```

```
<210> SEQ ID NO 7
<211> LENGTH: 567
<212> TYPE: DNA
<213> ORGANISM: Sugarcane mosaic virus

<400> SEQUENCE: 7
gggaagaaca aacgcagtag acaaaaaactt cgattcaaag aagcaagaga caacaaatat     60
gcatatgatg tcacaggatc ggaagaatgc cttggcgaga attttggaac agcctataca    120
aagaaaggta aaggaaaagg aactaaagtt ggactcggtg tgaagcagca taaattccat    180
atgatgtacg gtttcgatcc ccaagagtac aacctaattc ggtttgtcga tccactcacg    240
ggagcaactc ttgatgaaca aatccatgcc gatatacgct taattcaaga gcacttcgct    300
gaaattcgtg aggaggcagt gattaatgac acaattgaaa ggcagcagat ttacggcaat    360
cctggactac aagcattttt catacaaaat gggtcagcaa acgctctgag agttgattta    420
acaccacatt cacctacacg agttgtcaca ggtaataaca tagcagggtt cccagaatat    480
gaaggaacac ttcgtcagac tggaacagct ataactatac ccattggtca agtcccaatc    540
gcaaatgaag caggggttgc acacgag                                        567
```

```
<210> SEQ ID NO 8
<211> LENGTH: 726
<212> TYPE: DNA
<213> ORGANISM: Sugarcane mosaic virus

<400> SEQUENCE: 8
tcaaaatcca tgatgaacgg gttgggtgat tacacaccaa tatcgcaaca attgtgtcta     60
gtacaaaatg actcggatgg ggtaaagcgg aatgtatttt caattggata tggctcatat    120
cttatttcac cagcgcactt attcaaatat aacaatggtg aaataacaat tagatcatca    180
```

```
agaggattgt acaaaattcg taattctgtg gatttaaaat tacatccaat tgcacacaga    240
gacatggtca taattcaact cccaaaggat ttcccaccgt tcccaatgcg cttgaaattc    300
aaacaaccat cacgagatat gcgagtctgc ctagtaggtg tcaacttcca acagaattat    360
agcacttgca tcgtatcaga aagtagtgtg acagcaccaa aaggaaatgg agacttttgg    420
aaacattgga tatcaacagt cgacggtcaa tgtggactac cattggtaga tactaagagc    480
aaacatattg tcggaattca tagtcttgca tcaacaagtg gaaacactaa tttctttgtc    540
gctgtgcctg ggaactttaa tgaatacatc aatggacttg tgcaagcaaa taaatgggaa    600
aaaggatggc actataatcc gaatctcata tcctggtgtg gactaaattt agttgattct    660
gccccaaaag gtttgtttaa aacgtcaaaa ttggtagaag acttggacgc gagcgttgaa    720
gagcaa                                                              726
```

<210> SEQ ID NO 9
<211> LENGTH: 1563
<212> TYPE: DNA
<213> ORGANISM: Sugarcane mosaic virus

<400> SEQUENCE: 9

```
tgcaagatca ccgaaacatg gctcacagag caattacaag ataatttgca agtggttgcg     60
aaatgtccag gccaacttgt taccaagcat gttgttaagg gtcaatgccc acactttcaa    120
ttgtacttat caacacatga cgatgccaaa gaatacttcg cacccatgct tggaaaatac    180
gacaagagta ggcttaacag agcagctttt atcaaagaca tatcaaaata tgcaaaacca    240
atttatattg gagaaatcaa gtatgatatc tttgatagag ctgtacagcg ggttgtcaat    300
attctcaaaa atgttggaat gcaacaatgc gtttatgtca cagatgaaga agaaattttc    360
agatcactta acctgaacgc agctgtcgga gcattgtata caggaaagaa gaaaaattac    420
tttgaaaatt tttcaagcga agacaaagaa gagatcgtga tgagatcctg tgaacgtatt    480
tacaatgggc aacttggcgt atggaatgga tcgctcaaag ctgagatcag atcaatagag    540
aaaaccatgc tgaataagac tcgaaccttc acagcagccc cattagaaac tttgctcgga    600
ggaaaagtgt gcgtggatga ttttaataat caattctatt cacatcattt agaaggtcca    660
tggactgttg ggataacaaa attctatgga ggttggaatc gcttacttga gaagttacca    720
gaaggatggg tttactgcga tgctgacggg tctcaatttg atagttcgtt aacaccatat    780
ctcatcaatg cagtattaaa tattcgattg caatttatgg aagattggga tataggagcg    840
caaatgctaa agaacctgta cactgagatt gtttacacac caatcgcaac gccagacgga    900
tcaatcgtga agaaattcaa aggtaacaat agcggacaac cttctacagt agtggacaac    960
acattgatgg ttataatagc tttcaactat gccatgctat caagtggtat caaagaagaa   1020
gaaatcgata attgctgtag aatgtttgcg aatggtgatg acttactcct agcagtgcat   1080
cctgattttg agttcatttt agatgaattt caaaatcact ttgggaatct tgggctgaac   1140
ttcgaattta catcacgaac acgagacaaa tccgaactgt ggttcatgtc cacaagaggc   1200
atcaagtatg aaggaattta cataccaaag cttgagaaag aaagaatagt cgccatactt   1260
gaatgggatc gatcaaactt gcctgaacat aggttggaag ctatatgtgc agcgatggtt   1320
gaggcctggg gatattccga tctcgttcat gaaatacgaa agttctatgc gtggcttttg   1380
gaaatgcaac cttttgcaaa tctcgcaaaa gaagggttgg ccccatacat tgccgagaca   1440
gcactccgca atctctatct tggaacgggt atcaaagagg aagaaattga aaaatatctt   1500
```
aaacaattca ttaaggatct tcccggatac atagaagatt acaatgaaga tgtattccat 1560
cag 1563

<210> SEQ ID NO 10
<211> LENGTH: 987
<212> TYPE: DNA
<213> ORGANISM: Sugarcane mosaic virus

<400> SEQUENCE: 10
tcgggaactg ttgatgcggg tgcacaaggc ggcagtggaa gccaagggac aacaccacca 60
gcaacaggta gtggagcaaa accagccacc tcaggggcag gatctggtag tggcacagga 120
gctggaactg gtgtaactgg aggtcaagca aggactggca gtggcactgg gacgggatct 180
ggagcaaccg gaggccaatc aggatctgga agtggcactg aacaggttaa cacgggttca 240
gcaggaacta atgcaactgg aggccaaaga gatagggatg tggatgcagg tacaacagga 300
aaaatttctg taccaaagct caaggccatg tcaaagaaaa tgcgcttacc taaagcaaaa 360
ggaaaagatg tgctacattt ggattttcta ttgacataca aaccacaaca acaagacata 420
tcaaacacta gagcaaccaa ggaagagttt gatagatggt atgatgccat aaagaaggaa 480
tacgaaattg atgacacaca aatgacagtt gtcatgagtg gccttatggt atggtgcatc 540
gaaaatggtt gctcaccaaa cataaacgga aattggacaa tgatggatga agatgaacaa 600
agggtctttc cactcaaacc ggtcattgag aatgcatctc caactttccg acaaattatg 660
catcatttca gtgatgcagc tgaagcgtac atagagtaca gaaactctac tgagcgatat 720
atgccaagat acggacttca gcgcaatctc accgactata gcttagcacg gtatgcattt 780
gatttctatg aaatgacttc acgcacacct gctagagcta aagaagccca catgcagatg 840
aaagccgcag cagttcgtgg ttcaaacaca cgactgttcg gtttggacgg aaatgtcggc 900
gagactcagg agaatacaga gagacacaca gctggcgatg ttagtcgcaa catgcactct 960
ctgttgggag tgcagcagca ccactag 987

<210> SEQ ID NO 11
<211> LENGTH: 9642
<212> TYPE: DNA
<213> ORGANISM: Sugarcane mosaic virus

<400> SEQUENCE: 11
aaaaacaaca aaactcaaca caacacaaca aaacacaacc aagcaaatcc aatttacttg 60
cgctcagatt gtagtgaacg gctcgaacga aacggttctt cgagatcact ctctgattct 120
tcctcatctt tcaatttctt tcgaaagaaa tggcgggaac gtggacctac gtgacacgta 180
agtggcagcc agatgttaac aacgatcgtc acattaaaag agtgatggaa atgtttgcag 240
caaaacatca acattactca gaagaacagc gacttgccca taatatgaaa ttattgagga 300
aggcaagtgt tgtaagcgtt gagcctgcga aaccaaagca gaagcaggca actcaacaga 360
tgtgggttga gaaatgtgat cacaatcctg ttgatcactt agtatatcca cgacttggaa 420
aatccgcgaa caaagcagat atgagtatta aaagtgcatc tgtaagcaaa ctaaccagag 480
agattttaga aatctcaaag gttagcggcc ttaaggttga actaattgat aaacgaaaaa 540
gattcaaaac acagttatca atcaaaaggt tcaatggcaa aaatttcctc cactgcaaaa 600
cgaatcacga aaacaattta tttaagagga aagacatagc cattgggcac aaatggtttc 660
caacgattga agccattgct agatgctata gcacgatgaa tcgagaagaa ctacaaagcc 720
tttatagagg gagcagtggt ctcacattca ttcaaaacga tgaattgttc attgtcagag 780

```
gaagaatgaa tggtgaactt gtcaatagct tgtacgagac aaatcgggtt ttggatattg      840
agcactacgc agatccccag gctaacgatt tctggagggg atacacaaat gcttacgtag      900
agaatcgtaa catttcgact actcatacag agcacacccc tacaatcaat ctagaagaat      960
gtggaaaacg aatggctcta ctcgagatac tatttcactc tacattcaaa attacatgca     1020
agacatgcaa cattgatgat cttgaattat cggatgatga atttggagct aaactctaca     1080
agaatttgca acgtatcgaa gagaaacaac gagagtatct tgcaaaggat caaaaactat     1140
ccagaatgat acaatttatc aaagaaaggt gcaatccaaa attttcgcat ttaccaacgc     1200 tatgcaagt tgcggaaaca atagggcact atactgataa ccagtcaaag caaataatgg     1260
atattagcga agcgctcatc aaagttaata ctctgactcc tgatgatgct atgaaagcaa     1320
gcgcagcgtt acttgaagtg tcgcgatggt ataagaatcg taaggagtca ctcaaaactg     1380
actcattgga atcttttaga aataaaatat caccaaagag tacaataaat gcagctttaa     1440
tgtgcgataa tcaattggat aaaaatgcaa attttgtatg gggtaatagg gaataccacg     1500
ccaaacgatt tttcgcaaac tattttgaag cagtggatcc cacagatgca tatgaaaagc     1560
acgtcacacg gttcaaccct aatggtcaac gaaagttatc aataggaaag ttagttatcc     1620
cactagactt tcaaaagatt agagaatcat tgttggact ctcgataaat agacaaccgc      1680
tggataaatg ttgtgttagc aagatcgaag gagggtatat atacccatgt tgctgcgtca     1740
caacagaatt tggtaaacca gcatactctg agataatacc tccaacgaaa gggcatataa     1800
caataggcaa ttctattgat ccaaagattg tggacttgcc aaatacaaca ccacccagca     1860
tgtacattgc taaggatggg tattgctata tcaacatctt tttagcagcc atgatcaacg     1920
ttaatgaaga atctgccaag gattacacga aattttttgag ggacgaacta gttgagcgtc     1980
tcggaaagtg gccaaagctt aaagacgtag caacagcgtg ttatgcatta tctgtaatgt     2040
ttccagaaat taagaatgct gagctacctc caattctagt tgaccatgaa aataaatcaa     2100
tgcacgtaat tgattcatat ggttcactaa gcgttggatt tcacatatta aaagcaagca     2160
cgattggtca attaatcaaa tttcaatatg agtctatgga tagtgaaatg cgcgaataca     2220
tagtaggagg aactctcaca caacagacat tcaacacact tcttaagatg cttacgaaaa     2280
acatgttcaa accagagcgc atcaagcaga taattgaaga ggaacccttc ttacttatga     2340
tggcgattgc gtctccaacg gtattaatag cactatataa taattgttat attgagcaag     2400
ctatgacata ctggatcgtt aagaatcaag gagttgcagc catattcgca caactcgaag     2460
cattagccaa gaaaacatcc caggctgagc tattagttct acaaatgcag atacttgaaa     2520
aagcatctaa ccaattaaga ttagcagttt caggacttag ccatatcgac ccagcaaagc     2580
gacttttgtg gtcacacctt gaagcgatgt caacacgatc agaaatgaac aaggagttaa     2640
tagctgaggg gtatgcacta tatgacgagc gcctatacac cctgatggaa aaaagttacg     2700
tagatcaatt aaaccaatca tgggcagaat tgtcatactg tggaaaattt tcagcaatat     2760
ggcgtgtgtt cagagtcagg aagtattaca aaccgtcttt aaccgtgaga aaaagcgtag     2820
atttaggcgc tgtatacaat atatcagcta cgcatctaat atcagattta gcgcggaaaa     2880
gtcaagatca agtcagctct actttaacca aactccgcaa cggtttctat gataaattag     2940
agaaagttag aatacgaact ataaaaacgg tttattggtt tatacctgat atatttagac     3000
tcgtgcacat attcatagtt ttgagtttat taactaccat cgctaacact atcatagtaa     3060
ctatgaatga ctacaagaaa ttgaagaagc aacaaagaga agacgaatat gaagcagaaa     3120
```

```
ttaacgaagt tcgcagaatc cattctacct taatggaaga gcggaaggac aatctgacgt    3180
gtgaacaatt tattgagtat atgcgtcaaa atcatccacg gctagttgaa gcaacactgg    3240
acttaactca cacaggtgtc atacatgaag ggaaatccaa tctcgaaacc aatttggaac    3300
aggcaatggc agttggaacc ttgataacaa tgatacttga tccacagaaa agcgatgctg    3360
tctataaggt gttgaacaaa atgcggacag taattagtac aattgaacaa aacgtcccat    3420
tcccttcagt gaatttctcc aacatcttaa cacctccagt ggcacaacag agtgtagatg    3480
ttgatgagcc attaacactt agcactgata aaaatttaac aatagacttt gacacaaatc    3540
aagatttacc tgccgataca ttcagtaatg atgtgacatt tgaagattgg tggtcaaatc    3600
aattaagcaa caacagaaca gtgccacact accgacttgg gggaaagttc attgaattca    3660
cacgagaaaa cgcagcccac acgagcatcg aacttgcaca ctcaaacatt gagagggaat    3720
tcttgcttag aggagcagtc ggctcgggaa atccactggg gttaccatac catcttagca    3780
tgcgcggaaa agtgcttcta ctagagccta caagaccgct agctgagaac gtgtgtaggc    3840
aactacaagg accgccattt aacgtaagtc caactcttca aatgcgtgga ttaagttctt    3900
ttggatgcac tccaatcaca atcatgacat ctggttttgc attgcacatg tacgcaaata    3960
atccagataa aatatctgag tacgatttca taatctttga tgaatgtcat ataatggaag    4020
caccagcgat ggccttttat tgcttactca aagaatatga atatcgagga aaaattatca    4080
aggtatcagc tacgcctcca ggaagggagt gtgaattcac aacacaacat ccagtagaca    4140
tccatgtttg tgagaatcta actcagcaac agtttgttat ggaactcggg actggttcaa    4200
ccgcagatgc tacgaagtac ggaaataata tcttagttta tgtagcaagc tataatgacg    4260
tcgattcatt gtcgcaagca ctagtcgaac ttaaattttc cgtaatcaaa gtggatggcc    4320
gaacaatgaa acaaaacaca acaggaatca ttacaaacgg taccgcacaa agaagtgtt    4380 ttgttgtcgc aacgaatata attgagaatg gcgtcacact agatattgat gttgttgtcg    4440
acttcggact taaggtctca gctgacttgg acgttgacaa cagggcggta ttgtataaac    4500
gcgtaagtat atcatatggt gaacgcatac aacgattggg tcgtgttggc agaaataaac    4560
ctggtacagt tattcgaatc ggaaaaacaa tgaaaggttt gcaggaaatt ccagcaatga    4620
tcgcaacaga agcagccttc atgtgtttcg cttacggtct taaagttatc actcataatg    4680
tttcaacgac ccatcttgca aagtgcacag ttaaacaagc gagaaccatg atgcaatttg    4740
aattatcacc atttgtcatg gctgagctcg ttaagtttga tggttcaatg catccacaaa    4800
tacatgaggc actagtaaaa tacaaactta gagattctgt cataatgctc agaccgaatg    4860
cacttccaag ggtcaattta cataattggc ttacagcccg agattataat agaataggat    4920
gttcattaga actcgaagac cacgtcaaaa ttccgtacta cattagggga gttcctgaca    4980
agttgtatgg aaagctatat gatattatct tacagtatag tccaactagt tgctacggta    5040
gactatcaag tgcgtgtgca ggtaaagtag catatactct gcgaactgat ccattttcac    5100
ttccaagaac aatagcaata attaatgcct taatcacgga ggagtatgcg aagagagatc    5160
actatcgtaa catgatttca aacccatctt catcacacgc attctcactc aatgggttgg    5220
tgtctatgat cgctactaga tatatgaaag accatacaaa ggagaatatt gacaaactca    5280
ttagagtgcg tgatcaatta cttgagtttc aaggtactgg aatgcaattt caagatccat    5340
cagaactcat ggaaattggg gctctcaaca cagttattca ccaaggaatg gacgcaactg    5400
cagcttgtat tgggttacaa ggacgatgga atgcttcact tatacaacgc gatctcctga    5460
ttgcaggtgg agtttttatc ggaggcattt tgatgatgtg gagcctattt actaaatgga    5520
```

```
gtaacacaaa tgtctcacat caggggaaga acaaacgcag tagacaaaaa cttcgattca    5580
aagaagcaag agacaacaaa tatgcatatg atgtcacagg atcggaagaa tgccttggcg    5640
agaattttgg aacagcctat acaaagaaag gtaaaggaaa aggaactaaa gttggactcg    5700
gtgtgaagca gcataaattc catatgatgt acggtttcga tccccaagag tacaacctaa    5760
ttcggtttgt cgatccactc acgggagcaa ctcttgatga acaaatccat gccgatatac    5820
gcttaattca agagcacttc gctgaaattc gtgaggaggc agtgattaat gacacaattg    5880
aaaggcagca gatttacggc aatcctggac tacaagcatt tttcatacaa aatgggtcag    5940
caaacgctct gagagttgat ttaacaccac attcacctac acgagttgtc acaggtaata    6000
acatagcagg gttcccagaa tatgaaggaa cacttcgtca gactggaaca gctataacta    6060
tacccattgg tcaagtccca atcgcaaatg aagcaggggt tgcacacgag tcaaaatcca    6120
tgatgaacgg gttgggtgat tacacaccaa tatcgcaaca attgtgtcta gtacaaaatg    6180
actcggatgg ggtaaagcgg aatgtatttt caattggata tggctcatat cttatttcac    6240
cagcgcactt attcaaatat aacaatggtg aaataacaat tagatcatca agaggattgt    6300
acaaaattcg taattctgtg gatttaaaat tacatccaat tgcacacaga gacatggtca    6360
taattcaact cccaaaggat ttcccaccgt tcccaatgcg cttgaaattc aaacaaccat    6420
cacgagatat gcgagtctgc ctagtaggtg tcaacttcca acagaattat agcacttgca    6480
tcgtatcaga aagtagtgtg acagcaccaa aaggaaatgg agacttttgg aaacattgga    6540
tatcaacagt cgacggtcaa tgtggactac cattggtaga tactaagagc aaacatattg    6600
tcggaattca tagtcttgca tcaacaagtg aaaacactaa tttctttgtc gctgtgcctg    6660
ggaactttaa tgaatacatc aatggacttg tgcaagcaaa taaatgggaa aaggatggc     6720 actataatcc gaatctcata tcctggtgtg gactaaattt agttgattct gccccaaaag    6780 gtttgttta aacgtcaaaa ttggtagaag acttggacgc gagcgttgaa gagcaatgca    6840
agatcaccga acatggctc acagagcaat tacaagataa tttgcaagtg gttgcgaaat    6900
gtccaggcca acttgttacc aagcatgttg ttaagggtca atgcccacac tttcaattgt    6960
acttatcaac acatgacgat gccaaagaat acttcgcacc catgcttgga aaatacgaca    7020
agagtaggct taacagagca gcttttatca aagacatatc aaaatatgca aaaccaattt    7080
atattggaga aatcaagtat gatatctttg atagagctgt acagcgggtt gtcaatattc    7140
tcaaaaatgt tggaatgcaa caatgcgttt atgtcacaga tgaagaagaa atttcagat     7200 cacttaacct gaacgcagct gtcggagcat tgtatacagg aaagaagaaa attactttg     7260 aaaattttc aagcgaagac aaagaagaga tcgtgatgag atcctgtgaa cgtatttaca    7320
atgggcaact tggcgtatgg aatggatcgc tcaaagctga gatcagatca atagagaaaa    7380
ccatgctgaa taagactcga accttcacag cagccccatt agaaactttg ctcggaggaa    7440
aagtgtgcgt ggatgatttt aataatcaat tctattcaca tcatttagaa ggtccatgga    7500
ctgttgggat aacaaaattc tatggaggtt ggaatcgctt acttgagaag ttaccagaag    7560
gatgggttta ctgcgatgct gacgggtctc aatttgatag ttcgttaaca ccatatctca    7620
tcaatgcagt attaaatatt cgattgcaat ttatggaaga ttgggatata ggagcgcaaa    7680
tgctaaagaa cctgtacact gagattgttt acacaccaat cgcaacgcca gacggatcaa    7740
tcgtgaagaa attcaaaggt aacaatagcg gacaaccttc tacagtagtg gacaacacat    7800
tgatggttat aatagctttc aactatgcca tgctatcaag tggtatcaaa gaagaagaaa    7860
```

```
tcgataattg ctgtagaatg tttgcgaatg gtgatgactt actcctagca gtgcatcctg    7920
attttgagtt catttttagat gaatttcaaa atcactttgg gaatcttggg ctgaacttcg    7980
aatttacatc acgaacacga gacaaatccg aactgtggtt catgtccaca agaggcatca    8040
agtatgaagg aatttacata ccaaagcttg agaaagaaag aatagtcgcc atacttgaat    8100
gggatcgatc aaacttgcct gaacataggt tggaagctat atgtgcagcg atggttgagg    8160
cctggggata ttccgatctc gttcatgaaa tacgaaagtt ctatgcgtgg cttttggaaa    8220
tgcaaccttt tgcaaatctc gcaaaagaag ggttggcccc atacattgcc gagacagcac    8280
tccgcaatct ctatcttgga acgggtatca agaggaaga aattgaaaaa tatcttaaac     8340
aattcattaa ggatcttccc ggatacatag aagattacaa tgaagatgta ttccatcagt    8400
cgggaactgt tgatgcgggt gcacaaggcg gcagtggaag ccaagggaca acaccaccag    8460
caacaggtag tggagcaaaa ccagccacct caggggcagg atctggtagt ggcacaggag    8520
ctggaactgg tgtaactgga ggtcaagcaa ggactggcag tggcactggg acgggatctg    8580
gagcaaccgg aggccaatca ggatctggaa gtggcactga acaggttaac acgggttcag    8640
caggaactaa tgcaactgga ggccaaagag ataggggatgt ggatgcaggt acaacaggaa    8700
aaatttctgt accaaagctc aaggccatgt caaagaaaat gcgcttacct aaagcaaaag    8760
gaaaagatgt gctacatttg gattttctat tgacatacaa accacaacaa caagacatat    8820
caaacactag agcaaccaag gaagagtttg atagatggta tgatgccata agaaggaat    8880 acgaaattga tgacacacaa atgacagttg tcatgagtgg ccttatggta tggtgcatcg    8940
aaaatggttg ctcaccaaac ataaacggaa attggacaat gatggatgaa gatgaacaaa    9000 gggtcttttcc actcaaaccg gtcattgaga atgcatctcc aactttccga caaattatgc    9060
atcatttcag tgatgcagct gaagcgtaca tagagtacag aaactctact gagcgatata    9120
tgccaagata cggacttcag cgcaatctca ccgactatag cttagcacgg tatgcatttg    9180
atttctatga aatgacttca cgcacacctg ctagagctaa agaagcccac atgcagatga    9240
aagccgcagc agttcgtggt tcaaacacac gactgttcgg tttggacgga aatgtcggcg    9300
agactcagga gaatacagag agacacacag ctggcgatgt tagtcgcaac atgcactctc    9360
tgttgggagt gcagcagcac cactagtctc ctggaaaccc tgtttgcagt accaataata    9420
tgtactaata tatagtattt tagtgaggtt ttacctcgtc tttactgttt tattacgtat    9480
gtatttaaag cgtgaaccag tctgcaacat acagggttgg acccagtgtg ttctggtgta    9540
gcgtgtacta gcgtcgagcc atgagatgga ctgcactggg tgtggttttg ccacttgtgt    9600
tgcgagtctc ttggtgagag acaaaaaaaa aaaaaaaaaa aa                       9642
```

<210> SEQ ID NO 12
<211> LENGTH: 18
<212> TYPE: DNA
<213> ORGANISM: Artificial Sequence
<220> FEATURE:
<223> OTHER INFORMATION: Syntheic construct
<400> SEQUENCE: 12

```
agatctcccg ggcgtacg                                                     18
```

<210> SEQ ID NO 13
<211> LENGTH: 12
<212> TYPE: DNA
<213> ORGANISM: Artificial Sequence
<220> FEATURE:
<223> OTHER INFORMATION: Syntheic construct

<400> SEQUENCE: 13
ccgcggcccg gg																12

<210> SEQ ID NO 14
<211> LENGTH: 24
<212> TYPE: DNA
<213> ORGANISM: Artificial Sequence
<220> FEATURE:
<223> OTHER INFORMATION: Syntheic construct

<400> SEQUENCE: 14
gggccctgtt taaacgcctg cagg															24

<210> SEQ ID NO 15
<211> LENGTH: 24
<212> TYPE: DNA
<213> ORGANISM: Artificial Sequence
<220> FEATURE:
<223> OTHER INFORMATION: Syntheic construct

<400> SEQUENCE: 15
gaggacgtgt ttcaccaatc cgca															24

<210> SEQ ID NO 16
<211> LENGTH: 9684
<212> TYPE: DNA
<213> ORGANISM: Artificial Sequence
<220> FEATURE:
<223> OTHER INFORMATION: Syntheic construct

<400> SEQUENCE: 16
aaaaacaaca aaactcaaca caacacaaca aaacacaacc aagcaaatcc aatttacttg			60 cgctcagatt gtagtgaacg gctcgaacga aacggttctt cgagatcact ctctgattct			120 tcctcatctt tcaatttctt tcgaaagaaa tggcgggaac gtggacctac gtgacacgta			180 agtggcagcc agatgttaac aacgatcgtc acattaaaag agtgatggaa atgtttgcag			240 caaaacatca acattactca gaagaacagc gacttgccca taatatgaaa ttattgagga			300 aggcaagtgt tgtaagcgtt gagcctgcga aaccaaagca gaagcaggca actcaacaga			360 tgtgggttga gaaatgtgat cacaatcctg ttgatcactt agtatatcca cgacttggaa			420 aatccgcgaa caaagcagat atgagtatta aaagtgcatc tgtaagcaaa ctaaccagag			480 agattttaga aatctcaaag gttagcggcc ttaaggttga actaattgat aaacgaaaaa			540 gattcaaaac acagttatca atcaaaaggt tcaatggcaa aaatttcctc cactgcaaaa			600 cgaatcacga aaacaattta tttaagagga aagacatagc cattgggcac aaatggtttc			660 caacgattga agccattgct agatgctata gcacgatgaa tcgagaagaa ctacaaagcc			720 tttatagagg gagcagtggt ctcacattca ttcaaaacga tgaattgttc attgtcagag			780 gaagaatgaa tggtgaactt gtcaatagct tgtacgagac aaatcgggtt ttggatattg			840 agcactacgc aagatctccc gggcgtacgg aggacgtgtt tcaccaatcc gcagatcccc			900 aggctaacga tttctggagg ggatacacaa atgcttacgt agagaatcgt aacatttcga			960 ctactcatac agagcacacc cctacaatca atctagaaga atgtgaaaaa cgaatggctc			1020 tactcgagat actatttcac tctacattca aaattacatg caagacatgc aacattgatg			1080 atcttgaatt atcggatgat gaatttggag ctaaactcta caagaatttg caacgtatcg			1140 aagagaaaca acgagagtat cttgcaaagg atcaaaaact atccagaatg atacaatttat			1200

```
tcaaagaaag gtgcaatcca aaattttcgc atttaccaac gctatggcaa gttgcggaaa      1260
caatagggca ctatactgat aaccagtcaa agcaaataat ggatattagc gaagcgctca      1320
tcaaagttaa tactctgact cctgatgatg ctatgaaagc aagcgcagcg ttacttgaag      1380
tgtcgcgatg gtataagaat cgtaaggagt cactcaaaac tgactcattg gaatctttta      1440
gaaataaaat atcaccaaag agtacaataa atgcagcttt aatgtgcgat aatcaattgg      1500
ataaaaatgc aaattttgta tggggtaata gggaatacca cgccaaacga ttttcgcaa       1560 actattttga agcagtggat cccacagatg catatgaaaa gcacgtcaca cggttcaacc      1620
ctaatggtca acgaaagtta tcaataggaa agttagttat cccactagac tttcaaaaga      1680
ttagagaatc atttgttgga ctctcgataa atagacaacc gctggataaa tgttgtgtta      1740
gcaagatcga aggagggtat atatacccat gttgctgcgt cacaacagaa tttggtaaac      1800
cagcatactc tgagataata cctccaacga aagggcatat aacaataggc aattctattg      1860
atccaaagat tgtggacttg ccaaatacaa caccacccag catgtacatt gctaaggatg      1920
ggtattgcta tatcaacatc ttttagcag ccatgatcaa cgttaatgaa gaatctgcca       1980
aggattacac gaattttttg agggacgaac tagttgagcg tctcggaaag tggccaaagc      2040
ttaaagacgt agcaacagcg tgttatgcat tatctgtaat gtttccagaa attaagaatg      2100
ctgagctacc tccaattcta gttgaccatg aaaataaatc aatgcacgta attgattcat      2160
atggttcact aagcgttgga tttcacatat aaaaagcaag cacgattggt caattaatca      2220
aatttcaata tgagtctatg gatagtgaaa tgcgcgaata catagtagga ggaactctca      2280
cacaacagac attcaacaca cttcttaaga tgcttacgaa aaacatgttc aaaccagagc      2340
gcatcaagca gataattgaa gaggaaccct tcttacttat gatggcgatt gcgtctccaa      2400
cggtattaat agcactatat aataattgtt atattgagca agctatgaca tactggatcg      2460
ttaagaatca aggagttgca gccatattcg cacaactcga agcattagcc aagaaaacat      2520
cccaggctga gctattagtt ctacaaatgc agatacttga aaaagcatct aaccaattaa      2580
gattagcagt ttcaggactt agccatatcg acccagcaaa gcgacttttg tggtcacacc      2640
ttgaagcgat gtcaacacga tcagaaatga caaggagtt aatagctgag gggtatgcac       2700
tatatgacga gcgcctatac accctgatgg aaaaaagtta cgtagatcaa ttaaaccaat      2760
catgggcaga attgtcatac tgtggaaaat tttcagcaat atggcgtgtg ttcagagtca      2820
ggaagtatta caaaccgtct ttaaccgtga gaaaaagcgt agatttaggc gctgtataca      2880
atatatcagc tacgcatcta atatcagatt tagcgcggaa aagtcaagat caagtcagct      2940
ctactttaac caaactccgc aacggtttct atgataaatt agagaaagtt agaatacgaa      3000
ctataaaaac ggtttattgg tttatacctg atatattag actcgtgcac atattcatag       3060
ttttgagttt attaactacc atcgctaaca ctatcatagt aactatgaat gactacaaga      3120
aattgaagaa gcaacaaaga gaagacgaat atgaagcaga aattaacgaa gttcgcagaa      3180
tccattctac cttaatggaa gagcggaagg acaatctgac gtgtgaacaa tttattgagt      3240
atatgcgtca aaatcatcca cggctagttg aagcaacact ggacttaact cacacaggtg      3300
tcatacatga agggaaatcc aatctcgaaa ccaatttgga acaggcaatg gcagttggaa      3360
ccttgataac aatgatactt gatccacaga aaagcgatgc tgtctataag gtgttgaaca      3420
aaatgcggac agtaattagt acaattgaac aaaacgtccc attcccttca gtgaatttct      3480
ccaacatctt aacacctcca gtggcacaac agagtgtaga tgttgatgag ccattaacac      3540
ttagcactga taaaaattta acaatagact ttgacacaaa tcaagattta cctgccgata      3600
```

```
cattcagtaa tgatgtgaca tttgaagatt ggtggtcaaa tcaattaagc aacaacagaa   3660
cagtgccaca ctaccgactt gggggaaagt tcattgaatt cacacgagaa aacgcagccc   3720
acacgagcat cgaacttgca cactcaaaca ttgagaggga attcttgctt agaggagcag   3780
tcggctcggg aaaatccact gggttaccat accatcttag catgcgcgga aaagtgcttc   3840
tactagagcc tacaagaccg ctagctgaga acgtgtgtag gcaactacaa ggaccgccat   3900
ttaacgtaag tccaactctt caaatgcgtg gattaagttc ttttggatgc actccaatca   3960
caatcatgac atctggtttt gcattgcaca tgtacgcaaa taatccagat aaaatatctg   4020
agtacgattt cataatcttt gatgaatgtc atataatgga agcaccagcg atggcctttt   4080
attgcttact caaagaatat gaatatcgag gaaaaattat caaggtatca gctacgcctc   4140
caggaaggga gtgtgaattc acaacacaac atccagtaga catccatgtt tgtgagaatc   4200
taactcagca acagtttgtt atggaactcg ggactggttc aaccgcagat gctacgaagt   4260
acggaaataa tatcttagtt tatgtagcaa gctataatga cgtcgattca ttgtcgcaag   4320
cactagtcga acttaaattt tccgtaatca agtggatgg ccgaacaatg aaacaaaaca   4380
caacaggaat cattacaaac ggtaccgcac aaaagaagtg ttttgttgtc gcaacgaata   4440
taattgagaa tggcgtcaca ctagatattg atgttgttgt cgacttcgga cttaaggtct   4500
cagctgactt ggacgttgac aacagggcgg tattgtataa acgcgtaagt atatcatatg   4560
gtgaacgcat acaacgattg ggtcgtgttg gcagaaataa acctggtaca gttattcgaa   4620
tcggaaaaac aatgaaaggt ttgcaggaaa ttccagcaat gatcgcaaca gaagcagcct   4680
tcatgtgttt cgcttacggt cttaaagtta tcactcataa tgtttcaacg acccatcttg   4740
caaagtgcac agtaaacaa gcagagaacca tgatgcaatt tgaattatca ccatttgtca   4800
tggctgagct cgttaagttt gatggttcaa tgcatccaca aatacatgag gcactagtaa   4860
aatacaaact tagagattct gtcataatgc tcagaccgaa tgcacttcca agggtcaatt   4920
tacataattg gcttacagcc cgagattata atagaatagg atgttcatta gaactcgaag   4980
accacgtcaa aattccgtac tacattaggg gagttcctga caagttgtat ggaaagctat   5040
atgatattat cttacagtat agtccaacta gttgctacgg tagactatca agtgcgtgtg   5100
caggtaaagt agcatatact ctgcgaactg atccattttc acttccaaga acaatagcaa   5160
taattaatgc cttaatcacg gaggagtatg cgaagagaga tcactatcgt aacatgattt   5220
caaacccatc ttcatcacac gcattctcac tcaatgggtt ggtgtctatg atcgctacta   5280
gatatatgaa agaccataca aaggagaata ttgacaaact cattagagtg cgtgatcaat   5340
tacttgagtt tcaaggtact ggaatgcaat tcaagatcc atcagaactc atggaaattg   5400
gggctctcaa cacagttatt caccaaggaa tggacgcaac tgcagcttgt attgggttac   5460
aaggacgatg gaatgcttca cttatacaac gcgatctcct gattgcaggt ggagttttta   5520
tcggaggcat tttgatgatg tggagcctat ttactaaatg gagtaacaca aatgtctcac   5580
atcaggggaa gaacaaacgc agtagacaaa aacttcgatt caaagaagca agagacaaca   5640
aatatgcata tgatgtcaca ggatcggaag aatgccttgg cgagaatttt ggaacagcct   5700
atacaaagaa aggtaaagga aaaggaacta agtggact cggtgtgaag cagcataaat   5760
tccatatgat gtacggtttc gatccccaag agtacaacct aattcggttt gtcgatccac   5820
tcacgggagc aactcttgat gaacaaatcc atgccgatat acgcttaatt caagagcact   5880
tcgctgaaat tcgtgaggag gcagtgatta atgacacaat tgaaaggcag cagatttacg   5940
```

-continued

```
gcaatcctgg actacaagca tttttcatac aaaatgggtc agcaaacgct ctgagagttg      6000
atttaacacc acattcacct acacgagttg tcacaggtaa taacatagca gggttcccag      6060
aatatgaagg aacacttcgt cagactggaa cagctataac tatacccatt ggtcaagtcc      6120
caatcgcaaa tgaagcaggg gttgcacacg agtcaaaatc catgatgaac gggttgggtg      6180
attacacacc aatatcgcaa caattgtgtc tagtacaaaa tgactcggat ggggtaaagc      6240
ggaatgtatt ttcaattgga tatggctcat atcttatttc accagcgcac ttattcaaat      6300
ataacaatgg tgaaataaca attagatcat caagaggatt gtacaaaatt cgtaattctg      6360
tggatttaaa attacatcca attgcacaca gagacatggt cataattcaa ctcccaaagg      6420
atttcccacc gttcccaatg cgcttgaaat tcaaacaacc atcacgagat atgcgagtct      6480
gcctagtagg tgtcaacttc aacagaatt atagcacttg catcgtatca gaaagtagtg       6540
tgacagcacc aaaaggaaat ggagactttt ggaaacattg gatatcaaca gtcgacggtc      6600
aatgtggact accattggta gatactaaga gcaaacatat tgtcggaatt catagtcttg      6660
catcaacaag tggaaacact aatttctttg tcgctgtgcc tgggaacttt aatgaataca      6720
tcaatggact tgtgcaagca aataaatggg aaaaggatg gcactataat ccgaatctca       6780
tatcctggtg tggactaaat ttagttgatt ctgccccaaa aggtttgttt aaaacgtcaa      6840
aattggtaga agacttggac gcgagcgttg aagagcaatg caagatcacc gaaacatggc      6900
tcacagagca attacaagat aatttgcaag tggttgcgaa atgtccaggc caacttgtta      6960
ccaagcatgt tgttaagggt caatgcccac actttcaatt gtacttatca acacatgacg      7020
atgccaaaga atacttcgca cccatgcttg gaaaatacga caagagtagg cttaacagag      7080
cagcttttat caaagacata tcaaaatatg caaaaccaat ttatattgga gaaatcaagt      7140
atgatatctt tgatagagct gtacagcggg ttgtcaatat tctcaaaaat gttggaatgc      7200
aacaatgcgt ttatgtcaca gatgaagaag aaattttcag atcacttaac ctgaacgcag      7260
ctgtcggagc attgtataca ggaagagaaga aaaattactt tgaaaatttt tcaagcgaag      7320
acaaagaaga gatcgtgatg agatcctgtg aacgtattta caatgggcaa cttggcgtat      7380
ggaatggatc gctcaaagct gagatcagat caatagagaa aaccatgctg aataagactc      7440
gaaccttcac agcagcccca ttagaaactt tgctcggagg aaaagtgtgc gtggatgatt      7500
ttaataatca attctattca catcatttag aaggtccatg gactgttggg ataacaaaat      7560
tctatggagg ttggaatcgc ttacttgaga agttaccaga aggatgggtt tactgcgatg      7620
ctgacgggtc tcaatttgat agttcgttaa caccatatct catcaatgca gtattaaata      7680
ttcgattgca atttatggaa gattgggata taggagcgca aatgctaaag aacctgtaca      7740
ctgagattgt ttacacacca atcgcaacgc cagacggatc aatcgtgaag aaattcaaag      7800
gtaacaatag cggacaacct tctacagtag tggacaacac attgatggtt ataatagctt      7860
tcaactatgc catgctatca agtggtatca agaagaaga atcgataat tgctgtagaa        7920 tgtttgcgaa tggtgatgac ttactcctag cagtgcatcc tgattttgag ttcattttag      7980
atgaatttca aaatcacttt gggaatcttg gctgaactt cgaatttaca tcacgaacac       8040
gagacaaatc cgaactgtgg ttcatgtcca caagaggcat caagtatgaa ggaatttaca      8100
taccaaagct tgagaaagaa agaatagtcg ccatacttga atgggatcga tcaaacttgc      8160
ctgaacatag gttggaagct atatgtgcag cgatggttga ggcctgggga tattccgatc      8220
tcgttcatga aatacgaaag ttctatgcgt ggctttggga aatgcaacct tttgcaaatc      8280
tcgcaaaaga agggttggcc ccatacattg ccgagacagc actccgcaat ctctatcttg      8340
```

```
gaacgggtat caaagaggaa gaaattgaaa aatatcttaa acaattcatt aaggatcttc    8400
ccggatacat agaagattac aatgaagatg tattccatca gtcgggaact gttgatgcgg    8460
gtgcacaagg cggcagtgga agccaaggga caacaccacc agcaacaggt agtggagcaa    8520
aaccagccac ctcaggggca ggatctggta gtggcacagg agctggaact ggtgtaactg    8580
gaggtcaagc aaggactggc agtggcactg gacgggatc tggagcaacc ggaggccaat     8640
caggatctgg aagtggcact gaacaggtta acacgggttc agcaggaact aatgcaactg    8700
gaggccaaag agatagggat gtggatgcag gtacaacagg aaaaatttct gtaccaaagc    8760
tcaaggccat gtcaaagaaa atgcgcttac ctaaagcaaa aggaaaagat gtgctacatt    8820
tggattttct attgacatac aaaccacaac aacaagacat atcaaacact agagcaacca    8880
aggaagagtt tgatagatgg tatgatgcca taaagaagga atacgaaatt gatgacacac    8940
aaatgacagt tgtcatgagt ggccttatgg tatggtgcat cgaaaatggt tgctcaccaa    9000
acataaacgg aaattggaca atgatggatg aagatgaaca aagggtcttt ccactcaaac    9060
cggtcattga gaatgcatct ccaactttcc gacaaattat gcatcatttc agtgatgcag    9120
ctgaagcgta catagagtac agaaactcta ctgagcgata tatgccaaga tacgacttc    9180 agcgcaatct caccgactat agcttagcac ggtatgcatt tgatttctat gaaatgactt    9240
cacgcacacc tgctagagct aaagaagccc acatgcagat gaaagccgca gcagttcgtg    9300
gttcaaacac acgactgttc ggtttggacg gaaatgtcgg cgagactcag gagaatacag    9360
agagacacac agctggcgat gttagtcgca acatgcactc tctgttggga gtgcagcagc    9420
accactagtc tcctggaaac cctgtttgca gtaccaataa tatgtactaa tatatagtat    9480
tttagtgagg ttttacctcg tctttactgt tttattacgt atgtatttaa agcgtgaacc    9540
agtctgcaac atacagggtt ggacccagtg tgttctggtg tagcgtgtac tagcgtcgag    9600
ccatgagatg gactgcactg ggtgtggttt tgccacttgt gttgcgagtc tcttggtgag    9660
agacaaaaaa aaaaaaaaaa aaaa                                          9684
```

<210> SEQ ID NO 17
<211> LENGTH: 9678
<212> TYPE: DNA
<213> ORGANISM: Artificial Sequence
<220> FEATURE:
<223> OTHER INFORMATION: Syntheic construct

<400> SEQUENCE: 17

```
aaaaacaaca aaactcaaca caacacaaca aaacacaacc aagcaaatcc aatttacttg      60
cgctcagatt gtagtgaacg gctcgaacga aacggttctt cgagatcact ctctgattct     120
tcctcatctt tcaatttctt tcgaaagaaa tggcgggaac gtggacctac gtgacacgta     180
agtggcagcc agatgttaac aacgatcgtc acattaaaag agtgatggaa atgtttgcag     240
caaaacatca acattactca gaagaacagc gacttgccca taatatgaaa ttattgagga     300
aggcaagtgt tgtaagcgtt gagcctgcga aaccaaagca gaagcaggca actcaacaga     360
tgtgggttga gaaatgtgat cacaatcctg ttgatcactt agtatatcca cgacttggaa     420
aatccgcgaa caaagcagat atgagtatta aagtgcatc tgtaagcaaa ctaaccagag     480
agattttaga aatctcaaag gttagcggcc ttaaggttga actaattgat aaacgaaaaa     540
gattcaaaac acagttatca atcaaaaggt tcaatgcaa aaatttcctc cactgcaaaa      600
cgaatcacga aacaattta tttaagagga aagacatagc cattgggcac aaatggtttc     660
```

```
caacgattga agccattgct agatgctata gcacgatgaa tcgagaagaa ctacaaagcc      720
tttatagagg gagcagtggt ctcacattca ttcaaaacga tgaattgttc attgtcagag      780
gaagaatgaa tggtgaactt gtcaatagct tgtacgagac aaatcgggtt ttggatattg      840
agcactacgc accgcggccc ggggaggacg tgtttcacca atccgcagat ccccaggcta      900
acgatttctg gagggatac acaaatgctt acgtagagaa tcgtaacatt tcgactactc       960
atacagagca caccctaca atcaatctag aagaatgtgg aaaacgaatg gctctactcg      1020
agatactatt tcactctaca ttcaaaatta catgcaagac atgcaacatt gatgatcttg     1080
aattatcgga tgatgaattt ggagctaaac tctacaagaa tttgcaacgt atcgaagaga     1140
aacaacgaga gtatcttgca aaggatcaaa aactatccag aatgatacaa tttatcaaag     1200
aaaggtgcaa tccaaaattt tcgcatttac caacgctatg gcaagttgcg aaacaatag      1260 ggcactatac tgataaccag tcaaagcaaa taatggatat tagcgaagcg ctcatcaaag     1320
ttaatactct gactcctgat gatgctatga agcaagcgc agcgttactt gaagtgtcgc      1380
gatggtataa gaatcgtaag gagtcactca aaactgactc attggaatct tttagaaata    1440
aaatatcacc aaagagtaca ataaatgcag ctttaatgtg cgataatcaa ttggataaaa    1500
atgcaaattt tgtatggggt aatagggaat accacgccaa acgatttttc gcaaactatt    1560
ttgaagcagt ggatcccaca gatgcatatg aaaagcacgt cacacggttc aaccctaatg   1620
gtcaacgaaa gttatcaata ggaaagttag ttatccccact agactttcaa aagattagag   1680
aatcatttgt tggactctcg ataaatagac aaccgctgga taaatgttgt gttagcaaga    1740
tcgaaggagg gtatatatac ccatgttgct gcgtcacaac agaatttggt aaaccagcat    1800
actctgagat aatacctcca acgaagggc atataacaat aggcaattct attgatccaa     1860
agattgtgga cttgccaaat acaacaccac ccagcatgta cattgctaag gatgggtatt    1920
gctatatcaa catctttta gcagccatga tcaacgttaa tgaagaatct gccaaggatt     1980
acacgaaatt tttgagggac gaactagttg agcgtctcgg aaagtggcca aagcttaaag    2040
acgtagcaac agcgtgttat gcattatctg taatgtttcc agaaattaag aatgctgagc    2100
tacctccaat tctagttgac catgaaaata aatcaatgca cgtaattgat tcatatggtt   2160
cactaagcgt tggatttcac atattaaaag caagcacgat tggtcaatta atcaaatttc    2220
aatatgagtc tatggatagt gaaatgcgcg aatacatagt aggaggaact ctcacacaac    2280
agacattcaa cacacttctt aagatgctta cgaaaaacat gttcaaacca gagcgcatca   2340
agcagataat tgaagaggaa ccccttcttac ttatgatggc gattgcgtct ccaacggtat    2400
taatagcact atataataat tgttatattg agcaagctat gacatactgg atcgttaaga    2460
atcaaggagt tgcagccata ttcgcacaac tcgaagcatt agccaagaaa acatcccagg    2520
ctgagctatt agttctacaa atgcagatac ttgaaaaagc atctaaccaa ttaagattag    2580
cagtttcagg acttagccat atcgacccag caaagcgact tttgtggtca cacccttgaag  2640 cgatgtcaac acgatcagaa atgaacaagg agttaatagc tgaggggtat gcactatatg   2700
acgagcgcct atacaccctg atggaaaaaa gttacgtaga tcaattaaac caatcatggg    2760
cagaattgtc atactgtgga aaattttcag caatatggcg tgtgttcaga gtcaggaagt    2820
attacaaacc gtctttaacc gtgagaaaaa gcgtagattt aggcgctgta tacaatatat    2880
cagctacgca tctaatatca gatttagcgc ggaaaagtca agatcaagtc agctctactt    2940
taaccaaact ccgcaacggt ttctatgata aattagagaa agttagaata cgaactataa    3000
aaacggttta ttggtttata cctgatatat ttagactcgt gcacatattc atagtttga     3060
```

```
gtttattaac taccatcgct aacactatca tagtaactat gaatgactac aagaaattga   3120
agaagcaaca aagagaagac gaatatgaag cagaaattaa cgaagttcgc agaatccatt   3180
ctaccttaat ggaagagcgg aaggacaatc tgacgtgtga acaatttatt gagtatatgc   3240
gtcaaaatca tccacggcta gttgaagcaa cactggactt aactcacaca ggtgtcatac   3300
atgaagggaa atccaatctc gaaaccaatt tggaacaggc aatggcagtt ggaaccttga   3360
taacaatgat acttgatcca cagaaaagcg atgctgtcta aggtgttg aacaaaatgc     3420 ggacagtaat tagtacaatt gaacaaaacg tcccattccc ttcagtgaat ttctccaaca   3480
tcttaacacc tccagtggca caacagagtg tagatgttga tgagccatta acacttagca   3540
ctgataaaaa tttaacaata gactttgaca caaatcaaga tttacctgcc gatacattca   3600
gtaatgatgt gacatttgaa gattggtggt caaatcaatt aagcaacaac agaacagtgc   3660
cacactaccg acttggggga aagttcattg aattcacacg agaaaacgca gcccacacga   3720
gcatcgaact tgcacactca acattgaga gggaattctt gcttagagga gcagtcggct    3780
cgggaaaatc cactgggtta ccataccatc ttagcatgcg cggaaaagtg cttctactag   3840
agcctacaag accgctagct gagaacgtgt gtaggcaact acaaggaccg ccatttaacg   3900
taagtccaac tcttcaaatg cgtggattaa gttcttttgg atgcactcca atcacaatca   3960
tgacatctgg ttttgcattg cacatgtacg caaataatcc agataaaata tctgagtacg   4020
atttcataat ctttgatgaa tgtcatataa tggaagcacc agcgatggcc ttttattgct   4080
tactcaaaga atatgaatat cgaggaaaaa ttatcaaggt atcagctacg cctccaggaa   4140
gggagtgtga attcacaaca caacatccag tagacatcca tgtttgtgag aatctaactc   4200
agcaacagtt tgttatggaa ctcgggactg gttcaaccgc agatgctacg aagtacggaa   4260
ataatatctt agtttatgta gcaagctata atgacgtcga ttcattgtcg caagcactag   4320
tcgaacttaa attttccgta atcaaagtgg atggccgaac aatgaaacaa acacaacag    4380 gaatcattac aaacggtacc gcacaaaaga agtgttttgt tgtcgcaacg aatataattg   4440
agaatggcgt cacactagat attgatgttg ttgtcgactt cggacttaag gtctcagctg   4500
acttggacgt tgacaacagg gcggtattgt ataaacgcg aagtatatca tatggtgaac    4560
gcatacaacg attgggtcgt gttggcagaa ataaacctgg tacagttatt cgaatcggaa   4620
aaacaatgaa aggtttgcag gaaattccag caatgatcgc aacagaagca gccttcatgt   4680
gtttcgctta cggtcttaaa gttatcactc ataatgtttc aacgacccat cttgcaaagt   4740
gcacagttaa acaagcgaga accatgatgc aatttgaatt atcaccattt gtcatggctg   4800
agctcgttaa gtttgatggt tcaatgcatc cacaaataca tgaggcacta gtaaaataca   4860
aacttagaga ttctgtcata atgctcagac cgaatgcact tccaagggtc aatttacata   4920
attggcttac agcccgagat tataatagaa taggatgttc attagaactc gaagaccacg   4980
tcaaaattcc gtactacatt aggggagttc ctgacaagtt gtatgaaag ctatatgata    5040 ttatcttaca gtatagtcca actagttgct acggtagact atcaagtgcg tgtgcaggta   5100
aagtagcata tactctgcga actgatccat tttcacttcc aagaacaata gcaataatta   5160
atgccttaat cacggaggag tatgcgaaga gagatcacta tcgtaacatg atttcaaacc   5220
catcttcatc acacgcattc tcactcaatg ggttggtgtc tatgatcgct actagatata   5280
tgaaagacca tacaaaggag aatattgaca aactcattag agtgcgtgat caattacttg   5340
agtttcaagg tactggaatg caatttcaag atccatcaga actcatggaa attggggctc   5400
```

```
tcaacacagt tattcaccaa ggaatggacg caactgcagc ttgtattggg ttacaaggac    5460
gatggaatgc ttcacttata caacgcgatc tcctgattgc aggtggagtt tttatcggag    5520
gcattttgat gatgtggagc ctatttacta aatggagtaa cacaaatgtc tcacatcagg    5580
ggaagaacaa acgcagtaga caaaaacttc gattcaaaga agcaagagac aacaaatatg    5640
catatgatgt cacaggatcg gaagaatgcc ttggcgagaa ttttggaaca gcctatacaa    5700
agaaaggtaa aggaaaagga actaaagttg gactcggtgt gaagcagcat aaattccata    5760
tgatgtacgg tttcgatccc caagagtaca acctaattcg gtttgtcgat ccactcacgg    5820
gagcaactct tgatgaacaa atccatgccg atatacgctt aattcaagag cacttcgctg    5880
aaattcgtga ggaggcagtg attaatgaca caattgaaag gcagcagatt tacggcaatc    5940
ctggactaca agcattttc atacaaaatg ggtcagcaaa cgctctgaga gttgatttaa    6000
caccacattc acctacacga gttgtcacag gtaataacat agcagggttc ccagaatatg    6060
aaggaacact tcgtcagact ggaacagcta taactatacc cattggtcaa gtcccaatcg    6120
caaatgaagc agggggttgca cacgagtcaa atccatgat gaacggggttg ggtgattaca    6180 caccaatatc gcaacaattg tgtctagtac aaaatgactc ggatggggta agcggaatg    6240 tattttcaat tggatatggc tcatatctta tttccaccagc gcacttattc aaatataaca    6300
atggtgaaat aacaattaga tcatcaagag gattgtacaa aattcgtaat tctgtggatt    6360
taaaattaca tccaattgca cacagagaca tggtcataat tcaactccca aaggatttcc    6420
caccgttccc aatgcgcttg aaattcaaac aaccatcacg agatatgcga gtctgcctag    6480
taggtgtcaa cttccaacag aattatagca cttgcatcgt atcagaaagt agtgtgacag    6540
caccaaaagg aaatggagac ttttggaaac attggatatc aacagtcgac ggtcaatgtg    6600
gactaccatt ggtagatact aagagcaaac atattgtcgg aattcatagt cttgcatcaa    6660
caagtggaaa cactaatttc tttgtcgctg tgcctgggaa ctttaatgaa tacatcaatg    6720
gacttgtgca agcaaataaa tgggaaaaag gatggcacta taatccgaat ctcatatcct    6780
ggtgtggact aaatttagtt gattctgccc caaaaggttt gtttaaaacg tcaaaattgg    6840
tagaagactt ggacgcgagc gttgaagagc aatgcaagat caccgaaaca tggctcacag    6900
agcaattaca agataatttg caagtggttg cgaaatgtcc aggccaactt gttaccaagc    6960
atgttgttaa gggtcaatgc ccacactttc aattgtactt atcaacacat gacgatgcca    7020
aagaatactt cgcacccatg cttggaaaat acgacaagag taggcttaac agagcagctt    7080
ttatcaaaga catatcaaaa tatgcaaaac caatttatat tggagaaatc aagtatgata    7140
tctttgatag agctgtacag cgggttgtca atattctcaa aaatgttgga atgcaacaat    7200
gcgtttatgt cacagatgaa gaagaaattt tcagatcact taacctgaac gcagctgtcg    7260
gagcattgta tacaggaaag aagaaaaatt actttgaaaa ttttttcaagc gaagacaaag    7320 aagagatcgt gatgagatcc tgtgaacgta tttacaatgg gcaacttggc gtatggaatg    7380
gatcgctcaa agctgagatc agatcaatag agaaaaccat gctgaataag actcgaacct    7440
tcacagcagc cccattagaa actttgctcg gaggaaaagt gtgcgtggat gatttttaata    7500 atcaattcta ttcacatcat ttagaaggtc catggactgt ggggataaca aaattctatg    7560
gaggttggaa tcgcttactt gagaagttac cagaaggatg ggtttactgc gatgctgacg    7620
ggtctcaatt tgatagttcg ttaacaccat atctcatcaa tgcagtatta atattcgat    7680 tgcaattttat ggaagattgg gatataggag cgcaaatgct aaagaacctg tacactgaga    7740
ttgtttacac accaatcgca acgccagacg gatcaatcgt gaagaaattc aaaggtaaca    7800
```

| atagcggaca accttctaca gtagtggaca acacattgat ggttataata gctttcaact | 7860 |
| atgccatgct atcaagtggt atcaaagaag aagaaatcga taattgctgt agaatgtttg | 7920 |
| cgaatggtga tgacttactc ctagcagtgc atcctgattt tgagttcatt ttagatgaat | 7980 |
| ttcaaaatca ctttgggaat cttgggctga acttcgaatt tacatcacga acacgagaca | 8040 |
| aatccgaact gtggttcatg tccacaagag gcatcaagta tgaaggaatt tacataccaa | 8100 |
| agcttgagaa agaagaata gtcgccatac ttgaatggga tcgatcaaac ttgcctgaac | 8160 |
| ataggttgga agctatatgt gcagcgatgg ttgaggcctg ggatattcc gatctcgttc | 8220 |
| atgaaatacg aaagttctat gcgtggcttt tggaaatgca accttttgca aatctcgcaa | 8280 |
| aagaagggtt ggccccatac attgccgaga cagcactccg caatctctat cttggaacgg | 8340 |
| gtatcaaaga ggaagaaatt gaaaaatatc ttaaacaatt cattaaggat cttcccggat | 8400 |
| acatagaaga ttacaatgaa gatgtattcc atcagtcggg aactgttgat gcgggtgcac | 8460 |
| aaggcggcag tggaagccaa gggacaacac caccagcaac aggtagtgga gcaaaaccag | 8520 |
| ccacctcagg ggcaggatct ggtagtggca caggagctgg aactggtgta actggaggtc | 8580 |
| aagcaaggac tggcagtggc actgggacgg gatctggagc aaccggaggc caatcaggat | 8640 |
| ctggaagtgg cactgaacag gttaacacgg gttcagcagg aactaatgca actggaggcc | 8700 |
| aaagagatag ggatgtggat gcaggtacaa caggaaaaat ttctgtacca aagctcaagg | 8760 |
| ccatgtcaaa gaaaatgcgc ttacctaaag caaaggaaa agatgtgcta catttggatt | 8820 |
| ttctattgac atacaaacca caacaacaag acatatcaaa cactagagca accaaggaag | 8880 |
| agtttgatag atggtatgat gccataaaga aggaatacga aattgatgac acacaaatga | 8940 |
| cagttgtcat gagtggcctt atggtatggt gcatcgaaaa tggttgctca ccaaacataa | 9000 |
| acggaaattg gacaatgatg gatgaagatg aacaaagggt cttcccactc aaaccggtca | 9060 |
| ttgagaatgc atctccaact ttccgacaaa ttatgcatca tttcagtgat gcagctgaag | 9120 |
| cgtacataga gtacagaaac tctactgagc gatatatgcc aagatacgga cttcagcgca | 9180 |
| atctcaccga ctatagctta gcacggtatg catttgattt ctatgaaatg acttcacgca | 9240 |
| cacctgctag agctaaagaa gcccacatgc agatgaaagc cgcagcagtt cgtggttcaa | 9300 |
| acacacgact gttcggtttg gacggaaatg tcggcgagac tcaggagaat acagagagac | 9360 |
| acacagctgg cgatgttagt cgcaacatgc actctctgtt gggagtgcag cagcaccact | 9420 |
| agtctcctgg aaaccctgtt tgcagtacca ataatatgta ctaatatata gtattttagt | 9480 |
| gaggttttac ctcgtcttta ctgttttatt acgtatgtat ttaaagcgtg aaccagtctg | 9540 |
| caacatacag ggttggaccc agtgtgttct ggtgtagcgt gtactagcgt cgagccatga | 9600 |
| gatggactgc actgggtgtg gttttgccac ttgtgttgcg agtctcttgg tgagagacaa | 9660 |
| aaaaaaaaaa aaaaaaa | 9678 |

<210> SEQ ID NO 18
<211> LENGTH: 9690
<212> TYPE: DNA
<213> ORGANISM: Artificial Sequence
<220> FEATURE:
<223> OTHER INFORMATION: Syntheic construct

<400> SEQUENCE: 18

| aaaaacaaca aaactcaaca caacacaaca aaacacaacc aagcaaatcc aatttacttg | 60 |
| cgctcagatt gtagtgaacg gctcgaacga aacggttctt cgagatcact ctctgattct | 120 |

```
tcctcatctt tcaatttctt tcgaaagaaa tggcgggaac gtggacctac gtgacacgta    180
agtggcagcc agatgttaac aacgatcgtc acattaaaag agtgatggaa atgtttgcag    240
caaaacatca acattactca gaagaacagc gacttgccca atatgaaa ttattgagga     300 aggcaagtgt tgtaagcgtt gagcctgcga accaaagca gaagcaggca actcaacaga    360
tgtgggttga gaaatgtgat cacaatcctg ttgatcactt agtatatcca cgacttggaa    420
aatccgcgaa caaagcagat atgagtatta aaagtgcatc tgtaagcaaa ctaaccagag    480
agattttaga atctcaaag gttagcggcc ttaaggttga actaattgat aaacgaaaaa     540
gattcaaaac acagttatca atcaaaaggt tcaatggcaa aaatttcctc cactgcaaaa    600
cgaatcacga aacaatttta tttaagagga aagacatagc cattgggcac aaatggtttc    660
caacgattga agccattgct agatgctata gcacgatgaa tcgagaagaa ctacaaagcc    720
tttatagagg gagcagtggt ctcacattca ttcaaaacga tgaattgttc attgtcagag    780
gaagaatgaa tggtgaactt gtcaatagct tgtacgagac aaatcgggtt ttggatattg    840
agcactacgc agggccctgt ttaaacgcct gcagggagga cgtgtttcac caatccgcag    900
atccccaggc taacgatttc tggaggggat acacaaatgc ttacgtagag aatcgtaaca    960
tttcgactac tcatacagag cacacccta caatcaatct agaagaatgt ggaaaacgaa    1020
tggctctact cgagatacta tttcactcta cattcaaaat tacatgcaag acatgcaaca    1080
ttgatgatct tgaattatcg gatgatgaat ttggagctaa actctacaag aatttgcaac    1140
gtatcgaaga gaaacaacga gagtatcttg caaaggatca aaaactatcc agaatgatac    1200
aatttatcaa agaaaggtgc aatccaaaat tttcgcattt accaacgcta tggcaagttg    1260
cggaaacaat agggcactat actgataacc agtcaaagca ataatggat attagcgaag     1320 cgctcatcaa agttaatact ctgactcctg atgatgctat gaaagcaagc gcagcgttac    1380
ttgaagtgtc gcgatggtat aagaatcgta aggagtcact caaaactgac tcattggaat    1440
cttttagaaa taaatatca ccaaagagta caataaatgc agctttaatg tgcgataatc     1500
aattggataa aaatgcaaat tttgtatggg gtaataggga ataccacgcc aaacgatttt    1560
tcgcaaacta ttttgaagca gtggatccca cagatgcata tgaaaagcac gtcacacggt    1620
tcaaccctaa tggtcaacga aagttatcaa taggaaagtt agttatccca ctagactttc    1680
aaaagattag agaatcattt gttggactct cgataaatag acaaccgctg gataaatgtt    1740
gtgttagcaa gatcgaagga gggtatatat acccatgttg ctgcgtcaca acagaatttg    1800
gtaaaccagc atactctgag ataataccctc caacgaaagg gcatataaca ataggcaatt    1860
ctattgatcc aaagattgtg gacttgccaa atacaacacc cccagcatg tacattgcta     1920 aggatgggta ttgctatatc aacatctttt tagcagccat gatcaacgtt aatgaagaat    1980
ctgccaagga ttacacgaaa ttttttgaggg acgaactagt tgagcgtctc ggaaagtggc    2040
caaagcttaa agacgtagca acagcgtgtt atgcattatc tgtaatgttt ccagaaatta    2100
agaatgctga gctacctcca attctagttg accatgaaaa taaatcaatg cacgtaattg    2160
attcatatgg ttcactaagc gttggatttc acatattaaa agcaagcacg attggtcaat    2220
taatcaaatt tcaatatgag tctatggata gtgaaatgcg cgaatacata gtaggaggaa    2280
ctctcacaca acagacattc aacacacttc ttaagatgct tacgaaaaac atgttcaaac    2340
cagagcgcat caagcagata attgaagagg aacccttctt acttatgatg gcgattgcgt    2400
ctccaacggt attaatagca ctatataata attgttatat tgagcaagct atgacatact    2460
ggatcgttaa gaatcaagga gttgcagcca tattcgcaca actcgaagca ttagccaaga    2520
```

-continued

| | |
|---|---|
| aaacatccca ggctgagcta ttagttctac aaatgcagat acttgaaaaa gcatctaacc | 2580 |
| aattaagatt agcagtttca ggacttagcc atatcgaccc agcaaagcga cttttgtggt | 2640 |
| cacaccttga agcgatgtca acacgatcag aaatgaacaa ggagttaata gctgaggggt | 2700 |
| atgcactata tgacgagcgc ctatacaccc tgatggaaaa aagttacgta gatcaattaa | 2760 |
| accaatcatg ggcagaattg tcatactgtg gaaaattttc agcaatatgg cgtgtgttca | 2820 |
| gagtcaggaa gtattacaaa ccgtctttaa ccgtgagaaa aagcgtagat ttaggcgctg | 2880 |
| tatacaatat atcagctacg catctaatat cagatttagc gcggaaaagt caagatcaag | 2940 |
| tcagctctac tttaaccaaa ctccgcaacg gtttctatga taaattagag aaagttagaa | 3000 |
| tacgaactat aaaaacggtt tattggttta tacctgatat atttagactc gtgcacatat | 3060 |
| tcatagtttt gagtttatta actaccatcg ctaacactat catagtaact atgaatgact | 3120 |
| acaagaaatt gaagaagcaa caaagagaag acgaatatga agcagaaatt aacgaagttc | 3180 |
| gcagaatcca ttctacctta atggaagagc ggaaggacaa tctgacgtgt gaacaattta | 3240 |
| ttgagtatat gcgtcaaaat catccacggc tagttgaagc aacactggac ttaactcaca | 3300 |
| caggtgtcat acatgaaggg aaatccaatc tcgaaaccaa tttggaacag gcaatggcag | 3360 |
| ttggaaccTt gataacaatg atacttgatc cacagaaaag cgatgctgtc tataaggtgt | 3420 |
| tgaacaaaat gcggacagta attagtacaa ttgaacaaaa cgtcccattc ccttcagtga | 3480 |
| atttctccaa catcttaaca cctccagtgg cacaacagag tgtagatgtt gatgagccat | 3540 |
| taacacttag cactgataaa aatttaacaa tagactttga cacaaatcaa gatttacctg | 3600 |
| ccgatacatt cagtaatgat gtgacatttg aagattggtg gtcaaatcaa ttaagcaaca | 3660 |
| acagaacagt gccacactac cgacttgggg gaaagttcat tgaattcaca cgagaaaacg | 3720 |
| cagcccacac gagcatcgaa cttgcacact caaacattga gagggaattc ttgcttagag | 3780 |
| gagcagtcgg ctcgggaaaa tccactgggt taccatacca tcttagcatg cgcggaaaag | 3840 |
| tgcttctact agagcctaca agaccgctag ctgagaacgt gtgtaggcaa ctacaaggac | 3900 |
| cgccatttaa cgtaagtcca actcttcaaa tgcgtggatt aagttctttt ggatgcactc | 3960 |
| caatcacaat catgacatct ggttttgcat tgcacatgta cgcaaataat ccagataaaa | 4020 |
| tatctgagta cgatttcata atctttgatg aatgtcatat aatggaagca ccagcgatgg | 4080 |
| ccttttattg cttactcaaa gaatatgaat atcgaggaaa aattatcaag gtatcagcta | 4140 |
| cgcctccagg aagggagtgt gaattcacaa cacaacatcc agtagacatc catgtttgtg | 4200 |
| agaatctaac tcagcaacag tttgttatgg aactcggacg tggttcaacc gcagatgcta | 4260 |
| cgaagtacgg aaataatatc ttagtttatg tagcaagcta taatgacgtc gattcattgt | 4320 |
| cgcaagcact agtcgaactt aaattttccg taatcaaagt ggatggccga acaatgaaac | 4380 |
| aaaacacaac aggaatcatt acaaacggta ccgcacaaaa gaagtgtttt gttgtcgcaa | 4440 |
| cgaatataat tgagaatggc gtcacactag atattgatgt tgttgtcgac ttcgacttaa | 4500 |
| aggtctcagc tgacttggac gttgacaaca gggcggtatt gtataaacgc gtaagtatat | 4560 |
| catatggtga acgcatacaa cgattgggtc gtgttggcag aaataaacct ggtacagtta | 4620 |
| ttcgaatcgg aaaaacaatg aaaggtttgc aggaaattcc agcaatgatc gcaacagaag | 4680 |
| cagccttcat gtgtttcgct tacggtctta agttatcac tcataatgtt tcaacgaccc | 4740 |
| atcttgcaaa gtgcacagtt aaacaagcga gaaccatgat gcaatttgaa ttatcaccat | 4800 |
| ttgtcatggc tgagctcgtt aagtttgatg gttcaatgca tccacaaata catgaggcac | 4860 |

```
tagtaaaata caaacttaga gattctgtca taatgctcag accgaatgca cttccaaggg    4920
tcaatttaca taattggctt acagcccgag attataatag aataggatgt tcattagaac    4980
tcgaagacca cgtcaaaatt ccgtactaca ttaggggagt tcctgacaag ttgtatggaa    5040
agctatatga tattatctta cagtatagtc caactagttg ctacggtaga ctatcaagtg    5100
cgtgtgcagg taaagtagca tatactctgc gaactgatcc attttcactt ccaagaacaa    5160
tagcaataat taatgcctta atcacggagg agtatgcgaa gagagatcac tatcgtaaca    5220
tgatttcaaa cccatcttca tcacacgcat tctcactcaa tgggttggtg tctatgatcg    5280
ctactagata tatgaaagac catacaaagg agaatattga caaactcatt agagtgcgtg    5340
atcaattact tgagttttcaa ggtactggaa tgcaattttca agatccatca gaactcatgg    5400
aaattggggc tctcaacaca gttattcacc aaggaatgga cgcaactgca gcttgtattg    5460
ggttacaagg acgatggaat gcttcactta tacaacgcga tctcctgatt gcaggtggag    5520
tttttatcgg aggcattttg atgatgtgga gcctatttac taaatggagt aacacaaatg    5580
tctcacatca ggggaagaac aaacgcagta gacaaaaact tcgattcaaa gaagcaagag    5640
acaacaaata tgcatatgat gtcacaggat cggaagaatg ccttggcgag aatttttggaa    5700 cagcctatac aaagaaaggt aaaggaaaag gaactaaagt tggactcggt gtgaagcagc    5760
ataaattcca tatgatgtac ggtttcgatc cccaagagta caacctaatt cggtttgtcg    5820
atccactcac gggagcaact cttgatgaac aaatccatgc cgatatacgc ttaattcaag    5880
agcacttcgc tgaaattcgt gaggaggcag tgattaatga cacaattgaa aggcagcaga    5940
tttacggcaa tcctggacta caagcatttt tcatacaaaa tgggtcagca aacgctctga    6000
gagttgattt aacaccacat tcacctacac gagttgtcac aggtaataac atagcagggt    6060
tcccagaata tgaaggaaca cttcgtcaga ctggaacagc tataactata cccattggtc    6120
aagtcccaat cgcaaatgaa gcaggggttg cacacgagtc aaaatccatg atgaacgggt    6180
tgggtgatta cacaccaata tcgcaacaat tgtgtctagt acaaaatgac tcggatgggg    6240
taaagcggaa tgtattttca attggatatg gctcatatct tatttcacca gcgcacttat    6300
tcaaatataa caatggtgaa ataacaatta gatcatcaag aggattgtac aaaattcgta    6360
attctgtgga tttaaaatta catccaattg cacacagaga catggtcata attcaactcc    6420
caaaggattt cccaccgttc ccaatgcgct tgaaattcaa acaaccatca cgagatatgc    6480
gagtctgcct agtaggtgtc aacttccaac agaattatag cacttgcatc gtatcagaaa    6540
gtagtgtgac agcaccaaaa ggaaatggag acttttggaa acattggata tcaacagtcg    6600
acggtcaatg tggactacca ttggtagata ctaagagcaa acatattgtc ggaattcata    6660
gtcttgcatc aacaagtgga aacactaatt tctttgtcgc tgtgcctggg aactttaatg    6720
aatacatcaa tggacttgtg caagcaaata atgggaaaa aggatggcac tataatccga    6780
atctcatatc ctggtgtgga ctaaatttag ttgattctgc cccaaaaggt ttgtttaaaa    6840
cgtcaaaatt ggtagaagac ttggacgcga gcgttgaaga gcaatgcaag atcaccgaaa    6900
catggctcac agagcaatta caagataatt tgcaagtggt tgcgaaatgt ccaggccaac    6960
ttgttaccaa gcatgttgtt aagggtcaat gcccacactt tcaattgtac ttatcaacac    7020
atgacgatgc caaagaatac ttcgcaccca tgcttggaaa atacgacaag agtaggctta    7080
acagagcagc ttttatcaaa gacatatcaa aatatgcaaa accaatttat attggagaaa    7140
tcaagtatga tatctttgat agagctgtac agcgggttgt caatattctc aaaaatgttg    7200
gaatgcaaca atgcgtttat gtcacagatg aagaagaaat tttcagatca cttaacctga    7260
```

| | |
|---|---|
| acgcagctgt cggagcattg tatacaggaa agaagaaaaa ttactttgaa aattttcaa | 7320 |
| gcgaagacaa agaagagatc gtgatgagat cctgtgaacg tatttacaat gggcaacttg | 7380 |
| gcgtatggaa tggatcgctc aaagctgaga tcagatcaat agagaaaacc atgctgaata | 7440 |
| agactcgaac cttcacagca gccccattag aaactttgct cggaggaaaa gtgtgcgtgg | 7500 |
| atgattttaa taatcaattc tattcacatc atttagaagg tccatggact gttgggataa | 7560 |
| caaaattcta tggaggttgg aatcgcttac ttgagaagtt accagaagga tgggtttact | 7620 |
| gcgatgctga cgggtctcaa tttgatagtt cgttaacacc atatctcatc aatgcagtat | 7680 |
| taaatattcg attgcaattt atggaagatt gggatatagg agcgcaaatg ctaaagaacc | 7740 |
| tgtacactga gattgtttac acaccaatcg caacgccaga cggatcaatc gtgaagaaat | 7800 |
| tcaaaggtaa caatagcgga caaccttcta cagtagtgga caacacattg atggttataa | 7860 |
| tagcttcaa ctatgccatg ctatcaagtg gtatcaaaga agaagaaatc gataattgct | 7920 |
| gtagaatgtt tgcgaatggt gatgacttac tcctagcagt gcatcctgat tttgagttca | 7980 |
| ttttagatga atttcaaaat cactttggga atcttgggct gaacttcgaa tttacatcac | 8040 |
| gaacacgaga caaatccgaa ctgtggttca tgtccacaag aggcatcaag tatgaaggaa | 8100 |
| tttacatacc aaagcttgag aaagaaagaa tagtcgccat acttgaatgg gatcgatcaa | 8160 |
| acttgcctga acataggttg gaagctatat gtgcagcgat ggttgaggcc tggggatatt | 8220 |
| ccgatctcgt tcatgaaata cgaaagttct atgcgtggct tttggaaatg caaccttttg | 8280 |
| caaatctcgc aaaagaaggg ttggccccat acattgccga cagcactc cgcaatctct | 8340 |
| atcttggaac gggtatcaaa gaggaagaaa ttgaaaaata tcttaaacaa ttcattaagg | 8400 |
| atcttcccgg atacatagaa gattacaatg aagatgtatt ccatcagtcg ggaactgttg | 8460 |
| atgcgggtgc acaaggcggc agtggaagcc aagggacaac accaccagca acaggtagtg | 8520 |
| gagcaaaacc agccacctca ggggcaggat ctggtagtgg cacaggagct ggaactggtg | 8580 |
| taactggagg tcaagcaagg actggcagtg gcactgggac gggatctgga gcaaccggag | 8640 |
| gccaatcagg atctggaagt ggcactgaac aggttaacac gggttcagca ggaactaatg | 8700 |
| caactggagg ccaaagagat agggatgtgg atgcaggtac aacaggaaaa atttctgtac | 8760 |
| caaagctcaa ggccatgtca agaaaatgc gcttacctaa agcaaaagga aaagatgtgc | 8820 |
| tacatttgga ttttctattg acatacaaac cacaacaaca agacatatca aacactagag | 8880 |
| caaccaagga agagtttgat agatggtatg atgccataaa gaaggaatac gaaattgatg | 8940 |
| acacacaaat gacagttgtc atgagtggcc ttatggtatg gtgcatcgaa aatggttgct | 9000 |
| caccaaacat aaacggaaat tggacaatga tggatgaaga tgaacaaagg gtctttccac | 9060 |
| tcaaaccggt cattgagaat gcatctccaa ctttccgaca aattatgcat catttcagtg | 9120 |
| atgcagctga agcgtacata gagtacagaa actctactga gcgatatatg ccaagatacg | 9180 |
| gacttcagcg caatctcacc gactatagct tagcacggta tgcatttgat ttctatgaaa | 9240 |
| tgacttcacg cacacctgct agagctaaag aagcccacat gcagatgaaa gccgcagcag | 9300 |
| ttcgtggttc aaacacacga ctgttcggtt tggacggaaa tgtcggcgag actcaggaga | 9360 |
| atacagagag acacacagct ggcgatgtta gtcgcaacat gcactctctg ttgggagtgc | 9420 |
| agcagcacca ctagtctcct ggaaaccctg tttgcagtac caataatatg tactaatata | 9480 |
| tagtatttta gtgaggtttt acctcgtctt tactgttta ttacgtatgt atttaaagcg | 9540 |
| tgaaccagtc tgcaacatac agggttggac ccagtgtgtt ctggtgtagc gtgtactagc | 9600 |

-continued

| | |
|---|---:|
| gtcgagccat gagatggact gcactgggtg tggttttgcc acttgtgttg cgagtctctt | 9660 |
| ggtgagagac aaaaaaaaaa aaaaaaaaaa | 9690 |

<210> SEQ ID NO 19
<211> LENGTH: 14395
<212> TYPE: DNA
<213> ORGANISM: Artificial Sequence
<220> FEATURE:
<223> OTHER INFORMATION: Syntheic construct

<400> SEQUENCE: 19

| | |
|---|---:|
| cataagtgcg gcgacgatag tcatgccccg cgcccaccgg aaggagctga ctgggttgaa | 60 |
| ggctctcaag ggcatcggtc gagcggccgc cctccaaaaa tatcaaagat acagtctcag | 120 |
| aagaccaaag ggcaattgag acttttcaac aaagggtaat atccggaaac ctcctcggat | 180 |
| tccattgccc agctatctgt cactttattg tgaagatagt ggaaaaggaa ggtggctcct | 240 |
| acaaatgcca tcattgcgat aaaggaaagg ccatcgttga agatgcctct gccgacagtg | 300 |
| gtcccaaaga tggaccccca cccacgagga gcatcgtgga aaaagaagac gttccaacca | 360 |
| cgtcttcaaa gcaagtggat tgatgtgata ctccaaaaat atcaaagata cagtctcaga | 420 |
| agaccaaagg gcaattgaga cttttcaaca aagggtaata tccggaaacc tcctcggatt | 480 |
| ccattgccca gctatctgtc actttattgt gaagatagtg aaaaggaag gtggctccta | 540 |
| caaatgccat cattgcgata aaggaaaggc catcgttgaa gatgcctctg ccgacagtgg | 600 |
| tcccaaagat ggaccccac ccacgaggag catcgtggaa aaagaagacg ttccaaccac | 660 |
| gtcttcaaag caagtggatt gatgtgatat ccactgac gtaagggatg acgcacaatc | 720 |
| ccactatcct tcgcaagacc cttcctctat ataaggaagt tcatttcatt tggagaggaa | 780 |
| aaacaacaaa actcaacaca acacaacaaa acacaaccaa gcaaatccaa tttacttgcg | 840 |
| ctcagattgt agtgaacggc tcgaacgaaa cggttcttcg agatcactct ctgattcttc | 900 |
| ctcatctttc aatttctttc gaaagaaatg gcgggaacgt ggacctacgt gacacgtaag | 960 |
| tggcagccag atgttaacaa cgatcgtcac attaaagag tgatggaaat gtttgcagca | 1020 |
| aaacatcaac attactcaga agaacagcga cttgcccata atatgaaatt attgaggaag | 1080 |
| gcaagtgttg taagcgttga gcctgcgaaa ccaaagcaga agcaggcaac tcaacagatg | 1140 |
| tgggttgaga atgtgatca caatcctgtt gatcacttag tatatccacg acttggaaaa | 1200 |
| tccgcgaaca aagcagatat gagtattaaa agtgcatctg taagcaaact aaccagagag | 1260 |
| attttagaaa tctcaaaggt tagcggcctt aaggttgaac taattgataa cgaaaaaga | 1320 |
| ttcaaaacac agttatcaat caaaaggttc aatggcaaaa atttcctcca ctgcaaaacg | 1380 |
| aatcacgaaa acaatttatt taagaggaaa gacatagcca ttgggcacaa atggtttcca | 1440 |
| acgattgaag ccattgctag atgctatagc acgatgaatc gagaagaact acaaagcctt | 1500 |
| tatagaggga gcagtggtct cacattcatt caaaacgatg aattgttcat tgtcagagga | 1560 |
| agaatgaatg gtgaacttgt caatagcttg tacgagacaa atcgggtttt ggatattgag | 1620 |
| cactacgcaa gatctcccgg gcgtacggag gacgtgtttc accaatccgc agatccccag | 1680 |
| gctaacgatt tctggagggg atacacaaat gcttacgtag agaatcgtaa catttcgact | 1740 |
| actcatacag agcacacccc tacaatcaat ctagaagaat gtggaaaacg aatggctcta | 1800 |
| ctcgagatac tatttcactc tacattcaaa attacatgca agacatgcaa cattgatgat | 1860 |
| cttgaattat cggatgatga atttggagct aaactctaca agaatttgca acgtatcgaa | 1920 |
| gagaaacaac gagagtatct tgcaaaggat caaaaactat ccagaatgat acaatttatc | 1980 |

```
aaagaaaggt gcaatccaaa attttcgcat ttaccaacgc tatggcaagt tgcggaaaca    2040 ataggggcact atactgataa ccagtcaaag caaataatgg atattagcga agcgctcatc   2100
aaagttaata ctctgactcc tgatgatgct atgaaagcaa gcgcagcgtt acttgaagtg    2160
tcgcgatggt ataagaatcg taaggagtca ctcaaaactg actcattgga atcttttaga   2220
aataaaatat caccaaagag tacaataaat gcagctttaa tgtgcgataa tcaattggat    2280
aaaaatgcaa attttgtatg gggtaatagg gaataccacg ccaaacgatt tttcgcaaac   2340
tattttgaag cagtggatcc cacagatgca tatgaaaagc acgtcacacg gttcaaccct    2400
aatggtcaac gaaagttatc aataggaaag ttagttatcc cactagactt tcaaaagatt   2460
agagaatcat tgttggact ctcgataaat agacaaccgc tggataaatg ttgtgttagc     2520
aagatcgaag gagggtatat atacccatgt tgctgcgtca caacagaatt tggtaaacca   2580
gcatactctg agataatacc tccaacgaaa gggcatataa caataggcaa ttctattgat    2640
ccaaagattg tggacttgcc aaaatacaaca ccacccagca tgtacattgc taaggatggg  2700
tattgctata tcaacatctt tttagcagcc atgatcaacg ttaatgaaga atctgccaag    2760
gattacacga aattttttgag ggacgaacta gttgagcgtc tcggaaagtg gccaaagctt  2820
aaagacgtag caacagcgtg ttatgcatta tctgtaatgt ttccagaaat taagaatgct    2880
gagctacctc caattctagt tgaccatgaa aataaatcaa tgcacgtaat tgattcatat   2940
ggttcactaa gcgttggatt tcacatatta aaagcaagca cgattggtca attaatcaaa    3000
tttcaatatg agtctatgga tagtgaaatg cgcgaataca tagtaggagg aactctcaca   3060
caacagacat tcaacacact tcttaagatg cttacgaaaa acatgttcaa accagagcgc    3120
atcaagcaga taattgaaga ggaacccttc ttacttatga tggcgattgc gtctccaacg   3180
gtattaatag cactatataa taattgttat attgagcaag ctatgacata ctggatcgtt    3240
aagaatcaag gagttgcagc catattcgca caactcgaag cattagccaa gaaaacatcc   3300
caggctgagc tattagttct acaaatgcag atacttgaaa aagcatctaa ccaattaaga    3360
ttagcagttt caggacttag ccatatcgac ccagcaaagc gacttttgtg gtcacacctt   3420
gaagcgatgt caacacgatc agaaatgaac aaggagttaa tagctgaggg gtatgcacta    3480
tatgacgagc gcctatacac cctgatggaa aaaagttacg tagatcaatt aaaccaatca   3540
tgggcagaat tgtcatactg tggaaaattt tcagcaatat ggcgtgtgtt cagagtcagg    3600
aagtattaca aaccgtcttt aaccgtgaga aaaagcgtag atttaggcgc tgtatacaat   3660
atatcagcta cgcatctaat atcagattta gcgcggaaaa gtcaagatca agtcagctct    3720 acttttaacca aactccgcaa cggtttctat gataaattag agaaagttag aatacgaact   3780
ataaaaacgg tttattggtt tatacctgat atatttagac tcgtgcacat attcatagtt    3840
ttgagtttat taactaccat cgctaacact atcatagtaa ctatgaatga ctacaagaaa   3900
ttgaagaagc aacaaagaga agacgaatat gaagcagaaa ttaacgaagt tcgcagaatc    3960
cattctacct taatggaaga gcggaaggac aatctgacgt gtgaacaatt tattgagtat   4020
atgcgtcaaa atcatccacg gctagttgaa gcaacactgg acttaactca cacaggtgtc    4080
atacatgaag ggaaatccaa tctcgaaacc aatttggaac aggcaatggc agttggaacc   4140
ttgataacaa tgatacttga tccacagaaa agcgatgctg tctataaggt gttgaacaaa    4200
atgcggacag taattagtac aattgaacaa aacgtcccat tcccttcagt gaatttctcc   4260
aacatcttaa caccctccagt ggcacaacag agtgtagatg ttgatgagcc attaacactt   4320
```

```
agcactgata aaaatttaac aatagacttt gacacaaatc aagatttacc tgccgataca    4380
ttcagtaatg atgtgacatt tgaagattgg tggtcaaatc aattaagcaa caacagaaca    4440
gtgccacact accgacttgg gggaaagttc attgaattca cacgagaaaa cgcagcccac    4500
acgagcatcg aacttgcaca ctcaaacatt gagagggaat tcttgcttag aggagcagtc    4560
ggctcgggaa aatccactgg gttaccatac catcttagca tgcgcggaaa agtgcttcta    4620
ctagagccta caagaccgct agctgagaac gtgtgtaggc aactacaagg accgccattt    4680
aacgtaagtc caactcttca aatgcgtgga ttaagttctt ttggatgcac tccaatcaca    4740
atcatgacat ctggttttgc attgcacatg tacgcaaata atccagataa aatatctgag    4800
tacgatttca taatctttga tgaatgtcat ataatggaag caccagcgat ggccttttat    4860
tgcttactca aagaatatga atatcgagga aaaattatca aggtatcagc tacgcctcca    4920
ggaagggagt gtgaattcac aacacaacat ccagtagaca tccatgtttg tgagaatcta    4980
actcagcaac agtttgttat ggaactcggg actggttcaa ccgcagatgc tacgaagtac    5040
ggaaataata tcttagttta tgtagcaagc tataatgacg tcgattcatt gtcgcaagca    5100
ctagtcgaac ttaaattttc cgtaatcaaa gtggatggcc gaacaatgaa acaaaacaca    5160
acaggaatca ttacaaacgg taccgcacaa agaagtgtt ttgttgtcgc aacgaatata    5220
attgagaatg gcgtcacact agatattgat gttgttgtcg acttcggact taaggtctca    5280
gctgacttgg acgttgacaa cagggcggta ttgtataaac gcgtaagtat atcatatggt    5340
gaacgcatac aacgattggg tcgtgttggc agaaataaac ctggtacagt tattcgaatc    5400
ggaaaaacaa tgaaaggttt gcaggaaatt ccagcaatga tcgcaacaga agcagccttc    5460
atgtgtttcg cttacggtct taaagttatc actcataatg tttcaacgac ccatcttgca    5520
aagtgcacag ttaaacaagc gagaaccatg atgcaatttg aattatcacc atttgtcatg    5580
gctgagctcg ttaagtttga tggttcaatg catccacaaa tacatgaggc actagtaaaa    5640
tacaaactta gagattctgt cataatgctc agaccgaatg cacttccaag ggtcaattta    5700
cataattggc ttacagcccg agattataat agaataggat gttcattaga actcgaagac    5760
cacgtcaaaa ttccgtacta cattagggga gttcctgaca agttgtatgg aaagctatat    5820
gatattatct tacagtatag tccaactagt tgctacggta gactatcaag tgcgtgtgca    5880
ggtaaagtag catatactct gcgaactgat ccattttcac ttccaagaac aatagcaata    5940
attaatgcct taatcacgga ggagtatgcg aagagagatc actatcgtaa catgatttca    6000
aacccatctt catcacacgc attctcactc aatgggttgg tgtctatgat cgctactaga    6060
tatatgaaag accatacaaa ggagaatatt gacaaactca ttagagtgcg tgatcaatta    6120
cttgagtttc aaggtactgg aatgcaattt caagatccat cagaactcat ggaaattggg    6180
gctctcaaca cagttattca ccaaggaatg gacgcaactg cagcttgtat tgggttacaa    6240
ggacgatgga atgcttcact tatacaacgc gatctcctga ttgcaggtgg agttttatc    6300 ggaggcattt tgatgatgtg gagcctattt actaaatgga gtaacacaaa tgtctcacat    6360
caggggaaga acaaacgcag tagacaaaaa cttcgattca agaagcaag agacaacaaa    6420 tatgcatatg atgtcacagg atcggaagaa tgccttggcg agaattttgg aacagcctat    6480
acaaagaaag gtaaaggaaa aggaactaaa gttggactcg gtgtgaagca gcataaattc    6540
catatgatgt acggtttcga tcccaagag tacaacctaa ttcggtttgt cgatccactc    6600
acgggagcaa ctcttgatga acaaatccat gccgatatac gcttaattca agagcacttc    6660
gctgaaattc gtgaggaggc agtgattaat gacacaattg aaaggcagca gatttacggc    6720
```

```
aatcctggac tacaagcatt tttcatacaa aatgggtcag caaacgctct gagagttgat      6780
ttaacaccac attcacctac acgagttgtc acaggtaata acatagcagg gttcccagaa      6840
tatgaaggaa cacttcgtca gactggaaca gctataacta tacccattgg tcaagtccca      6900
atcgcaaatg aagcaggggt tgcacacgag tcaaaatcca tgatgaacgg gttgggtgat      6960
tacacaccaa tatcgcaaca attgtgtcta gtacaaaatg actcggatgg ggtaaagcgg      7020
aatgtatttt caattggata tggctcatat cttatttcac cagcgcactt attcaaaatat     7080 aacaatggtg aaataacaat tagatcatca agaggattgt acaaaattcg taattctgtg      7140
gatttaaaat tacatccaat tgcacacaga gacatggtca taattcaact cccaaaggat      7200
ttcccaccgt tcccaatgcg cttgaaattc aaacaaccat cacgagatat gcgagtctgc      7260
ctagtaggtg tcaacttcca acagaattat agcacttgca tcgtatcaga aagtagtgtg      7320
acagcaccaa aaggaaatgg agactttggg aaacattgga tatcaacagt cgacggtcaa      7380
tgtggactac cattggtaga tactaagagc aaacatattg tcggaattca tagtcttgca      7440
tcaacaagtg aaacactaa tttctttgtc gctgtgcctg ggaactttaa tgaatacatc       7500
aatggacttg tgcaagcaaa taatgggaa aaaggatggc actataatcc gaatctcata      7560
tcctggtgtg gactaaattt agttgattct gccccaaaag gtttgtttaa aacgtcaaaa      7620
ttggtagaag acttggacgc gagcgttgaa gagcaatgca agatcaccga acatggctc       7680 acagagcaat tacaagataa tttgcaagtg gttgcgaaat gtccaggcca acttgttacc      7740
aagcatgttg ttaagggtca atgcccacac tttcaattgt acttatcaac acatgacgat      7800
gccaaagaat acttcgcacc catgcttgga aaatacgaca agagtaggct taacagagca      7860
gcttttatca aagacatatc aaaatatgca aaaccaattt atattggaga atcaagtat       7920 gatatctttg atagagctgt acagcgggtt gtcaatattc tcaaaaatgt tggaatgcaa      7980
caatgcgttt atgtcacaga tgaagaagaa attttcagat cacttaaccct gaacgcagct      8040 gtcggagcat tgtatacagg aaagaagaaa aattactttg aaaattttcc aagcgaagac      8100
aaagaagaga tcgtgatgag atcctgtgaa cgtatttaca atgggcaact tggcgtatgg      8160
aatggatcgc tcaaagctga gatcagatca atagagaaaa ccatgctgaa taagactcga      8220
accttcacag cagcccccat tagaaacttg ctcggaggaa aagtgtgcgt ggatgatttt      8280
aataatcaat tctattcaca tcattaagaa ggtccatgga ctgttgggat aacaaaattc      8340
tatggaggtt ggaatcgctt acttgagaag ttaccagaag gatgggttta ctgcgatgct      8400
gacgggtctc aatttgatag ttcgttaaca ccatatctca tcaatgcagt attaaatatt      8460
cgattgcaat ttatggaaga ttgggatata ggagcgcaaa tgctaaagaa cctgtacact      8520
gagattgttt acacaccaat cgcaacgcca gacggatcaa tcgtgaagaa attcaaaggt      8580
aacaatagcg acaaccttc tacagtagtg acaacacat tgatggttat aatagctttc       8640
aactatgcca tgctatcaag tggtatcaaa gaagaagaaa tcgataattg ctgtagaatg      8700
tttgcgaatg gtgatgactt actcctagca gtgcatcctg atttgagtt cattttagat       8760 gaatttcaaa atcactttgg gaatcttggg ctgaacttcg aatttacatc acgaacacga      8820
gacaaatccg aactgtggtt catgtccaca agaggcatca agtatgaagg aatttacata      8880
ccaaagcttg agaaagaaag aatagtcgcc atacttgaat gggatcgatc aaacttgcct      8940
gaacataggt ggaagctat atgtgcagcg atggttgagg cctggggata ttccgatctc      9000
gttcatgaaa tacgaaagtt ctatgcgtgg ctttttggaa tgcaaccttt tgcaaatctc      9060
```

```
gcaaaagaag ggttggcccc atacattgcc gagacagcac tccgcaatct ctatcttgga    9120
acgggtatca aagaggaaga aattgaaaaa tatcttaaac aattcattaa ggatcttccc    9180
ggatacatag aagattacaa tgaagatgta ttccatcagt cgggaactgt tgatgcgggt    9240
gcacaaggcg gcagtggaag ccaagggaca acaccaccag caacaggtag tggagcaaaa    9300
ccagccacct caggggcagg atctggtagt ggcacaggag ctggaactgg tgtaactgga    9360
ggtcaagcaa ggactggcag tggcactggg acgggatctg gagcaaccgg aggccaatca    9420
ggatctggaa gtggcactga acaggttaac acgggttcag caggaactaa tgcaactgga    9480
ggccaaagag atagggatgt ggatgcaggt acaacaggaa aaatttctgt accaaagctc    9540
aaggccatgt caaagaaaat gcgcttacct aaagcaaaag gaaagatgt gctacatttg     9600 gattttctat tgacatacaa accacaacaa caagacatat caaacactag agcaaccaag    9660
gaagagtttg atagatggta tgatgccata aagaaggaat acgaaattga tgacacacaa    9720
atgacagttg tcatgagtgg ccttatggta tggtgcatcg aaaatggttg ctcaccaaac    9780
ataaacggaa attggacaat gatggatgaa gatgaacaaa gggtctttcc actcaaaccg    9840
gtcattgaga atgcatctcc aactttccga caaattatgc atcatttcag tgatgcagct    9900
gaagcgtaca tagagtacag aaactctact gagcgatata tgccaagata cggacttcag    9960
cgcaatctca ccgactatag cttagcacgg tatgcatttg atttctatga aatgacttca   10020
cgcacacctg ctagagctaa agaagcccac atgcagatga aagccgcagc agttcgtggt   10080
tcaaacacac gactgttcgg tttggacgga aatgtcggcg agactcagga gaatacagag   10140
agacacacag ctggcgatgt tagtcgcaac atgcactctc tgttgggagt gcagcagcac   10200
cactagtctc ctggaaaccc tgtttgcagt accaataata tgtactaata tatagtattt   10260
tagtgaggtt ttacctcgtc tttactgttt tattacgtat gtatttaaag cgtgaaccag   10320
tctgcaacat acagggttgg acccagtgtg ttctggtgta gcgtgtacta gcgtcgagcc   10380
atgagatgga ctgcactggg tgtggttttg ccacttgtgt tgcgagtctc ttggtgagag   10440
acaaaaaaaa aaaaaaaaaa aacctggatc ctaggttcac aaagtgtcat cgatagctcg   10500
aatttccccg atcgttcaaa catttggcaa taaagtttct taagattgaa tcctgttgcc   10560
ggtcttgcga tgattatcat ataatttctg ttgaattacg ttaagcatgt aataattaac   10620
atgtaatgca tgacgttatt tatgagatgg gttttatga ttagagtccc gcaattatac    10680
atttaatacg cgatagaaaa caaaatatag cgcgcaaact aggataaatt atcgcgcgcg   10740
gtgtcatcta tgttactaga tcgggaattc ttgaagacga aagggcctcg tgatacgcct   10800 attttatag gttaatgtca tgataataat ggtttcttag acgtcaggtg gcacttttcg    10860
gggaaatgtg cgcggaaccc ctatttgttt attttttctaa atacattcaa atatgtatcc   10920
gctcatgaga caataaccct gataaatgct tcaataatat tgaaaaagga agagtatgag   10980
tattcaacat ttccgtgtcg cccttattcc cttttttgcg cattttgcc ttcctgtttt     11040 tgctcaccca gaaacgctgg tgaaagtaaa agatgctgaa gatcagttgg gtgcacgagt   11100
gggttacatc gaactggatc tcaacagcgg taagatcctt gagagttttc gccccgaaga   11160
acgttttcca atgatgagca cttttaaagt tctgctatgt ggcgcggtat tatcccgtgt   11220
tgacgccggg caagagcaac tcggtcgccg catacactat tctcagaatg acttggttga   11280
gtactcacca gtcacagaaa agcatcttac ggatggcatg acagtaagag aattatgcag   11340
tgctgccata accatgagtg ataacactgc ggccaactta cttctgacaa cgatcggagg   11400
accgaaggag ctaaccgctt ttttgcacaa catgggggat catgtaactc gccttgatcg   11460
```

```
ttgggaaccg gagctgaatg aagccatacc aaacgacgag cgtgacacca cgatgcctgc   11520
agcaatggca acaacgttgc gcaaactatt aactggcgaa ctacttactc tagcttcccg   11580
gcaacaatta atagactgga tggaggcgga taaagttgca ggaccacttc tgcgctcggc   11640
ccttccggct ggctggttta ttgctgataa atctggagcc ggtgagcgtg gtctcgcgcg   11700
tatcattgca gcactggggc cagatggtaa gccctcccgt atcgtagtta tctacacgac   11760
ggggagtcag gcaactatgg atgaacgaaa tagacagatc gctgagatag gtgcctcact   11820
gattaagcat tggtaactgt cagaccaagt ttactcatat atactttaga ttgatttaaa   11880
acttcatttt taatttaaaa ggatctaggt gaagatcctt tttgataatc tcatgaccaa   11940
aatcccttaa cgtgagtttt cgttccactg agcgtcagac cccgtagaaa agatcaaagg   12000
atcttcttga tccttttt tctgcgcgt aatctgctgc ttgcaaacaa aaaaaccacc   12060
gctaccagcg gtggtttgtt tgccggatca agagctacca actctttttc cgaaggtaac   12120
tggcttcagc agagcgcaga taccaaatac tgtccttcta gtgtagccgt agttaggcca   12180
ccacttcaag aactctgtag caccgcctac atacctcgct ctgctaatcc tgttaccagt   12240
ggctgctgcc agtggcgata gtcgtgtct taccggggttg gactcaagac gatagttacc   12300
ggataaggcg cagcggtcgg gctgaacggg gggttcgtgc acacagccca gcttggagcg   12360
aacgacctac accgaactga gatacctaca gcgtgagcta tgagaaagcg ccacgcttcc   12420
cgaagggaga aaggcggaca ggtatccggt aagcggcagg gtcggaacag gagagcgcac   12480
gagggagctt ccaggggggaa acgcctggta tctttatagt cctgtcgggt ttcgccacct   12540
ctgacttgag cgtcgatttt tgtgatgctc gtcaggggg cggagcctat ggaaaaacgc   12600
cagcaacgcg gcctttttac ggttcctggc cttttgctgg ccttttgctc acatgttctt   12660
tcctgcgtta tcccctgatt ctgtggataa ccgtattacc gcctttgagt gagctgatac   12720
cgctcgccgc agccgaacga ccgagcgcag cgagtcagtg agcgaggaag cggaagagcg   12780
cctgatgcgg tattttctcc ttacgcatct gtgcggtatt tcacaccgca tatggtgcac   12840
tctcagtaca atctgctctg atgccgcata gttaagccag tatacactcc gctatcgcta   12900
cgtgactggg tcatggctgc gccccgacac ccgccaacac ccgctgacgc gccctgacgg   12960
gcttgtctgc tcccggcatc cgcttacaga caagctgtga ccgtctccgg gagctgcatg   13020
tgtcagaggt tttcaccgtc atcaccgaaa cgcgcgaggc agctgcggta aagctcatca   13080
gcgtggtcgt gaagcgattc acagatgtct gcctgttcat ccgcgtccag ctcgttgagt   13140
ttctccagaa gcgttaatgt ctggcttctg ataaagcggg ccatgttaag gcggttttt   13200 tcctgtttgg tcactgatgc ctccgtgtaa gggggatttc tgttcatggg ggtaatgata   13260
ccgatgaaac gagagaggat gctcacgata cgggttactg atgatgaaca tgcccggtta   13320
ctggaacgtt gtgagggtaa acaactggcg gtatggatgc ggcgggacca gagaaaaatc   13380
actcagggtc aatgccagcg cttcgttaat acagatgtag gtgttccaca gggtagccag   13440
cagcatcctg cgatgcagat ccggaacata atggtgcagg gcgctgactt ccgcgtttcc   13500
agactttacg aaaacacgaa accgaagacc attcatgttg ttgctcaggt cgcagacgtt   13560
ttgcagcagc agtcgcttca cgttcgctcg cgtatcggtg attcattctg ctaaccagta   13620
aggcaacccc gccagcctag ccgggtcctc aacgacagga gcacgatcat cgcacccgt   13680 ggccaggacc caacgctgcc cgagatgcgc cgcgtgcggc tgctggagat ggcggacgcg   13740
atggatatgt tctgccaagg gttggtttgc gcattcacag ttctccgcaa gaattgattg   13800
```

```
gctccaattc ttggagtggt gaatccgtta gcgaggtgcc gccggcttcc attcaggtcg    13860
aggtggcccg gctccatgca ccgcgacgca acgcggggag gcagacaagg tatagggcgg    13920
cgcctacaat ccatgccaac ccgttccatg tgctcgccga ggcggcataa atcgccgtga    13980
cgatcagcgg tccaatgatc gaagttaggc tggtaagagc cgcgagcgat ccttgaagct    14040
gtccctgatg gtcgtcatct acctgcctgg acagcatggc ctgcaacgcg gcatcccga    14100 tgccgccgga agcgagaaga atcataatgg ggaaggccat ccagcctcgc gtcgcgaacg    14160
ccagcaagac gtagcccagc gcgtcggccg ccatgccggc gataatggcc tgcttctcgc    14220
cgaaacgttt ggtggcggga ccagtgacga aggcttgagc gagggcgtgc aagattccga    14280
ataccgcaag cgacaggccg atcatcgtcg cgctccagcg aaagcggtcc tcgccgaaaa    14340
tgacccagag cgctgccggc acctgtccta cgagttgcat gataaagaag acagt         14395

<210> SEQ ID NO 20
<211> LENGTH: 14389
<212> TYPE: DNA
<213> ORGANISM: Artificial Sequence
<220> FEATURE:
<223> OTHER INFORMATION: Syntheic construct

<400> SEQUENCE: 20
cataagtgcg gcgacgatag tcatgccccg cgcccaccgg aaggagctga ctgggttgaa      60
ggctctcaag ggcatcggtc gagcggccgc cctccaaaaa tatcaaagat acagtctcag     120
aagaccaaag ggcaattgag acttttcaac aaagggtaat atccggaaac ctcctcggat     180
tccattgccc agctatctgt cactttattg tgaagatagt ggaaaaggaa ggtggctcct     240
acaaatgcca tcattgcgat aaaggaaagg ccatcgttga agatgcctct gccgacagtg     300
gtcccaaaga tggaccccca cccacgagga gcatcgtgga aaaagaagac gttccaacca     360
cgtcttcaaa gcaagtggat tgatgtgata ctccaaaaat atcaaagata cagtctcaga     420
agaccaaagg gcaattgaga cttttcaaca aagggtaata tccggaaacc tcctcggatt     480
ccattgccca gctatctgtc actttattgt gaagatagtg gaaaaggaag gtggctccta     540
caaatgccat cattgcgata aaggaaaggc catcgttgaa gatgcctctg ccgacagtgg     600
tcccaaagat ggaccccac ccacgaggag catcgtggaa aaagaagacg ttccaaccac      660
gtcttcaaag caagtggatt gatgtgatat ctccactgac gtaagggatg acgcacaatc     720
ccactatcct tcgcaagacc cttcctctat ataaggaagt tcatttcatt tggagaggaa     780
aaacaacaaa actcaacaca acacaacaaa acacaaccaa gcaaatccaa tttacttgcg     840
ctcagattgt agtgaacggc tcgaacgaaa cggttcttcg agatcactct ctgattcttc     900
ctcatctttc aatttctttc gaaagaaatg gcgggaacgt ggacctacgt gacacgtaag     960
tggcagccag atgttaacaa cgatcgtcac attaaaagag tgatggaaat gtttgcagca    1020
aaacatcaac attactcaga agaacagcga cttgcccata atatgaaatt attgaggaag    1080
gcaagtgttg taagcgttga gcctgcgaaa ccaaagcaga agcaggcaac tcaacagatg    1140
tgggttgaga atgtgatca caatcctgtt gatcacttag tatatccacg acttggaaaa    1200
tccgcgaaca agcagatat gagtattaaa agtgcatctg taagcaaact aaccagagag    1260
attttagaaa tctcaaaggt tagcggcctt aaggttgaac taattgataa acgaaaaga    1320 ttcaaaacac agttatcaat caaaaggttc aatggcaaaa attttcctcca ctgcaaaacg    1380 aatcacgaaa acaatttatt taagaggaaa gacatagcca ttgggcacaa atggtttcca    1440
acgattgaag ccattgctag atgctatagc acgatgaatc gagaagaact acaaagcctt    1500
```

```
tatagaggga gcagtggtct cacattcatt caaaacgatg aattgttcat tgtcagagga    1560
agaatgaatg gtgaacttgt caatagcttg tacgagacaa atcgggtttt ggatattgag    1620
cactacgcac cgcggcccgg ggaggacgtg tttcaccaat ccgcagatcc ccaggctaac    1680
gatttctgga ggggatacac aaatgcttac gtagagaatc gtaacatttc gactactcat    1740
acagagcaca cccctacaat caatctagaa gaatgtggaa aacgaatggc tctactcgag    1800
atactatttc actctacatt caaaattaca tgcaagacat gcaacattga tgatcttgaa    1860
ttatcggatg atgaatttgg agctaaactc tacaagaatt tgcaacgtat cgaagagaaa    1920
caacgagagt atcttgcaaa ggatcaaaaa ctatccagaa tgatacaatt tatcaaagaa    1980
aggtgcaatc caaatttttc gcatttacca acgctatggc aagttgcgga acaatagggg    2040
cactatactg ataaccagtc aaagcaaata atggatatta gcgaagcgct catcaaagtt    2100
aatactctga ctcctgatga tgctatgaaa gcaagcgcag cgttacttga agtgtcgcga    2160
tggtataaga atcgtaagga gtcactcaaa actgactcat tggaatcttt tagaaataaa    2220
atatcaccaa agagtacaat aaatgcagct ttaatgtgcg ataatcaatt ggataaaaat    2280
gcaaattttg tatgggggtaa tagggaatac cacgccaaac gattttttcgc aaactatttt    2340 gaagcagtgg atcccacaga tgcatatgaa aagcacgtca cacggttcaa ccctaatggt    2400
caacgaaagt tatcaatagg aaagttagtt atcccactag actttcaaaa gattagagaa    2460
tcatttgttg gactctcgat aaatagacaa ccgctggata aatgttgtgt tagcaagatc    2520
gaaggagggt atatataccc atgttgctgc gtcacaacag aatttggtaa accagcatac    2580
tctgagataa tacctccaac gaaagggcat ataacaatag gcaattctat tgatccaaag    2640
attgtggact tgccaaatac aacaccaccc agcatgtaca ttgctaagga tgggtattgc    2700
tatatcaaca tcttttttagc agccatgatc aacgttaatg aagaatctgc caaggattac    2760
acgaaatttt tgagggacga actagttgag cgtctcggaa agtggccaaa gcttaaagac    2820
gtagcaacag cgtgttatgc attatctgta atgtttccag aaattaagaa tgctgagcta    2880
cctccaattc tagttgacca tgaaaataaa tcaatgcacg taattgattc atatggttca    2940
ctaagcgttg gatttcacat attaaaagca agcacgattg gtcaattaat caaatttcaa    3000
tatgagtcta tggatagtga aatgcgcgaa tacatagtag gaggaactct cacacaacag    3060
acattcaaca cacttcttaa gatgcttacg aaaaacatgt tcaaaccaga gcgcatcaag    3120
cagataattg aagaggaacc cttcttactt atgatggcga ttgcgtctcc aacggtatta    3180
atagcactat ataataattg ttatattgag caagctatga catactggat cgttaagaat    3240
caaggagttg cagccatatt cgcacaactc gaagcattag ccaagaaaac atcccaggct    3300
gagctattag ttctacaaat gcagatactt gaaaaagcat ctaaccaatt aagattagca    3360
gtttcaggac ttagccatat cgacccagca aagcgacttt tgtggtcaca ccttgaagcg    3420
atgtcaacac gatcagaaat gaacaaggag ttaatagctg aggggtatgc actatatgac    3480
gagcgcctat acaccctgat ggaaaaaagt tacgtagatc aattaaacca atcatgggca    3540
gaattgtcat actgtggaaa attttcagca atatggcgtg tgttcagagt caggaagtat    3600
tacaaaccgt ctttaaccgt gagaaaaagc gtagatttag cgcgctgtata caatatatca    3660 gctacgcatc taatatcaga tttagcgcgg aaaagtcaag atcaagtcag ctctacttta    3720
accaaactcc gcaacggttt ctatgataaa ttagagaaag ttagaatacg aactataaaa    3780
acggtttatt ggtttatacc tgatatattt agactcgtgc acatattcat agttttgagt    3840
```

```
ttattaacta ccatcgctaa cactatcata gtaactatga atgactacaa gaaattgaag    3900
aagcaacaaa gagaagacga atatgaagca gaaattaacg aagttcgcag aatccattct    3960
accttaatgg aagagcggaa ggacaatctg acgtgtgaac aatttattga gtatatgcgt    4020
caaaatcatc cacggctagt tgaagcaaca ctggacttaa ctcacacagg tgtcatacat    4080
gaagggaaat ccaatctcga aaccaatttg gaacaggcaa tggcagttgg aaccttgata    4140
acaatgatac ttgatccaca gaaaagcgat gctgtctata aggtgttgaa caaaatgcgg    4200
acagtaatta gtacaattga acaaaacgtc ccattcctt cagtgaattt ctccaacatc    4260
ttaacacctc cagtggcaca acagagtgta gatgttgatg agccattaac acttagcact    4320
gataaaaatt taacaataga ctttgacaca aatcaagatt tacctgccga tacattcagt    4380
aatgatgtga catttgaaga ttggtggtca aatcaattaa gcaacaacag aacagtgcca    4440
cactaccgac ttgggggaaa gttcattgaa ttcacacgag aaaacgcagc ccacacgagc    4500
atcgaacttg cacactcaaa cattgagagg gaattcttgc ttagaggagc agtcggctcg    4560
ggaaaatcca ctgggttacc ataccatctt agcatgcgcg gaaaagtgct tctactagag    4620
cctacaagac cgctagctga gaacgtgtgt aggcaactac aaggaccgcc atttaacgta    4680
agtccaactc ttcaaatgcg tggattaagt tcttttggat gcactccaat cacaatcatg    4740
acatctggtt ttgcattgca catgtacgca aataatccag ataaaatatc tgagtacgat    4800
ttcataatct ttgatgaatg tcatataatg gaagcaccag cgatggcctt ttattgctta    4860
ctcaaagaat atgaatatcg aggaaaaatt atcaaggtat cagctacgcc tccaggaagg    4920
gagtgtgaat tcacaacaca acatccagta gacatccatg tttgtgagaa tctaactcag    4980
caacagtttg ttatggaact cgggactggt tcaaccgcag atgctacgaa gtacggaaat    5040
aatatcttag tttatgtagc aagctataat gacgtcgatt cattgtcgca agcactagtc    5100
gaacttaaat tttccgtaat caaagtggat ggccgaacaa tgaaacaaaa cacaacagga    5160
atcattacaa acggtaccgc acaaaagaag tgttttgttg tcgcaacgaa tataattgag    5220
aatggcgtca cactagatat tgatgttgtt gtcgacttcg gacttaaggt ctcagctgac    5280
ttggacgttg acaacagggc ggtattgtat aaacgcgtaa gtatatcata tggtgaacgc    5340
atacaacgat tgggtcgtgt tggcagaaat aaacctggta cagttattcg aatcggaaaa    5400
acaatgaaag gtttgcagga aattccagca atgatcgcaa cagaagcagc cttcatgtgt    5460
ttcgcttacg gtcttaaagt tatcactcat aatgtttcaa cgacccatct tgcaaagtgc    5520
acagttaaac aagcgagaac catgatgcaa tttgaattat caccatttgt catggctgag    5580
ctcgttaagt ttgatggttc aatgcatcca caaatacatg aggcactagt aaaatacaaa    5640
cttagagatt ctgtcataat gctcagaccg aatgcacttc aagggtcaa tttacataat    5700
tggcttacag cccgagatta aatagaata ggatgttcat tagaactcga agaccacgtc    5760
aaaattccgt actacattag gggagttcct gacaagttgt atggaaagct atatgatatt    5820
atcttacagt atagtccaac tagttgctac ggtagactat caagtgcgtg tgcaggtaaa    5880
gtagcatata ctctgcgaac tgatccattt tcacttccaa gaacaatagc aataattaat    5940
gccttaatca cggaggagta tgcgaagaga gatcactatc gtaacatgat ttcaaaccca    6000
tcttcatcac acgcattctc actcaatggg ttggtgtcta tgatcgctac tagatatatg    6060
aaagaccata caaaggagaa tattgacaaa ctcattagag tgcgtgatca attacttgag    6120
tttcaaggta ctggaatgca atttcaagat ccatcagaac tcatggaaat tggggctctc    6180
aacacagtta ttcaccaagg aatggacgca actgcagctt gtattgggtt acaaggacga    6240
```

```
tggaatgctt cacttataca acgcgatctc ctgattgcag gtggagtttt tatcggaggc   6300
attttgatga tgtggagcct atttactaaa tggagtaaca caaatgtctc acatcagggg   6360
aagaacaaac gcagtagaca aaaacttcga ttcaaagaag caagagacaa caaatatgca   6420
tatgatgtca caggatcgga agaatgcctt ggcgagaatt ttggaacagc ctatacaaag   6480
aaaggtaaag gaaaaggaac taaagttgga ctcggtgtga agcagcataa attccatatg   6540
atgtacggtt tcgatcccca agagtacaac ctaattcggt tgtcgatcc actcacggga    6600 gcaactcttg atgaacaaat ccatgccgat atacgcttaa ttcaagagca cttcgctgaa   6660
attcgtgagg aggcagtgat taatgacaca attgaaaggc agcagattta cggcaatcct   6720
ggactacaag cattttttcat acaaaatggg tcagcaaacg ctctgagagt tgatttaaca   6780
ccacattcac ctacacgagt tgtcacaggt aataacatag cagggttccc agaatatgaa   6840
ggaacacttc gtcagactgg aacagctata actataccca ttggtcaagt cccaatcgca   6900
aatgaagcag gggttgcaca cgagtcaaaa tccatgatga acgggttggg tgattacaca   6960
ccaatatcgc aacaattgtg tctagtacaa aatgactcgg atggggtaaa gcggaatgta   7020
ttttcaattg gatatggctc atatcttatt tcaccagcgc acttattcaa atataacaat   7080
ggtgaaataa caattagatc atcaagagga ttgtacaaaa ttcgtaattc tgtggattta   7140
aaattacatc caattgcaca cagagacatg gtcataattc aactcccaaa ggatttccca   7200
ccgttcccaa tgcgcttgaa attcaaacaa ccatcacgag atatgcgagt ctgcctagta   7260
ggtgtcaact tccaacagaa ttatagcact tgcatcgtat cagaaagtag tgtgacagca   7320
ccaaaaggaa atggagactt ttggaaacat tggatatcaa cagtcgacgg tcaatgtgga   7380
ctaccattgg tagatactaa gagcaaacat attgtcggaa ttcatagtct tgcatcaaca   7440
agtggaaaca ctaatttctt tgtcgctgtg cctgggaact ttaatgaata catcaatgga   7500
cttgtgcaag caaataaatg ggaaaaagga tggcactata atccgaatct catatcctgg   7560
tgtggactaa atttagttga ttctgcccca aaaggtttgt ttaaaacgtc aaaattggta   7620
gaagacttgg acgcgagcgt tgaagagcaa tgcaagatca ccgaaacatg gctcacagag   7680
caattacaag ataatttgca agtggttgcg aaatgtccag gccaacttgt taccaagcat   7740
gttgttaagg gtcaatgccc acactttcaa ttgtacttat caacacatga cgatgccaaa   7800
gaatacttcg cacccatgct tggaaaatac gacaagagta ggcttaacag agcagctttt   7860
atcaaagaca tatcaaaata tgcaaaacca atttatattg gagaaatcaa gtatgatatc   7920
tttgatagag ctgtacagcg ggttgtcaat attctcaaaa atgttggaat gcaacaatgc   7980
gtttatgtca cagatgaaga agaaattttc agatcactta acctgaacgc agctgtcgga   8040
gcattgtata caggaaagaa gaaaaattac tttgaaaatt tttcaagcga agacaaagaa   8100
gagatcgtga tgagatcctg tgaacgtatt tacaatgggc aacttggcgt atggaatgga   8160
tcgctcaaag ctgagatcag atcaatagag aaaaccatgc tgaataagac tcgaaccttc   8220
acagcagccc cattagaaac tttgctcgga ggaaaagtgt gcgtggatga ttttaataat   8280
caattctatt cacatcattt agaaggtcca tggactgttg ggataacaaa attctatgga   8340
ggttggaatc gcttacttga aagttacca gaaggatggg tttactgcga tgctgacggg   8400
tctcaatttg atagttcgtt aacaccatat ctcatcaatg cagtattaaa tattcgattg   8460
caatttatgg aagattggga tagagagcg caaatgctaa agaacctgta cactgagatt   8520
gtttacacac caatcgcaac gccagacgga tcaatcgtga agaaattcaa aggtaacaat   8580
```

```
agcggacaac cttctacagt agtggacaac acattgatgg ttataatagc tttcaactat    8640
gccatgctat caagtggtat caaagaagaa gaaatcgata attgctgtag aatgtttgcg    8700
aatggtgatg acttactcct agcagtgcat cctgattttg agttcatttt agatgaattt    8760
caaaatcact ttgggaatct tgggctgaac ttcgaattta catcacgaac acgagacaaa    8820
tccgaactgt ggttcatgtc cacaagaggc atcaagtatg aaggaattta cataccaaag    8880
cttgagaaag aaagaatagt cgccatactt gaatgggatc gatcaaactt gcctgaacat    8940
aggttggaag ctatatgtgc agcgatggtt gaggcctggg gatattccga tctcgttcat    9000
gaaatacgaa agttctatgc gtggcttttg gaaatgcaac cttttgcaaa tctcgcaaaa    9060
gaagggttgg ccccatacat tgccgagaca gcactccgca atctctatct tggaacgggt    9120
atcaaagagg aagaaattga aaaatatctt aaacaattca ttaaggatct tcccggatac    9180
atagaagatt acaatgaaga tgtattccat cagtcgggaa ctgttgatgc gggtgcacaa    9240
ggcggcagtg gaagccaagg gacaacacca ccagcaacag gtagtggagc aaaaccagcc    9300
acctcagggg caggatctgg tagtggcaca ggagctggaa ctggtgtaac tggaggtcaa    9360
gcaaggactg gcagtggcac tgggacggga tctggagcaa ccggaggcca atcaggatct    9420
ggaagtggca ctgaacaggt taacacgggt tcagcaggaa ctaatgcaac tggaggccaa    9480
agagataggg atgtggatgc aggtacaaca ggaaaaattt ctgtaccaaa gctcaaggcc    9540
atgtcaaaga aaatgcgctt acctaaagca aaaggaaaag atgtgctaca tttggatttt    9600
ctattgacat acaaaccaca acaacaagac atatcaaaca ctagagcaac caaggaagag    9660
tttgatagat ggtatgatgc cataaagaag gaatacgaaa ttgatgacac acaaatgaca    9720
gttgtcatga gtggccttat ggtatggtgc atcgaaaatg gttgctcacc aaacataaac    9780
ggaaattgga caatgatgga tgaagatgaa caaagggtct ttccactcaa accggtcatt    9840
gagaatgcat ctccaacttt ccgacaaatt atgcatcatt tcagtgatgc agctgaagcg    9900
tacatagagt acagaaactc tactgagcga tatatgccaa gatacggact tcagcgcaat    9960
ctcaccgact atagcttagc acggtatgca tttgatttct atgaaatgac ttcacgcaca   10020
cctgctagag ctaaagaagc ccacatgcag atgaaagccg cagcagttcg tggttcaaac   10080
acacgactgt tcggtttgga cggaaatgtc ggcgagactc aggagaatac agagagacac   10140
acagctggcg atgttagtcg caacatgcac tctctgttgg gagtgcagca gcaccactag   10200
tctcctggaa accctgtttg cagtaccaat aatatgtact aatatatagt attttagtga   10260
ggttttacct cgtctttact gttttattac gtatgtattt aaagcgtgaa ccagtctgca   10320
acatacaggg ttggacccag tgtgttctgg tgtagcgtgt actagcgtcg agccatgaga   10380
tggactgcac tgggtgtggt tttgccactt gtgttgcgag tctcttggtg agagacaaaa   10440
aaaaaaaaaa aaaaaacctg gatcctaggt tcacaaagtg tcatcgatag ctcgaatttc   10500
cccgatcgtt caaacatttg gcaataaagt ttcttaagat tgaatcctgt tgccggtctt   10560
gcgatgatta tcatataatt tctgttgaat tacgttaagc atgtaataat taacatgtaa   10620
tgcatgacgt tatttatgag atgggttttt atgattagag tcccgcaatt atacatttaa   10680
tacgcgatag aaaacaaaat atagcgcgca aactaggata aattatcgcg cgcggtgtca   10740
tctatgttac tagatcggga attcttgaag acgaaagggc ctcgtgatac gcctattttt   10800
ataggttaat gtcatgataa taatggtttc ttagacgtca ggtggcactt ttcggggaaa   10860
tgtgcgcgga accctatttg tttatttttc taaatacatt caaatatgt  atccgctcat   10920
gagacaataa ccctgataaa tgcttcaata atattgaaaa aggaagagta tgagtattca   10980
```

```
acatttccgt gtcgcccttta ttccctttttt tgcggcatttt tgccttcctg tttttgctca   11040
cccagaaacg ctggtgaaag taaaagatgc tgaagatcag ttgggtgcac gagtgggtta   11100
catcgaactg gatctcaaca gcggtaagat ccttgagagt tttcgccccg aagaacgttt   11160
tccaatgatg agcacttttta aagttctgct atgtggcgcg gtattatccc gtgttgacgc   11220
cgggcaagag caactcggtc gccgcataca ctattctcag aatgacttgg ttgagtactc   11280
accagtcaca gaaaagcatc ttacggatgg catgacagta agagaattat gcagtgctgc   11340
cataaccatg agtgataaca ctgcggccaa cttacttctg acaacgatcg gaggaccgaa   11400
ggagctaacc gcttttttgc acaacatggg ggatcatgta actcgccttg atcgttggga   11460
accggagctg aatgaagcca taccaaacga cgagcgtgac accacgatgc ctgcagcaat   11520
ggcaacaacg ttgcgcaaac tattaactgg cgaactactt actctagctt cccggcaaca   11580
attaatagac tggatggagg cggataaagt tgcaggacca cttctgcgct cggcccttcc   11640
ggctggctgg tttattgctg ataaatctgg agccggtgag cgtgggtctc gcggtatcat   11700
tgcagcactg gggccagatg gtaagccctc ccgtatcgta gttatctaca cgacggggag   11760
tcaggcaact atgatgaac gaaatagaca gatcgctgag ataggtgcct cactgattaa   11820
gcattggtaa ctgtcagacc aagtttactc atatatactt tagattgatt taaaacttca   11880
tttttaattt aaaaggatct aggtgaagat cctttttgat aatctcatga ccaaaatccc   11940
ttaacgtgag ttttcgttcc actgagcgtc agaccccgta gaaaagatca aggatcttc   12000 ttgagatcct ttttttctgc gcgtaatctg ctgcttgcaa acaaaaaaac caccgctacc   12060
agcggtggtt tgtttgccgg atcaagagct accaactctt tttccgaagg taactggctt   12120
cagcagagcg cagataccaa atactgtcct tctagtgtag ccgtagttag gccaccactt   12180
caagaactct gtagcaccgc ctacatacct cgctctgcta atcctgttac cagtggctgc   12240
tgccagtggc gataagtcgt gtcttaccgg gttggactca agacgatagt taccggataa   12300
ggcgcagcgg tcgggctgaa cggggggttc gtgcacacag cccagcttgg agcgaacgac   12360
ctacaccgaa ctgagatacc tacagcgtga gctatgagaa agcgccacgc ttcccgaagg   12420
gagaaaggcg gacaggtatc cggtaagcgg cagggtcgga acaggagagc gcacgaggga   12480
gcttccaggg ggaaacgcct ggtatcttta tagtcctgtc gggtttcgcc acctctgact   12540
tgagcgtcga ttttttgtgat gctcgtcagg ggggcggagc ctatggaaaa acgccagcaa   12600
cgcggccttt ttacggttcc tggccttttg ctggcctttt gctcacatgt tctttcctgc   12660
gttatcccct gattctgtgg ataaccgtat taccgccttt gagtgagctg ataccgctcg   12720
ccgcagccga acgaccgagc gcagcgagtc agtgagcgag gaagcggaag agcgcctgat   12780
gcggtatttt ctccttacgc atctgtgcgg tatttcacac cgcatatggt gcactctcag   12840
tacaatctgc tctgatgccg catagttaag ccagtataca ctccgctatc gctacgtgac   12900
tgggtcatgg ctgcgccccg acacccgcca cacccgctg acgcgccctg acgggcttgt   12960
ctgctcccgg catccgctta cagacaagct gtgaccgtct ccgggagctg catgtgtcag   13020
aggttttcac cgtcatcacc gaaacgcgcg aggcagctgc ggtaaagctc atcagcgtgg   13080
tcgtgaagcg attcacagat gtctgcctgt tcatccgcgt ccagctcgtt gagtttctcc   13140
agaagcgtta atgtctggct tctgataaag cgggccatgt taagggcggt tttttcctgt   13200
ttggtcactg atgcctccgt gtaaggggga tttctgttca tggggtaat gataccgatg   13260 aaacgagaga ggatgctcac gatacgggtt actgatgatg aacatgcccg gttactggaa   13320
```

```
cgttgtgagg gtaaacaact ggcggtatgg atgcggcggg accagagaaa aatcactcag    13380
ggtcaatgcc agcgcttcgt taatacagat gtaggtgttc cacagggtag ccagcagcat    13440
cctgcgatgc agatccggaa cataatggtg cagggcgctg acttccgcgt ttccagactt    13500
tacgaaacac ggaaaccgaa gaccattcat gttgttgctc aggtcgcaga cgttttgcag    13560
cagcagtcgc ttcacgttcg ctcgcgtatc ggtgattcat tctgctaacc agtaaggcaa    13620
ccccgccagc ctagccgggt cctcaacgac aggagcacga tcatgcgcac ccgtggccag    13680
gacccaacgc tgcccgagat gcgccgcgtg cggctgctgg agatggcgga cgcgatggat    13740
atgttctgcc aagggttggt ttgcgcattc acagttctcc gcaagaattg attggctcca    13800
attcttggag tggtgaatcc gttagcgagg tgccgccggc ttccattcag gtcgaggtgg    13860
cccggctcca tgcaccgcga cgcaacgcgg ggaggcagac aaggtatagg gcggcgccta    13920
caatccatgc caacccgttc catgtgctcg ccgaggcggc ataaatcgcc gtgacgatca    13980
gcggtccaat gatcgaagtt aggctggtaa gagccgcgag cgatccttga agctgtccct    14040
gatggtcgtc atctacctgc ctggacagca tggcctgcaa cgcgggcatc ccgatgccgc    14100
cggaagcgag aagaatcata atggggaagg ccatccagcc tcgcgtcgcg aacgccagca    14160
agacgtagcc cagcgcgtcg gccgccatgc cggcgataat ggcctgcttc tcgccgaaac    14220
gtttggtggc gggaccagtg acgaaggctt gagcgagggc gtgcaagatt ccgaataccg    14280
caagcgacag gccgatcatc gtcgcgctcc agcgaaagcg gtcctcgccg aaaatgaccc    14340
agagcgctgc cggcacctgt cctacgagtt gcatgataaa gaagacagt              14389
```

<210> SEQ ID NO 21
<211> LENGTH: 20771
<212> TYPE: DNA
<213> ORGANISM: Artificial Sequence
<220> FEATURE:
<223> OTHER INFORMATION: Syntheic construct

<400> SEQUENCE: 21

```
gagagtgtcg tgctccacca tgttgcataa gtgcggcgac gatagtcatg ccccgcgccc      60
accggaagga gctgactggg ttgaaggctc tcaagggcat cggtcgagcg gccgccctcc     120
aaaaatatca agatacagt ctcagaagac caaagggcaa ttgagacttt tcaacaaagg      180
gtaatatccg gaaacctcct cggattccat tgcccagcta tctgtcactt tattgtgaag     240
atagtggaaa aggaaggtgg ctcctacaaa tgccatcgtt gcgataaagg aaaggccatc     300
gttgaagatg cctctgccga cagtggtccc aaagatggac ccccacccac gaggagcatc     360
gtggaaaaag aagacgttcc aaccacgtct tcaaagcaag tggattgatg tgatactcca     420
aaaatatcaa agatacagtc tcagaagacc aaagggcaat tgagactttt caacaaaggg     480
taatatccgg aaacctcctc ggattccatt gcccagctat ctgtcacttt attgtgaaga     540
tagtggaaaa ggaaggtggc tcctacaaat gccatcattg cgataaagga agggccatcg     600
ttgaagatgc ctctgccgac agtggtccca agatggacc cccacccacg aggagcatcg     660
tggaaaaaga agacgttcca accacgtctt caaagcaagt ggattgatgt gatatctcca     720
ctgacgtaag gatgacgca caatcccact atccttcgca agacccttcc tctatataaa     780
ggaagttcat ttcatttggg gaggaaaaac aacaaaactc aacacaacac aacaaaacac     840
aaccaagcaa atccaattta cttgcgctca gattgtagtg aacggctcga acgaaacggt     900
tcttcgagat cactctctga ttcttcctca tctttcaatt tctttcgaaa gaaatggcgg     960
gaacgtggac ctacgtgaca cgtaagtggc agccagatgt taacaacgat cgtcacatta    1020
```

```
aaagagtgat ggaaatgttt gcagcaaaac atcaacatta ctcagaagaa cagcgacttg    1080
cccataatat gaaattattg aggaaggcaa gtgttgtaag cgttgagcct gcgaaaccaa    1140
agcagaagca ggcaactcaa cagatgtggg ttgagaaatg tgatcacaat cctgttgatc    1200
acttagtata tccacgactt ggaaaatccg cgaacaaagc agatatgagt attaaaagtg    1260
catctgtaag caaactaacc agagagattt tagaaatctc aaaggttagc ggccttaagg    1320
ttgaactaat tgataaacga aaagattca aacacagtt atcaatcaaa aggttcaatg    1380
gcaaaaattt cctccactgc aaaacgaatc acgaaaacaa tttatttaag aggaaagaca    1440
tagccattgg gcacaaatgg tttccaacga ttgaagccat tgctagatgc tatagcacga    1500
tgaatcgaga agaactacaa agcctttata gagggagcag tggtctcaca ttcattcaaa    1560
acgatgaatt gttcattgtc agaggaagaa tgaatggtga acttgtcaat agcttgtacg    1620
agacaaatcg ggttttggat attgagcact acgcagggcc ctgtttaaac gcctgcaggg    1680
aggacgtgtt tcaccaatcc gcagatcccc aggctaacga tttctggagg ggatacacaa    1740
atgcttacgt agagaatcgt aacatttcga ctactcatac agagcacacc cctacaatca    1800
atctagaaga atgtggaaaa cgaatggctc tactcgagat actatttcac tctacattca    1860
aaattacatg caagacatgc aacattgatg atcttgaatt atcggatgat gaatttggag    1920
ctaaactcta caagaatttg caacgtatcg aagagaaaca acgagagtat cttgcaaagg    1980
atcaaaaact atccagaatg atacaattta tcaaagaaag gtgcaatcca aaattttcgc    2040
atttaccaac gctatggcaa gttgcggaaa caatagggca ctatactgat aaccagtcaa    2100
agcaaataat ggatattagc gaagcgctca tcaaagttaa tactctgact cctgatgatg    2160
ctatgaaagc aagcgcagcg ttacttgaag tgtcgcgatg gtataagaat cgtaaggagt    2220
cactcaaaac tgactcattg gaatcttta gaaataaaat atcaccaaag agtacaataa    2280
atgcagcttt aatgtgcgat aatcaattgg ataaaaatgc aaattttgta tggggtaata    2340
gggaatacca cgccaaacga ttttcgcaa actattttga agcagtggat cccacagatg    2400
catatgaaaa gcacgtcaca cggttcaacc ctaatggtca acgaaagtta tcaataggaa    2460
agttagttat cccactagac tttcaaaaga ttagagaatc atttgttgga ctctcgataa    2520
atagacaacc gctggataaa tgttgtgtta gcaagatcga aggagggtat atatacccat    2580
gttgctgcgt cacaacagaa tttggtaaac cagcatactc tgagtaaata cctccaacga    2640
aagggcatat aacataggc aattctattg atccaaagat tgtggacttg ccaaatacaa    2700
caccacccag catgtacatt gctaaggatg ggtattgcta tatcaacatc ttttagcag    2760 ccatgatcaa cgttaatgaa gaatctgcca aggattacac gaaattttg agggacgaac    2820 tagttgagcg tctcggaaag tggccaaagc ttaaagacgt agcaacagcg tgttatgcat    2880
tatctgtaat gtttccagaa attaagaatg ctgagctacc tccaattcta gttgaccatg    2940
aaaataaatc aatgcacgta attgattcat atggttcact aagcgttgga tttcacatat    3000
taaaagcaag cacgattggt caattaatca aatttcaata tgagtctatg gatagtgaaa    3060
tgcgcgaata catagtagga ggaactctca cacaacagac attcaacaca cttcttaaga    3120
tgcttacgaa aaacatgttc aaaccagagc gcatcaagca gataattgaa gaggaaccct    3180
tcttacttat gatggcgatt gcgtctccaa cggtattaat agcactatat aataattgtt    3240
atattgagca agctatgaca tactggatcg ttaagaatca aggagttgca gccatattcg    3300
cacaactcga agcattagcc aagaaaaacat cccaggctga gctattagtt ctacaaatgc    3360
```

```
agatacttga aaaagcatct aaccaattaa gattagcagt tcaggactt agccatatcg    3420 acccagcaaa gcgactttg tggtcacacc ttgaagcgat gtcaacacga tcagaaatga    3480
acaaggagtt aatagctgag gggtatgcac tatatgacga gcgcctatac accctgatgg    3540
aaaaaagtta cgtagatcaa ttaaaccaat catgggcaga attgtcatac tgtggaaaat    3600
tttcagcaat atggcgtgtg ttcagagtca ggaagtatta caaaccgtct ttaaccgtga    3660
gaaaaagcgt agatttaggc gctgtataca atatatcagc tacgcatcta atatcagatt    3720
tagcgcggaa aagtcaagat caagtcagct ctactttaac caaactccgc aacggtttct    3780
atgataaatt agagaaagtt agaatacgaa ctataaaaac ggtttattgg tttatacctg    3840
atatatttag actcgtgcac atattcatag ttttgagttt attaactacc atcgctaaca    3900
ctatcatagt aactatgaat gactacaaga aattgaagaa gcaacaaaga gaagacgaat    3960
atgaagcaga aattaacgaa gttcgcagaa tccattctac cttaatggaa gagcggaagg    4020
acaatctgac gtgtgaacaa tttattgagt atatgcgtca aaatcatcca cggctagttg    4080
aagcaacact ggacttaact cacacaggtg tcatacatga agggaaatcc aatctcgaaa    4140
ccaatttgga acaggcaatg gcagttggaa ccttgataac aatgatactt gatccacaga    4200
aaagcgatgc tgtctataag gtgttgaaca aaatgcggac agtaattagt acaattgaac    4260
aaaacgtccc attcccttca gtgaatttct ccaacatctt aacacctcca gtggcacaac    4320
agagtgtaga tgttgatgag ccattaacac ttagcactga taaaaattta acaatagact    4380
ttgacacaaa tcaagattta cctgccgata cattcagtaa tgatgtgaca tttgaagatt    4440
ggtggtcaaa tcaattaagc aacaacagaa cagtgccaca ctaccgactt ggggaaagt    4500 tcattgaatt cacacgagaa aacgcagccc acacgagcat cgaacttgca cactcaaaca    4560
ttgagaggga attcttgctt agaggagcag tcggctcggg aaaatccact gggttaccat    4620
accatcttag catgcgcgga aaagtgcttc tactagagcc tacaagaccg ctagctgaga    4680
acgtgtgtag gcaactacaa ggaccgccat ttaacgtaag tccaactctt caaatgcgtg    4740
gattaagttc ttttggatgc actccaatca caatcatgac atctggtttt gcattgcaca    4800
tgtacgcaaa taatccagat aaaatatctg agtacgattt cataatcttt gatgaatgtc    4860
atataatgga agcaccagcg atggcctttt attgcttact caaagaatat gaatatcgag    4920
gaaaaattat caaggtatca gctacgcctc caggaaggga gtgtgaattc acaacacaac    4980
atccagtaga catccatgtt tgtgagaatc taactcagca acagtttgtt atggaactcg    5040
ggactggttc aaccgcagat gctacgaagt acggaaataa tatcttagtt tatgtagcaa    5100
gctataatga cgtcgattca ttgtcgcaag cactagtcga acttaaattt tccgtaatca    5160
aagtggatgg ccgaacaatg aaacaaaaca caacaggaat cattacaaac ggtaccgcac    5220
aaaagaagtg ttttgttgtc gcaacgaata taattgagaa tggcgtcaca ctagatattg    5280
atgttgttgt cgacttcgga cttaaggtct cagctgactt ggacgttgac aacagggcgg    5340
tattgtataa acgcgtaagt atatcatatg gtgaacgcat acaacgattg ggtcgtgttg    5400
gcagaaataa acctggtaca gttattcgaa tcggaaaaac aatgaaaggt ttgcaggaaa    5460
ttccagcaat gatcgcaaca gaagcagcct tcatgtgttt cgcttacggt cttaaagtta    5520
tcactcataa tgtttcaacg acccatcttg caaagtgcac agttaaacaa gcgagaacca    5580
tgatgcaatt tgaattatca ccatttgtca tggctgagct cgttaagttt gatggttcaa    5640
tgcatccaca aatacatgag gcactagtaa aatacaaact tagagattct gtcataatgc    5700
tcagaccgaa tgcacttcca agggtcaatt tacataattg gcttacagcc cgagattata    5760
```

```
atagaatagg atgttcatta gaactcgaag accacgtcaa aattccgtac tacattaggg    5820
gagttcctga caagttgtat ggaaagctat atgatattat cttacagtat agtccaacta    5880
gttgctacgg tagactatca agtgcgtgtg caggtaaagt agcatatact ctgcgaactg    5940
atccattttc acttccaaga acaatagcaa taattaatgc cttaatcacg gaggagtatg    6000
cgaagagaga tcactatcgt aacatgattt caaacccatc ttcatcacac gcattctcac    6060
tcaatgggtt ggtgtctatg atcgctacta gatatatgaa agaccataca aaggagaata    6120
ttgacaaact cattagagtg cgtgatcaat tacttgagtt tcaaggtact ggaatgcaat    6180
ttcaagatcc atcagaactc atggaaattg gggctctcaa cacagttatt caccaaggaa    6240
tggacgcaac tgcagcttgt attgggttac aaggacgatg gaatgcttca cttatacaac    6300
gcgatctcct gattgcaggt ggagttttta tcggaggcat tttgatgatg tggagcctat    6360
ttactaaatg gagtaacaca aatgtctcac atcagggaa gaacaaacgc agtagacaaa    6420
aacttcgatt caaagaagca agagacaaca aatatgcata tgatgtcaca ggatcggaag    6480
aatgccttgg cgagaatttt ggaacagcct atacaaagaa aggtaaagga aaggaacta    6540 aagttggact cggtgtgaag cagcataaat tccatatgat gtacggtttc gatccccaag    6600
agtacaacct aattcggttt gtcgatccac tcacgggagc aactcttgat gaacaaatcc    6660
atgccgatat acgcttaatt caagagcact cgctgaaat tcgtgaggag gcagtgatta    6720
atgacacaat tgaaggcag cagatttacg gcaatcctgg actacaagca tttttcatac    6780
aaaatgggtc agcaaacgct ctgagagttg atttaacacc acattcacct acacgagttg    6840
tcacaggtaa taacatagca gggttcccag aatatgaagg aacacttcgt cagactggaa    6900
cagctataac tatacccatt ggtcaagtcc caatcgcaaa tgaagcaggg gttgcacacg    6960
agtcaaaatc catgatgaac gggttgggtg attacacacc aatatcgcaa caattgtgtc    7020
tagtacaaaa tgactcggat ggggtaaagc ggaatgtatt ttcaattgga tatggctcat    7080
atcttatttc accagcgcac ttattcaaat ataacaatgg tgaaataaca attagatcat    7140
caagaggatt gtacaaaatt cgtaattctg tggatttaaa attacatcca attgcacaca    7200
gagacatggt cataattcaa ctcccaaagg atttcccacc gttcccaatg cgcttgaaat    7260
tcaaacaacc atcacgagat atgcgagtct gcctagtagg tgtcaacttc aacagaatt    7320 atagcacttg catcgtatca gaaagtagtg tgacagcacc aaaaggaaat ggagactttt    7380
ggaaacattg gatatcaaca gtcgacggtc aatgtggact accattggta gatactaaga    7440
gcaaacatat tgtcggaatt catagtcttg catcaacaag tggaaacact aatttctttg    7500
tcgctgtgcc tgggaacttt aatgaataca tcaatggact tgtgcaagca aataaatggg    7560
aaaaaggatg gcactataat ccgaatctca tatcctggtg tggactaaat ttagttgatt    7620
ctgccccaaa aggtttgttt aaaacgtcaa aattggtaga agacttggac gcgagcgttg    7680
aagagcaatg caagatcacc gaaacatggc tcacagagca attacaagat aatttgcaag    7740
tggttgcgaa atgtccaggc caacttgtta ccaagcatgt tgttaagggt caatgcccac    7800
actttcaatt gtacttatca acacatgacg atgccaaaga atacttcgca cccatgcttg    7860
gaaaatacga caagagtagg cttaacagag cagcttttat caaagacata tcaaaatatg    7920
caaaaccaat ttatattgga gaaatcaagt atgatatctt tgatagagct gtacagcggg    7980
ttgtcaatat tctcaaaaat gttggaatgc aacaatgcgt ttatgtcaca gatgaagaag    8040 aaatttttcag atcacttaac ctgaacgcag ctgtcggagc attgtataca ggaaagaaga    8100
```

```
aaaattactt tgaaaatttt tcaagcgaag acaaagaaga gatcgtgatg agatcctgtg    8160
aacgtattta caatgggcaa cttggcgtat ggaatggatc gctcaaagct gagatcagat    8220
caatagagaa aaccatgctg aataagactc gaaccttcac agcagcccca ttagaaactt    8280
tgctcggagg aaaagtgtgc gtggatgatt ttaataatca attctattca catcatttag    8340
aaggtccatg gactgttggg ataacaaaat tctatggagg ttggaatcgc ttacttgaga    8400
agttaccaga aggatgggtt tactgcgatg ctgacgggtc tcaatttgat agttcgttaa    8460
caccatatct catcaatgca gtattaaata ttcgattgca atttatggaa gattgggata    8520
taggagcgca aatgctaaag aacctgtaca ctgagattgt ttacacacca atcgcaacgc    8580
cagacggatc aatcgtgaag aaattcaaag gtaacaatag cggacaacct tctacagtag    8640
tggacaacac attgatggtt ataatagctt tcaactatgc catgctatca agtggtatca    8700
aagaagaaga aatcgataat tgctgtagaa tgtttgcgaa tggtgatgac ttactcctag    8760
cagtgcatcc tgattttgag ttcatttag atgaatttca aaatcacttt gggaatcttg    8820
ggctgaactt cgaatttaca tcacgaacac gagacaaatc cgaactgtgg ttcatgtcca    8880
caagaggcat caagtatgaa ggaatttaca taccaaagct tgagaaagaa agaatagtcg    8940
ccatacttga atgggatcga tcaaacttgc ctgaacatag gttggaagct atatgtgcag    9000
cgatggttga ggcctgggga tattccgatc tcgttcatga aatacgaaag ttctatgcgt    9060
ggcttttgga aatgcaacct tttgcaaatc tcgcaaaaga agggttggcc ccatacattg    9120
ccgagacagc actccgcaat ctctatcttg gaacgggtat caaagaggaa gaaattgaaa    9180
aatatcttaa acaattcatt aaggatcttc ccggatacat agaagattac aatgaagatg    9240
tattccatca gtcgggaact gttgatgcgg gtgcacaagg cggcagtgga agccaaggga    9300
caacaccacc agcaacaggt agtggagcaa aaccagccac ctcaggggca ggatctggta    9360
gtggcacagg agctggaact ggtgtaactg gaggtcaagc aaggactggc agtggcactg    9420
ggacgggatc tggagcaacc ggaggccaat caggatctgg aagtggcact gaacaggtta    9480
acacgggttc agcaggaact aatgcaactg gaggccaaag agataggat gtggatgcag    9540 gtacaacagg aaaaatttct gtaccaaagc tcaaggccat gtcaaagaaa atgcgcttac    9600
ctaaagcaaa aggaaaagat gtgctacatt tggattttct attgacatac aaaccacaac    9660
aacaagacat atcaaacact agagcaacca aggaagagtt tgatagatgg tatgatgcca    9720
taaagaagga atacgaaatt gatgacacac aaatgacagt tgtcatgagt ggccttatgg    9780
tatggtgcat cgaaaatggt tgctcaccaa acataaacgg aaattggaca atgatggatg    9840
aagatgaaca aagggtcttt ccactcaaac cggtcattga gaatgcatct ccaactttcc    9900
gacaaattat gcatcatttc agtgatgcag ctgaagcgta catagagtac agaaactcta    9960
ctgagcgata tatgccaaga tacggacttc agcgcaatct caccgactat agcttagcac   10020
ggtatgcatt tgatttctat gaaatgactt cacgcacacc tgctagagct aaagaagccc   10080
acatgcagat gaaagccgca gcagttcgtg gttcaaacac acgactgttc ggtttggacg   10140
gaaatgtcgg cgagactcag gagaatacag agagacacac agctggcgat gttagtcgca   10200
acatgcactc tctgttggga gtgcagcagc accactagtc tcctggaaac cctgtttgca   10260
gtaccaataa tatgtactaa tatatagtat tttagtgagg ttttacctcg tctttactgt   10320
tttattacgt atgtatttaa agcgtgaacc agtctgcaac atacagggtt ggacccagtg   10380
tgttctggtg tagcgtgtac tagcgtcgag ccatgagatg gactgcactg ggtgtggttt   10440
tgccacttgt gttgcgagtc tcttggtgag agacaaaaaa aaaaaaaaaa aaaacctgga   10500
```

```
tcctaggttc acaaagtgtc atcgatagct cgaatttccc cgatcgttca acatttggc    10560
aataaagttt cttaagattg aatcctgttg ccggtcttgc gatgattatc ataattttc    10620
tgttgaatta cgttaagcat gtaataatta acatgtaatg catgacgtta tttatgagat   10680
gggttttat gattagagtc ccgcaattat acatttaata cgcgatagaa acaaaatat     10740
agcgcgcaaa ctaggataaa ttatcgcgcg cggtgtcatc tatgttacta gatcgggaat   10800
tcttgaagac gaaagggcct caacgctagc caccaccacc accaccacgt gtgaattaca   10860
ggtgaccagc tcgaatttcc ccgatcgttc aaacatttgg caataaagtt cttaagatt    10920
gaatcctgtt gccggtcttg cgatgattat catataattt ctgttgaatt acgttaagca   10980
tgtaataatt aacatgtaat gcatgacgtt atttatgaga tgggttttta tgattagagt   11040
cccgcaatta tacatttaat acgcgataga aacaaaata tagcgcgcaa actaggataa    11100
attatcgcgc gcggtgtcat ctatgttact agatcgggaa ttaaactatc agtgtttgac   11160
aggatatatt ggcgggtaaa cctaagagaa aagagcgttt attagaataa cggatattta   11220
aaagggcgtg aaaaggttta tccgttcgtc catttgtatg tgcatgccaa ccacagggtt   11280
cccctcggga tcaaagtact ttgatccaac ccctccgctg ctatagtgca gtcggcttct   11340
gacgttcagt gcagccgtct tctgaaaacg acatgtcgca caagtcctaa gttacgcgac   11400
aggctgccgc cctgcccttt tcctggcgtt ttcttgtcgc gtgttttagt cgcataaagt   11460
agaatacttg cgactagaac cggagacatt acgccatgaa caagagcgcc gccgctggcc   11520
tgctgggcta tgcccgcgtc agcaccgacg accaggactt gaccaaccaa cgggccgaac   11580
tgcacgcggc cggctgcacc aagctgtttt ccgagaagat caccggcacc aggcgcgacc   11640
gcccggagct ggccaggatg cttgaccacc tacgccctgg cgacgttgtg acagtgacca   11700
ggctagaccg cctggcccgc agcacccgcg acctactgga cattgccgag cgcatccagg   11760
aggccggcgc gggcctgcgt agcctggcag agccgtgggc cgacaccacc acgccggccg   11820
gccgcatggt gttgaccgtg ttcgccggca ttgccgagtt cgagcgttcc ctaatcatcg   11880
accgcacccg gagcgggcgc gaggccgcca aggcccgagg cgtgaagttt ggcccccgcc   11940
ctaccctcac cccggcacag atcgcgcacg cccgcgagct gatcgaccag gaaggccgca   12000
ccgtgaaaga ggcggctgca ctgcttggcg tgcatcgctc gaccctgtac cgcgcacttg   12060
agcgcagcga ggaagtgacg cccaccgagg ccaggcggcg cggtgccttc cgtgaggacg   12120
cattgaccga ggccgacgcc ctggcggccg ccgagaatga acgccaagag gaacaagcat   12180
gaaaccgcac caggacggcc aggacgaacc gtttttcatt accgaagaga tcgaggcgga   12240
gatgatcgcg gccgggtacg tgttcgagcc gccccgcgcac gtctcaaccg tgcggctgca   12300
tgaaatcctg gccggtttgt ctgatgccaa gctggcggcc tggccggcca gcttggccgc   12360
tgaagaaacc gagcgccgcc gtctaaaaag gtgatgtgta tttgagtaaa acagcttgcg   12420
tcatgcggtc gctgcgtata tgatgcgatg agtaaataaa caaatacgca aggggaacgc   12480
atgaaggtta tcgctgtact taaccagaaa ggcgggtcag gcaagacgac catcgcaacc   12540
catctagccc gcgccctgca actcgccggg gccgatgttc tgttagtcga ttccgatccc   12600
cagggcagtg cccgcgattg ggcggccgtg cgggaagatc aaccgctaac cgttgtcggc   12660
atcgaccgcc cgacgattga ccgcgacgtg aaggccatcg gccggcgcga cttcgtagtg   12720
atcgacggag cgccccaggc ggcggacttg gctgtgtccg cgatcaaggc agccgacttc   12780
gtgctgattc cggtgcagcc aagcccttac gacatatggg ccaccgccga cctggtggag   12840
```

```
ctggttaagc agcgcattga ggtcacggat ggaaggctac aagcggcctt tgtcgtgtcg    12900
cgggcgatca aaggcacgcg catcggcggt gaggttgccg aggcgctggc cgggtacgag    12960
ctgcccattc ttgagtcccg tatcacgcag cgcgtgagct acccaggcac tgccgccgcc    13020
ggcacaaccg ttcttgaatc agaacccgag ggcgacgctg cccgcgaggt ccaggcgctg    13080
gccgctgaaa ttaaatcaaa actcatttga gttaatgagg taaagagaaa atgagcaaaa    13140
gcacaaacac gctaagtgcc ggccgtccga gcgcacgcag cagcaaggct gcaacgttgg    13200
ccagcctggc agacacgcca gccatgaagc gggtcaactt tcagttgccg gcggaggatc    13260
acaccaagct gaagatgtac gcggtacgcc aaggcaagac cattaccgag ctgctatctg    13320
aatacatcgc gcagctacca gagtaaatga gcaaatgaat aaatgagtag atgaattta    13380
gcggctaaag gaggcggcat ggaaaatcaa gaacaaccag gcaccgacgc cgtggaatgc    13440
cccatgtgtg gaggaacggg cggttggcca ggcgtaagcg gctgggttgc ctgccggccc    13500
tgcaatggca ctggaacccc caagcccgag gaatcggcgt gagcggtcgc aaaccatccg    13560
gcccggtaca aatcggcgcg cgctgggtg atgacctggt ggagaagttg aaggccgcgc    13620
aggccgccca gcggcaacgc atcgaggcag aagcacgccc cggtgaatcg tggcaagcgg    13680
ccgctgatcg aatccgcaaa gaatcccggc aaccgccggc agccggtgcg ccgtcgatta    13740
ggaagccgcc caagggcgac gagcaaccag attttttcgt tccgatgctc tatgacgtgg    13800
gcacccgcga tagtcgcagc atcatggacg tggccgtttt ccgtctgtcg aagcgtgacc    13860
gacgagctgg cgaggtgatc cgctacgagc ttccagacgg gcacgtagag gtttccgcag    13920
ggccggccgg catggccagt gtgtgggatt acgacctggt actgatggcg gtttcccatc    13980
taaccgaatc catgaaccga taccgggaag ggaagggaga caagcccggc cgcgtgttcc    14040
gtccacacgt tgcggacgta ctcaagttct gccggcgagc cgatggcgga aagcagaaag    14100
acgacctggt agaaacctgc attcggttaa acaccacgca cgttgccatg cagcgtacga    14160
agaaggccaa gaacggccgc ctggtgacgg tatccgaggg tgaagccttg attagccgct    14220
acaagatcgt aaagagcgaa accgggcggc cggagtacat cgagatcgag ctagctgatt    14280
ggatgtaccg cgagatcaca gaaggcaaga acccggacgt gctgacggtt caccccgatt    14340
acttttttgat cgatcccggc atcggccgtt ttctctaccg cctggcacgc cgcgccgcag    14400
gcaaggcaga agccagatgg ttgttcaaga cgatctacga acgcagtggc agcgccggag    14460
agttcaagaa gttctgtttc accgtgcgca agctgatcgg gtcaaatgac ctgccggagt    14520
acgatttgaa ggaggaggcg gggcaggctg gcccgatcct agtcatgcgc taccgcaacc    14580
tgatcgaggg cgaagcatcc gccggttcct aatgtacgga gcagatgcta gggcaaattg    14640
ccctagcagg ggaaaaggt cgaaaaggtc tctttcctgt ggatagcacg tacattggga    14700
acccaaagcc gtacattggg aaccggaacc cgtacattgg gaacccaaag ccgtacattg    14760
ggaaccggtc acacatgtaa gtgactgata taaaagagaa aaaaggcgat ttttccgcct    14820
aaaactcttt aaaacttatt aaaactctta aaacccgcct ggcctgtgca taactgtctg    14880
gccagcgcac agccgaagag ctgcaaaaag cgcctaccct tcggtcgctg cgctcccta    14940
gccccgccgc ttcgcgtcgg cctatcgcgg ccgctggccg ctcaaaaatg ctggcctac    15000
ggccaggcaa tctaccaggg cgcggacaag ccgcgccgtc gccactcgac cgccggcgcc    15060
cacatcaagg caccctgcct cgcgcgtttc ggtgatgacg gtgaaaacct ctgacacatg    15120
cagctcccgg agacggtcac agcttgtctg taagcggatg ccgggagcag acaagcccgt    15180
cagggcgcgt cagcgggtgt tggcgggtgt cggggcgcag ccatgaccca gtcacgtagc    15240
```

```
gatagcggag tgtatactgg cttaactatg cggcatcaga gcagattgta ctgagagtgc   15300
accatatgcg gtgtgaaata ccgcacagat gcgtaaggag aaaataccgc atcaggcgct   15360
cttccgcttc ctcgctcact gactcgctgc gctcggtcgt tcggctgcgg cgagcggtat   15420
cagctcactc aaaggcggta atacggttat ccacagaatc aggggataac gcaggaaaga   15480
acatgtgagc aaaaggccag caaaaggcca ggaaccgtaa aaaggccgcg ttgctggcgt   15540
ttttccatag gctccgcccc cctgacgagc atcacaaaaa tcgacgctca agtcagaggt   15600
ggcgaaaccc gacaggacta taaagatacc aggcgtttcc ccctggaagc tccctcgtgc   15660
gctctcctgt tccgaccctg ccgcttaccg gatacctgtc cgcctttctc ccttcgggaa   15720
gcgtggcgct ttctcatagc tcacgctgta ggtatctcag ttcggtgtag gtcgttcgct   15780
ccaagctggg ctgtgtgcac gaaccccccg ttcagcccga ccgctgcgcc ttatccggta   15840
actatcgtct tgagtccaac ccggtaagac acgacttatc gccactggca gcagccactg   15900
gtaacaggat tagcagagcg aggtatgtag gcggtgctac agagttcttg aagtggtggc   15960
ctaactacgg ctacactaga aggacagtat ttggtatctg cgctctgctg aagccagtta   16020
ccttcggaaa aagagttggt agctcttgat ccggcaaaca aaccaccgct ggtagcggtg   16080
gtttttttgt ttgcaagcag cagattacgc gcagaaaaaa aggatctcaa gaagatcctt   16140
tgatcttttc tacggggtct gacgctcagt ggaacgaaaa ctcacgttaa gggattttgg   16200
tcatgcattc tagggaaggt gcgaacaagt ccctgatatg agatcatgtt tgtcatctgg   16260
agccatagaa cagggttcat catgagtcat caacttacct tcgccgacag tgaattcagc   16320
agtaagcgcc gtcagaccag aaaagagatt ttcttgtccc gcatggagca gattctgcca   16380
tggcaaaaca tggtggaagt catcgagccg ttttaccccca aggctggtaa tggccggcga   16440
ccttatccgc tggaaaccat gctacgcatt cactgcatgc agcattggta caacctgagc   16500
gatggcgcga tggaagatgc tctgtacgaa atcgcctcca tgcgtctgtt tgcccggtta   16560
tccctggata gcgccttgcc ggaccgcacc accatcatga atttccgcca cctgctggag   16620
cagcatcaac tggcccgcca attgttcaag accatcaatc gctggctggc cgaagcaggc   16680
gtcatgatga ctcaaggcac cttggtcgat gccaccatca ttgaggcacc cagctcgacc   16740
aagaacaaag agcagcaacg cgatccggag atgcatcaga ccaagaaagg caatcagtgg   16800
cactttggca tgaaggccca cattggtgtc gatgccaaga gtggcctgac ccacagcctg   16860
gtcaccaccg cggccaacga gcatgacctc aatcagctgg gtaatctgct gcatggagag   16920
gagcaatttg tctcagccga tgccggctac caaggggcgc cacagcgcga ggagctggcc   16980
gaggtggatg tggactggct gatcgccgag cgccccggca aggtaagaac cttgaaacag   17040
catccacgca agaacaaaac ggccatcaac atcgaataca tgaaagccag catccgggcc   17100
agggtggagc acccatttcg catcatcaag cgacagttcg gcttcgtgaa agccagatac   17160
aaggggttgc tgaaaacga taaccaactg gcgatgttat tcacgctggc caacctgttt   17220
cgggcggacc aaatgatacg tcagtgggag agatctcact aaaaactggg gataacgcct   17280
taaatggcga agaacggtc taaataggct gattcaaggc atttacggga gaaaaaatcg   17340
gctcaaacat gaagaaatga aatgactgag tcagccgaga agaatttccc cgcttattcg   17400
caccttccct aggtactaaa acaattcatc cagtaaaata taatatttta ttttctccca   17460
atcaggcttg atccccagta agtcaaaaaa tagctcgaca tactgttctt ccccgatatc   17520
ctccctgatc gaccggacgc agaaggcaat gtcataccac ttgtccgccc tgccgcttct   17580
```

```
cccaagatca ataaagccac ttactttgcc atctttcaca aagatgttgc tgtctcccag    17640
gtcgccgtgg gaaaagacaa gttcctcttc gggcttttcc gtctttaaaa aatcatacag    17700
ctcgcgcgga tctttaaatg gagtgtcttc ttcccagttt tcgcaatcca catcggccag    17760
atcgttattc agtaagtaat ccaattcggc taagcggctg tctaagctat tcgtataggg    17820
acaatccgat atgtcgatgg agtgaaagag cctgatgcac tccgcataca gctcgataat    17880
cttttcaggg ctttgttcat cttcatactc ttccgagcaa aggacgccat cggcctcact    17940
catgagcaga ttgctccagc catcatgccg ttcaaagtgc aggacctttg gaacaggcag    18000
ctttccttcc agccatagca tcatgtcctt ttcccgttcc acatcatagg tggtcccttt    18060
ataccggctg tccgtcattt ttaaatatag gtttcattt tctcccacca gcttatatac    18120
cttagcagga gacattcctt ccgtatcttt tacgcagcgg tatttttcga tcagttttt     18180 caattccggt gatattctca ttttagccat ttattattc cttcctcttt tctacagtat     18240
ttaaagatac cccaagaagc taattataac aagacgaact ccaattcact gttccttgca    18300
ttctaaaacc ttaaatacca gaaaacagct tttcaaagt tgttttcaaa gttggcgtat     18360
aacatagtat cgacggagcc gattttgaaa ccgcggtgat cacaggcagc aacgctctgt    18420
catcgttaca atcaacatgc taccctccgc gagatcatcc gtgtttcaaa cccggcagct    18480
tagttgccgt tcttccgaat agcatcggta acatgagcaa agtctgccgc cttacaacgg    18540
ctctcccgct gacgccgtcc cggactgatg ggctgcctgt atcgagtggt gattttgtgc    18600
cgagctgccg gtcggggagc tgttggctgg ctggtggcag gatatattgt ggtgtaaaca    18660
aattgacgct tagacaactt aataacacat gcggacgtt tttaatgtac tgaattaacg     18720
ccgaattaat tcggggatc tggattttag tactggattt tggttttagg aattagaaat     18780
tttattgata gaagtatttt acaaatacaa atacatacta agggtttctt atatgctcaa    18840
cacatgagcg aaaccctata ggaaccctaa ttcccttatc tgggaactac tcacacatta    18900
ttatggagaa actcgagctt gtcgatcgac agatcccggt cggcatctac tctatttctt    18960
tgccctcgga cgagtgctgg ggcgtcggtt tccactatcg gcgagtactt ctacacagcc    19020
atcggtccag acggccgcgc ttctgcgggc gatttgtgta cgcccgacag tcccggctcc    19080
ggatcggacg attgcgtcgc atcgaccctg cgcccaagct gcatcatcga aattgccgtc    19140
aaccaagctc tgatagagtt ggtcaagacc aatgcggagc atatacgccc ggagtcgtgg    19200
cgatcctgca agctccggat gcctccgctc gaagtagcgc gtctgctgct ccatacaagc    19260
caaccacggc ctccagaaga agatgttggc gacctcgtat tgggaatccc cgaacatcgc    19320
ctcgctccag tcaatgaccg ctgttatgcg gccattgtcc gtcaggacat tgttggagcc    19380
gaaatccgcg tgcacgaggt gccggacttc ggggcagtcc tcggcccaaa gcatcagctc    19440
atcgagagcc tgcgcgacgg acgcactgac ggtgtcgtcc atcacagttt gccagtgata    19500
cacatgggga tcagcaatcg cgcatatgaa atcacgccat gtagtgtatt gaccgattcc    19560
ttgcggtccg aatgggccga acccgctcgt ctggctaaga tcggccgcag cgatcgcatc    19620
catagcctcc gcgaccggtt gtagaacagc gggcagttcg gtttcaggca ggtcttgcaa    19680
cgtgacaccc tgtgaacggc gggagatgca ataggtcagg ctctcgctaa actcccccaat    19740 gtcaagcact tccggaatcg ggagcgcggc cgatgcaaag tgccgataaa cataacgatc    19800
tttgtagaaa ccatcggcgc agctatttac ccgcaggaca tatccacgcc ctcctacatc    19860
gaagctgaaa gcacgagatt cttcgccctc cgagagctgc atcaggtcgg agacgctgtc    19920
gaacttttcg atcagaaact tctcgacaga cgtcgcggtg agttcaggct ttttcatatc    19980
```

-continued

```
tcattgcccc ccggatctgc gaaagctcga gagagataga tttgtagaga gagactggtg  20040
atttcagcgt gtcctctcca aatgaaatga acttccttat atagaggaag gtcttgcgaa  20100
ggatagtggg attgtgcgtc atcccttacg tcagtggaga tatcacatca atccacttgc  20160
tttgaagacg tggttggaac gtcttctttt tccacgatgc tcctcgtggg tgggggtcca  20220
tctttgggac cactgtcggc agaggcatct tgaacgatag cctttccttt atcgcaatga  20280
tggcatttgt aggtgccacc ttccttttct actgtccttt tgatgaagtg acagatagct  20340
gggcaatgga atccgaggag gtttcccgat attacccttt gttgaaaagt ctcaatagcc  20400
ctttggtctt ctgagactgt atctttgata ttcttggagt agacgagagt gtcgtgctcc  20460
accatgttat cacatcaatc cacttgcttt gaagacgtgg ttggaacgtc ttcttttttcc 20520
acgatgctcc tcgtgggtgg gggtccatct ttgggaccac tgtcggcaga ggcatcttga  20580
acgatagcct ttcctttatc gcaatgatgg catttgtagg tgccaccttc cttttctact  20640
gtccttttga taaagtgaca gatagctggg caatggaatc cgaggaggtt tccggatatt  20700
acccttgtt gaaaagtctc aattgcccctt tggtcttctg agactgtatc tttgatattc  20760
ttggagtaga c                                                        20771

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
aaaaacaaca aaactcaaca caacacaaca aaa                                33

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
tgctttgttc gcggattttc ca                                            22

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
gagggagcag tggtctca                                                 18

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
cgcgcatttc actatccata ga                                            22

<210> SEQ ID NO 26
```

```
<211> LENGTH: 24
<212> TYPE: DNA
<213> ORGANISM: Artificial Sequence
<220> FEATURE:
<223> OTHER INFORMATION: Primer

<400> SEQUENCE: 26
acaatatatc agctacgcat ctaa                                         24

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
ttagatgcgt agctgatata ttgt                                         24

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
agctctactt taaccaaact ccg                                          23

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
cggagtttgg ttaaagtaga gct                                          23

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
tgacacctgt gtgagttaag t                                            21

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
tgaagattgg tggtcaaatc aa                                           22

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
```
tagaggagca gtcggctcgg gaa                                                  23

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
ttcccgagcc gactgctcct cta                                                  23

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gagaatggcg tcacactaga                                                      20

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
cgattgggtc gtgttggca                                                       19

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
atgaaagatc acacgaagga                                                      20

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
ggctctcaac acagttattc a                                                    21

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
tcggatctgc ttacactaag aa                                                   22

<210> SEQ ID NO 39
<211> LENGTH: 22
<212> TYPE: DNA

```
<213> ORGANISM: Artificial Sequence
<220> FEATURE:
<223> OTHER INFORMATION: Primer

<400> SEQUENCE: 39
tagcaggttt cccagagtat ga                                              22

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
agtgtaacag caccaaaagg aa                                              22

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
acaagtggga aaaggatgg ca                                               22

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
tgccatcctt tttcccactt gt                                              22

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
tatgacaaaa gcagattaaa caga                                            24

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
gtcgacaaca cactcatggt                                                 20

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
ggcaacttgg cgtatggaa                                                  19
```

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
gaaaatgcgc ttacctaaag caa            23

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
gtgtcatcaa tttcgtattc ct             22

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
caatctcacc gactatagct ta             22

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
tggcatcata ccatctatca aact           24

<210> SEQ ID NO 50
<211> LENGTH: 42
<212> TYPE: DNA
<213> ORGANISM: Artificial Sequence
<220> FEATURE:
<223> OTHER INFORMATION: Primer

<400> SEQUENCE: 50
tttttttttt tttttttttt gtctctcacc aagagactcg ca    42

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51
acgcacaatc ccactatc                  18

<210> SEQ ID NO 52
<211> LENGTH: 19
<212> TYPE: DNA
<213> ORGANISM: Artificial Sequence
<220> FEATURE:

<223> OTHER INFORMATION: Primer

<400> SEQUENCE: 52
agaccggcaa caggattca                                                    19

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gaacgtggac ctacgtgaca                                                   20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gtgagaccac tgctccctct                                                   20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
tagggaatac cacgccaaac                                                   20

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
cgcgcatttc actatccata ga                                                22

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
tgatccacag aaaagcgatg                                                   20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
cggaattttg acgtggtctt                                                   20

```
<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
ccagaatatg aaggaacact tc                                              22

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
tcatcaccat tcgcaaacat                                                 20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
gcaaatctcg caaagaagg                                                  20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
ccaagagact cgcaacacaa                                                 20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
aaggagctga ctgggttgaa                                                 20

<210> SEQ ID NO 64
<211> LENGTH: 49
<212> TYPE: DNA
<213> ORGANISM: Artificial Sequence
<220> FEATURE:
<223> OTHER INFORMATION: Primer

<400> SEQUENCE: 64
acacgtcctc cgtacgcccg ggagatcttg cgtagtgctc aatatccaa                 49

<210> SEQ ID NO 65
<211> LENGTH: 49
<212> TYPE: DNA
<213> ORGANISM: Artificial Sequence
<220> FEATURE:
<223> OTHER INFORMATION: Primer
```

<400> SEQUENCE: 65
cgggcgtacg gaggacgtgt ttcaccaatc cgcagatccc caggctaac        49

<210> SEQ ID NO 66
<211> LENGTH: 45
<212> TYPE: DNA
<213> ORGANISM: Artificial Sequence
<220> FEATURE:
<223> OTHER INFORMATION: Primer

<400> SEQUENCE: 66
aaacacgtcc tccccgggcc gcggtgcgta gtgctcaata tccaa            45

<210> SEQ ID NO 67
<211> LENGTH: 45
<212> TYPE: DNA
<213> ORGANISM: Artificial Sequence
<220> FEATURE:
<223> OTHER INFORMATION: Primer

<400> SEQUENCE: 67
cccggggagg acgtgtttca ccaatccgca gatccccagg ctaac            45

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
gcatgtcttg catgtaattt tga                                    23

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
ttcacatcat ttagaaggtc ca                                     22

<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
ccttgtgcac ccgtatcaa                                         19

<210> SEQ ID NO 71
<211> LENGTH: 19
<212> TYPE: DNA
<213> ORGANISM: Artificial Sequence
<220> FEATURE:
<223> OTHER INFORMATION: Primer

<400> SEQUENCE: 71
ttgatacggg tgcacaagg                                         19

<210> SEQ ID NO 72
<211> LENGTH: 20

```
<212> TYPE: DNA
<213> ORGANISM: Artificial Sequence
<220> FEATURE:
<223> OTHER INFORMATION: Primer

<400> SEQUENCE: 72
tacaccagtt ccagctcctg                                            20

<210> SEQ ID NO 73
<211> LENGTH: 29
<212> TYPE: DNA
<213> ORGANISM: Artificial Sequence
<220> FEATURE:
<223> OTHER INFORMATION: Primer

<400> SEQUENCE: 73
gaagatctat ggtccgtcct gtagaaacc                                  29

<210> SEQ ID NO 74
<211> LENGTH: 27
<212> TYPE: DNA
<213> ORGANISM: Artificial Sequence
<220> FEATURE:
<223> OTHER INFORMATION: Primer

<400> SEQUENCE: 74
ccgcgtacgt tgtttgcctc cctgctg                                    27

<210> SEQ ID NO 75
<211> LENGTH: 30
<212> TYPE: DNA
<213> ORGANISM: Artificial Sequence
<220> FEATURE:
<223> OTHER INFORMATION: Primer

<400> SEQUENCE: 75
tccccgcgga tggtccgtcc tgtagaaacc                                 30

<210> SEQ ID NO 76
<211> LENGTH: 27
<212> TYPE: DNA
<213> ORGANISM: Artificial Sequence
<220> FEATURE:
<223> OTHER INFORMATION: Primer

<400> SEQUENCE: 76
tccccgcggt tgtttgcctc cctgctg                                    27

<210> SEQ ID NO 77
<211> LENGTH: 28
<212> TYPE: DNA
<213> ORGANISM: Artificial Sequence
<220> FEATURE:
<223> OTHER INFORMATION: Primer

<400> SEQUENCE: 77
gaagatctat ggtgagcaag ggagagga                                   28

<210> SEQ ID NO 78
<211> LENGTH: 29
<212> TYPE: DNA
<213> ORGANISM: Artificial Sequence
<220> FEATURE:
<223> OTHER INFORMATION: Primer

<400> SEQUENCE: 78
```
ccgcgtacgc ttgtacagct cgtccatgc                               29

<210> SEQ ID NO 79
<211> LENGTH: 29
<212> TYPE: DNA
<213> ORGANISM: Artificial Sequence
<220> FEATURE:
<223> OTHER INFORMATION: Primer

<400> SEQUENCE: 79
tccccgcgga tggtgagcaa gggagagga                               29

<210> SEQ ID NO 80
<211> LENGTH: 29
<212> TYPE: DNA
<213> ORGANISM: Artificial Sequence
<220> FEATURE:
<223> OTHER INFORMATION: Primer

<400> SEQUENCE: 80
tccccgcggc ttgtacagct cgtccatgc                               29

<210> SEQ ID NO 81
<211> LENGTH: 26
<212> TYPE: DNA
<213> ORGANISM: Artificial Sequence
<220> FEATURE:
<223> OTHER INFORMATION: Primer

<400> SEQUENCE: 81
tcccccggga tgagcccaga acgacg                                  26

<210> SEQ ID NO 82
<211> LENGTH: 26
<212> TYPE: DNA
<213> ORGANISM: Artificial Sequence
<220> FEATURE:
<223> OTHER INFORMATION: Primer

<400> SEQUENCE: 82
tcccccgggg atctcggtga cgggca                                  26

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
cctgaagatc accctgtgct                                         20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
gcagtctcca gctcctgttc                                         20

<210> SEQ ID NO 85
<211> LENGTH: 60
<212> TYPE: DNA
<213> ORGANISM: Artificial Sequence

```
<220> FEATURE:
<223> OTHER INFORMATION: Synthetic construct

<400> SEQUENCE: 85
attgagcact acgcaagatc tcccgggcgt acggaggacg tgtttcacca atccgcagat      60

<210> SEQ ID NO 86
<211> LENGTH: 20
<212> TYPE: PRT
<213> ORGANISM: Artificial Sequence
<220> FEATURE:
<223> OTHER INFORMATION: Synthetic construct

<400> SEQUENCE: 86

Ile Glu His Tyr Ala Arg Ser Pro Gly Arg Thr Glu Asp Val Phe His
1               5                   10                  15

Gly Ser Ala Asp
            20

<210> SEQ ID NO 87
<211> LENGTH: 54
<212> TYPE: DNA
<213> ORGANISM: Artificial Sequence
<220> FEATURE:
<223> OTHER INFORMATION: Synthetic construct

<400> SEQUENCE: 87
attgagcact acgcaccgcg gcccggggag gacgtgtttc accaatccgc agat           54

<210> SEQ ID NO 88
<211> LENGTH: 18
<212> TYPE: PRT
<213> ORGANISM: Artificial Sequence
<220> FEATURE:
<223> OTHER INFORMATION: Synthetic construct

<400> SEQUENCE: 88

Ile Glu His Tyr Ala Pro Gly Arg Arg Glu Asp Val Phe His Gly Ser
1               5                   10                  15

Ala Asp
```